United States Patent
McCauley et al.

(10) Patent No.: US 9,994,587 B2
(45) Date of Patent: Jun. 12, 2018

(54) HIV PROTEASE INHIBITORS

(71) Applicant: MERCK CANADA INC., Kirkland, Québec (CA)

(72) Inventors: John A. McCauley, Maple Glen, PA (US); David Jonathan Bennett, Winchester, MA (US); Christopher J. Bungard, Lansdale, PA (US); Thomas J. Greshock, Collegeville, PA (US); M. Katharine Holloway, Lansdale, PA (US); Peter D. Williams, Harleysville, PA (US); Christian Beaulieu, Laval (CA); Sheldon Crane, Ile Perrot (CA); Stephanie Lessard, St-Jean-sur-Richelieu (CA); Daniel Mckay, Milton, MA (US); Carmela Molinaro, Colonia, NJ (US); Oscar Miguel Moradei, Burlington, MA (US); Vijayasaradhi Sivalenka, Singapore (SG); Vouy Linh Truong, Pierrefonds (CA); Satyanarayana Tummanapalli, Singapore (SG)

(73) Assignees: Merck Sharp & Dohme Corp., Rahway, NJ (US); Merck Canada Inc., Kirkland, Province of Quebec (CA)

( * ) Notice: Subject to any disclaimer, the term of this patent is extended or adjusted under 35 U.S.C. 154(b) by 0 days. days.

(21) Appl. No.: 15/123,111

(22) PCT Filed: Mar. 2, 2015

(86) PCT No.: PCT/US2015/018267
§ 371 (c)(1),
(2) Date: Sep. 1, 2016

(87) PCT Pub. No.: WO2015/134366
PCT Pub. Date: Sep. 11, 2015

(65) Prior Publication Data
US 2017/0217986 A1    Aug. 3, 2017

Related U.S. Application Data

(60) Provisional application No. 61/948,697, filed on Mar. 6, 2014.

(51) Int. Cl.
| | | |
|---|---|---|
| C07D 498/10 | (2006.01) | |
| C07D 265/30 | (2006.01) | |
| A61K 31/5375 | (2006.01) | |
| C07D 413/12 | (2006.01) | |
| A61K 31/5377 | (2006.01) | |
| C07D 417/14 | (2006.01) | |

(Continued)

(52) U.S. Cl.
CPC ........ C07D 498/10 (2013.01); A61K 31/5375 (2013.01); A61K 31/5377 (2013.01); A61K 31/5386 (2013.01); A61K 45/06 (2013.01); C07D 265/30 (2013.01); C07D 265/36 (2013.01); C07D 413/06 (2013.01); C07D 413/12 (2013.01); C07D 413/14 (2013.01); C07D 417/14 (2013.01); C07D 471/04 (2013.01); C07D 487/04 (2013.01)

(58) Field of Classification Search
CPC ...................................................... C07D 498/10
See application file for complete search history.

(56) References Cited

U.S. PATENT DOCUMENTS

| | | |
|---|---|---|
| 4,252,801 A | 2/1981 | Hauck et al. |
| 5,196,438 A | 3/1993 | Martin et al. |

(Continued)

FOREIGN PATENT DOCUMENTS

| | | |
|---|---|---|
| WO | 200138332 A1 | 5/2001 |
| WO | 2014043019 A1 | 3/2014 |

OTHER PUBLICATIONS

Post-exposure prophylaxis HIV [online], retrieved from the internet on May 13, 2017; URL: http://www.webmd.com/hiv-aids/post-exposure-prophylaxis.*

(Continued)

*Primary Examiner* — Shawquia Jackson
(74) *Attorney, Agent, or Firm* — Carol S. Quagliato; John C. Todaro

(57) ABSTRACT

The present invention is directed to 2,6-morpholine derivatives of Formula (I): and pharmaceutically acceptable salts thereof, wherein $Z^1$, $Z^2$, $V^1$, $V^2$, $V^3$, $R^6$, $R^{6A}$, and X are defined herein. The invention also relates to methods of using the 2,6-morpholine derivatives of the invention for the inhibition of HV protease, the inhibition of HV replication, the prophylaxis of infection by HIV, the treatment of infection by HIV, and the prophylaxis, treatment, and delay in the onset or progression of AIDS. The compounds and their salts can be employed as ingredients in pharmaceutical compositions, optionally in combination with other antivirals, immunomodulators, antibiotics or vaccines.

17 Claims, No Drawings

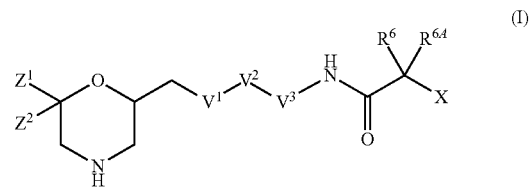

(I)

(51) Int. Cl.
*C07D 413/14* (2006.01)
*C07D 487/04* (2006.01)
*C07D 471/04* (2006.01)
*C07D 413/06* (2006.01)
*C07D 265/36* (2006.01)
*A61K 31/5386* (2006.01)
*A61K 45/06* (2006.01)

(56) References Cited

U.S. PATENT DOCUMENTS

| | | | |
|---|---|---|---|
| 5,413,999 | A | 5/1995 | Vacca et al. |
| 5,484,801 | A | 1/1996 | Al-Razzak et al. |
| 5,484,926 | A | 1/1996 | Dressman et al. |
| 5,585,397 | A | 12/1996 | Tung et al. |
| 5,650,412 | A | 7/1997 | Kim et al. |
| 5,852,195 | A | 12/1998 | Romines et al. |
| 8,497,383 | B2 | 7/2013 | Coburn et al. |
| 9,079,834 | B2 | 7/2015 | Boyd et al. |
| 9,133,157 | B2 | 9/2015 | Boyd et al. |
| 9,187,415 | B2 | 11/2015 | Moradei et al. |
| 9,315,475 | B2 | 4/2016 | Beaulieu et al. |
| 2002/0077338 | A1 | 6/2002 | Dressman et al. |
| 2003/0055071 | A1 | 3/2003 | Anthony et al. |
| 2010/0093811 | A1 | 4/2010 | Coburn et al. |
| 2016/0159752 | A1 | 6/2016 | Williams et al. |
| 2016/0296527 | A1 | 10/2016 | McCauley et al. |
| 2016/0311786 | A1 | 10/2016 | McCauley et al. |
| 2017/0073354 | A1 | 3/2017 | Williams et al. |

OTHER PUBLICATIONS

Landovitz, et al. N. Engl. J. Med. 2009, 361:18, 1768-75.*
Berge, S.M., et al.,, "Pharmaceutical Salts", J. Pharm. Sci, 1977, pp. 1-19, vol. 66, No. 1.
Bingham, A.L., et al., "Over One Hundred Solvates of sulfathiazole", Chem. Commun., 2001, pp. 603-604.
Caira, M.R., et al.,, "Preparation and Crystal Characterization of a Polymorph, a Monohydrate, and an Ethyl Acetate Solvate of the Antifungal Fluconazole", J. Pharmaceutical Sci., 2004, pp. 601-611, vol. 93, No. 3.
Frankel, A.D., et al., "HIV-1: Fifteen Proteins and an RNA", Annu. Rev. Biochem., 1998, pp. 1-25, vol. 67, US.
Gould, P.L., Salt Selections for Basic Drugs, Intl J. Pharmaceutics, 1986, pp. 201-217, vol. 33.
Gulick, R.M., et al. "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337.
Hammer, S.C., et al.,, "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11.
Kohl, N.E., et al.,, "Active Human Immunodeficiency Virus Protease is Required for Viral Infectivity", Proc. Natl. Acad. Sci., 1988, pp. 4686-4690, vol. 85.
PCT International Preliminary Report on Patentability, dated Sep. 6, 2016—PCT/US2015/018267, International Filing Date Mar. 2, 2015.
Pearl, L.H., et al.,, "A Structural Model for the Retroviral Proteases", Nature, 1987, pp. 351-354, vol. 329.
Power, M.D.,, et al. "Nucleotide Sequence of SRV-1, a Type D Simian", Science, 1986, pp. 1567-1572, vol. 231.
PubChem. Compound Summary for CID 41291344. Create Date: May 30, 2009.
PubChem. Compound Summary for CID 64532853. Create Date: Oct. 23, 2012.
Ratner, L., et al.,, "Complete Nucleotide Sequence of AIDS Virus, HTLV-III", Nature, 1985, pp. 277-284, vol. 313.
Toh, H., et al.,, "Close Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5.
Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No., US.

* cited by examiner

HIV PROTEASE INHIBITORS

CROSS-REFERENCE TO RELATED APPLICATIONS

This application claims the benefit of U.S. Provisional Application Ser. No. 61/948,697, filed Mar. 6, 2014, the contents of which are herein incorporated by reference in their entirety.

FIELD OF THE INVENTION

The present invention is directed to certain 2,6-morpholine derivatives and their pharmaceutically acceptable salts. Some of these derivatives are HIV protease inhibitors. The compounds are useful for the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

Human immunodeficiency virus (HIV) is a retrovirus which is the etiological agent of acquired immunodeficiency syndrome (AIDS) and its precursor AIDS-related complex ("ARC"), a syndrome characterized by symptoms such as persistent generalized lymphadenopathy, fever and weight loss. AIDS is characterized by the destruction of the immune system, particularly CD4 T-cells, with attendant susceptibility to opportunistic infections. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al. (Proc. Natl Acad. Sci. 85: 4686-4690 (1988)) demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

The HIV genome is made up of single-stranded RNA which comprises several genes that code for structural proteins common to all retroviruses and additional genes that code for accessory proteins specific to HIV (A. D. Frankel and J. A. T. Young, *Annu. Rev. Biochem.* 67:1-25 (1998)). Open reading frames encoding structural proteins include the pol gene (Ratner et al., *Nature* 313: 277-284 (1985)), which encodes reverse transcriptase, integrase and HIV protease, the gag gene, which encodes the core proteins of the virion (Toh et al., *EMBO J.* 4: 1267-1272 (1985); Power et al., *Science* 231: 1567-72 (1986); Pearl et al., *Nature* 329: 351-54 (1987)), and the env gene, which encodes gp120 (surface) and gp41 (TM/transmembrane).

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 337: 725-733 (1997) and Gulick et al., *New England J. Med.* 337: 734-739 (1997).

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

In one aspect, the present invention provides Compounds of Formula (I):

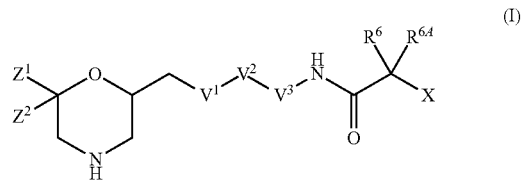

or a pharmaceutically acceptable salt or prodrug thereof, wherein:

$V^1$ is a bond, $CH_2$, or O;

$V^2$ is $CH_2$;

$V^3$ is $CH_2$; or alternatively, $V^2$ and $V^3$ may come together to form (i) a phenyl group, which is optionally substituted with up to 4 occurrences of $X^D$, or (ii) HetA; wherein $V^2$ is C or CH and $V^3$ is C, CH, or N;

X is H or $NR^1R^2$;

each occurrence of $X^D$ is independently selected from halo, hydroxy, =O, $C_1$-$C_4$ alkyl, $C_1$-$C_4$ alkoxy, —$S(O)_k$—$C_1$-$C_4$ alkyl, $CF_3$, CN, $C_0$-$C_4$ alkyl-phenyl;

each k is independently 0, 1 or 2;

$Z^1$ is selected from the group consisting of:

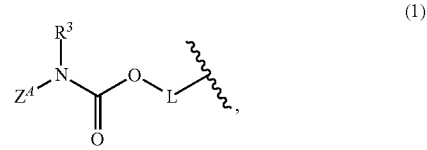

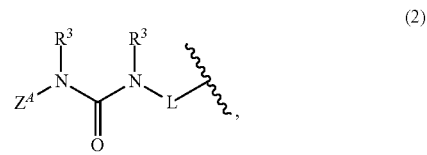

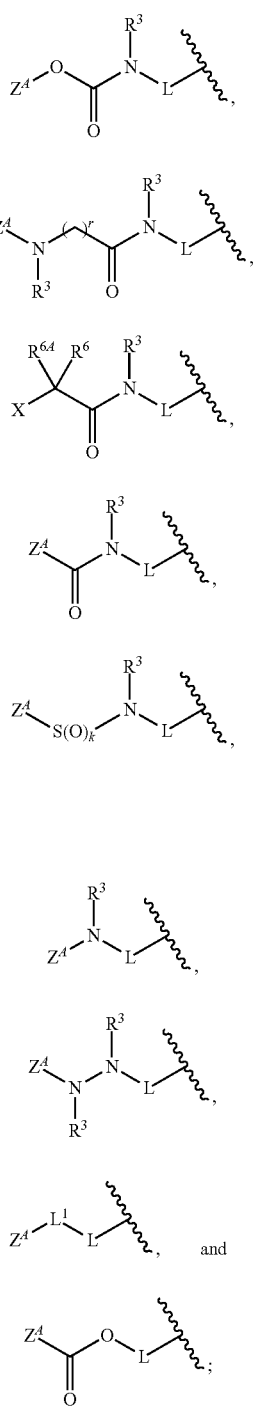

L is a linker selected from
(a) a bond,
(b) —$C_1$-$C_3$ alkylene-,
(c) —$C_2$-$C_4$ alkenylene-,
(d) —$CH_2$—$CF_2$—
(e) —C(O)—,
(f) —$CH_2$—C(O)—,
(g) —$CH_2$—$CH_2$—C(O)—, and

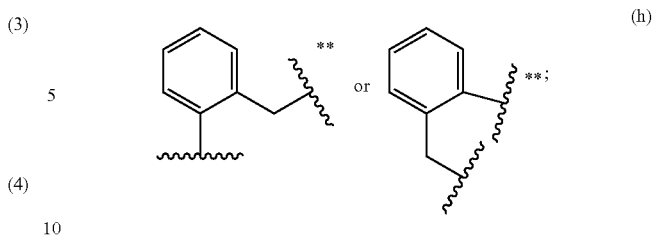

$L^1$ is selected from the group consisting of: S, S(O), $S(O)_2$, O, $C_1$-$C_3$ alkylene, and a bond;
each r is independently 1, 2, 3 or 4;
$Z^A$ is selected from the group consisting of:
(1) hydrogen,
(2) $C_1$-$C_{10}$ alkyl,
(3) $C_2$-$C_{10}$ alkenyl,
(4) $C_2$-$C_{10}$ alkynyl,
(5) $C_3$-$C_7$ cycloalkyl,
(6) AryA,
(7) HetB, and
(8) HetC,
wherein said $C_1$-$C_{10}$ alkyl, $C_2$-$C_{10}$ alkenyl, $C_2$-$C_{10}$ alkynyl, and $C_3$-$C_7$ cycloalkyl, are optionally substituted with 1 to 6 substituents independently selected from the group consisting of: fluoro, hydroxyl, carbomoyl, $C_3$-$C_6$ cycloalkyl, C(O)O—$C_1$-$C_6$ alkyl, C(O)OH, C(O)—$C_1$-$C_6$ alkyl, N(H)—$C_1$-$C_6$ alkyl, N(—$C_1$-$C_6$ alkyl)$_2$, AryA, HetB and HetC;
each $R^3$ is independently H or $C_1$-$C_6$ alkyl;
$Z^2$ is H; or alternatively $Z^1$ and $Z^2$, together with the carbon atom to which they are attached may form a spirocyclic 3- to 6-membered monocyclic heterocycloalkyl group, a spirocyclic 5- or 6-membered monocyclic heterocycloalkenyl group, or a spirocyclic 3- to 6-membered cycloalkyl group; wherein said 3- to 6-membered monocyclic heterocycloalkyl group, said 5- or 6-membered monocyclic heterocycloalkenyl group, or said 3- to 6-membered cycloalkyl group may be optionally substituted with $X^A$ from one up to the maximum number of substitutable positions as allowed by valence;
$R^6$ is selected from:

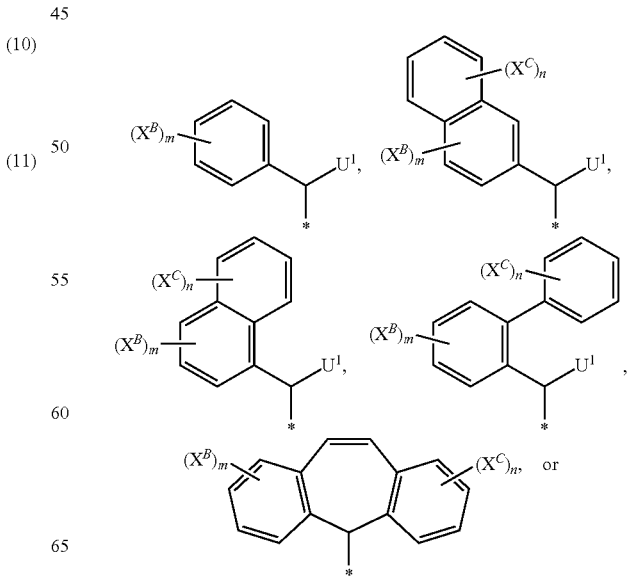

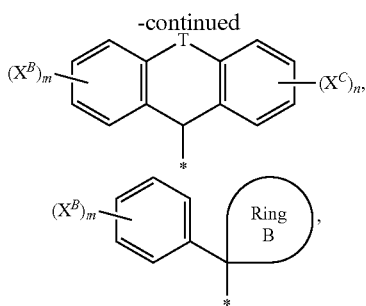

wherein the asterisk (*) denotes the point of attachment to the rest of the compound and $U^1$ is selected from (1) H, (2) $C_1$-$C_{10}$ alkyl, wherein said $C_1$-$C_{10}$ alkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (3) $C_3$-$C_7$ cycloalkyl, wherein said $C_3$-$C_7$ cycloalkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (4) AryA, (5) HetB, (6) HetC, (7) $C_1$-$C_{10}$ alkyl substituted with AryA, (8) $C_1$-$C_{10}$ alkyl substituted with HetB, and (9) $C_1$-$C_{10}$ alkyl substituted with HetC; and Ring B is selected from $C_3$-$C_7$ cycloalkyl, HetB, and HetC, wherein $C_3$-$C_7$ cycloalkyl is optionally substituted with 1 to 4 substituents independently selected from halo, OH, $C_1$-$C_4$ alkyl, $C_1$-$C_4$ fluorolkyl and $C_1$-$C_4$ alkoxy;

$R^{6A}$ is selected from H or $C_1$-$C_6$ alkyl;

alternatively, $R^6$ and $R^{6A}$ together with the carbon to which they are attached form a $C_3$-$C_6$ cycloalkyl, which is optionally substituted with phenyl, wherein the phenyl is optionally substituted with from 1 to 3 $X^E$;

each occurrence of $X^A$, $X^B$, $X^C$, $X^E$, $Y^B$ and $Y^C$ are independently selected from the group consisting of:
(1) $C_1$-$C_6$ alkyl,
(2) $C_3$-$C_6$ cycloalkyl,
(3) $C_1$-$C_6$ haloalkyl,
(4) OH,
(5) O—$C_1$-$C_6$ alkyl,
(6) O—$C_1$-$C_6$ haloalkyl,
(7) O—$C_3$-$C_6$ cycloalkyl,
(8) SH,
(9) S—$C_1$-$C_6$ alkyl,
(10) S—$C_1$-$C_6$ haloalkyl,
(11) S—$C_3$-$C_6$ cycloalkyl,
(12) halo,
(13) CN,
(14) $NO_2$,
(15) $NH_2$,
(16) N(H)—$C_1$-$C_6$ alkyl,
(17) N(—$C_1$-$C_6$ alkyl)$_2$,
(18) N(H)C(O)—$C_1$-$C_6$ alkyl,
(19) N(H)CH(O),
(20) CH(O),
(21) C(O)—$C_1$-$C_6$ alkyl,
(22) C(O)OH,
(23) C(O)O—$C_1$-$C_6$ alkyl,
(24) C(O)$NH_2$,
(25) C(O)N(H)—$C_1$-$C_6$ alkyl,
(26) C(O)N(—$C_1$-$C_6$ alkyl)$_2$,
(27) C(O)N(H)C(O)—$C_1$-$C_6$ alkyl,
(28) C(O)N(H)CH(O)
(29) $SO_2H$,
(30) $SO_2$—$C_1$-$C_6$ alkyl;
(31) phenyl, benzyl or phenoxy, each optionally substituted with 1 to 5 substituents independently selected from halo and $C_1$-$C_6$ alkyl,
(32) HetD, —O-HetD or —$CH_2$—HetD,
(33) trimethylsilyl,
(34) $C_2$-$C_6$ alkenyl, and
(35) $SO_2$—$NH_2$
wherein $C_1$-$C_6$ alkyl in each instance of (1), (3) (5), (6), (9), (10), (16), (17), (18), (21), (23), (25), (26), (27), (30), and (31) and $C_2$-$C_6$ alkenyl of (34) above is optionally substituted with 1 to 6 substituents independently selected from the group consisting of:
(a) $C_1$-$C_6$ haloalkyl,
(b) OH
(c) O—$C_1$-$C_6$ alkyl,
(d) O—$C_1$-$C_6$ haloalkyl,
(e) O—$C_3$-$C_6$ cycloalkyl,
(f) SH,
(g) S—$C_1$-$C_6$ alkyl,
(h) halo,
(i) CN,
(j) $NO_2$,
(k) $NH_2$,
(l) N(H)—$C_{1-6}$ alkyl,
(m) N(—$C_1$-$C_6$ alkyl)$_2$,
(n) C(O)—$C_1$-$C_6$ alkyl,
(o) C(O)OH,
(p) C(O)O—$C_1$-$C_6$ alkyl, and
(q) $SO_2$—$C_1$-$C_6$ alkyl;

m is an integer equal to 0, 1, 2, or 3;
n is an integer equal to 0, 1, 2, or 3;
$R^1$ is H, $C_1$-$C_6$ alkyl, $C_3$-$C_6$ cycloalkyl, $C_1$-$C_6$ alkyl substituted with $C_3$-$C_6$ cycloalkyl, C(O)—$R^7$ or $SO_2$—$R^7$;
$R^2$ is H, $C_1$-$C_6$ alkyl, $C_1$-$C_6$ haloalkyl and $C_3$-$C_6$ cycloalkyl;
$R^7$ is:
(1) $C_1$-$C_6$ alkyl,
(2) $C_3$-$C_6$ cycloalkyl,
(3) $C_1$-$C_6$ alkyl substituted with $C_3$-$C_6$ cycloalkyl,
(4) O—$C_1$-$C_6$ alkyl,
(5) O—$C_1$-$C_6$ alkyl substituted with O—$C_1$-$C_6$ alkyl,
(6) O—$C_1$-$C_6$ fluoroalkyl,
(7) C(O)O—$C_1$-$C_6$ alkyl,
(8) $C_1$-$C_6$ alkyl substituted with C(O)O—$C_1$-$C_6$ alkyl,
(9) $C_1$-$C_6$ alkyl substituted with C(O)OH,
(10) $C_1$-$C_6$ alkyl substituted with C(O)—$C_1$-$C_6$ alkyl,
(11) N(H)—$C_1$-$C_6$ alkyl,
(12) N(—$C_1$-$C_6$ alkyl)$_2$,
(13) $C_1$-$C_6$ alkyl substituted with $NH_2$, N(H)—$C_1$-$C_6$ alkyl, or N(—$C_1$-$C_6$ alkyl)$_2$,
(14) AryA,
(15) $C_1$-$C_6$ alkyl substituted with AryA,
(16) O—$C_1$-$C_6$ alkyl substituted with AryA,
(17) HetB,
(18) $C_1$-$C_6$ alkyl substituted with HetB,
(19) O—$C_1$-$C_6$ alkyl substituted with HetB,
(20) HetC,
(21) O-HetC, or
(22) O—$C_1$-$C_6$ alkyl substituted with HetC;

each AryA is an aryl which is independently phenyl or naphthyl, wherein the phenyl or naphthyl is optionally substituted with $Y^B$ from one up to the maximum number of substitutable positions as allowed by valence;

each HetA is an independently a 5- or 6-membered monocyclic heteroaryl containing from 1 to 4 N, wherein the moncyclic ring is optionally substituted with up to 3 occurrences of $X^D$;

each HetB is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with $Y^C$ from one up to the maximum number of substitutable positions as allowed by valence; and each HetC is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with one or more substituents, up to the maxium number allowed by valance, each of which is independently halo, CN, $C_1$-$C_6$ alkyl, OH, oxo, O—$C_1$-$C_6$ alkyl, $C_1$-$C_6$ haloalkyl, O—$C_1$-$C_6$ haloalkyl, $C(O)NH_2$, C(O)N(H)—$C_1$-$C_6$ alkyl, C(O)N(—$C_1$-$C_6$ alkyl)$_2$, C(O)H, C(O)—$C_1$-$C_6$ alkyl, $CO_2H$, $CO_2$—$C_1$-$C_6$ alkyl, $SO_2H$, or $SO_2$—$C_1$-$C_6$ alkyl; and each HetD is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with 1 to 5 substituents independently selected from halo and $C_1$-$C_6$ alkyl.

The Compounds of Formula (I) (also referred to herein as the "2,6-morpholine derivatives") and pharmaceutically acceptable salts and prodrugs thereof can be useful, for example, for inhibiting HIV viral replication or replicon activity, or for treating or preventing HIV infection in a subject. Without being bound by any specific theory, it is believed that the 2,6-morpholine derivatives inhibit HIV viral replication by inhibiting HIV Protease.

Accordingly, the present invention includes methods for treating or preventing HIV infection in a subject, comprising administering to the subject an effective amount of at least one 2,6-morpholine derivative.

The details of the invention are set forth in the accompanying detailed description below. Illustrative methods and materials for practicing the invention described herein. Other embodiments, aspects and features of the present invention are either further described in or will be apparent from the ensuing description, examples and appended claims.

DETAILED DESCRIPTION OF THE INVENTION

The present invention relates to 2,6-morpholine derivatives, compositions comprising at least one 2,6-morpholine derivative, and methods of using the 2,6-morpholine derivatives for treating or preventing HIV infection in a patient.
Definitions and Abbreviations The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

The term "effective amount" as used herein, refers to an amount of a 2,6-morpholine derivative and/or an additional therapeutic agent, or a composition thereof that is effective in producing the desired therapeutic, ameliorative, inhibitory or preventative effect when administered to a patient suffering from a viral infection or virus-related disorder. The desired effect may be (1) the inhibition of HIV; (2) the treatment of HIV infection, (3) reduction of the likelihood, severity, or progression of symptoms of HIV infection; (4) the inhibition of HIV viral replication; (5) the inhibition of HIV viral production; and/or (6) reduction in the likelihood, severity, or progression of AIDS. In the combination therapies of the present invention, an effective amount can refer to each individual agent or to the combination as a whole, wherein the amounts of all agents administered are together effective, but wherein the component agent of the combination may not be present individually in an effective amount.

A "subject" or a "patient" is a human or non-human mammal. In one embodiment, a subject is a human. In another embodiment, a subject is a primate. In another embodiment, a subject is a monkey. In still another embodiment, a subject is a rhesus monkey.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_3$-C$_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkenylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein. An arylene group is divalent and either available bond on an arylene group can connect to either group flanking the arylene group. For example, the group "A-arylene-B," wherein the arylene group is:

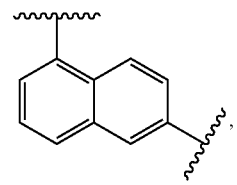 [SMILES: *c1ccc2c(*)cccc2c1]

is understood to represent both:

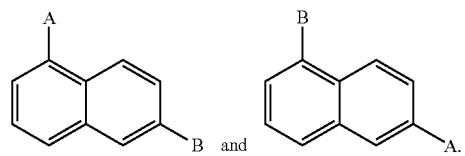

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

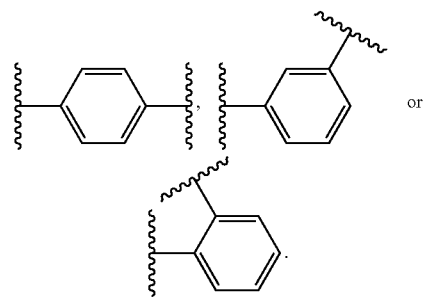

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from 5 to 10 ring carbon atoms. In another embodiment, a cycloalkyl contains from 3 to 7 ring atoms. In another embodiment, a cycloalkyl contains from 5 to 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

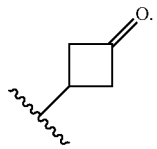 [SMILES: *C1CC(=O)C1]

The term "cycloalkenyl," as used herein, refers to a non-aromatic mono- or multicyclic ring system comprising from about 3 to about 10 ring carbon atoms and containing at least one endocyclic double bond. In one embodiment, a cycloalkenyl group is contains from about 3 to about 6 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein. A ring carbon atom of a cycloalkyl group may be functionalized as a carbonyl group. In one embodiment, a cycloalkenyl group is unsubstituted. In another embodiment, a cycloalkenyl group is cyclopentenyl. In another embodiment, a cycloalkenyl group is cyclohexenyl. The term "$C_3$-$C_6$ cycloalkenyl" refers to a cycloalkenyl group having from 3 to 6 ring carbon atoms. Unless otherwise indicated, a cycloalkenyl group is unsubstituted.

The term "halo," as used herein, means —F, —Cl, —Br or —I. In one embodiment, a halo group is —F, —Cl or —Br. In another embodiment, a halo group is —F or —Cl. In another embodiment, a halo group is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 11 ring atoms. In another embodiment, a heteroaryl group is monocyclic and has 5 or 6 ring atoms. In another embodiment, a heteroaryl group is bicyclic and has from 9 to 11 ring atoms. A heteroaryl group can be optionally substituted by one or more "ring system substituents" which may be the same or different, and are as defined herein. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to 7 ring atoms. In another embodiment, a heterocycloalkyl group is monocyclic has from about 4 to about 8 ring atoms. In one embodiment, the 4- to 8-membered monocyclic heterocycloalkyl group can form a spirocycle at one of its ring carbon atoms with a separate 3- to 6-membered monocyclic heterocycloalkyl group, a separate 5- or 6-membered monocyclic heterocycloalkenyl group, or a separate 6- to 10-membered bicyclic heterocycloalkyl group. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like. The term "heterocycloalkyl" also encompasses a heterocycloalkyl group, as defined herein, which is fused to an aryl (e.g., benzene) or heteroaryl ring. A heterocycloalkyl group can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like.

A ring carbon atom of a heterocycloalkyl group may be functionalized as a carbonyl group. An illustrative example of such a heterocycloalkyl group is:

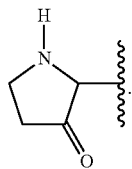

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Examples of ring system substituents, which are independently selected, include: alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)— alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

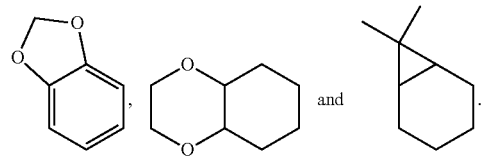

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^1$, $R^7$, etc.) occurs more than one time in any constituent or in any formula provided herein, e.g. Formula (I), its definition on each occurrence is independent of its definition at every other occurrence, unless otherwise indicated.

Unless otherwise noted, either available bond on a linker group can connect to either group flanking the linker group. For example, where L is —CH$_2$—CF$_2$—, the definition of L includes both A-CH$_2$—CF$_2$—B and A-CF$_2$—CH$_2$—B.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987)

Edward B. Roche, ed., American Pharmaceutical Association and Pergamon Press. The term "prodrug" means a compound (e.g., a drug precursor) that is transformed in vivo to provide a 2,6-morpholine derivative or a pharmaceutically acceptable salt of the compound. The transformation may occur by various mechanisms (e.g., by metabolic or chemical processes), such as, for example, through hydrolysis in blood. For example, if a 2,6-morpholine derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a 2,6-morpholine derivative contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a 2,6-morpholine derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$_5$ wherein $Y^4$ is H or methyl and $Y^5$ is mono-N— or di-N, N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halo, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 2,6-morpholine derivatives can form salts which are also within the scope of this invention. The term "salt(s)", as employed herein, denotes acidic salts formed with inorganic and/or organic acids, as well as basic salts formed with inorganic and/or organic bases. In addition, when a 2,6-morpholine derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 2,6-morpholine derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in

*The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 2,6-morpholine derivatives may be atropisomers (e.g., substituted biaryls) and are considered as part of this invention. Enantiomers can also be directly separated using chiral chromatographic techniques.

It is also possible that the 2,6-morpholine derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 2,6-morpholine derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 2,6-morpholine derivatives, and of the salts, solvates, hydrates, esters and prodrugs of the 2,6-morpholine derivatives, are intended to be included in the present invention.

The following abbreviations are used below and have the following meanings: 18-C-6 is 18-Crown-6 ($[C_2H_4O]_6$); Bn is benzyl; BOC or Boc is t-butyloxycarbonyl; $(BOC)_2O$ (or $BOC_2O$) is di-t-butyl carbonate; Bu is butyl; DCM is dichloromethane; DIAD is diisopropylazodicarboxylate; DMF is N,N-dimethylformamide; DMSO is dimethylsulfoxide; DMAP is N,N-dimethylamino pyridine; ES is electrospray (MS); EtOAc is ethyl acetate; EtOH is ethanol; $Et_2O$ is diethyl ether; $Et_3N$ (alternatively $NEt_3$) is triethylamine; h is hour(s); HATU is O-(7-Azabenzotriazol-1-yl)N,N,N',N'-tetramethyluronium hexafluorophosphate; HIV is human immunodeficiency virus; HPLC is high performance liquid chromatography; KO$^t$Bu is potassium tert-butoxide; LCMS is liquid chromatography/mass spectrometry; LRMS is low resolution mass spectroscopy; Me is methyl; min is minutes; MeOH is methanol; MS is mass spectrum; NBS is N-bromosuccinimide; MTBE is methyl tert-butyl ether; NMR is nuclear magnetic resonance; NOE is nuclear overhauser enhancement; Pd/C is palladium on carbon; PDC is pyridinium dichromate; $Pd_2dba_3$ is tris(dibenzylideneacetone) dipalladium; $Pd(OH)_2$ is palladium hydroxide; Py is pyridine; Ph is phenyl; SPE is solid phase extraction; TBAF is tetra n-butylammonium fluoride; TBDPS-Cl is tert-butyldiphenylsilyl; TEA is triethylamine; TFA is trifluoroacetic acid; THF is tetrahydrofuran, TMS is trimethylsilyl; and TMSCN is trimethylsilyl cyanide.

The Compounds of Formula (I):

The present invention provides 2,6-morpholine derivatives of Formula (I):

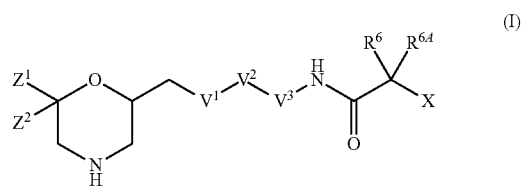

(I)

and pharmaceutically acceptable salts thereof, wherein $Z^1$, $Z^2$, $V^1$, $V^2$, $V^3$, $R^6$, $R^{6A}$, and X are as defined above for Compounds of Formula (I).

In embodiments of the invention (Embodiments E1-E3), $V^1$ is a bond (Embodiment E1), $CH_2$ (Embodiment E2), or O (Embodiment E3), and all other variables are as originally defined (i.e. as defined in Formula I in the Summary of the Invention).

In one embodiment (Embodiment E4), $V^2$ is $CH_2$, $V^3$ is $CH_2$, $V^1$ is as defined in any of Embodiments E1-E3, and all other variables are as originally defined.

In one embodiment (Embodiment E5), $V^2$ and $V^3$ come together to form a phenyl group, which is optionally substituted with up to 4 occurrences of $X^D$, $V^1$ is as defined in any of Embodiments E1-E3, and all other variables are as originally defined.

In sub-embodiments of Embodiment E5, the phenyl group is substituted with up to 3 occurrences of $X^D$, or up to two occurrences of $X^D$. In separate embodiments, the phenyl group is substituted with one occurrence of $X^D$, two occurrences of $X^D$, 3 occurrences of $X^D$, 4 occurrences of $X^D$, or is not substituted.

In further sub-embodiments of Embodiment E5, each occurrence of $X^D$ is independently selected from halo, hydroxy, =O, $C_1$-$C_4$ alkyl, $C_1$-$C_4$ alkoxy, —S(O)$_k$$C_1$-$C_4$ alkyl, $CF_3$, CN, and $C_0$-$C_4$ alkyl-phenyl. In other sub-embodiments, at least one $X^D$ is F. In still further embodiments, there is one occurrence of $X^D$ and $X^D$ is F. In embodiments when $X^D$ is $C_1$-$C_4$ alkyl-S(O)$_k$—, each K is independently 0, 1, or 2.

In one embodiment (Embodiment E6), $V^2$ and $V^3$ come together to form:

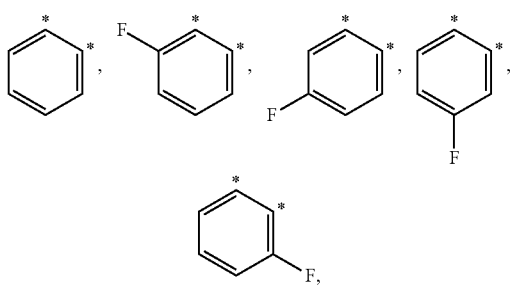

wherein the asterisk (*) denotes the point of attachment to the rest of the compound; wherein $V^1$ is as defined in any of Embodiments E1-E3, and all other variables are as originally defined.

In one embodiment (Embodiment E7), $V^2$ and $V^3$ come together to form HetA, wherein $V^2$ is C or CH and $V^3$ is C, CH, or N, $V^1$ is as defined in any of Embodiments E1-E3, and Het A and all other variables are as originally defined.

In one embodiment (Embodiment E8), $V^2$ and $V^3$ come together to form a 5-membered monocyclic heteroaryl containing from 1 to 4 N, wherein the monocyclic ring is optionally substituted with up to 3 occurrences of $X^D$, $V^1$ is as defined in any of Embodiments E1-E3, and all other variables are as originally defined.

In one embodiment (Embodiment E9), $V^2$ and $V^3$ come together to form a 6-membered monocyclic heteroaryl containing from 1 to 4 N, wherein the monocyclic ring is optionally substituted with up to 3 occurrences of $X^D$, $V^1$ is as defined in any of Embodiments E1-E3, and all other variables are as originally defined.

In a further embodiment of Embodiment 9, $V^3$ is N, one occurrence of $X^D$ is present, and $X^D$ is =O.

In further embodiments of Embodiments E8 or E9, the monocyclic ring contains 4 N, 3N, 2N, or 1N. In other embodiments, the monocyclic ring contains from 1 to 3 N, or 1 or 2 N.

In other embodiments of Embodiments E8 or E9, each occurrence of $X^D$ is independently selected from halo, hydroxy, =O, $C_1$-$C_4$ alkyl, $C_1$-$C_4$ alkoxy, $C_1$-$C_4$ alkyl-S(O)$_k$, $CF_3$, CN, and $C_0$-$C_4$ alkyl-phenyl. In one embodiment, at least one $X^D$ is F. In one embodiment, at least one $X^D$ is =O. In still further embodiments, there is one occurrence of $X^D$ and $X^D$ is F. In embodiments when $X^D$ is $C_1$-$C_4$ alkyl-S(O)$_k$, each K is independently 0, 1, or 2.

In one embodiment (Embodiment E10), X is H, $V^1$ is as defined in any of Embodiments E1-E3, $V^2$ and $V^3$ are defined in any of Embodiments E4-E9, and all other variables are as originally defined.

In one embodiment (Embodiment E11), X is NR$^1$R$^2$; R$^1$ is selected from the group consisting of: H, $C_1$-$C_6$ alkyl, $C_3$-$C_6$ cycloalkyl, $C_1$-$C_6$ alkyl substituted with $C_3$-$C_6$ cycloalkyl, C(O)—R$^7$ or SO$_2$—R$^7$; R$^2$ is selected from the group consisting of: H, $C_1$-$C_6$ alkyl, $C_1$-$C_6$ haloalkyl and $C_3$-$C_6$cycloalkyl; $V^1$ is as defined in any of Embodiments E1-E3, $V^2$ and $V^3$ are defined in any of Embodiments E4-E9, and all other variables are as originally defined.

In one embodiment (Embodiment E12), X is:

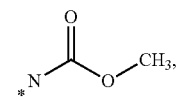

wherein the asterisk (*) denotes the point of attachment to the rest of the compound; $V^1$ is as defined in any of Embodiments E1-E3, $V^2$ and $V^3$ are defined in any of Embodiments E4-E9; and all other variables are as originally defined.

In one embodiment (Embodiment E13), X is NH$_2$, N(H)—CH$_2$—CF$_3$ or N(H)—C(O)—OR$^2$; $V^1$ is as defined in any of Embodiments E1-E3, $V^2$ and $V^3$ are defined in any of Embodiments E4-E9; and all other variables are as originally defined.

In one embodiment (Embodiment E14), R$^6$ is selected from:

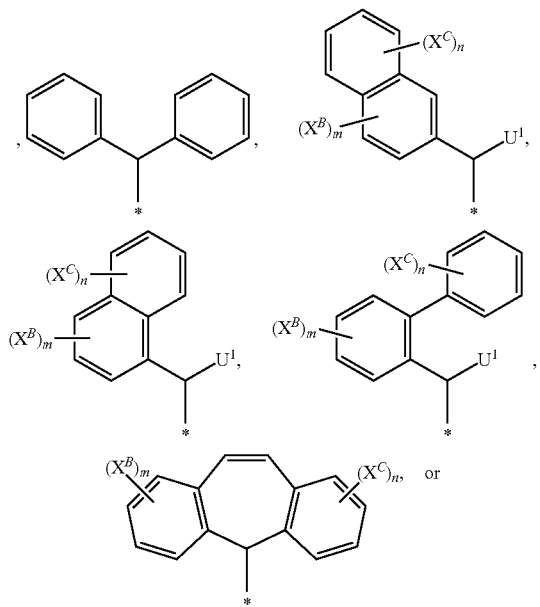

-continued

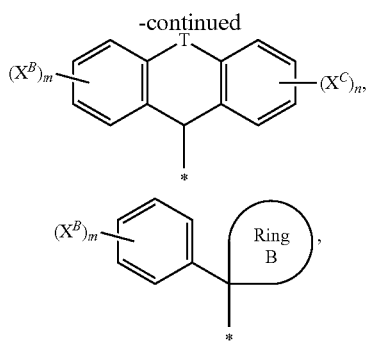

wherein the asterisk (*) denotes the point of attachment to the rest of the compound and $U^1$ is selected from (1) H, (2) $C_1$-$C_{10}$ alkyl, wherein said $C_1$-$C_{10}$ alkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (3) $C_3$-$C_7$ cycloalkyl, wherein said $C_3$-$C_7$ cycloalkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (4) AryA, (5) HetB, (6) HetC, (7) $C_1$-$C_{10}$ alkyl substituted with AryA, (8) $C_1$-$C_{10}$ alkyl substituted with HetB, and (9) $C_1$-$C_{10}$ alkyl substituted with HetC; and Ring B is selected from $C_3$-$C_7$ cycloalkyl, HetB, and HetC, wherein $C_3$-$C_7$ cycloalkyl is optionally substituted with 1 to 4 substituents independently selected from halo, OH, $C_1$-$C_4$ alkyl, $C_1$-$C_4$ fluorolkyl and $C_1$-$C_4$ alkoxy; $R^{6A}$ is selected from H or $C_1$-$C_6$ alkyl; $V^1$ is as defined in any of Embodiments E1-E3, $V^2$ and $V^3$ are defined in any of Embodiments E4-E9, X is defined in any of Embodiments E10-E13, and all other variables are as originally defined.

In one embodiment (Embodiment E15), $R^6$ is

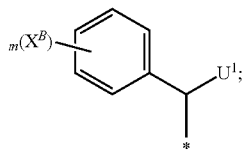

wherein U1 is selected from HetB or HetC; $R^{6A}$ is H; $V^1$ is as defined in any of Embodiments E1-E3, $V^2$ and $V^3$ are defined in any of Embodiments E4-E9, X is defined in any of Embodiments E10-E13, and all other variables are as originally defined.

In one embodiment (Embodiment E16), $R^6$ is:

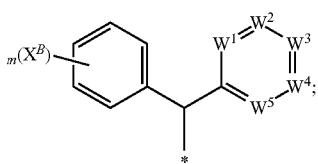

wherein $W^1$ to $W^5$ are independently $CR^5$ or N, with the proviso that no more than four of $W^1$ to $W^5$ are N, each $R^5$ is independently $X^C$ or H; $R^{6A}$ is H; $V^1$ is as defined in any of Embodiments E1-E3, $V^2$ and $V^3$ are defined in any of Embodiments E4-E9, X is defined in any of Embodiments E10-E13, and all other variables are as originally defined.

In one embodiment (Embodiment E17), $R^6$ is:

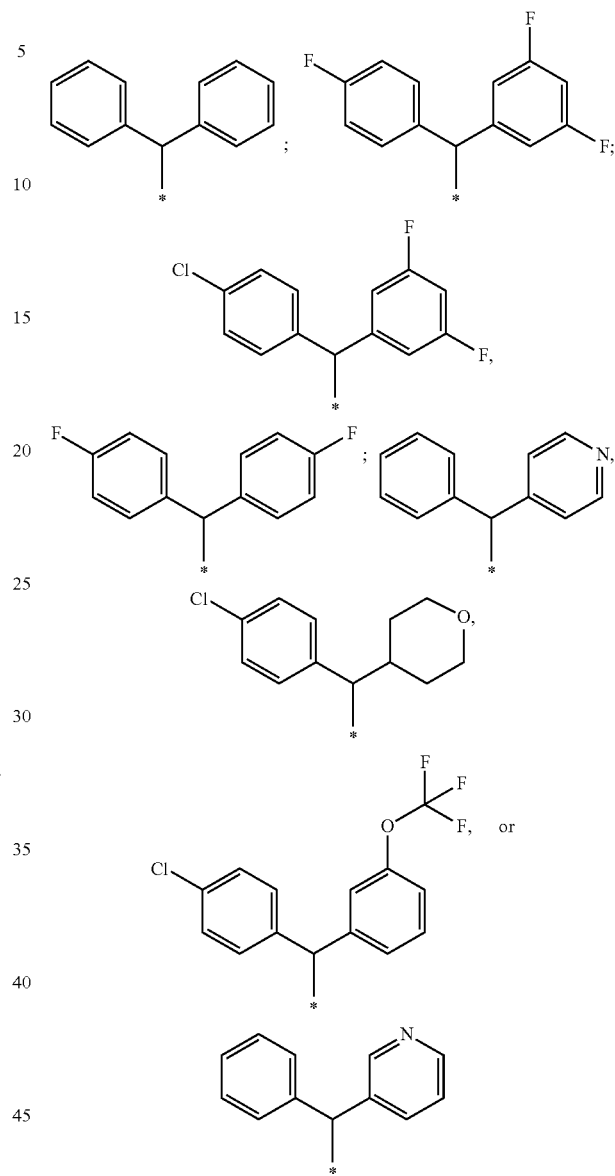

$R^{6A}$ is H; $V^1$ is as defined in any of Embodiments E1-E3, $V^2$ and $V^3$ are defined in any of Embodiments E4-E9, X is defined in any of Embodiments E10-E13, and all other variables are as originally defined.

In one embodiment (Embodiment E18), $R^6$ and $R^{6A}$ together with the carbon to which they are attached form a $C_3$-$C_6$ cycloalkyl, which is optionally substituted with phenyl, wherein the phenyl is optionally substituted with from 1 to 3 $X^E$; $V^1$ is as defined in any of Embodiments E1-E3, $V^2$ and $V^3$ are defined in any of Embodiments E4-E9, X is defined in any of Embodiments E10-E13, and all other variables are as originally defined.

In one embodiment (Embodiment E19), $Z^1$ and $Z^2$, together with the carbon atom to which they are attached, form a spirocyclic 3- to 6-membered monocyclic heterocycloalkyl group, a spirocyclic 5- or 6-membered monocyclic heterocycloalkenyl group, or a spirocyclic 3- to 6-membered cycloalkyl group; wherein said 3- to 6-membered monocyclic heterocycloalkyl group, said 5- or 6-membered monocyclic heterocycloalkenyl group, or said 3- to 6-membered cycloalkyl group may be optionally substituted with $X^A$ from one up to the maximum number of substitutable positions as allowed by valence; $R^6$ and $R^{6A}$ are defined in any of Embodiments E14-E18; $V^1$ is as defined in any of Embodiments E1-E3; $V^2$ and $V^3$ are defined in any of Embodiments E4-E9; X is defined in any of Embodiments E10-E13; and all other variables are as originally defined.

In sub-embodiments of Embodiment E19, the spirocyclic group is substituted with zero, one or two $X^A$, wherein each occurrence of $X^A$ is independently $C(O)$—$C_1$-$C_6$ alkyl, $SO_2$—$C_1$-$C_6$ alkyl, =O, $C_1$-$C_6$ alkyl or halo.

In one embodiment (Embodiment E20), $Z^1$ is selected from the group consisting of:

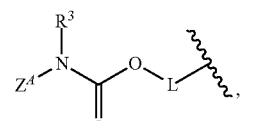 (1)

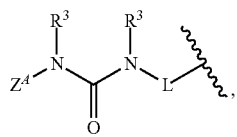 (2)

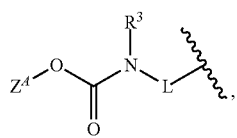 (3)

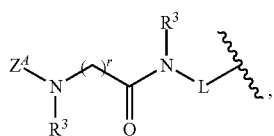 (4)

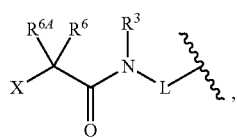 (5)

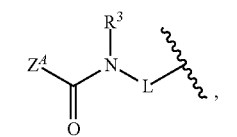 (6)

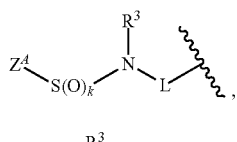 (7)

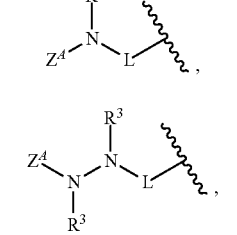 (8)

(9)

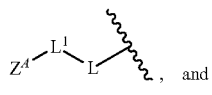 (10)

and

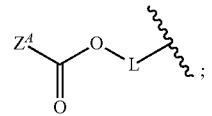 (11)

L is a linker selected from: (a) a bond, (b) —$C_1$-$C_3$ alkylene-, (c) —$C_2$-$C_4$ alkenylene-, (d) —$CH_2$—$CF_2$—, (e) —$C(O)$—, (f) —$CH_2$—$C(O)$—, and (g) —$CH_2$—$CH_2$—$C(O)$—;

$L^1$ is selected from the group consisting of: S, S(O), $S(O)_2$, O, $C_1$-$C_3$ alkylene, and a bond;

$Z^A$ is selected from the group consisting of: hydrogen, $C_1$-$C_{10}$ alkyl, $C_2$-$C_{10}$ alkenyl, $C_2$-$C_{10}$ alkynyl, $C_3$-$C_7$ cycloalkyl, AryA, HetB, and HetC, wherein said $C_1$-$C_{10}$ alkyl, $C_2$-$C_{10}$ alkenyl, $C_2$-$C_{10}$ alkynyl, and $C_3$-$C_7$ cycloalkyl, are optionally substituted with 1 to 6 substituents independently selected from the group consisting of: fluoro, hydroxyl, carbomoyl, $C_3$-$C_6$ cycloalkyl, $C(O)O$—$C_1$-$C_6$ alkyl, $C(O)OH$, $C(O)$—$C_1$-$C_6$ alkyl, $N(H)$—$C_1$-$C_6$ alkyl, $N(—C_1$-$C_6$ alkyl$)_2$, AryA, HetB and HetC; each $R^3$ is independently H or $C_1$-$C_6$ alkyl; $Z^2$ is H;

$R^6$ and $R^{6A}$ are defined in any of Embodiments E14-E18; $V^1$ is as defined in any of Embodiments E1-E3; $V^2$ and $V^3$ are defined in any of Embodiments E4-E9; X is defined in any of Embodiments E10-E13; and all other variables are as originally defined.

In sub-embodiments of Embodiment E20, $Z^A$ is selected from the group consisting of: $C_1$-$C_{10}$ alkyl, $C_2$-$C_{10}$ alkenyl, $C_2$-$C_{10}$ alkynyl, $C_3$-$C_7$ cycloalkyl, which are each optionally substituted with 1 to 6 substituents, 1 to 5 substituents, 1 to 4 substituents, or 1 to 3 substituents, as set forth in Embodiment E20.

In one embodiment (Embodiment E21), $Z^1$ is selected from the group consisting of:

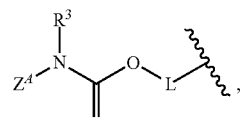 (1)

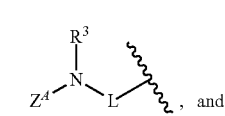 (2)

and

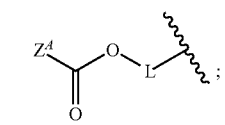 (3)

L is a linker selected from: (a) a bond, (b) —$CH_2$—, (c) —$CH_2$—$CF_2$—, and (d) —$CH_2CH_2$—; $Z^2$ is H;

$R^6$ and $R^{6A}$ are defined in any of Embodiments E14-E18; $V^1$ is as defined in any of Embodiments E1-E3; $V^2$ and $V^3$ are defined in any of Embodiments E4-E9; X is defined in any of Embodiments E10-E13; and all other variables are as originally defined.

In one embodiment (Embodiment E22), $Z^1$ is:

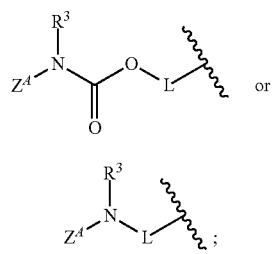

$R^3$ is H or CH$_3$, L is a linker selected from: (a) a bond, (b) —CH$_2$—, (c) —CH$_2$—CF$_2$—, and (d) —CH$_2$CH$_2$—; $Z^2$ is H; $R^6$ and $R^{6A}$ are defined in any of Embodiments E14-E18; $V^1$ is as defined in any of Embodiments E1-E3; $V^2$ and $V^3$ are defined in any of Embodiments E4-E9; X is defined in any of Embodiments E10-E13; and all other variables are as originally defined.

In one embodiment (Embodiment E23), $Z^1$ is:

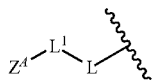

L is selected from: (a) a bond or (b) —CH$_2$—; $Z^2$ is H; $R^6$ and $R^{6A}$ are defined in any of Embodiments E14-E18; $V^1$ is as defined in any of Embodiments E1-E3; $V^2$ and $V^3$ are defined in any of Embodiments E4-E9; X is defined in any of Embodiments E10-E13; and all other variables are as originally defined.

In further embodiments of Embodiments E21-E23, $Z^A$ is AryA, HetB or HetC, wherein AryA is optionally substituted with from one to four $Y^B$, from one to three $Y^B$, one or two $Y^B$, or one $Y^B$; HetB is optionally substituted with from one to four $Y^C$, from one to three $Y^C$, one or two $Y^C$, or one $Y^C$; and HetC is optionally substituted with from one to four, from one to three, one or two, or one substituent, each of which is independently halo, CN, or C$_1$-C$_6$ alkyl.

One class of compounds of the invention (Class C-1) includes compounds of Formula (Ia):

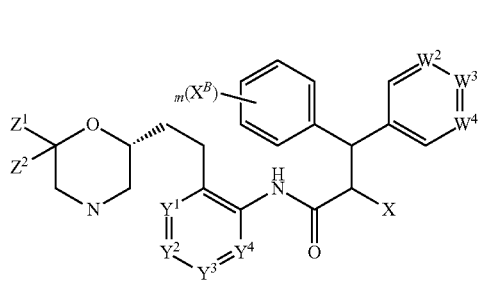

or a pharmaceutically acceptable salt thereof, wherein $Y^1$, $Y^2$, $Y^3$, and $Y^4$ are independently C(R$^4$) or N; $W^2$, $W^3$, and $W^4$ are independently CR$^5$ or N; each $R^5$ is independently $X^C$ or H;

each occurrence of $R^4$ is independently selected from H, halo, hydroxy, C$_1$-C$_4$ alkyl, C$_1$-C$_4$ alkoxy, C$_1$-C$_4$ alkyl-S(O)$_k$—, CF$_3$, CN, and benzyl; and Z1 and Z2 are as originally defined, or as defined in Embodiments E19-E23 or sub-embodiments.

Another class of compounds of the invention (Class C-2) includes compounds of Formula Ib):

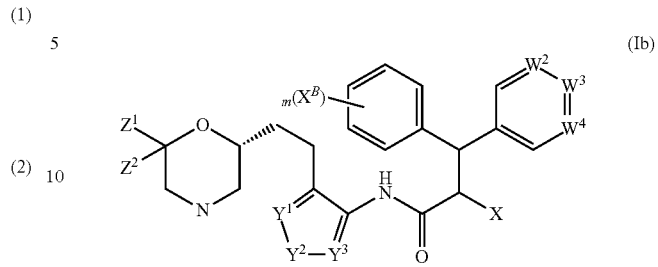

or a pharmaceutically acceptable salt thereof, wherein all variables except $R^4$ are as defined in Class C-1, and each occurrence of $R^4$ is independently selected from H, halo, hydroxy, C$_1$-C$_4$ alkyl, C$_1$-C$_4$ alkoxy, C$_1$-C$_4$ alkyl-S(O)$_k$—, CF$_3$, CN, =O, and benzyl.

In one embodiment of Class C-1 or Class C-2, $R^4$ is independently H or fluoro, each $X^B$ is independently selected from F, Cl, Br, —OCH$_3$, —CF$_3$, and —OCF$_3$, each $R^5$ is independently selected from H, F, Cl, Br, —OCH$_3$, —CF$_3$, and —OCF$_3$, and m is 0, 1 or 2.

In one embodiment of Class C-1 or Class C-2, each $X^B$ is independently F or Cl, and each $R^5$ is independently H, F, or Cl, provided that one $X^B$ group is present and substituted at the 4-position.

In one embodiment of Class C-1 or Class C-2, at least one of $Y^1$, $Y^2$, $Y^3$, and $Y^4$ is CF.

In another embodiment of Class C-1 or Class C-2, X is selected from: H, —NH$_2$, N(H)—CH$_2$—CF$_3$, and —N(H)—C(O)—OR$^2$.

In one embodiment of Class C-1 or Class C-2, $Z^1$ and $Z^2$, together with the carbon atom to which they are attached, form a spirocyclic 5- or 6-membered monocyclic heterocycloalkyl group, or a spirocyclic 5- or 6-membered cycloalkyl group; wherein said 5- or 6-membered monocyclic heterocycloalkyl group, or said 5- or 6-membered cycloalkyl group may be optionally substituted with one or two $X^A$, wherein each occurrence of $X^A$ is independently C(O)—C$_1$-C$_6$ alkyl, SO$_2$—C$_1$-C$_6$ alkyl, =O, C$_1$-C$_6$ alkyl, and halo.

In another embodiment of Class C-1 or Class C-2, $Z^1$ is

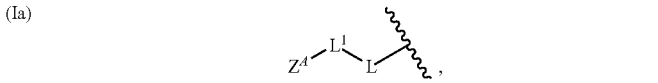

L is C$_1$-C$_3$ alkylene, CH$_2$CF$_2$, or a bond, and $Z^2$ is H.

In another embodiment of Class C-1 or Class C-2, $Z^2$ is H, and $Z^1$ is selected from the group consisting of:

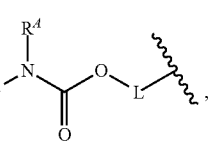

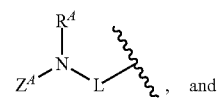

and

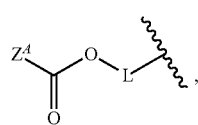

and

L is a linker selected from (a) a bond, (b) —CH$_2$—, (c) —CH$_2$—CF$_2$—, and (d) —CH$_2$CH$_2$—.

In further embodiments of Class C-1 or Class C-2, Z2 is H, Z1 is as defined in either of the previous two embodiments, and $Z^A$ is: (1) AryA optionally substituted with one or two substituents, independently selected from: (a) C$_1$-C$_6$ alkyl, (b) C$_1$-C$_6$ haloalkyl, (c) halo, (d) CN, (e) NO$_2$, (f) NH$_2$(g) SO$_2$—C$_1$-C$_6$ alkyl, (h) SO$_2$—NH$_2$, (i) phenyl, benzyl or phenoxy, each optionally substituted with 1 or 2 substituents selected from halo and C$_1$-C$_6$ alkyl, and (j) HetD, —O-HetD or —CH$_2$—HetD; (2) HetB, optionally substituted with one or two substituents, independently selected from: halo, C$_1$-C$_6$ alkyl, HetB, C$_1$-C$_6$ alkyl substituted with HetB, and phenyl; and (3) HetC, optionally substituted with one or two substituents, independently selected from: halo or C$_1$-C$_6$ alkyl.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt. It is understood that references to compounds would include the compound in its present form as well as in different forms, such as polymorphs, solvates and hydrates, as applicable.

It is further to be understood that the embodiments of compositions and methods provided as (a) through (k) above include all embodiments of the compounds, including such embodiments that result from combinations of embodiments.

Uses of the 2,6-Morpholine Derivatives:

The 2,6-morpholine derivatives and pharmaceutical compositions comprising said 2,6-morpholine derivatives are useful in human and veterinary medicine for treating or preventing HIV infection and/or the clinical manifestations thereof in a subject. In a specific embodiment, the 2,6-morpholine derivatives are inhibitors of HIV-1. In one embodiment, the clinical manifestation of the HIV infection has progressed to AIDS. In accordance with the invention, the 2,6-morpholine derivatives can be administered to a subject in need of treatment or prevention of HIV infection, or the clinical symptoms thereof.

The 2,6-morpholine derivatives can be useful in (1) the inhibition of HIV; (2) the treatment of HIV infection, (3) reduction of the likelihood, severity, or progression of symptoms of HIV infection; (4) the inhibition of HIV viral replication; (5) the inhibition of HIV viral production; and/or (6) reduction in the likelihood, severity, or progression of AIDS. For example, the 2,6-morpholine derivatives are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject comprising administering to the subject an effective amount of at least one 2,6-morpholine derivative or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In another specific embodiment, the present invention provides methods for treating AIDS in a subject comprising administering to the subject an effective amount of at least one 2,6-morpholine derivative or a pharmaceutically acceptable salt or prodrug thereof.

The 2,6-morpholine derivatives are also useful in the preparation and execution of screening assays for antiviral compounds. For example the 2,6-morpholine derivatives are useful for identifying resistant HIV cell lines harboring mutations, which are excellent screening tools for more powerful antiviral compounds. Furthermore, the 2,6-morpholine derivatives are useful in establishing or determining the binding site of other antivirals to the HIV Integrase by competitive inhibition.

Combination Therapy:

The invention also relates to methods for treating or preventing HIV infection or AIDS comprising administering to a patient an effective amount of a 2,6-morpholine derivative, a pharmaceutically acceptable carrier, and one or more additional therapeutic agents which are not 2,6-morpholine derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one 2,6-morpholine derivative (which may include two or more different 2,6-morpholine derivatives), or a pharmaceutically acceptable salt or prodrug thereof, and (ii) at least one additional therapeutic agent that is other than a 2,6-morpholine derivative, wherein the amounts administered are together effective to treat or prevent a viral infection or the clinical symptoms thereof.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2,6-morpholine derivative and an additional therapeutic agent may be present in fixed amounts (dosage amounts) in a single dosage unit (e.g., a capsule, a tablet and the like).

In one embodiment, the at least one 2,6-morpholine derivative is administered during a time when the additional therapeutic agent(s) exert their prophylactic or therapeutic effect, or vice versa.

In another embodiment, the at least one 2,6-morpholine derivative and the additional therapeutic agent(s) are administered in doses commonly employed when such agents are used as monotherapy for treating a viral infection.

In another embodiment, the at least one 2,6-morpholine derivative and the additional therapeutic agent(s) are administered in doses lower than the doses commonly employed when such agents are used as monotherapy for treating a viral infection.

In one embodiment, the at least one 2,6-morpholine derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

As noted herein, the invention is also directed to use of a compound of Formula I or a salt or prodrug thereof with one or more anti-HIV agents. An "anti-HIV agent" is any agent that is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, anti-infectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |

TABLE A-continued

| Name | Type |
|---|---|
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g. abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof. In another embodiment, the invention provides a method for the treatment or prophylaxis of infection by HIV or for the treatment, prophylaxis, or delay in the onset or progression of the clinical manifestation of HIV infection, e.g. AIDS, in a subject in need thereof, which comprises administering to the subject a pharmaceutical composition as described above.

It is understood that the scope of combinations of the compounds of this invention with anti-HIV agents is not limited to the HIV antivirals listed in Table A, but includes any combination with any pharmaceutical composition useful for the treatment or prophylaxis of HIV and/or the clinical symptoms thereof, e.g. AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the 2,6-morpholine derivative(s) and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration:

When administered to a subject, the 2,6-morpholine derivatives can be administered as a component of a composition that comprises a pharmaceutically acceptable carrier or vehicle. The present invention provides pharmaceutical compositions comprising an effective amount of at least one 2,6-morpholine derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with an oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or 2,6-morpholine derivatives are administered orally.

In another embodiment, the one or more 2,6-morpholine derivatives are administered intravenously.

In one embodiment, a pharmaceutical preparation comprising at least one 2,6-morpholine derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 2,6-morpholine derivative(s) by weight or volume. In various embodiments, the present compositions can contain, in one embodiment, from about 1% to about 70% or from about 5% to about 60% of the 2,6-morpholine derivative(s) by weight or volume.

The compounds of Formula I can be administered orally in a dosage range of 0.001 to 1000 mg/kg of mammal (e.g., human) body weight per day in a single dose or in divided doses. One exemplary dosage range is 0.01 to 500 mg/kg body weight per day orally in a single dose or in divided doses. Another exemplary dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2,6-morpholine derivatives will be regulated according to the judgment of the attending clinician considering such factors as age, condition and size of the subject as well as severity of the symptoms being treated.

Kits:

In one aspect, the present invention provides a kit comprising a therapeutically effective amount of at least one 2,6-morpholine derivative, or a pharmaceutically acceptable salt or prodrug of said compound and a pharmaceutically acceptable carrier, vehicle or diluent.

In another aspect the present invention provides a kit comprising an amount of at least one 2,6-morpholine derivative, or a pharmaceutically acceptable salt or prodrug of said compound and an amount of at least one additional therapeutic agent, e.g. the therapeutic agents listed above, wherein the amounts of the two or more active ingredients result in a desired therapeutic effect. In one embodiment, the one or more 2,6-morpholine derivative and the one or more additional therapeutic agents are provided in the same container. In one embodiment, the one or more 2,6-morpholine derivatives and the one or more additional therapeutic agents are provided in separate containers.

The compounds of the present invention can be readily prepared according to the following reaction schemes and examples, or modifications thereof, using readily available starting materials, reagents and conventional synthesis procedures. The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

In the examples that follow, when a nitrogen atom is depicted without the necessary hydrogen atoms to complete the valence, it is assumed those nitrogen atoms are present unless specifically depicted to the contrary.

A number of references have been cited herein, the entire disclosures of which are incorporated herein by reference.

EXAMPLE 1

Preparation of Compound 1 (Methyl N-[(1S)-1-[4-[(6S)-6-[(4-aminophenyl)sulfonylmethyl]morpholin-2-yl]butylcarbamoyl]-2,2-diphenyl-ethyl]carbamate)

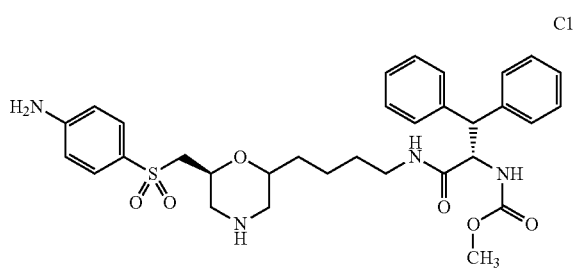 [SMILES: COC(=O)N[C@H](C(=O)NCCCCC1CNC[C@@H](CS(=O)(=O)c2ccc(N)cc2)O1)C(c1ccccc1)c1ccccc1]

Step 1—Synthesis of Compound Int-1a ((2S)-1-(benzylamino)-3-(benzyloxy)propan-2-ol)

To a solution of (2S)-2-[(benzyloxy)methyl]oxirane (1 eq.) in dichloromethane (0.6 M) at room temperature was added benzylamine (1 eq.) and Lithium Bis(trifluoromethanesulfonyl)imide (0.5 eq.) and the reaction mixture was stirred at room temperature for 12 hours. The reaction mixture was diluted with dichloromethane and aqueous saturated NaHCO$_3$ and aqueous layer was extracted with dichloromethane. The combined organic layers were dried over Na$_2$SO$_4$, filtered and concentrated. The crude product (Compound Int-1a) was used as such for the next step.

Step 2—Synthesis of Compound Int-1b (3-{benzyl[(2S)-3-(benzyloxy)-2-hydroxypropyl]amino}-2-chloropropanenitrile)

To a solution of Compound Int-1a (1 eq.) in t-butylmethyl ether (0.22 M) at room temperature was added 2-chloroacrylonitrile (1 eq.). The reaction mixture was heated to 50° C. and stirred for 16 hours. The reaction mixture was concentrated and used as such (Compound Int-1b) for the next step.

Step 3—Synthesis of Compound Int-1c ((6S)-4-benzyl-6-[(benzyloxy)methyl]morpholine-2-carbonitrile)

To a solution of compound Int-1b (1 eq.) in THF (0.2 M) at 0° C. was added 1M KOtBu in THF (1 eq.). The mixture was stirred for 2 hours at 0° C. and then heated to reflux for 3 hours. The reaction mixture was cooled to room temperature and saturated aqueous NH$_4$Cl was added. The aqueous layer was extracted with EtOAc. The combined organic layers were dried over Na$_2$SO$_4$, filtered and concentrated. The crude product was purified by automated SiO$_2$ flash chromatography system using solvent gradient of 5% EtOAc/Hex to 30% EtOAc/Hex to afford compound Int-1c.

Step 4—Synthesis of Compound Int-1d (ethyl (6S)-4-benzyl-6-[(benzyloxy)methyl]morpholine-2-carboxylate)

To a solution of compound Int-1c (1 eq.) in EtOH (0.2 M) at room temperature was added concentrated H$_2$SO$_4$ (12 eq.). The mixture was stirred at reflux for 48 hours, cooled to room temperature and concentrated to half of the original volume. The reaction mixture was then basified to pH 9 with saturated aqueous K$_2$CO$_3$ and extracted with Et$_2$O. The combined organic layers were dried over MgSO$_4$, filtered and concentrated and used as such (compound Int-1d) for the next step.

Step 5—Synthesis of Compound Int-1e ((2S)-2-[(benzyloxy)methyl]-6-(ethoxycarbonyl)morpholin-4-ium trifluoroacetate)

To a solution of compound Int-1d (1 eq.) in EtOH (0.15 M) at room temperature was added TFA (2 eq.) and 10% Pd/C (0.2 eq.). The reaction was degassed and then shaken in a parr apparatus under 50 psi of H$_2$ for 24 hours. The reaction mixture was filtered on celite and concentrated to afford compound Int-1e.

Step 6—Synthesis of Compound Int-1f (4-tert-butyl 2-ethyl (6S)-6-[(benzyloxy)methyl]morpholine-2,4-dicarboxylate)

To a solution of compound Int-1e (1 eq.) in a 1:1 mixture of THF/H$_2$O (0.1 M) at room temperature was added sodium bicarbonate (5 eq.) and Di-tert-butyl dicarbonate (1.5 eq.). The reaction mixture was stirred at room temperature for 16 hours and THF was removed by roto-vap. The aqueous layer was extracted with dichloromethane. The combined organic layers were washed with brine, dried over Na$_2$SO$_4$, filtered and concentrated. The crude product (compound Int-1f) was used as such for next step.

Step 7—Synthesis of Compound Int-1g (4-tert-butyl 2-ethyl (6S)-6-(hydroxymethyl)morpholine-2,4-dicarboxylate)

To a solution of compound Int-1f (1 eq.) in EtOAc (0.5 M) at room temperature was added 10% Pd/C (0.2 eq.). The reaction was degassed and then shaken in a parr apparatus under 50 psi of H$_2$ for 24 hours. The reaction mixture was filtered on celite and concentrated to afford compound Int-1g.

Step 8—Synthesis of Compound Int-1h (4-tert-butyl 2-ethyl (6S)-6-({[tert-butyl(diphenyl)silyl]oxy}methyl)morpholine-2,4-dicarboxylate)

To a solution of compound Int-1g (1 eq.) in dichloromethane (0.2 M) at room temperature was added TBDPS-Cl (1.2 eq.), triethylamine (2 eq.) and DMAP (0.2 eq.). The reaction mixture was stirred at room temperature for 6 hours and diluted with aqueous 1N HCl. The aqueous layer was extracted with dichloromethane. The combined organic layers were dried over Na$_2$SO$_4$, filtered and concentrated. The crude product was purified by automated SiO$_2$ flash chromatography system using solvent gradient of 10% EtOAc/Hex to 50% EtOAc/Hex to afford compound Int-1h.

Step 9—Synthesis of Compound Int-1i (tert-butyl (2S)-2-({[tert-butyl(diphenyl)silyl]oxy}methyl)-6-(hydroxymethyl)morpholine-4-carboxylate)

To a solution of compound Int-1h (1 eq.) in THF (0.1 M) at 0° C. was added LiBH$_4$ (2M in THF) (2 eq.) and MeOH (1 eq.). The reaction mixture was stirred at room temperature for 16 hours, poured into water and extracted with EtOAc. The combined organic layers were washed with 1N HCl, dried over Na$_2$SO$_4$, filtered and concentrated. The crude product (compound Int-1i) was used as such for next step.

Step 10—Synthesis of Compound Int-1j (tert-butyl (2S)-2-({[tert-butyl(diphenyl)silyl]oxy}methyl)-6-formylmorpholine-4-carboxylate)

To oxalyl chloride (1.2 eq.) in dichloromethane (0.1 eq.) at −78° C. was added DMSO (2.4 eq.) dropwise. The mixture was stirred at −78° C. for 30 minutes and a solution of compound Int-1i (1 eq.) in THF (0.2 M) was then added over 5 minutes. The reaction mixture was stirred at −78° C. for 90 minutes and triethylamine (5 eq.) was added. The reaction mixture was stirred at −78° C. for an additional 60 minutes, water was added and the mixture was warmed to room temperature. The aqueous layer was extracted with dichloromethane. The combined organic layers were washed with 1N HCl, water and 1M Na$_2$CO$_3$, dried over Na$_2$SO$_4$, filtered and concentrated. The crude product (compound Int-1j) was used as such for next step.

Step 11—Synthesis of Compound Int-1k (tert-butyl (2S)-2-({[tert-butyl(diphenyl)silyl]oxy}methyl)-6-[(1E)-3-oxoprop-1-en-1-yl]morpholine-4-carboxylate)

To a solution of compound Int-1j (1 eq.) in THF (0.1 eq.) at room temperature was added (triphenyl-$\lambda^5$-phosphanylidene)acetaldehyde (1.1 eq.). The mixture was stirred at 50° C. for 12 hours, filtered on celite and concentrated. The crude product was purified by automated SiO$_2$ flash chromatography system using solvent gradient of 10% EtOAc/Hex to 40% EtOAc/Hex to afford compound Int-1k.

Step 12—Synthesis of Compound Int-1L (tert-butyl (2S)-2-({[tert-butyl(diphenyl)silyl]oxy}methyl)-6-(3-oxopropyl)morpholine-4-carboxylate)

To a solution of compound Int-1k (1 eq.) in EtOAc (0.2 M) at room temperature was added 10% Pd/C (0.1 eq.). The reaction was degassed and then shaken in a parr apparatus under 30 psi of H$_2$ for 3 hours. The reaction mixture was filtered on celite and concentrated to afford compound Int-1L.

Step 13—Synthesis of Compound Int-1m (tert-butyl (2S)-2-({[tert-butyl(diphenyl)silyl]oxy}methyl)-6-[(3E)-4-nitrobut-3-en-1-yl]morpholine-4-carboxylate)

To a solution of compound Int-1L in toluene (0.06 M) at room temperature was added nitromethane (10 eq.) and 1,1,3,3-tetramethylguanidine (0.1 eq.). The mixture was stirred at room temperature for 1 hour and methanesulfonyl chloride (1.8 eq.) was added. Triethylamine (1.8 eq.) was then added and the reaction was stirred at room temperature for 1 hour. The reaction was diluted with Et$_2$O and aqueous saturated NaHCO$_3$. The aqueous layer was extracted with Et$_2$O and the combined organic layers were dried over Na$_2$SO$_4$, filtered and concentrated. The crude product was purified by automated SiO$_2$ flash chromatography system using solvent gradient of 0% EtOAc/Hex to 40% EtOAc/Hex to afford compound Int-1m.

Step 14—Synthesis of Compound Int-1n (tert-butyl (6S)-2-(4-aminobutyl)-6-({[tert-butyl(diphenyl)silyl]oxy}methyl)morpholine-4-carboxylate)

To a solution of compound Int-1m (1 eq.) in MeOH (0.1 M) at room temperature was added 10% Pd/C (0.1 eq.). The reaction was degassed and then shaken in a parr apparatus under 50 psi of H$_2$ for 3 hours. The reaction mixture was filtered on celite and concentrated to afford compound Int-1n.

Step 15—Synthesis of Compound Int-1o (tert-butyl (2S)-2-({[tert-butyl(diphenyl)silyl]oxy}methyl)-6-(4-{[N-(methoxycarbonyl)-β-phenyl-L-phenylalanyl]amino}butyl)morpholine-4-carboxylate)

To a solution of compound Int-1n in a 5:1 mixture of THF/H$_2$O (0.1 M) at room temperature was added NaHCO$_3$ (5 eq.) and 2,5-dioxopyrrolidin-1-yl N-(methoxycarbonyl)-β-phenyl-L-phenylalaninate (1 eq.). The mixture was stirred for 16 hours, diluted with EtOAc and water and the aqueous layer was extracted with EtOAc. The combined organic layers were washed with saturated aqueous NaHCO$_3$, brine, 1N aqueous HCl and brine, dried over Na$_2$SO$_4$, filtered and concentrated. The crude product was purified by automated SiO$_2$ flash chromatography system using solvent gradient of 20% EtOAc/Hex to 100% EtOAc/Hex to afford compound Int-1o.

Step 16—Synthesis of Compound Int-1p (tert-butyl (2S)-2-(hydroxymethyl)-6-(4-{[N-(methoxycarbonyl)-β-phenyl-L-phenylalanyl]amino}butyl)morpholine-4-carboxylate)

To a solution of compound Int-1o in THF (0.15 M) at room temperature was added TBAF (1M in THF) (1.5 eq.). The mixture was stirred at room temperature for 2 hours, diluted with EtOAc and brine and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 40% EtOAc/Hex to 100% EtOAc/Hex to afford compound Int-1p.

Step 17—Synthesis of Compound Int-1q (tert-butyl (6S)-2-(4-{[N-(methoxycarbonyl)-β-phenyl-L-phenylalanyl]amino}butyl)-6-{[(4-nitrophenyl)sulfanyl]methyl}morpholine-4-carboxylate)

To a solution of compound Int-1p in THF (0.05 M) at room temperature was added para-nitrothiophenol (8 eq.) and triphenylphosphine (8 eq.). The mixture was stirred for 5 minutes and DIAD (8 eq.) was added. The mixture was stirred at room temperature for 16 hours and concentrated under reduced pressure. The crude product was purified by automated SiO$_2$ flash chromatography system using solvent gradient of 0% EtOAc/Hex to 50% EtOAc/Hex to afford compound Int-1q.

Step 18—Synthesis of Compound Int-1r (tert-butyl (6S)-2-(4-{[N-(methoxycarbonyl)-β-phenyl-L-phenylalanyl]amino}butyl)-6-{[(4-nitrophenyl)sulfonyl]methyl}morpholine-4-carboxylate)

To a solution of compound Int-1q in a 6:1 mixture of EtOH/H$_2$O (0.02 M) at room temperature was added sodium tungstate dihydrate (1 eq.) and hydrogen peroxide (30%) (5 eq.). The mixture was stirred at room temperature for 16 hours and concentrated. The residue was diluted with EtOAc and saturated aqueous NaHCO$_3$ and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% to 10% MeOH/CH$_2$Cl$_2$ to afford compound Int-1r.

Step 19-Syntheis of Compound Int-1s (tert-butyl (2S)-2-{[(4-aminophenyl)sulfonyl]methyl}-6-(4-{[N-(methoxycarbonyl)-β-phenyl-L-phenylalanyl]amino}butyl)morpholine-4-carboxylate)

To a solution of compound Int-1r in a 2:1 mixture of EtOH/H$_2$O (0.02 M) at room temperature was added iron (powder) (10 eq.) and NH$_4$Cl (1 eq.). The mixture was stirred at reflux for 2 hours, cooled to room temperature and filtered on celite. The filtrate was concentrated under reduced pressure. The residue was diluted with EtOAc and saturated aqueous NaHCO$_3$ and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% to 5% MeOH/CH$_2$Cl$_2$ to afford compound Int-1s.

Step 20-Synthesis of Compound 1 (N-{4-[(6S)-6-{[(4-aminophenyl)sulfonyl]methyl}morpholin-2-yl]butyl}-Nα-(methoxycarbonyl)-β-phenyl-L-phenylalaninamide)

To a solution of compound Int-1s in a 1: mixture of CH$_2$Cl$_2$/TFA (0.1 M) was stirred at room temperature for 1 hour. The reaction mixture was concentrated under reduced pressure and the residue was co-evaporated twice with heptane and triturated in Et$_2$O to afford the compound 1 as a TFA salt.

M+1, +ESI=609.2

EXAMPLE 2

Preparation of Compound 2 (methyl N-[(1S)-1-benzhydryl-2-[3-[(6S)-6-[(4-chlorophenyl)sulfanylmethyl]morpholin-2-yl]propylamino]-2-oxo-ethyl]carbamate)

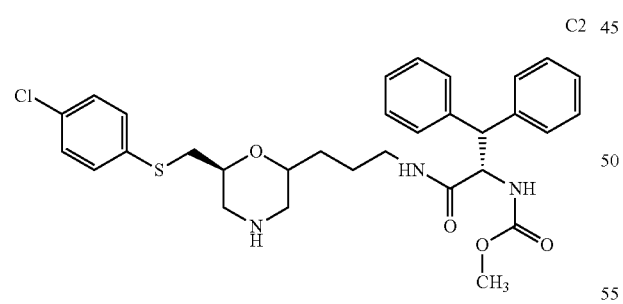

Step 1-Synthesis of Compound Int-2a (tert-butyl (6S)-2-[3-(benzylamino)propyl]-6-({[tert-butyl(diphenyl)silyl]oxy}methyl)morpholine-4-carboxylate)

To a solution of compound Int-1L (1 eq.) in MeOH (0.15 M) at room temperature was added benzylamine (1 eq.). The reaction mixture was stirred at room temperature for 2 hours and concentrated to dryness under reduced pressure. The residue was diluted in dry THF (0.15 M) and NaBH$_4$ (1 eq.) was added, followed by the addition of MeOH (2 eq.). The reaction mixture was stirred for 2 hours at room temperature, diluted with EtOAc and saturated aqueous NaHCO$_3$. The aqueous layer was extracted with EtOAc. The combined organic layers were washed with brine and 1N HCl, dried over Na$_2$SO$_4$, filtered and concentrated. The crude product was used as such (compound Int-2a) for the next step.

Step 2—Synthesis of Compound Int-2b (tert-butyl (6S)-2-(3-aminopropyl)-6-({[tert-butyl(diphenyl)silyl]oxy}methyl)morpholine-4-carboxylate)

To a solution of compound Int-2a (1 eq) in MeOH (0.1 M) at room temperature was added 20% Pd(OH)$_2$ (0.1 eq.). The reaction was degassed and then shaken in a parr apparatus under 50 psi of H$_2$ for 24 hours. The reaction mixture was filtered on celite and concentrated to afford compound Int-2b.

Step 3-Synthesis of Compound 2 (methyl N-[(1S)-1-benzhydryl-2-[3-[(6S)-6-[(4-chlorophenyl)sulfanylmethyl]morpholin-2-yl]propylamino]-2-oxo-ethyl]carbamate)

Compound 2 was prepared from compound Int-2b by following procedures from steps 15-17 and 20 described in Example 1 and using the appropriate reagents.

M+1, +ESI=582.2

EXAMPLE 3

Preparation of Compound 3 (methyl N-[(1S)-1-benzhydryl-2-[3-[(6S)-6-[(4-chloro-2-methyl-phenyl)sulfanylmethyl]morpholin-2-yl]propylamino]-2-oxo-ethyl]carbamate)

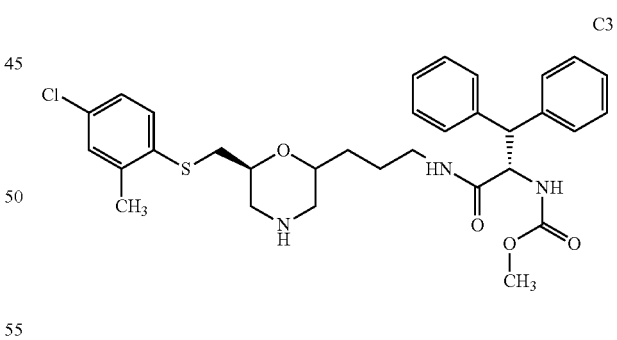

Step 1-Synthesis of Compound 3 (methyl N-[(1S)-1-benzhydryl-2-[3-[(6S)-6-[(4-chloro-2-methyl-phenyl)sulfanylmethyl]morpholin-2-yl]propylamino]-2-oxo-ethyl]carbamate)

Compound 3 was prepared from Compound Int-2b by following procedures described in Example 2 and using the appropriate reagents.

M+1, +ESI=596.2

EXAMPLE 4

Preparation of Compound 4 (methyl N-[(1S)-1-benzhydryl-2-[[2-[2-[(6S)-6-(2-naphthylsulfonylmethyl)morpholin-2-yl]ethyl]phenyl]amino]-2-oxo-ethyl]carbamate)

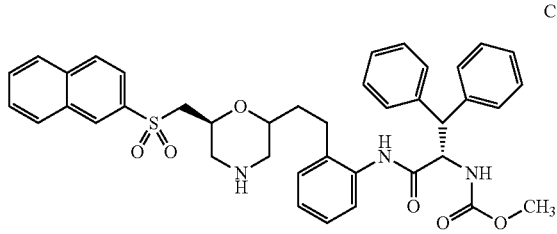

C-4

Step 1—Synthesis of Compound Int-4a (tert-butyl (2S)-2-({[tert-butyl(diphenyl)silyl]oxy}methyl)-6-[(E)-2-(2-nitrophenyl)ethenyl]morpholine-4-carboxylate)

To a solution of compound Int-1j (1 eq.) in DME (0.2 M) at room temperature was added (2-nitrobenzyl)(triphenyl)phosphonium bromide (1.1 eq.), potassium carbonate (2 eq.) and 18-C-6 (0.1 eq.). The reaction mixture was stirred at room temperature for 12 hours, filtered on celite and the filtrate was concentrated under reduced pressure. The crude product was purified by automated $SiO_2$ flash chromatography system using solvent gradient of 10% to 40% EtOAc/Hex to afford compound Int-4a.

Step 2—Synthesis of Compound Int-4b (tert-butyl (6S)-2-[2-(2-aminophenyl)ethyl]-6-({[tert-butyl(diphenyl)silyl]oxy}methyl)morpholine-4-carboxylate)

To a solution of compound Int-4a (1 eq.) in EtOAc (0.15 M) at room temperature was added 10% Pd/C (0.2 eq.). The reaction was degassed and then shaken in a parr apparatus under 1 atmosphere of $H_2$ for 16 hours. The reaction mixture was filtered on celite and concentrated to afford compound Int-4b.

Step 3—Synthesis of Compound Int-4c (tert-butyl (2S)-2-({[tert-butyl(diphenyl)silyl]oxy}methyl)-6-[2-(2-{[N-(methoxycarbonyl)-β-phenyl-L-phenylalanyl]amino}phenyl)ethyl]morpholine-4-carboxylate)

To a solution of compound Int-4b (1 eq.) in DMF (0.15 M) at room temperature was added N-(methoxycarbonyl)-β-phenyl-L-phenylalanine (1.1 eq.), HATU (1.4 eq.) and 2,6-lutidine (3 eq.). The reaction mixture was stirred at room temperature for 16 hours and diluted with EtOAc and saturated aqueous $NaHCO_3$. The aqueous layer was extracted with EtOAc. The combined organic layers were washed with brine and 1N aqueous HCl, dried over $Na_2SO_4$, filtered and concentrated. The crude product was purified by automated $SiO_2$ flash chromatography system using solvent gradient of 10% to 80% EtOAc/Hex to afford compound Int-4c.

Step 4—Synthesis of Compound Int-4d (tert-butyl (2S)-2-(hydroxymethyl)-6-[2-(2-{[N-(methoxycarbonyl)-β-phenyl-L-phenylalanyl]amino}phenyl)ethyl]morpholine-4-carboxylate)

To a solution of compound Int-4c in THF (0.1 M) at room temperature was added TBAF (1M in THF) (1.5 eq.). The mixture was stirred at room temperature for 2 hours, diluted with EtOAc and brine and the aqueous layer was extracted with EtOAc. The combined organic layers were washed with brine, dried over $Na_2SO_4$, filtered and concentrated. The crude product was purified by automated $SiO_2$ flash chromatography system using solvent gradient of 40% EtOAc/Hex to 100% EtOAc/Hex to afford the compound Int-4d.

Step 5-Synthesis of Compound 4 (methyl N-[(1S)-1-benzhydryl-2-[[2-[2-[(6S)-6-(2-naphthylsulfonylmethyl)morpholin-2-yl]ethyl]phenyl]amino]-2-oxo-ethyl]carbamate)

Compound 4 was prepared from compound Int-4d by following procedures from steps 17-18 and 20 described in Example 1 and using the appropriate reagents.

M+1, +ESI=692.2

EXAMPLE 5

Preparation of Compound 5 (methyl N-[(1S)-1-benzhydryl-2-[[2-[2-[(6S)-6-[(4-chlorophenoxy)methyl]morpholin-2-yl]ethyl]phenyl]amino]-2-oxo-ethyl]carbamate)

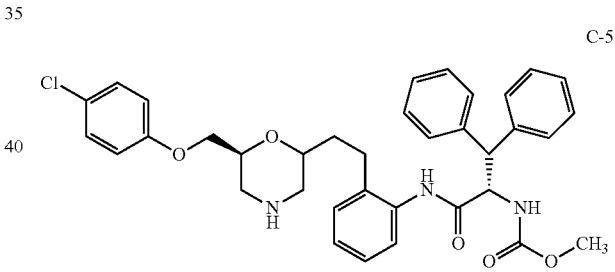

C-5

Step 1—Synthesis of Compound 5 (methyl N-[(1S)-1-benzhydryl-2-[[2-[2-[(6S)-6-[(4-chlorophenoxy)methyl]morpholin-2-yl]ethyl]phenyl]amino]-2-oxo-ethyl]carbamate)

Compound 5 was prepared from compound Int-4d by following procedures from steps 17 and 20 described in Example 1 and using the appropriate reagents. Alternatively, the TFA salt could be neutralized with aqueous saturated $NaHCO_3$, extracted with EtOAc, dried over $Na_2SO_4$, filtered and concentrated and then purified by automated $SiO_2$ flash chromatography system using solvent gradient of 0% to 10% MeOH/$CH_2Cl_2$ to afford compound 5.

M+1, +ESI=629.2

EXAMPLE 6

Preparation of Compound 6 (methyl N-[(1S)-1-benzhydryl-2-[[2-[2-[(6S)-6-[(4-chlorophenyl)sulfanylmethyl]morpholin-2-yl]ethyl]phenyl]amino]-2-oxo-ethyl]carbamate)

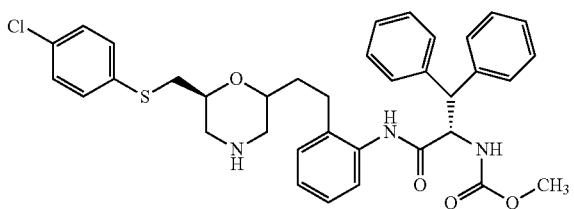

C-6

Step 1: Synthesis of Compound 6 (methyl N-[(1S)-1-benzhydryl-2-[[2-[2-[(6S)-6-[(4-chlorophenyl)sulfanylmethyl]morpholin-2-yl]ethyl]phenyl]amino]-2-oxo-ethyl]carbamate)

Compound 6 was prepared from compound Int-4d by following procedures from steps 17 and 20 described in Example 1 and using the appropriate reagents. Alternatively, the TFA salt could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford compound 6.

M+1, +ESI=644.2

EXAMPLE 7

Preparation of Compound 7 (methyl N-[(1S)-1-benzhydryl-2-[[2-[2-[(2R,6S)-6-[(4-chlorophenyl)sulfanylmethyl]morpholin-2-yl]ethyl]phenyl]amino]-2-oxo-ethyl]carbamate)

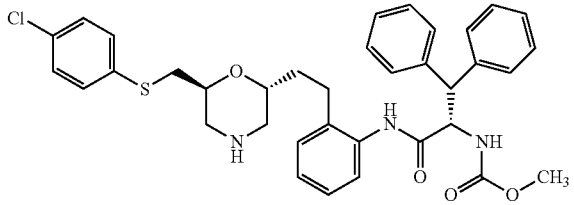 [SMILES: COC(=O)N[C@H](C(=O)Nc1ccccc1CC[C@@H]1CNC[C@@H](CSc2ccc(Cl)cc2)O1)C(c1ccccc1)c1ccccc1]

Step 1—Synthesis of Compound Int-7a (1-[(2E)-4-chlorobut-2-en-1-yl]-4-nitrobenzene)

To a solution of 4-nitrophenol (1 eq.) in DMF (0.7 M) at room temperature was added sodium hydride (1 eq.) and the mixture was stirred for 30 minutes. The resulting mixture was then slowly added to a solution of (2E)-1,4-dichlorobut-2-ene (4 eq.). The reaction mixture was stirred at room temperature for 48 hours and diluted with H$_2$O. The aqueous layer was extracted with tert-butylmethyl ether. The combined organic layers were washed with brine and water, dried over MgSO$_4$, filtered and concentrated. The crude product was purified by automated SiO$_2$ flash chromatography system using solvent gradient of 0% to 30% EtOAc/Hex to afford the compound Int-7a.

Step 2—Synthesis of Compound Int-7b ((2E)-N-benzyl-4-(4-nitrophenyl)but-2-en-1-amine)

To a solution of benzylamine (4 eq.) and sodium iodide (0.1 eq.) in DMSO (0.3 M) at 50° C. was added compound Int-7a (1 eq.) and the mixture was stirred at 50° C. for 2 hours. The reaction mixture was cooled to room temperature and diluted with H$_2$O. The aqueous layer was extracted with tert-butylmethyl ether. The combined organic layers were washed with brine and water, dried over MgSO$_4$, filtered and concentrated. The crude product was purified by automated SiO$_2$ flash chromatography system using solvent gradient of 0% to 5% MeOH/CH$_2$Cl$_2$ to afford the compound Int-7b.

Step 3—Synthesis of Compound Int-7c (2S)-1-{benzyl[(2E)-4-(4-nitrophenoxy)but-2-en-1-yl]amino}-3-{[tert-butyl(dimethyl)silyl]oxy}propan-2-ol To a solution of compound Int-7b (1 eq.) in dichloromethane (0.15 M) at room temperature was added tert-butyl(dimethyl)[(2S)-oxiran-2-ylmethoxy]silane (1 eq.) and lithium bis(trifluoromethanesulfonyl)imide (0.5 eq.). The mixture was stirred at room temperature for 12 hours and diluted with aqueous saturated NaHCO$_3$. The aqueous layer was extracted with CH$_2$Cl$_2$. The combined organic layers were dried over Na$_2$SO4, filtered and concentrated. The crude product was purified by automated SiO$_2$ flash chromatography system using solvent gradient of 20% to 80% EtOAc/Hex to afford compound Int-7c.

Step 4—Synthesis of Compound Int-7d (2S,6R)-4-benzyl-2-({[tert-butyl(dimethyl)silyl]oxy}methyl)-6-ethenylmorpholine To a solution of compound Int-7c (1 eq.) in dichloromethane (0.05 M) at room temperature was added triethylamine (1.5 eq.). The reaction mixture was degassed prior to the addition of Pd$_2$(dba)$_3$.CHCl$_3$ (0.04 eq.) and (1S,2S)-(−)-1,2-diaminocyclohexane-N,N'-Bis(2'-diphenylphosphinobenzoyl) (0.01 eq.). The mixture was stirred at room temperature for 12 hours and concentrated under reduced pressure. The crude product was purified by automated SiO$_2$ flash chromatography system using solvent gradient of 0% to 40% EtOAc/Hex to afford compound Int-7d.

Step 5—Synthesis of Compound Int-7e (1-[(2S,6S)-4-benzyl-6-({[tert-butyl(dimethyl)silyl]oxy}methyl)morpholin-2-yl]ethane-1,2-diol)

To a solution of compound Int-7d in a 1:1 mixture of acetone/water (0.15 M) at room temperature were added osmium tetroxide (0.05 eq.) and 4-methylmorpholine 4-oxide (0.05 eq.). The mixture was stirred at room temperature for 16 hours, concentrated under reduced pressure and diluted with aqueous saturated NaHCO$_3$. The aqueous layer was extracted with EtOAc and the combined organic layers were dried over Na$_2$SO$_4$, filtered and concentrated. The crude product (compound Int-7e) was used as such for the next step.

Step 6—Synthesis of Compound Int-7f ((2S,6S)-4-benzyl-6-({[tert-butyl(dimethyl)silyl]oxy}methyl)morpholine-2-carbaldehyde)

To a solution of compound Int-7e in a 3:1 mixture of THF/water (0.1 M) at room temperature was added sodium periodate (2.5 eq.). The mixture was stirred at room temperature for 2 hours and diluted with water. The aqueous layer was extracted with $Et_2O$ and the combined organic layers were dried over $MgSO_4$, filtered and concentrated. The crude product (compound Int-7f) was used as such for the next step.

Step 7—Synthesis of Compound Int-7g ((2S,6R)-4-benzyl-2-({[tert-butyl(dimethyl)silyl]oxy}methyl)-6-[(E)-2-(2-nitrophenyl)ethenyl]morpholine)

To a solution of compound Int-7f (1 eq.) in DME (0.2 M) at room temperature was added (2-nitrobenzyl)(triphenyl)phosphonium bromide (1.1 eq.), potassium carbonate (2 eq.) and 18-C-6 (0.1 eq.). The reaction mixture was stirred at room temperature for 12 hours, filtered on celite and the filtrate was concentrated under reduced pressure. The crude product was purified by automated $SiO_2$ flash chromatography system using solvent gradient of 10% to 80% EtOAc/Hex to afford compound Int-7g.

Step 8—Synthesis of Compound Int-7h (2-{2-[(2R,6S)-6-({[tert-butyl(dimethyl)silyl]oxy}methyl)morpholin-2-yl]ethyl}aniline)

To a solution of compound Int-7g (1 eq.) in MeOH (0.15 M) at room temperature was added 10% Pd/C (0.2 eq.). The reaction was degassed and then shaken in a parr apparatus under 50 psi of $H_2$ for 16 hours. The reaction mixture was filtered on celite and concentrated to afford compound Int-7h.

Step 9—Synthesis of Compound Int-7i (tert-butyl (2R,6S)-2-[2-(2-aminophenyl)ethyl]-6-({[tert-butyl(dimethyl)silyl]oxy}methyl)morpholine-4-carboxylate)

To a solution of compound Int-7h (1 eq.) in a 1:1 mixture of THF/$H_2O$ (0.1 M) at room temperature was added sodium bicarbonate (5 eq.) and Di-tert-butyl dicarbonate (1.5 eq.). The reaction mixture was stirred at room temperature for 16 hours and THF was removed by roto-vap. The aqueous layer was extracted with dichloromethane. The combined organic layers were washed with brine, dried over $Na_2SO_4$, filtered and concentrated. The crude product (compound Int-7i) was used as such for next step.

Step 10—Synthesis of Compound Int-7j (tert-butyl (2S,6R)-2-({[tert-butyl(dimethyl)silyl]oxy}methyl)-6-[2-(2-{[N-(methoxycarbonyl)-β-phenyl-L-phenylalanyl]amino}phenyl)ethyl]morpholine-4-carboxylate)

To a solution of compound Int-7i (1 eq.) in DMF (0.15 M) at room temperature was added N-(methoxycarbonyl)-β-phenyl-L-phenylalanine (1.1 eq.), HATU (1.4 eq.) and 2,6-lutidine (3 eq.). The reaction mixture was stirred at room temperature for 16 hours and diluted with EtOAc and saturated aqueous $NaHCO_3$. The aqueous layer was extracted with EtOAc. The combined organic layers were washed with brine and 1N aqueous HCl, dried over $Na_2SO_4$, filtered and concentrated. The crude product was purified by automated $SiO_2$ flash chromatography system using solvent gradient of 10% to 80% EtOAc/Hex to afford the compound Int-7j.

Step 11—Synthesis of Intermediate Compound Int-7k (tert-butyl (2S,6R)-2-(hydroxymethyl)-6-[2-(2-{[N-(methoxycarbonyl)-β-phenyl-L-phenylalanyl]amino}phenyl)ethyl]morpholine-4-carboxylate)

To a solution of compound Int-7j in THF (0.1 M) at room temperature was added TBAF (1M in THF) (1.5 eq.). The mixture was stirred at room temperature for 2 hours, diluted with EtOAc and brine and the aqueous layer was extracted with EtOAc. The combined organic layers were washed with brine, dried over $Na_2SO_4$, filtered and concentrated. The crude product was purified by automated $SiO_2$ flash chromatography system using solvent gradient of 0-5% MeOH/$CH_2Cl_2$ to afford the compound Int-7k.

Step 12—Synthesis of Compound Int-7L (tert-butyl (2S,6R)-2-{[(4-chlorophenyl)sulfanyl]methyl}-6-[2-(2-{[N-(methoxycarbonyl)-β-phenyl-L-phenylalanyl]amino}phenyl)ethyl]morpholine-4-carboxylate)

To a solution of compound Int-7k in Toluene (0.1 M) at room temperature was added para-nitrothiophenol (1.5 eq.) and cyanomethylenetributylphosphorane (2 eq.). The mixture was degassed, stirred at 80° C. for 2 hours and concentrated under reduced pressure. The crude product was purified by automated $SiO_2$ flash chromatography system using solvent gradient of 10% EtOAc/Hex to 100% EtOAc/Hex to afford the compound Int-7L.

Step 13—Synthesis of Compound 7 (N-(2-{2-[(2R,6S)-6-{[(4-chlorophenyl)sulfanyl]methyl}morpholin-2-yl]ethyl}phenyl)-Nα-(methoxycarbonyl)-β-phenyl-L-phenylalaninamide)

A solution of compound Int-7L in a 1:1 mixture of $CH_2Cl_2$/TFA (0.1 M) was stirred at room temperature for 1 hour. The reaction mixture was concentrated under reduced pressure and the residue was co-evaporated twice with heptane and triturated in $Et_2O$ to afford the desired product (compound 7) as a TFA salt. Alternatively, the TFA salt, after concentration, could be neutralized with aqueous saturated $NaHCO_3$, extracted with EtOAc, dried over $Na_2SO_4$, filtered and concentrated and then purified by automated $SiO_2$ flash chromatography system using solvent gradient of 0% to 10% MeOH/$CH_2Cl_2$ to afford the desired compound. Alternatively, the free base could be purified by filtration on SCX SPE cartridge made of pTSA-$SiO_2$ eluted first with MeOH to remove non basic impurities and eluted then with 10% $NH_4OH$/MeOH to elute the free base and afford the desired compound after concentration under reduced pressure.

M+1, +ESI=644.2

Examples 8 to 55 were prepared using the appropriate phenol or thiophenol and by following the procedures described in Example 7.

| Ex. | Structure | IUPAC name | LCMS data |
|---|---|---|---|
| 8 | 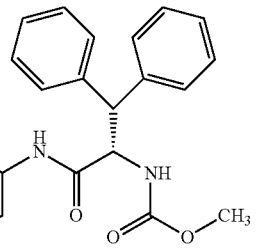 | methyl N-[(1S)-1-benzhydryl-2-[[2-[2-[(2R,6S)-6-[(4-bromophenyl)sulfanylmethyl]morpholin-2-yl]ethyl]phenyl]amino]-2-oxo-ethyl]carbamate | M + 1, +ESI = 689.2 |
| 9 | 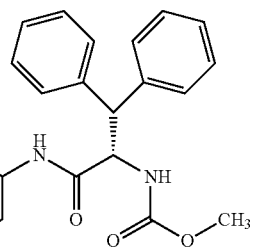 | methyl N-[(1S)-1-benzhydryl-2-[[2-[2-[(2R,6S)-6-[(4-bromophenoxy)methyl]morpholin-2-yl]ethyl]phenyl]amino]-2-oxo-ethyl]carbamate | M + 1, +ESI = 674.2 |
| 10 | 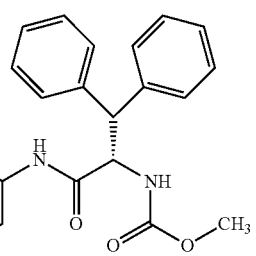 | methyl N-[(1S)-1-benzhydryl-2-[[2-[2-[(2R,6S)-6-[(4-bromo-2-nitro-phenoxy)methyl]morpholin-2-yl]ethyl]phenyl]amino]-2-oxo-ethyl]carbamate | M + 1, +ESI = 719.2 |
| 11 | 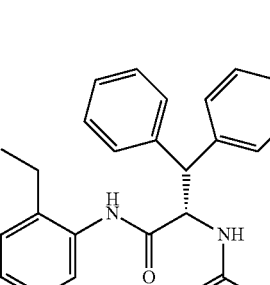 | methyl N-[(1S)-1-benzhydryl-2-oxo-2-[[2-[2-[(2R,6S)-6-[(4-phenylphenoxy)methyl]morpholin-2-yl]ethyl]phenyl]amino]ethyl]carbamate | M + 1, +ESI = 670.3 |
| 12 | 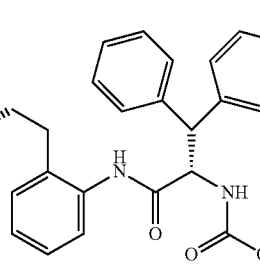 | methyl N-[(1S)-1-benzhydryl-2-[[2-[2-[(2R,6S)-6-[(4-benzylphenoxy)methyl]morpholin-2-yl]ethyl]phenyl]amino]-2-oxo-ethyl]carbamate | M + 1, +ESI = 684.4 |
| 13 | 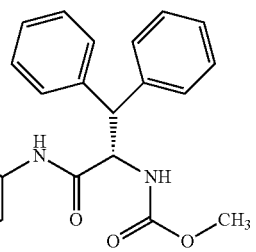 | methyl N-[(1S)-1-[[2-[2-[(2R,6S)-6-[(2-amino-4-bromo-phenoxy)methyl]morpholin-2-yl]ethyl]phenyl]carbamoyl]-2,2-diphenyl-ethyl]carbamate | M + 1, +ESI = 687.2 |

-continued

| Ex. | Structure | IUPAC name | LCMS data |
|---|---|---|---|
| 14 | 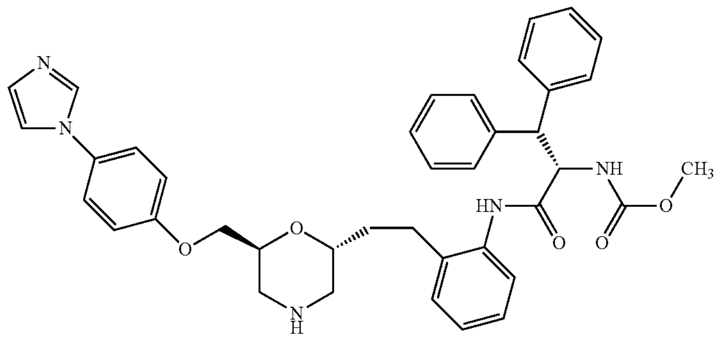 [SMILES: COC(=O)N[C@H](C(=O)Nc1ccccc1CC[C@@H]1CNC[C@@H](COc2ccc(-n3ccnc3)cc2)O1)C(c1ccccc1)c1ccccc1] | methyl N-[(1S)-1-benzhydryl-2-[[2-[2-[(2R,6S)-6-[(4-imidazol-1-ylphenoxy)methyl]morpholin-2-yl]ethyl]phenyl]amino]-2-oxo-ethyl]carbamate | M + 1, +ESI = 661.3 |
| 15 | 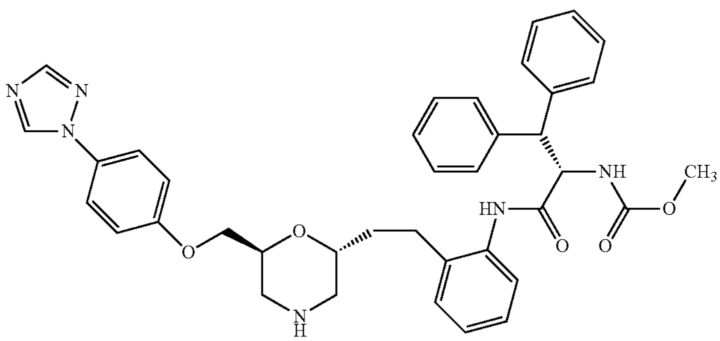 [SMILES: COC(=O)N[C@H](C(=O)Nc1ccccc1CC[C@@H]1CNC[C@@H](COc2ccc(-n3cncn3)cc2)O1)C(c1ccccc1)c1ccccc1] | methyl N-[(1S)-1-benzhydryl-2-oxo-2-[[2-[2-[(2R,6S)-6-[[4-(1,2,4-triazol-1-yl)phenoxy]methyl]morpholin-2-yl]ethyl]phenyl]amino]ethyl]carbamate | M + 1, +ESI = 661.3 |
| 16 | 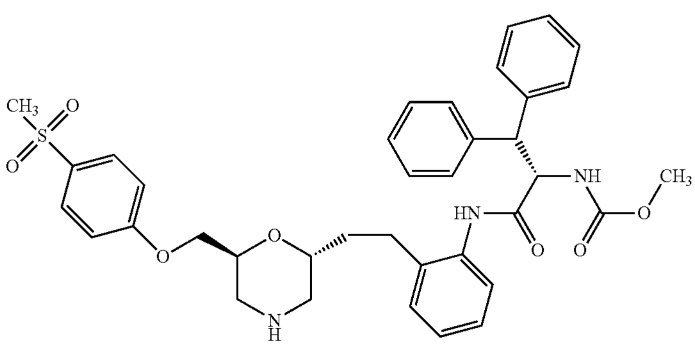 | methyl N-[(1S)-1-benzhydryl-2-[[2-[2-[(2R,6S)-6-[(4-methylsulfonylphenoxy)methyl]morpholin-2-yl]ethyl]phenyl]amino]-2-oxo-ethyl]carbamate | M + 1, +ESI = 672.2 |
| 17 | 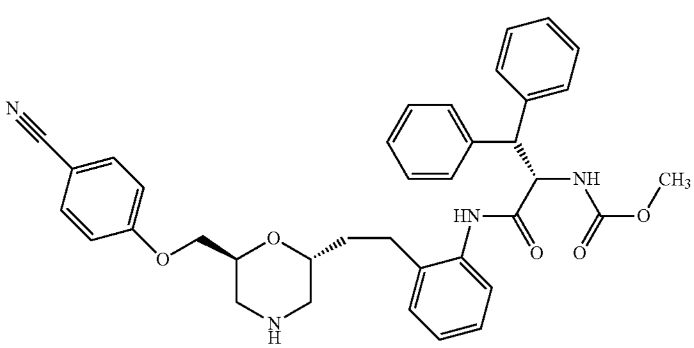 [SMILES: COC(=O)N[C@H](C(=O)Nc1ccccc1CC[C@@H]1CNC[C@@H](COc2ccc(C#N)cc2)O1)C(c1ccccc1)c1ccccc1] | methyl N-[(1S)-1-benzhydryl-2-[[2-[2-[(2R,6S)-6-[(4-cyanophenoxy)methyl]morpholin-2-yl]ethyl]phenyl]amino]-2-oxo-ethyl]carbamate | M + 1, +ESI = 619.3 |

-continued

| Ex. | Structure | IUPAC name | LCMS data |
|---|---|---|---|
| 18 | 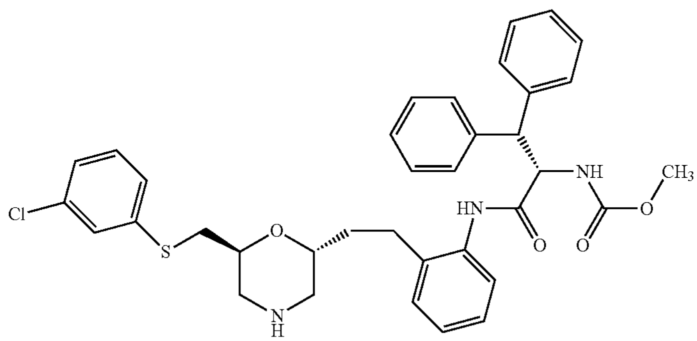 [SMILES: COC(=O)N[C@H](C(=O)Nc1ccccc1CC[C@@H]1CNC[C@@H](CSc2cccc(Cl)c2)O1)C(c1ccccc1)c1ccccc1] | methyl N-[(1S)-1-benzhydryl-2-[[2-[2-[(2R,6S)-6-[(3-chlorophenyl)sulfanylmethyl]morpholin-2-yl]ethyl]phenyl]amino-2-oxo-ethyl]carbamate | M + 1, +ESI = 644.2 |
| 19 | 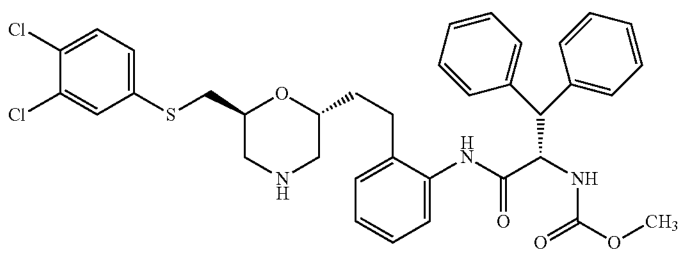 [SMILES: COC(=O)N[C@H](C(=O)Nc1ccccc1CC[C@@H]1CNC[C@@H](CSc2ccc(Cl)c(Cl)c2)O1)C(c1ccccc1)c1ccccc1] | methyl N-[(1S)-1-benzhydryl-2-[[2-[2-[(2R,6S)-6-[(3,4-dichlorophenyl)sulfanylmethyl]morpholin-2-yl]ethyl]phenyl]amino]-2-oxo-ethyl]carbamate | M + 1, +ESI = 678.1 |
| 20 | 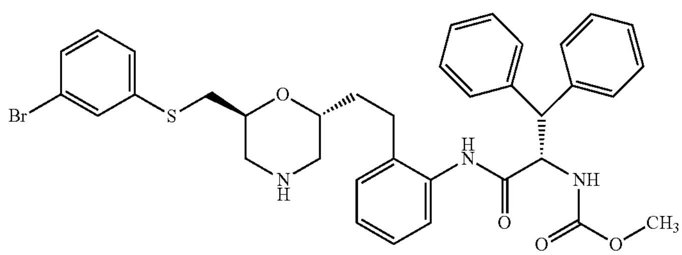 [SMILES: COC(=O)N[C@H](C(=O)Nc1ccccc1CC[C@@H]1CNC[C@@H](CSc2cccc(Br)c2)O1)C(c1ccccc1)c1ccccc1] | methyl N-[(1S)-1-benzhydryl-2-[[2-[2-[(2R,6S)-6-[(3-bromophenyl)sulfanylmethyl]morpholin-2-yl]ethyl]phenyl]amino-2-oxo-ethyl]carbamate | M + 1, +ESI = 688.2 |
| 21 | 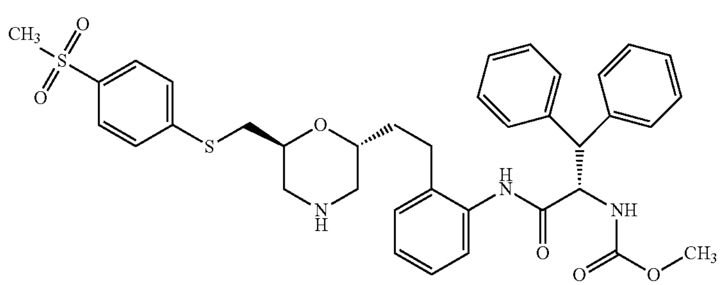 | methyl N-[(1S)-1-benzhydryl-2-[[2-[2-[(2R,6S)-6-[(4-methylsulfonylphenyl)sulfanylmethyl]morpholin-2-yl]ethyl]phenyl]amino]-2-oxo-ethyl]carbamate | M + 1, +ESI = 688.2 |
| 22 | 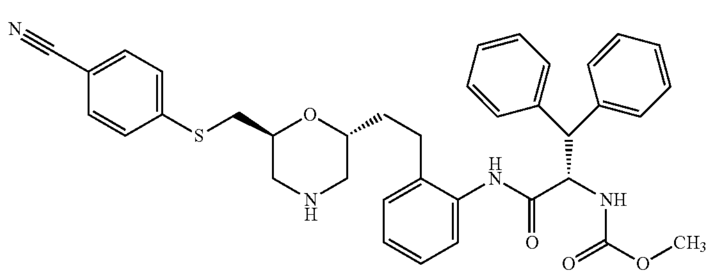 | methyl N-[(1S)-1-benzhydryl-2-[[2-[2-[(2R,6S)-6-[(4-cyanophenyl)sulfanylmethyl]morpholin-2-yl]ethyl]phenyl]amino]-2-oxo-ethyl]carbamate | M + 1, +ESI = 635.2 |

-continued

| Ex. | Structure | IUPAC name | LCMS data |
|---|---|---|---|
| 23 | 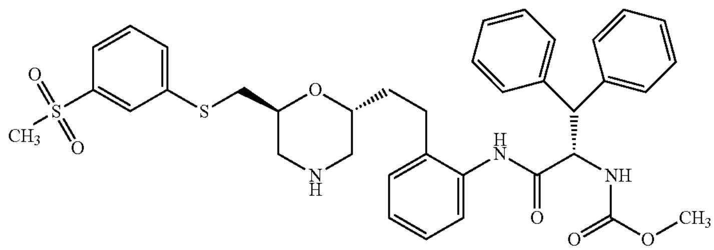 | methyl N-[(1S)-1-benzhydryl-2-[[2-[2-[(2R,6S)-6-[(3-methylsulfonylphenyl)sulfanylmethyl]morpholin-2-yl]ethyl]phenyl]amino]-2-oxo-ethyl]carbamate | M + 1, +ESI = 688.2 |
| 24 | 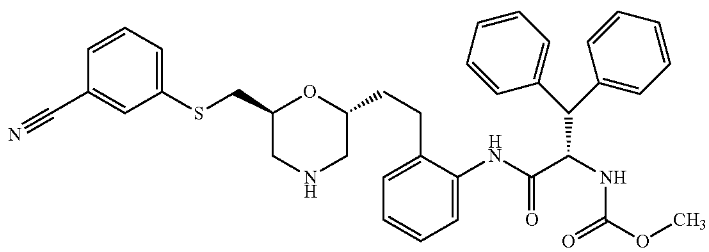 [SMILES: COC(=O)N[C@H](C(=O)Nc1ccccc1CC[C@@H]1CNC[C@@H](CSc2cccc(C#N)c2)O1)C(c1ccccc1)c1ccccc1] | methyl N-[(1S)-1-benzhydryl-2-[[2-[2-[(2R,6S)-6-[(3-cyanophenyl)sulfanylmethyl]morpholin-2-yl]ethyl]phenyl]amino]-2-oxo-ethyl]carbamate | M + 1, +ESI = 635.2 |
| 25 | 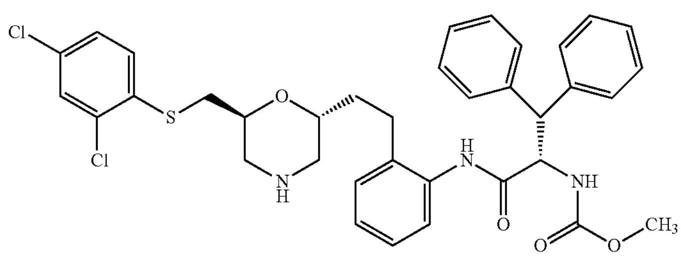 [SMILES: COC(=O)N[C@H](C(=O)Nc1ccccc1CC[C@@H]1CNC[C@@H](CSc2ccc(Cl)cc2Cl)O1)C(c1ccccc1)c1ccccc1] | methyl N-[(1S)-1-benzhydryl-2-[[2-[2-[(2R,6S)-6-[(2,4-dichlorophenyl)sulfanylmethyl]morpholin-2-yl]ethyl]phenyl]amino]-2-oxo-ethyl]carbamate | M + 1, +ESI = 678.1 |
| 26 | 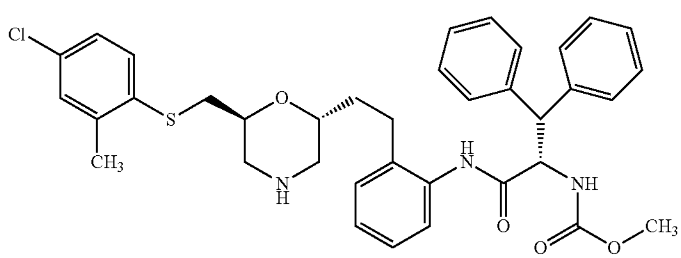 [SMILES: COC(=O)N[C@H](C(=O)Nc1ccccc1CC[C@@H]1CNC[C@@H](CSc2ccc(Cl)cc2C)O1)C(c1ccccc1)c1ccccc1] | methyl N-[(1S)-1-benzhydryl-2-[[2-[2-[(2R,6S)-6-[(4-chloro-2-methyl-phenyl)sulfanylmethyl]morpholin-2-yl]ethyl]phenyl]amino]-2-oxo-ethyl]carbamate | M + 1, +ESI = 658.2 |
| 27 | 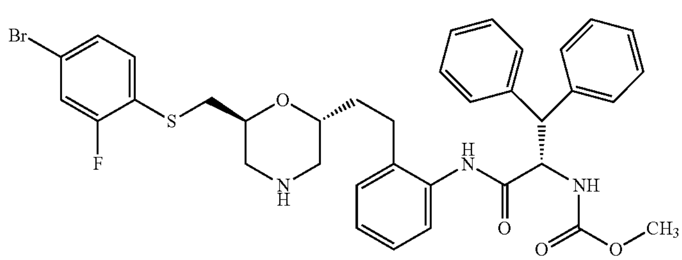 | methyl N-[(1S)-1-benzhydryl-2-[[2-[2-[(2R,6S)-6-[(4-bromo-2-fluoro-phenyl)sulfanylmethyl]morpholin-2-yl]ethyl]phenyl]amino]-2-oxo-ethyl]carbamate | M + 1, +ESI = 706.2 |
| 28 | 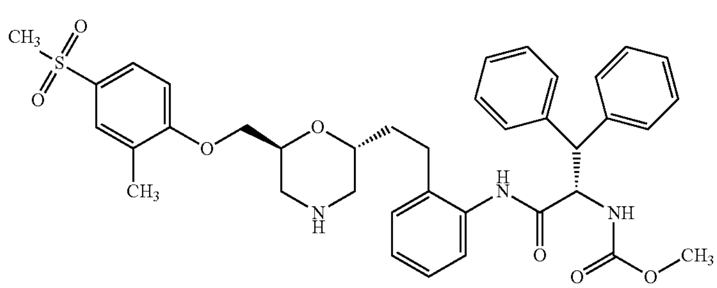 | methyl N-[(1S)-1-benzhydryl-2-[[2-[2-[(2R,6S)-6-[(2-methyl-4-methylsulfonyl-phenoxy)methyl]morpholin-2-yl]ethyl]phenyl]amino]-2-oxo-ethyl]carbamate | M + 1, +ESI = 686.2 |

-continued

| Ex. | Structure | IUPAC name | LCMS data |
|---|---|---|---|
| 29 | 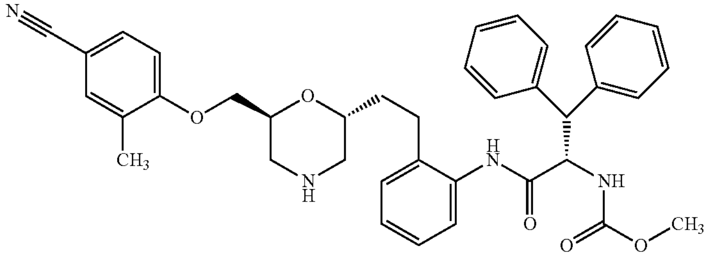 [SMILES: COC(=O)N[C@H](C(=O)Nc1ccccc1CC[C@@H]1CNC[C@@H](COc2ccc(C#N)cc2C)O1)C(c1ccccc1)c1ccccc1] | methyl N-[(1S)-1-benzhydryl-2-[[2-[2-[(2R,6S)-6-[(4-cyano-2-methyl-phenoxy)methyl]morpholin-2-yl]ethyl]phenyl]amino]-2-oxo-ethyl]carbamate | M + 1, +ESI = 633.3 |
| 30 | 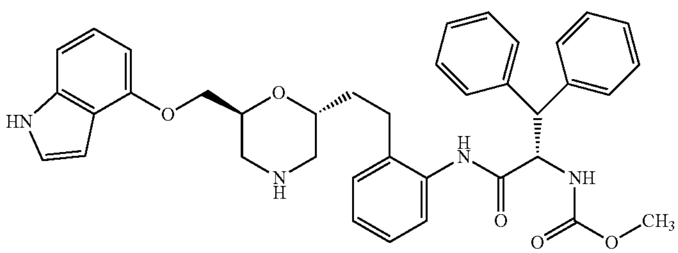 [SMILES: COC(=O)N[C@H](C(=O)Nc1ccccc1CC[C@@H]1CNC[C@@H](COc2cccc3[nH]ccc23)O1)C(c1ccccc1)c1ccccc1] | methyl N-[(1S)-1-benzhydryl-2-[[2-[2-[(2R,6S)-6-(1H-indol-4-yloxymethyl)morpholin-2-yl]ethyl]phenyl]amino]-2-oxo-ethyl]carbamate | M + 1, +ESI = 633.3 |
| 31 | 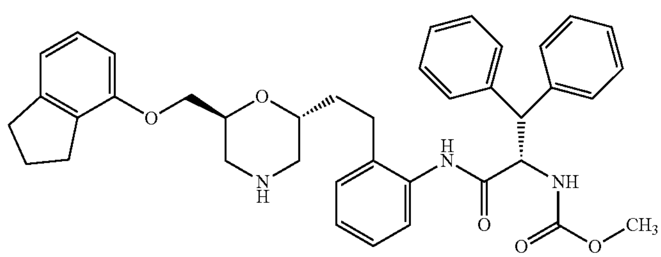 [SMILES: COC(=O)N[C@H](C(=O)Nc1ccccc1CC[C@@H]1CNC[C@@H](COc2cccc3c2CCC3)O1)C(c1ccccc1)c1ccccc1] | methyl N-[(1S)-1-benzhydryl-2-[[2-[2-[(2R,6S)-6-(indan-4-yloxymethyl)morpholin-2-yl]ethyl]phenyl]amino]-2-oxo-ethyl]carbamate | M + 1, +ESI = 634.3 |
| 32 | 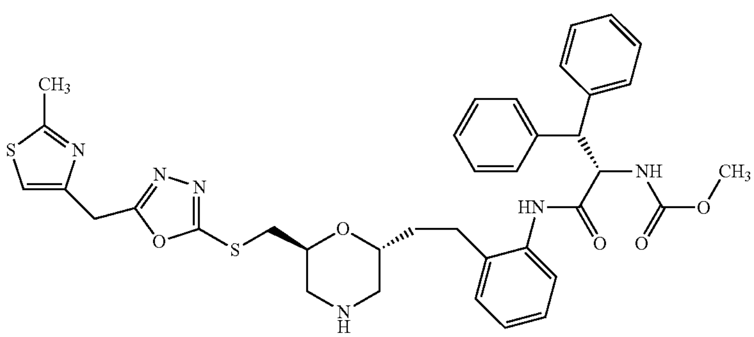 [SMILES: COC(=O)N[C@H](C(=O)Nc1ccccc1CC[C@@H]1CNC[C@@H](CSc2nnc(Cc3csc(C)n3)o2)O1)C(c1ccccc1)c1ccccc1] | methyl N-[(1S)-1-benzhydryl-2-[[2-[2-[(2R,6S)-6-[[5-[(2-methylthiazol-4-yl)methyl]-1,3,4-oxadiazol-2-yl]sulfanylmethyl]morpholin-2-yl]ethyl]phenyl]amino]-2-oxo-ethyl]carbamate | M + 1, +ESI = 713.2 |
| 33 | 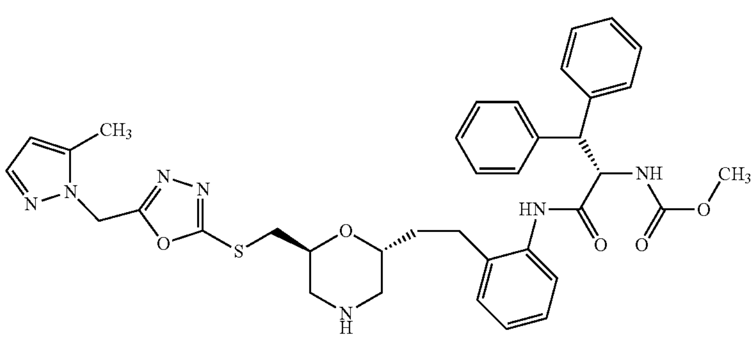 [SMILES: COC(=O)N[C@H](C(=O)Nc1ccccc1CC[C@@H]1CNC[C@@H](CSc2nnc(Cn3nccc3C)o2)O1)C(c1ccccc1)c1ccccc1] | methyl N-[(1S)-1-benzhydryl-2-[[2-[2-[(2R,6S)-6-[[5-[(5-methylpyrazol-1-yl)methyl]-1,3,4-oxadiazol-2-yl]sulfanylmethyl]morpholin-2-yl]ethyl]phenyl]amino]-2-oxo-ethyl]carbamate | M + 1, +ESI = 696.3 |

| Ex. | Structure | IUPAC name | LCMS data |
|---|---|---|---|
| 34 | 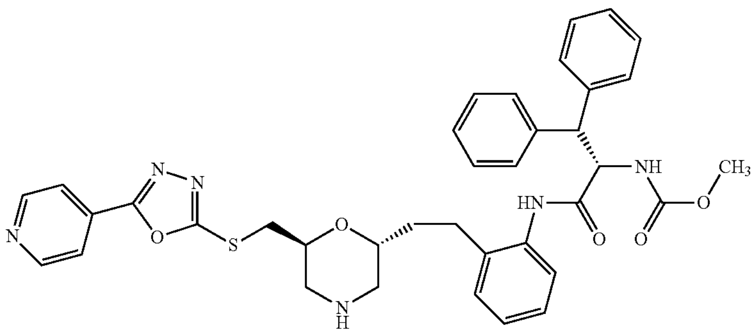 [SMILES: COC(=O)N[C@H](C(=O)Nc1ccccc1CC[C@@H]1CNC[C@@H](CSc2nnc(-c3ccncc3)o2)O1)C(c1ccccc1)c1ccccc1] | methyl N-[(1S)-1-benzhydryl-2-oxo-2-[[2-[2-[(2R,6S)-6-[[5-(4-pyridyl)-1,3,4-oxadiazol-2-yl]sulfanylmethyl]morpholin-2-yl]ethyl]phenyl]amino]ethyl]carbamate | M + 1, +ESI = 679.2 |
| 35 | 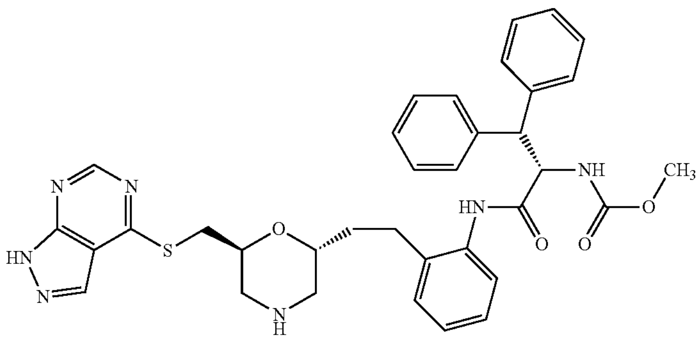 [SMILES: COC(=O)N[C@H](C(=O)Nc1ccccc1CC[C@@H]1CNC[C@@H](CSc2ncnc3[nH]ncc23)O1)C(c1ccccc1)c1ccccc1] | methyl N-[(1S)-1-benzhydryl-2-oxo-2-[[2-[2-[(2R,6S)-6-(1H-pyrazolo[3,4-d]pyrimidin-4-ylsulfanylmethyl)morpholin-2-yl]ethyl]phenyl]amino]ethyl]carbamate | M + 1, +ESI = 652.3 |
| 36 | 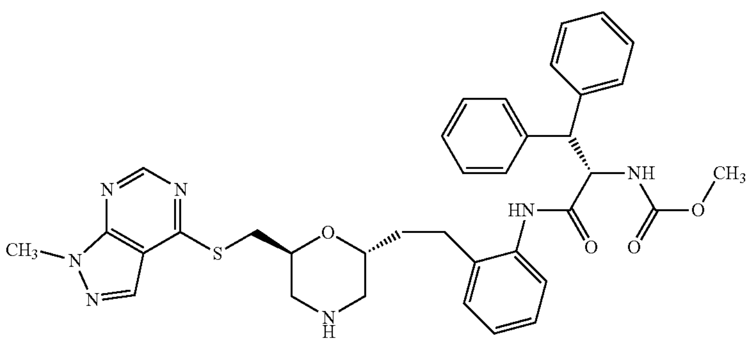 | methyl N-[(1S)-1-benzhydryl-2-[[2-[2-[(2R,6S)-6-[(1-methylpyrazolo[3,4-d]pyrimidin-4-yl)sulfanylmethyl]morpholin-2-yl]ethyl]phenyl]amino]-2-oxo-ethyl]carbamate | M + 1, +ESI = 666.3 |
| 37 | 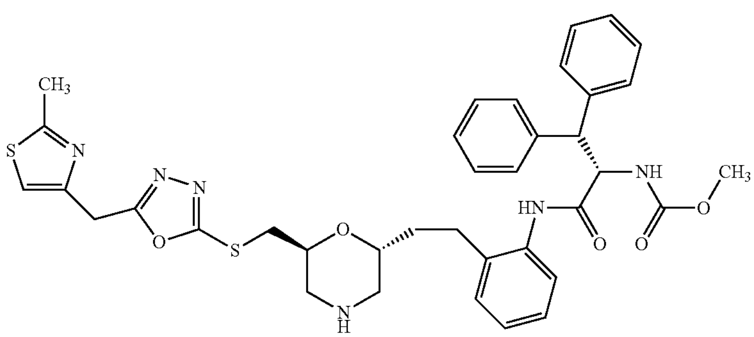 | methyl N-[(1S)-1-benzhydryl-2-[[2-[2-[(2R,6S)-6-[[5-[(2-methylthiazol-4-yl)methyl]-1,3,4-oxadiazol-2-yl]oxymethyl]morpholin-2-yl]ethyl]phenyl]amino]-2-oxo-ethyl]carbamate | M + 1, +ESI = 697.2 |
| 38 | 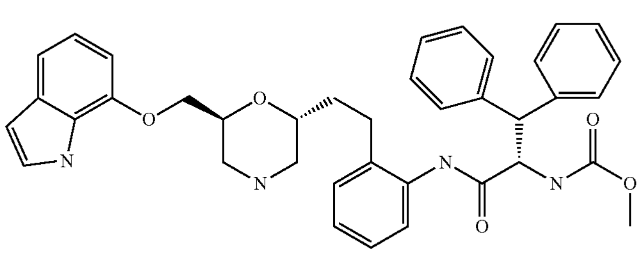 [SMILES: COC(=O)N[C@H](C(=O)Nc1ccccc1CC[C@@H]1CNC[C@@H](COc2cccc3cc[nH]c23)O1)C(c1ccccc1)c1ccccc1] | N-[2-(2-{(2R,6S)-6-[(1H-indol-7-yloxy)methyl]morpholin-2-yl}ethyl)phenyl]-Nα-(methoxycarbonyl)-b-phenyl-L-phenylalaninamide | M + 1, +ESI = 633.3 |

-continued

| Ex. | Structure | IUPAC name | LCMS data |
|---|---|---|---|
| 39 | 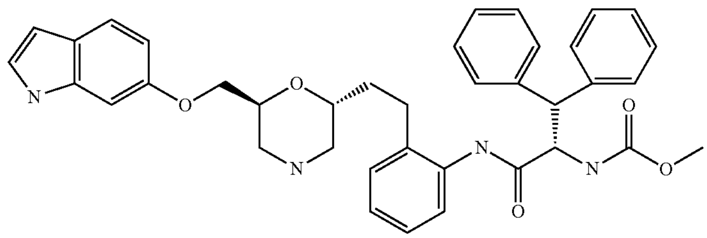 [SMILES: COC(=O)N[C@H](C(=O)Nc1ccccc1CC[C@@H]1CNC[C@@H](COc2ccc3cc[nH]c3c2)O1)C(c1ccccc1)c1ccccc1] | N-[2-(2-{(2R,6S)-6-[(1H-indol-6-yloxy)methyl]morpholin-2-yl}ethyl)phenyl]-Nα-(methoxycarbonyl)-b-phenyl-L-phenylalaninamide | M + 1, +ESI = 633.4 |
| 40 | 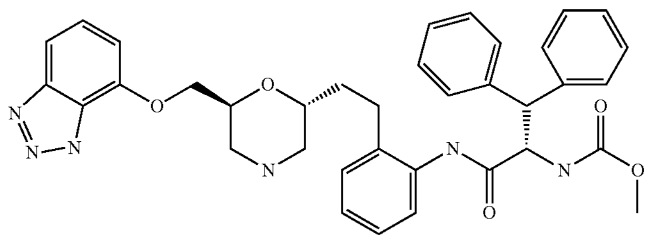 [SMILES: COC(=O)N[C@H](C(=O)Nc1ccccc1CC[C@@H]1CNC[C@@H](COc2cccc3nn[nH]c23)O1)C(c1ccccc1)c1ccccc1] | N-[2-(2-{(2R,6S)-6-[(1H-benzotriazol-7-yloxy)methyl]morpholin-2-yl}ethyl)phenyl]-Nα-(methoxycarbonyl)-b-phenyl-L-phenylalaninamide | M + 1, +ESI = 635.3 |
| 41 | 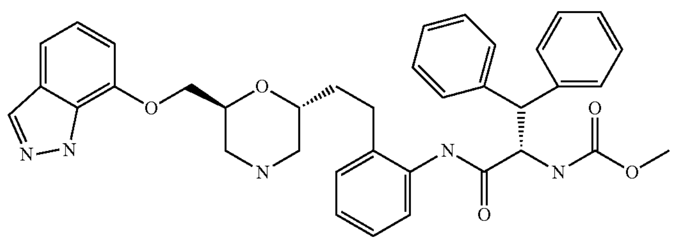 [SMILES: COC(=O)N[C@H](C(=O)Nc1ccccc1CC[C@@H]1CNC[C@@H](COc2cccc3cn[nH]c23)O1)C(c1ccccc1)c1ccccc1] | N-[2-(2-{(2R,6S)-6-[(1H-indazol-7-yloxy)methyl]morpholin-2-yl}ethyl)phenyl]-Nα-(methoxycarbonyl)-b-phenyl-L-phenylalaninamide | M + 1, +ESI = 634.3 |
| 42 | 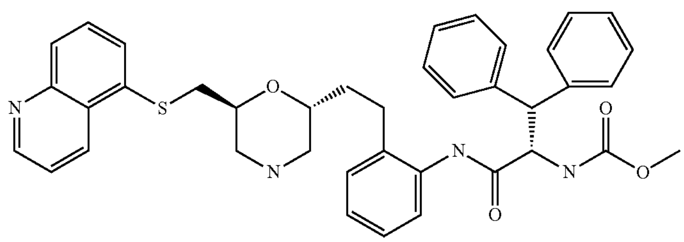 [SMILES: COC(=O)N[C@H](C(=O)Nc1ccccc1CC[C@@H]1CNC[C@@H](CSc2cccc3ncccc23)O1)C(c1ccccc1)c1ccccc1] | methyl [(2S)-1-oxo-3,3-diphenyl-1-{[2-(2-{(2R,6S)-6-[(quinolin-5-ylsulfanyl)methyl]morpholin-2-yl}ethyl)phenyl]amino}propan-2-yl]carbamate | M + 1, +ESI = 661 |
| 43 | 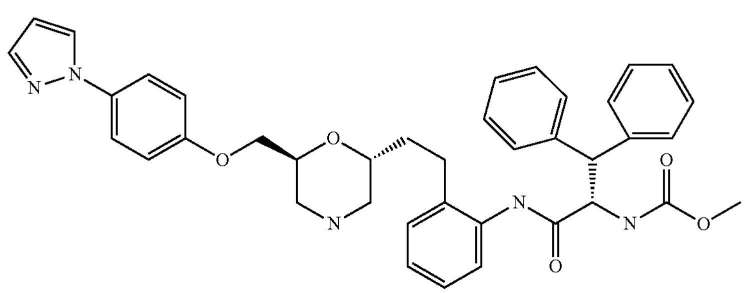 [SMILES: COC(=O)N[C@H](C(=O)Nc1ccccc1CC[C@@H]1CNC[C@@H](COc2ccc(-n3cccn3)cc2)O1)C(c1ccccc1)c1ccccc1] | N-α-(methoxycarbonyl)-β-phenyl-N-(2-{2-[(2R,6S)-6-{[4-(1H-pyrazol-1-yl)phenoxy]methyl}morpholin-2-yl]ethyl}phenyl)-L-phenylalaninamide | M + 1, +ESI = 660 |
| 44 | 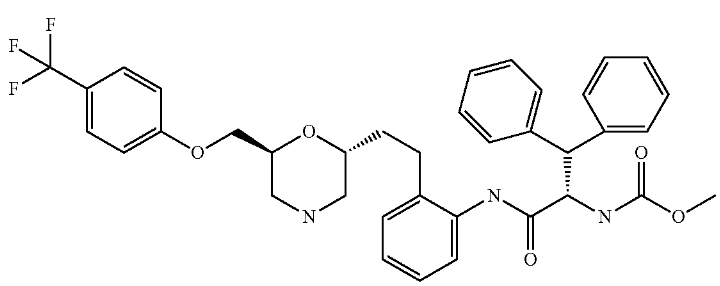 [SMILES: COC(=O)N[C@H](C(=O)Nc1ccccc1CC[C@@H]1CNC[C@@H](COc2ccc(C(F)(F)F)cc2)O1)C(c1ccccc1)c1ccccc1] | N-α-(methoxycarbonyl)-β-phenyl-N-(2-{2-[(2R,6S)-6-{[4-(trifluoromethyl)phenoxy]methyl}morpholin-2-yl]ethyl}phenyl)-L-phenylalaninamide | M + 1, +ESI = 662.2 |

| Ex. | Structure | IUPAC name | LCMS data |
|---|---|---|---|
| 45 | 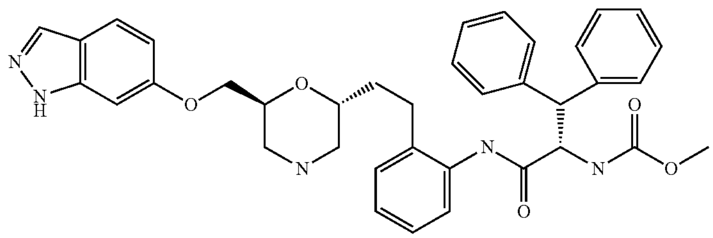 [SMILES: COC(=O)N[C@H](C(=O)Nc1ccccc1CC[C@@H]1CNC[C@@H](COc2ccc3cn[nH]c3c2)O1)C(c1ccccc1)c1ccccc1] | N-[2-(2-{(2R,6S)-6-[(1H-indazol-6-yloxy)methyl]morpholin-2-yl}ethyl)phenyl]-Nα-(methoxycarbonyl)-β-phenyl-L-phenylalaninamide | M + 1, +ESI = 634.3 |
| 46 | 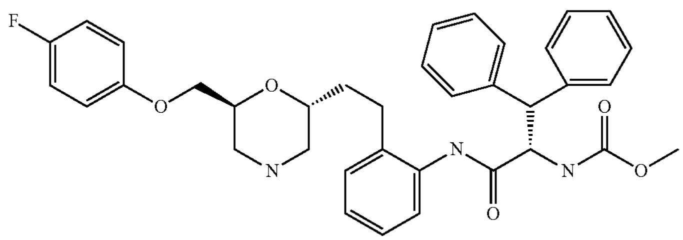 [SMILES: COC(=O)N[C@H](C(=O)Nc1ccccc1CC[C@@H]1CNC[C@@H](COc2ccc(F)cc2)O1)C(c1ccccc1)c1ccccc1] | N-[2-(2-{(2R,6S)-6-[(4-fluorophenoxy)methyl]morpholin-2-yl}ethyl)phenyl]-Nα-(methoxycarbonyl)-β-phenyl-L-phenylalaninamide | M + 1, +ESI = 612.2 |
| 47 | 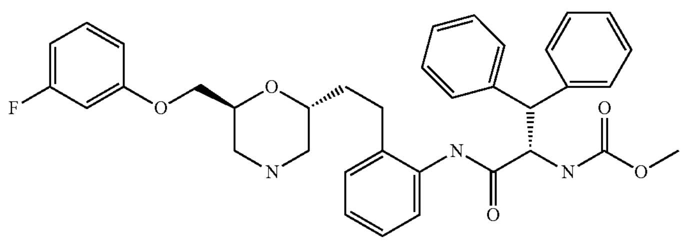 [SMILES: COC(=O)N[C@H](C(=O)Nc1ccccc1CC[C@@H]1CNC[C@@H](COc2cccc(F)c2)O1)C(c1ccccc1)c1ccccc1] | N-[2-(2-{(2R,6S)-6-[(3-fluorophenoxy)methyl]morpholin-2-yl}ethyl)phenyl]-Nα-(methoxycarbonyl)-β-phenyl-L-phenylalaninamide | M + 1, +ESI = 612.2 |
| 48 | 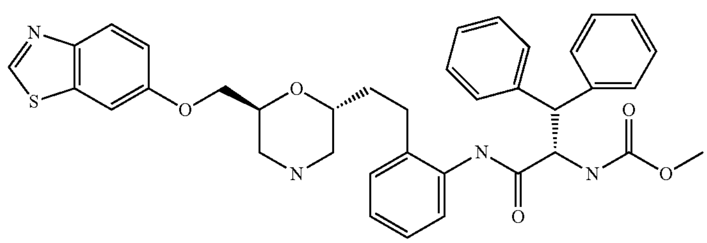 [SMILES: COC(=O)N[C@H](C(=O)Nc1ccccc1CC[C@@H]1CNC[C@@H](COc2ccc3ncsc3c2)O1)C(c1ccccc1)c1ccccc1] | N-[2-(2-{(2R,6S)-6-[(1,3-benzothiazol-6-yloxy)methyl]morpholin-2-yl}ethyl)phenyl]-Nα-(methoxycarbonyl)-β-phenyl-L-phenylalaninamide | M + 1, +ESI = 651.2 |
| 49 | 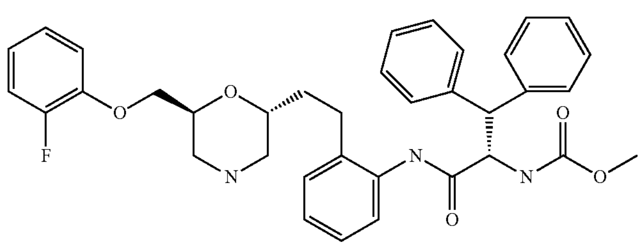 [SMILES: COC(=O)N[C@H](C(=O)Nc1ccccc1CC[C@@H]1CNC[C@@H](COc2ccccc2F)O1)C(c1ccccc1)c1ccccc1] | N-[2-(2-{(2R,6S)-6-[(2-fluorophenoxy)methyl]morpholin-2-yl}ethyl)phenyl]-Nα-(methoxycarbonyl)-β-phenyl-L-phenylalaninamide | M + 1, +ESI = 612.2 |
| 50 | 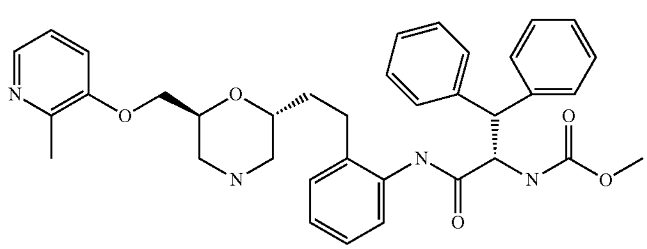 [SMILES: COC(=O)N[C@H](C(=O)Nc1ccccc1CC[C@@H]1CNC[C@@H](COc2cccnc2C)O1)C(c1ccccc1)c1ccccc1] | N-α-(methoxycarbonyl)-N-(2-{2-[(2R,6S)-6-{[(2-methylpyridin-3-yl)oxy]methyl}morpholin-2-yl]ethyl}phenyl)-β-phenyl-L-phenylalaninamide | M + 1, +ESI = 609.2 |

| Ex. | Structure | IUPAC name | LCMS data |
|---|---|---|---|
| 51 | 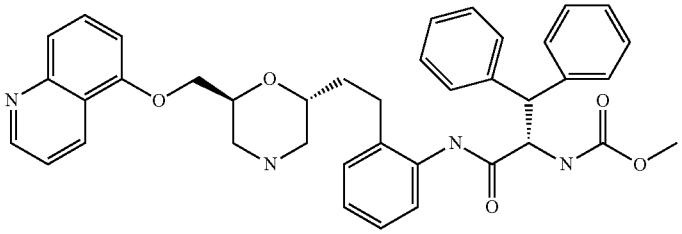 | methyl [(2S)-1-oxo-3,3-diphenyl-1-{[2-[2-{(2R,6S)-6-[(quinolin-5-yloxy)methyl]morpholin-2-yl}ethyl]phenyl]amino}propan-2-yl]carbamate | M + 1, +ESI = 645.2 |
| 52 | 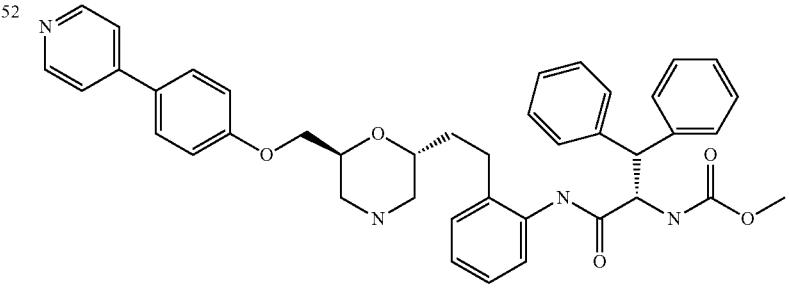 | N-α-(methoxycarbonyl)-β-phenyl-N-(2-{2-[(2R,6S)-6-{[4-(pyridin-4-yl)phenoxy]methyl}morpholin-2-yl]ethyl}phenyl)-L-phenylalaninamide | M + 1, +ESI = 671.3 |
| 53 | 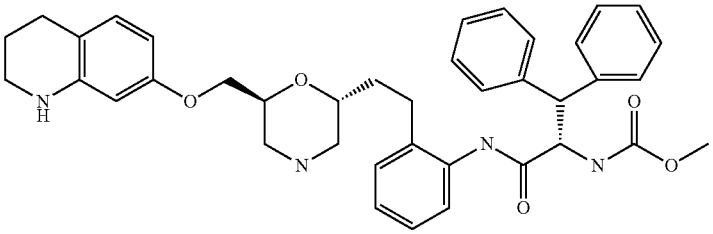 [SMILES: COC(=O)N[C@H](C(=O)Nc1ccccc1CC[C@@H]1CNC[C@@H](COc2ccc3c(c2)NCCC3)O1)C(c1ccccc1)c1ccccc1] | methyl [(2S)-1-oxo-3,3-diphenyl-1-{[2-(2-{(2R,6S)-6-[(1,2,3,4-tetrahydroquinolin-7-yloxy)methyl]morpholin-2-yl}ethyl)phenyl]amino}propan-2-yl]carbamate | M + 1, +ESI = 649.3 |
| 54 | 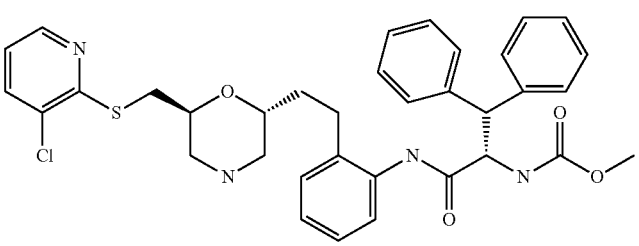 | N-(2-{2-[(2R,6S)-6-{[(3-chloropyridin-2-yl)sulfanyl]methyl}morpholin-2-yl]ethyl}phenyl)-Nα-(methoxycarbonyl)-β-phenyl-L-phenylalaninamide | M + 1, +ESI = 645.1 |
| 55 | 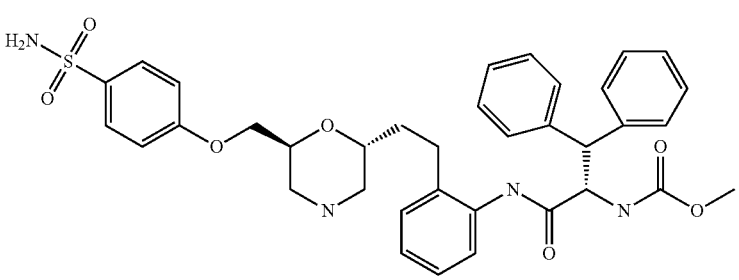 [SMILES: COC(=O)N[C@H](C(=O)Nc1ccccc1CC[C@@H]1CNC[C@@H](COc2ccc(S(N)(=O)=O)cc2)O1)C(c1ccccc1)c1ccccc1] | N-α-(methoxycarbonyl)-β-phenyl-N-[2-(2-{(2R,6S)-6-[(4-sulfamoylphenoxy)methyl]morpholin-2-yl}ethyl)phenyl]-L-phenylalaninamide | M + 1, +ESI = 673.3 |

EXAMPLE 56

Preparation of Compound 56 (methyl N-[(1S)-1-benzhydryl-2-[[2-[2-[(2R,6S)-6-[(4-chlorophenyl)sulfonylmethyl]morpholin-2-yl]ethyl]phenyl]amino]-2-oxo-ethyl]carbamate)

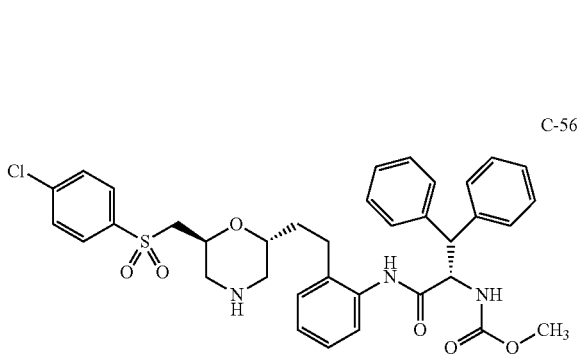 [SMILES: COC(=O)N[C@H](C(=O)Nc1ccccc1CC[C@@H]1CNC[C@@H](CS(=O)(=O)c2ccc(Cl)cc2)O1)C(c1ccccc1)c1ccccc1]

C-56

Step 1: Synthesis of Intermediate Compound Int-56a (tert-butyl (2S,6R)-2-{[(4-chlorophenyl)sulfonyl]methyl}-6-[2-(2-{[N-(methoxycarbonyl)-β-phenyl-L-phenylalanyl]amino}phenyl)ethyl]morpholine-4-carboxylate)

To a solution of compound Int-7L (tert-butyl (2S,6R)-2-{[(4-chlorophenyl)sulfanyl]methyl}-6-[2-(2-{[N-(methoxycarbonyl)-β-phenyl-L-phenylalanyl]amino}phenyl)ethyl]morpholine-4-carboxylate) in a 5:1 mixture of EtOH/H$_2$O (0.03 M) at room temperature was added sodium tungstate dihydrate (1 eq.) and hydrogen peroxide (30%) (5 eq.). The mixture was stirred at room temperature for 16 hours and concentrated. The residue was diluted with EtOAc and saturated aqueous NaHCO$_3$ and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% to 10% MeOH/CH$_2$Cl$_2$ to afford compound Int-56a.

Step 2: Synthesis of Compound 56 (methyl N-[(1S)-1-benzhydryl-2-[[2-[2-[(2R,6S)-6-[(4-chlorophenyl)sulfonylmethyl]morpholin-2-yl]ethyl]phenyl]amino]-2-oxo-ethyl]carbamate)

Compound 56 was prepared from intermediate compound Int-56a by following procedures from step 13 described in Example 7.

M+1, +ESI=676.15

EXAMPLE 57

Preparation of Compound 57 (methyl N-[(1S)-1-benzhydryl-2-[[2-[2-[(2R,6S)-6-[(4-chlorophenyl)sulfinylmethyl]morpholin-2-yl]ethyl]phenyl]amino]-2-oxo-ethyl]carbamate)

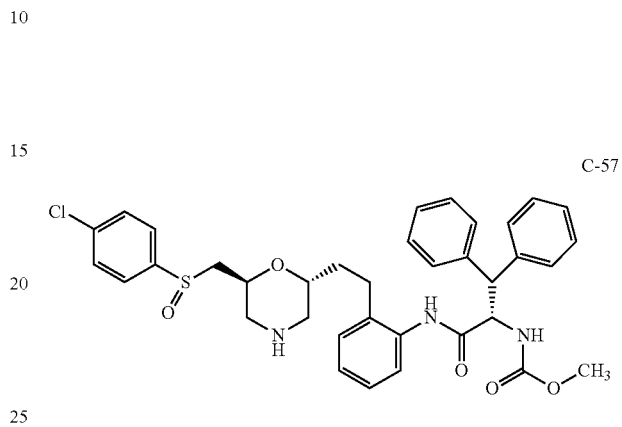

C-57

Step 1—Synthesis of Intermediate Compound Int-57a (tert-butyl (2S,6R)-2-{[(4-chlorophenyl)sulfinyl]methyl}-6-[2-(2-{[N-(methoxycarbonyl)-β-phenyl-L-phenylalanyl]amino}phenyl)ethyl]morpholine-4-carboxylate)

To a solution of Compound Int-7L (tert-butyl (2S,6R)-2-{[(4-chlorophenyl)sulfanyl]methyl}-6-[2-(2-{[N-(methoxycarbonyl)-β-phenyl-L-phenylalanyl]amino}phenyl)ethyl]morpholine-4-carboxylate) in a 5:1 mixture of EtOH/H$_2$O (0.03 M) at room temperature was added sodium tungstate dihydrate (0.2 eq.) and hydrogen peroxide (30%) (2 eq.). The mixture was stirred at room temperature for 1 hour and concentrated. The residue was diluted with EtOAc and saturated aqueous NaHCO$_3$ and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% to 10% MeOH/CH$_2$Cl$_2$ to afford the compound Int-57a.

Step 2-Synthesis of Compound 57 (methyl N-[(1S)-1-benzhydryl-2-[[2-[2-[(2R,6S)-6-[(4-chlorophenyl)sulfinylmethyl]morpholin-2-yl]ethyl]phenyl]amino]-2-oxo-ethyl]carbamate)

Compound 57 was prepared from Int-57a by following procedures from step 13 described in Example 7.

M+1, +ESI=660.25

EXAMPLE 58

Preparation of Compound 58 (methyl N-[(1S)-1-benzhydryl-2-[[2-[[(2S,6S)-6-[(4-chlorophenyl)sulfanylmethyl]morpholin-2-yl]methoxy]phenyl]amino]-2-oxo-ethyl]carbamate)

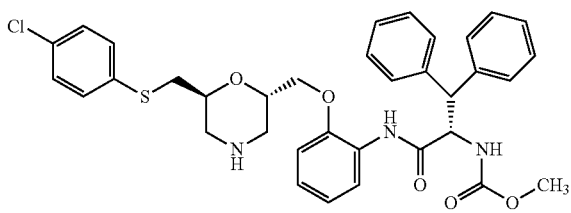

C-58

Step 1-Synthesis of Intermediate Compound Int-58a ((2S,6S)-4-benzyl-2-({[tert-butyl(dimethyl)silyl]oxy}methyl)-6-[(2-nitrophenoxy)methyl]morpholine)

To a solution of [(2S,6S)-4-benzyl-6-({[tert-butyl(dimethyl)silyl]oxy}methyl)morpholin-2-yl]methanol in CH$_2$Cl$_2$ (0.06 M) at room temperature was added 2-nitrophenol (2 eq.) and triphenylphosphine (2 eq.). The mixture was stirred for 5 minutes and DIAD (2 eq.) was added. The mixture was stirred at room temperature for 3 hours and concentrated under reduced pressure. The crude product was purified by automated SiO$_2$ flash chromatography system using solvent gradient of 0% EtOAc/Hex to 60% EtOAc/Hex to afford compound Int-58a.

Step 2: Synthesis of Compound 58 (methyl N-[((1S)-1-benzhydryl-2-[[2-[[(2S,6S)-6-[(4-chlorophmethenyl)sulfanylmethyl]morpholin-2-yl]methxy]phenyol]amino]-2-oxo-ethy]carbamate)

Compound was prepared from intermediate compound Int-58a by following procedures from steps 8 to 13 described in Example 7.
M+1, +ESI=646.2

EXAMPLE 59

Preparation of Compound 59 (methyl N-[(1S)-1-benzhydryl-2-[[2-[2-[(2R,6S)-6-[(4-chlorophenyl)methoxymethyl]morpholin-2-yl]ethyl]phenyl]amino]-2-oxo-ethyl]carbamate)

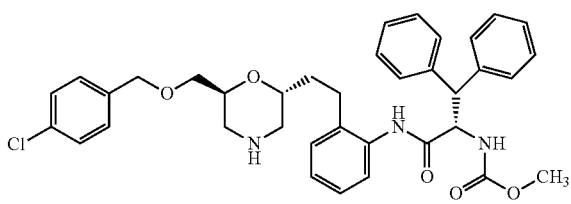

C-59

Step 1-Synthesis of Intermediate Compound Int-59a (tert-butyl (2S,6R)-2-{[(4-chlorobenzyl)oxy]methyl}-6-[2-(2-{[N-(methoxycarbonyl)-β-phenyl-L-phenylalanyl]amino}phenyl)ethyl]morpholine-4-carboxylate)

To a solution of Intermediate compound Int-7k (1 eq.) in acetonitrile (0.1 M) was added silver oxide (5 eq) and 4-chlorobenzylbromide (2 eq). The reaction mixture was stirred at 50° C. for 24 hours, filtered on celite and concentrated. The crude product was purified by automated SiO$_2$ flash chromatography system using solvent gradient of 10% EtOAc/Hex to 80% EtOAc/Hex to afford the compound Int-59a.

Step 2-Synthesis of Compound 59 (methyl N-[(1S)-1-benzhydryl-2-[[2-[2-[(2R,6S)-6-[(4-chlorophenyl)methoxymethyl]morpholin-2-yl]ethyl]phenyl]amino]-2-oxo-ethyl]carbamate)

Compound 59 was prepared from Intermediate Compound Int-59a by following procedure from step 13 described in Example 7.
M+1, +ESI=642.3

EXAMPLE 60

Preparation of Compound 60 (N-[2-(2-{(2R,6R)-6-[(E)-2-(4-chlorophenyl)ethenyl]morpholin-2-yl}ethyl)phenyl]-Nα-(methoxycarbonyl)-β-phenyl-L-phenylalaniamide)

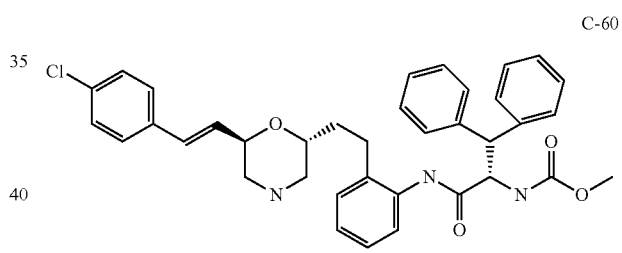

C-60

Step 1-Synthesis of Intermediate Compound Int-60a (tert-butyl (2S,6R)-2-formyl-6-[2-(2-{[N-(methoxycarbonyl)-β-phenyl-L-phenylalanyl]amino}phenyl)ethyl]morpholine-4-carboxylate)

To a solution of compound Int-7k (1.0 equiv.), 4-methylmorpholine 4-oxide (1.5 equiv.) and molecular sieves 4 Å (500 mg/mmol) in dichloromethane (0.1M) at −5° C. was added N,N,N-tripropylpropan-1-aminium oxido(trioxo)ruthenium (0.1 equiv.). The mixture was stirred for 1 hour, and upon completion the reaction mixture was filtered over a short silica gel pad and eluted with dichloromethane to afford the title compound (Int-60a). The crude product was used directly in the next step.

Step 2-Synthesis of Intermediate Compound Int-60b (tert-butyl (2R,6R)-2-[(E)-2-(4-chlorophenyl)ethenyl]-6-[2-(2-{[N-(methoxycarbonyl)-β-phenyl-L-phenylalanyl]amino}phenyl)ethyl]morpholine-4-carboxylate)

To (4-chlorobenzyl)(triphenyl)phosphonium chloride (5.0 equiv.) in tetrahydrofuran (0.05M) at room temperature was added potassium tert-butoxide (5.0 equiv.). The reaction mixture was stirred for one hour at this temperature and then compound Int-60a (1.0 equiv.) was added as a tetrahydrofuran solution (0.05M). The resulting solution was stirred at room temperature for two hours. Upon completion, a saturated aqueous solution of ammonium chloride was added, along with ethyl acetate. The aqueous layer was extracted with ethyl acetate three times. The organic layers were combined, dried over sodium sulfate, filtered and concentrated in vacuo. The residue was purified by an automated SiO₂ flash chromatography system using a solvent gradient of 0% to 60% ethyl acetate and hexanes.

Step 3-Synthesis of Compound 60 (N-[2-(2-{(2R,6R)-6-[(E)-2-(4-chlorophenyl)ethenyl]morpholin-2-yl}ethyl)phenyl]-Nα-(methoxycarbonyl)-β-phenyl-L-phenylalaninamide)

Compound 60 was prepared from compound Int-60b by following procedure from step 13 described in Example 7.
M+1 (+ESI)=624.2

EXAMPLE 61

Preparation of Compound 61 (N-α-(methoxycarbonyl)-N-(2-{2-[(2R,6R)-6-{(E)-2-[4-(methylsulfonyl)phenyl]ethenyl}morpholin-2-yl]ethyl}phenyl)-β-phenyl-L-phenylalaninamide)

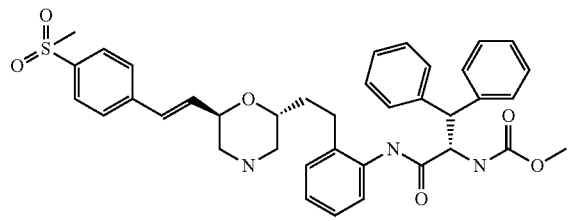

C-61

Compound 61 was prepared using same procedure as for Example 60 and using [4-(methylsulfonyl)benzyl](triphenyl)phosphonium chloride (5.0 equiv.) as Wittig reagent precursor.
M+1 (+ESI)=668.2

EXAMPLE 62

Preparation of Compound 62 (N-[2-(2-{(2R,6R)-6-[2-(4-chlorophenyl)ethyl]morpholin-2-yl}ethyl)phenyl]-Nα-(methoxycarbonyl)-β-phenyl-L-phenylalaninamide)

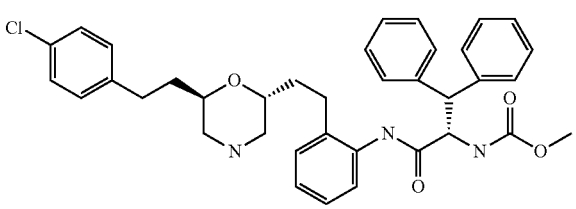

C-62

Step 1-Synthesis of Intermediate Compound Int-62a (tert-butyl (2R,6R)-2-[2-(4-chlorophenyl)ethyl]-6-[2-(2-{[N-(methoxycarbonyl)-β-phenyl-L-phenylalanyl]amino}phenyl)ethyl]morpholine-4-carboxylate)

Compound Int-60b (1.0 equiv.) was dissolved in degassed methanol (0.015M) and palladium on charcoal 10% Wt (4.0 equiv.) was added. The reaction mixture was stirred under 1 atm of hydrogen gas at room temperature for 8 hours. Upon completion, the reaction mixture was degassed with nitrogen, filtered over celite and rinsed with dichloromethane and methanol. The filtrate was concentrated in vacuo. The residue obtained was purified by an automated SiO₂ flash chromatography system using a solvent gradient of 10% to 70% ethyl acetate and hexanes to afford the desired compound (Int-62a).

Step 2-Synthesis of Compound 62 (N-[2-(2-{(2R,6R)-6-[2-(4-chlorophenyl)ethyl]morpholin-2-yl}ethyl)phenyl]-Nα-(methoxycarbonyl)-β-phenyl-L-phenylalaninamide)

Compound 62 was prepared from intermediate compound Int-62a by following the same procedure described in Step 13 Example 7 to afford the title compound.
M+1 (+ESI)=626.2

EXAMPLE 63

Preparation of Compound 63 (N-[2-(2-{(2R,6R)-6-[2-(4-cyanophenyl)ethyl]morpholin-2-yl}ethyl)phenyl]-N-α-(methoxycarbonyl)-β-phenyl-L-phenylalaninamide)

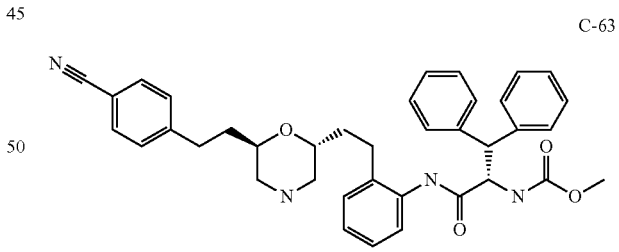

C-63

Step 1-Synthesis of Compound 63 (N-[2-(2-{(2R,6R)-6-[2-(4-cyanophenyl)ethyl]morpholin-2-yl}ethyl)phenyl]-N-α-(methoxycarbonyl)-β-phenyl-L-phenylalaninamide)

Compound 63 was prepared from compound Int-60a using the same procedure as described in Examples 60 and 62 using (4-cyanobenzyl)(triphenyl)phosphonium chloride (5.0 equiv.) as Wittig reagent precursor.
M+1 (+ESI)=617.3

EXAMPLE 64

Preparation of Compound 64 (N-[2-(2-{(2R,6R)-6-[2-(4-cyanophenoxy)ethyl]morpholin-2-yl}ethyl)phenyl]-Nα-(methoxycarbonyl)-β-phenyl-L-phenylalaninamide)

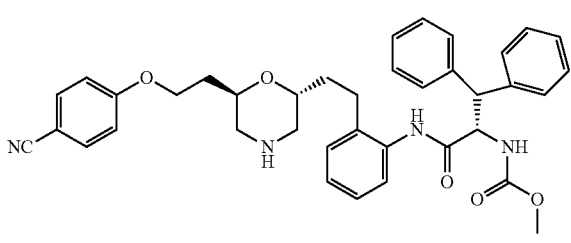

C-64

Step 1-Synthesis of Intermediate Compound Int-64a ((2S,6R)-4-(tert-butoxycarbonyl)-6-[2-(2-{[N-(methoxycarbonyl)-b-phenyl-L-phenylalanyl]amino}phenyl)ethyl]morpholine-2-carboxylic acid)

To a solution of intermediate compound Int-7k (1 eq) in DMF (0.1M) at room temperature was added PDC (10 eq) and 4A molecular sieve (1 g/mmol of substrate). The reaction mixture was stirred at room temperature for 16 hours. The reaction mixture was then filtered on a celite and the celite pad was washed with EtOAc and water. The filtrate was extracted with EtOAc. The combined organic layers were washed with 1N aqueous HCl and brine, dried over Na$_2$SO$_4$, filtered and concentrated. The crude product (Int-64a) was used as such for next step.

Step 2-Synthesis of Intermediate Compound Int-64b (tert-butyl (2S,6R)-2-(diazoacetyl)-6-[2-(2-{[N-(methoxycarbonyl)-β-phenyl-L-phenylalanyl]amino}phenyl)ethyl]morpholine-4-carboxylate)

To a stirred solution of intermediate compound Int-64a (1 eq) in THF (0.1M) at 0° C. was added triethylamine (1.1 eq) and isobutyl chloroformate (1.05). The reaction mixture was stirred at 0° C. for 30 minutes. The reaction mixture was then allowed to stand at room temperature for 30 minutes, and filtered through celite. To the filtrate was added a freshly prepared diazomethane over 30 minutes. The mixture was stirred at room temperature for 90 minutes. The solvent was evaporated and the residue obtained was purified by an automated SiO$_2$ flash chromatography system using a solvent gradient of 0% to 80% ethyl acetate and hexanes to afford compound Int-64b.

Step 3-Synthesis of Intermediate Compound Int-64c (tert-butyl (2R,6R)-2-[2-(2-{[N-(methoxycarbonyl)-β-phenyl-L-phenylalanyl]amino}phenyl)ethyl]-6-(2-methoxy-2-oxoethyl)morpholine-4-carboxylate)

To a stirred solution of intermediate compound Int-64b (1 eq) in methanol (0.1M) at 0° C. was added a solution of silver benzoate (0.3 eq) in triethylamine (11 eq). The reaction mixture was stirred at room temperature for 90 minutes. The solvent was evaporated and the residue was purified by an automated SiO$_2$ flash chromatography system using a solvent gradient of 0% to 80% ethyl acetate and hexanes to afford compound Int-64c.

Step 4-Synthesis of Intermediate Compound Int-64d ({(2R,6R)-4-(tert-butoxycarbonyl)-6-[2-(2-{[N-(methoxycarbonyl)-3-phenyl-L-phenylalanyl]amino}phenyl)ethyl]morpholin-2-yl}acetic acid)

To a stirred solution of intermediate compound Int-64c (1 eq) in a 1:2 mixture of MeOH and THF (0.1M) at 0° C. was added 1N LiOH (1.5 eq). The reaction mixture was stirred at room temperature for 3 hours. The reaction mixture was poured into potassium phosphate buffer pH=4, and extracted with ethyl acetate. The combined organic layers were washed with brine, dried with MgSO$_4$ and concentrated under vacuum to afford the compound Int-64d.

Step 5-Synthesis of Intermediate Compound Int-64e (tert-butyl (2R,6R)-2-(2-hydroxyethyl)-6-[2-(2-{[N-(methoxycarbonyl)-3-phenyl-L-phenylalanyl]amino}phenyl)ethyl]morpholine-4-carboxylate)

To a stirred solution of intermediate compound Int-64d (1 eq) in DME (0.1 M) at −15° C. was added N-methylmorpholine (1.1 eq) and isobutyl chloroformate (1.1 eq). Internal temperature must be below −10° C. The reaction mixture was stirred at −15° C. for 30 minutes. The solids were quickly filtered and washed with DME. To the filtrate at −50° C. was carefully added sodium borohydride (1.3 eq) as a solution in water (1M) and the internal temperature must be below −15° C. After addition of hydride, acetone was added followed by water-ammonium chloride. The reaction mixture was extracted with EtOAc. The combined organic layers were washed with brine, dried with MgSO$_4$ and concentrated under vacuum. The residue was purified by an automated SiO$_2$ flash chromatography system using a solvent gradient of 0% to 100% ethyl acetate and hexanes to afford the compound Int-64e.

Step 6-Synthesis of Compound 64 (N-[2-(2-{(2R,6R)-6-[2-(4-cyanophenoxy)ethyl]morpholin-2-yl}ethyl)phenyl]-Nα-(methoxycarbonyl)-β-phenyl-L-phenylalaninamide)

Compound 64 was prepared from intermediate compound Int-64e according to the same procedure described in Step 12 and 13 of Example 7 and using the appropriate reagents to afford the title compound.
M+1 (+ESI)=633

EXAMPLE 65

Preparation of Compound 65 (N-[2-(2-{(2R,6S)-6-[2-(4-bromophenyl)-1,1-difluoroethyl]morpholin-2-yl}ethyl)phenyl]-Nα-(methoxycarbonyl)-β-phenyl-L-phenylalaninamide)

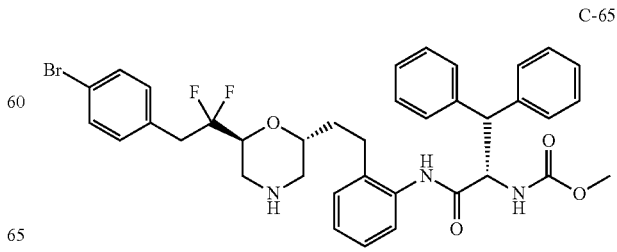

C-65

Step 1:-Synthesis of Intermediate Compound Int-65a (tert-butyl (2R,6S)-2-(2-{2-[(tert-butoxycarbonyl)amino]phenyl}ethyl)-6-({[tert-butyl(dimethyl)silyl]oxy}methyl)morpholine-4-carboxylate)

Intermediate compound Int-65a was obtained as a side product from mono-BOC protection of diamine 2-{2-[(2R,6S)-6-({[tert-butyl(dimethyl)silyl]oxy}methyl)morpholin-2-yl]ethyl}aniline following the procedure described in step 9 of Example 7 when 3 equivalents of Di-tert-butyl dicarbonate was used.

Step 2-Synthesis of Intermediate Compound Int-65b (tert-butyl (2R,6S)-2-(2-{2-[(tert-butoxycarbonyl)amino]phenyl}ethyl)-6-(hydroxymethyl)morpholine-4-carboxylate)

Intermediate compound Int-65b was prepared from intermediate compound Int-65a following the procedure described in step 11 Example 7.

Step 3-Synthesis of Intermediate Compound Int-65c ((2S,6R)-4-(tert-butoxycarbonyl)-6-(2-{2-[(tert-butoxycarbonyl)amino]phenyl}ethyl)morpholine-2-carboxylic acid)

A solution of intermediate compound Int-65b in dry DMF (0.14 M) was treated with solid 4A molecular sieves (245 weight %) and the suspension stirred under $N_2$ for 20 minutes, then solid PDC (9.8 eq.) was charged and the final dark mixture further stirred at room temperature for 3.5 hours, filtered through a pad of Celite, the filtrate diluted with EtOAc, washed with 5% $KHSO_4$, dried over $Na_2SO_4$, filtered and concentrated. The residue was purified by automated silicagel flash chromatography system eluted with 1% to 10% MeOH as a gradient, to afford compound Int-65c as grey solid.

Step 4-Synthesis of Intermediate Compound Int-65d (tert-butyl (2R,6S)-2-(2-{2-[(tert-butoxycarbonyl)amino]phenyl}ethyl)-6-[methoxy(methyl)carbamoyl]morpholine-4-carboxylate)

A mixture of intermediate compound Int-65c (1 eq.) and HATU (1.4 eq.) was dissolved in dry Py (0.16 M), stirred at room temperature under $N_2$ atmosphere for 12 minutes and then treated with solid N,O-dimethylhydroxylamine hydrochloride (4.1 eq.). The resulting amber solution was further stirred at room temperature under $N_2$ for 14 hours, diluted with EtOAc, washed with 5% $KHSO_4$ in water and then sat $NaHCO_3$, dried over $Na_2SO_4$, filtered and concentrated. The residue was purified by automated silicagel flash chromatography system, eluted with 0.3% to 10% MeOH as a gradient, to afford compound Int-65d as a beige solid.

Step 5-Synthesis of Intermediate Compound Int-65e (tert-butyl (2S,6R)-2-[(4-bromophenyl)acetyl]-6-(2-{2-[(tert-butoxycarbonyl)amino]phenyl}ethyl)morpholine-4-carboxylate)

A solution of intermediate compound Int-65d (1 eq.) in dry THF (0.033 M) stirred under $N_2$ atmosphere at external temperature of 0° C., was treated with a 0.25 M solution of 4-bromobenzylmagnesium bromide in ether (7.6 eq.), added dropwise over 7 minutes. The final mixture was then stirred at the same temperature for 5.5 hours. Quenching made by addition of saturated $NaHCO_3$, the mixture was then diluted ($CH_2Cl_2$), washed with sat $NaHCO_3$ plus brine, dried over $MgSO_4$, filtered and concentrated. The residue was purified by automated silicagel flash chromatography system eluted with 15% to 70% EtOAc in hexanes as a gradient, to afford compound Int-65e as light yellow foam.

Step 6-Synthesis of Intermediate Compound Int-65f (tert-butyl (2S,6R)-2-[2-(4-bromophenyl)-1,1-difluoroethyl]-6-(2-{2-[(tert-butoxycarbonyl)amino]phenyl}ethyl)morpholine-4-carboxylate)

A solution of intermediate compound Int-65e (1 eq) in dry DCM (0.082M) stirred at room temperature under $N_2$ was treated with neat morpholine-DAST (22 eq.) and the mixture stirred at the same temperature overnight. The mixture was diluted with $CH_2Cl_2$, quenched with dropwise addition of saturated $NaHCO_3$, poured on $CH_2Cl_2$ and washed with saturated NaHCO3, dried over MgSO4, filtered and concentrated. The residue was purified by automated silicagel flash chromatography system eluted with 10% to 60% EtOAc in hexanes as a gradient, to afford compound Int-65f as a white foam.

Step 7-Synthesis of Intermediate Compound Int-65g (2-(2-{(2R,6S)-6-[2-(4-bromophenyl)-1,1-difluoroethyl]morpholin-2-yl}ethyl)aniline)

Compound Int-65f was dissolved in a 2:1 solution of $CH_2Cl_2$:TFA (0.031 M), pre-prepared at 0° C. and added at the same temperature. The mixture was stirred for 2.5 hours at external temperature of 0° C., concentrated, diluted with DCM and washed with 5% KOH in brine, dried over $Na_2SO_4$, filtered and concentrated. The residue was purified by automated silicagel flash chromatography system eluted with 5% to 15% MeOH in $CH_2Cl_2$ as a gradient, to afford compound Int-65g as colorless oil.

Step 8-Synthesis of Intermediate Compound Int-65h (tert-butyl (2R,6S)-2-[2-(2-aminophenyl)ethyl]-6-[2-(4-bromophenyl)-1,1-difluoroethyl]morpholine-4-carboxylate)

A solution of compound Int-65g (1 eq.) in THF (0.023 M) was mixed with a solution of $NaHCO_3$ (4.9 eq.) in water (0.2 M) and the final mixture was treated with a solution of $BOC_2O$ (1.12 eq.) in THF (0.16 M). The suspension was stirred at room temperature for 2 hours, diluted with DCM, washed with brine, dried over $Na_2SO_4$, filtered and concentrated to render compound Int-65h, which was submitted to the next reaction without further purification.

Step 9-Synthesis of Intermediate Compound Int-65i (tert-butyl (2S,6R)-2-[2-(4-bromophenyl)-1,1-difluoroethyl]-6-[2-(2-{[N-(methoxy carbonyl)-β-phenyl-L-phenylalanyl]amino}phenyl)ethyl]morpholine-4-carboxylate)

Intermediate compound Int-65i was prepared from intermediate compound Int-65h following the procedure described in step 10 of Example 7.

Step 10-Synthesis of Compound 65 (N-[2-(2-{(2R,6S)-6-[2-(4-bromophenyl)-1,1-difluoroethyl]morpholin-2-yl}ethyl)phenyl]-Nα-(methoxycarbonyl)-β-phenyl-L-phenylalaninamide)

Compound 65 was prepared from intermediate compound Int-65i following the procedure described in step 13 of Example 7.

M+1 (+ESI)=708.1

EXAMPLE 66

Preparation of Compound 66 ((βS)—N-(2-{2-[(2R,6S)-6-{[(4-chlorophenyl)sulfanyl]methyl}morpholin-2-yl]ethyl}phenyl)-Nα-(methoxycarbonyl)-β-pyridin-3-yl-L-phenylalaninamide)

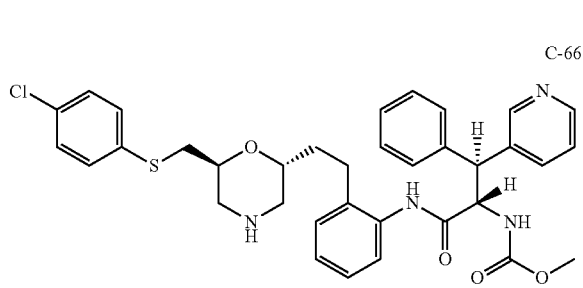 [SMILES: COC(=O)N[C@H](C(=O)Nc1ccccc1CC[C@@H]1CNC[C@@H](CSc2ccc(Cl)cc2)O1)[C@@H](c1ccccc1)c1cccnc1]

Step 1-Preparation of a mixture of methyl (2Z)-3-bromo-2-[(methoxycarbonyl)amino]-3-phenylprop-2-enoate and methyl (2E)-3-bromo-2-[(methoxycarbonyl)amino]-3-phenylprop-2-enoate Methyl (2Z)-2-[(methoxycarbonyl)amino]-3-phenylprop-2-enoate (1 eq) was dissolved in $CH_2Cl_2$ (0.3M). NBS (1.2 eq) was added in one portion and the mixture was stirred for 4 hours. TEA was added (1.1 eq) and the mixture was stirred overnight. Water was added to the mixture and the phases were separated using a phase separator cartridge from IST Biotage (Biotage AB, Uppsala, Sweden) and the organic layer was evaporated to dryness. A 3:1 mixture of E/Z isomers was obtained (favoring the Z isomer, determined by NOE). The reaction mixture was purified by automated $SiO_2$ flash chromatography system using solvent gradient of 0% to 60% EtOAc/Hex to afford a mixture of methyl (2Z)-3-bromo-2-[(methoxycarbonyl)amino]-3-phenylprop-2-enoate and methyl (2E)-3-bromo-2-[(methoxycarbonyl)amino]-3-phenylprop-2-enoate.

Step 2-Synthesis of Intermediate Compound Int-66a (methyl (2E)-2-[(methoxycarbonyl)amino]-3-phenyl-3-(pyridin-3-yl)prop-2-enoate)

A mixture of methyl (2Z)-3-bromo-2-[(methoxycarbonyl)amino]-3-phenylprop-2-enoate and methyl (2E)-3-bromo-2-[(methoxycarbonyl)amino]-3-phenylprop-2-enoate (1 eq), 3-pyridylboronic acid (1.5 eq), Pd2(dba)3 (0.04 eq) and tricyclohexylphosphonium tetrafluoroborate (0.1 eq) was weighed in a Schlenck tube. The tube was degassed under vacuum and filled with nitrogen 3 times. Dioxane (0.2M) and 1M aqueous $K_3PO_4$ (1.5 eq) were added and the mixture was heated to 100° C. for 4 hours. After the mixture was cooled to room temperature, water and $CH_2Cl_2$ were added and the resulting phases were separated on a phase separator cartridge from IST Biotage. The organic layer was concentrated to dryness and the mixture was purified by automated $SiO_2$ flash chromatography system using solvent gradient of 0% to 60% EtOAc/Hex. The first eluting isomer on silica gel was methyl (2E)-2-[(methoxycarbonyl)amino]-3-phenyl-3-(pyridin-3-yl)prop-2-enoate (Int-66a).

Step 3-Synthesis of Intermediate Compound Int-66b (Methyl (βS)—N-(methoxycarbonyl)-β-pyridin-3-yl-L-phenylalaninate)

In a glove box, bis(norbornadiene)rhodium(I) tetrafluoroborate (0.1 eq) and (R)-(−)-1-[(S)-(2-di-tert-butylphosphino)ferrocenyl]ethyldi-(4-trifluoromethylphenyl)phosphine (0.09 eq) were dissolved in $CH_2Cl_2$ (1 M) and stirred for 30 minutes. To the mixture was added (1 eq) intermediate compound Int-66a in MeOH (0.2 M) containing tetrafluoroboric acid-diethyl ether complex (1.2 eq) and put in a pressure bomb. The bomb was filled up with 400 psi of hydrogen and stirred over the weekend. Aqueous $Na_2CO_3$ was added and the phases were separated on a phase separator cartridge from IST Biotage. The organic layer was concentrated to dryness the crude mixture was purified by automated $SiO_2$ flash chromatography system using solvent gradient of 0% to 10% MeOH/$CH_2Cl_2$ to afford the desired product (Int-66b). The enantiomeric excess was determined by Chiral HPLC (Chiralpak OJ, 1.0 mL/min, Hexane:Ethanol: TEA (70:30:0.25), Tr (major) 6.47 min, Tr(minor) 5.22 min (94% e.e.).

Step 4-Synthesis of Intermediate Compound Int-66c ((βS)—N-(methoxycarbonyl)-β-pyridin-3-yl-L-phenylalanine)

Intermediate compound Int-66b (1 eq) was dissolved in a 2:1 mixture of THF and MeOH. 1M LiOH (3 eq) was added and the mixture was stirred overnight. The mixture was neutralized with 1N HCl and the solvents were removed. Purification was done by reversed phase HPLC on C18.

Step 5-Synthesis of Compound 66 ((βS)—N-(2-{2-[(2R,6S)-6-{[(4-chlorophenyl)sulfanyl]methyl}morpholin-2-yl]ethyl}phenyl)-Nα-(methoxycarbonyl)-β-pyridin-3-yl-L-phenylalaninamide)

Compound 66 was prepared from intermediate compound Int-7i and intermediate compound Int-66c using the same procedure as described in steps 10-13 of Example 7 using the appropriate reagents.

M+1 (+ESI)=646.2

Examples 67 to 70 were prepared by following the same procedures as described in Example 66 with the use of the appropriate reagents.

| Ex. | Structure | IUPAC name | LCMS data |
|---|---|---|---|
| 67 | 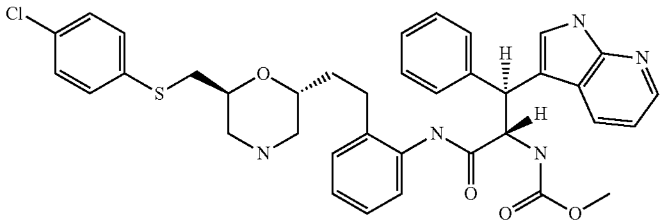 [SMILES: COC(=O)N[C@H](C(=O)Nc1ccccc1CC[C@@H]1CNC[C@@H](CSc2ccc(Cl)cc2)O1)[C@@H](c1ccccc1)c1c[nH]c2ncccc12] | (βS)-N-(2-{2-[(2R,6S)-6-{[(4-chlorophenyl)sulfanyl]methyl}morpholin-2-yl]ethyl}phenyl)-Nα-(methoxycarbonyl)-β-1H-pyrrolo[2,3-b]pyridin-3-yl-L-phenylalaninamide | M + 1, +ESI = 685 |
| 68 | 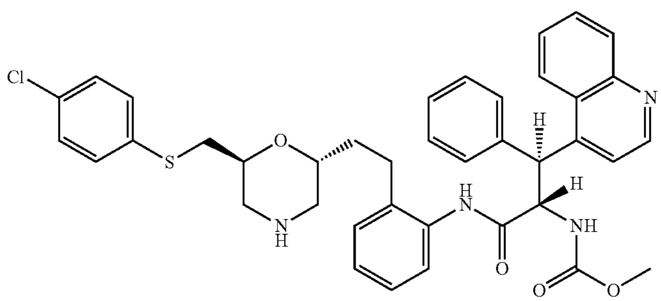 [SMILES: COC(=O)N[C@H](C(=O)Nc1ccccc1CC[C@@H]1CNC[C@@H](CSc2ccc(Cl)cc2)O1)[C@@H](c1ccccc1)c1ccnc2ccccc12] | methyl[(2S,3S)-1-[(2-{2-[(2R,6S)-6-{[(4-chlorophenyl)sulfanyl]methyl}morpholin-2-yl]ethyl}phenyl)amino]-1-oxo-3-phenyl-3-(quinolin-4-yl)propan-2-yl]carbamate | M + 1, +ESI = 696.1 |
| 69 | 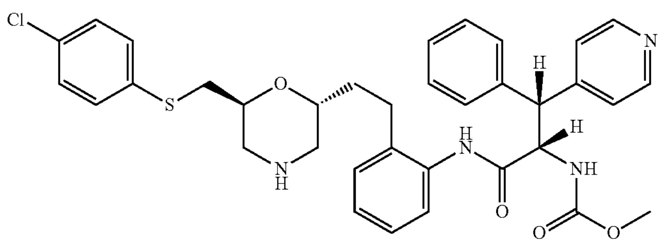 [SMILES: COC(=O)N[C@H](C(=O)Nc1ccccc1CC[C@@H]1CNC[C@@H](CSc2ccc(Cl)cc2)O1)[C@H](c1ccccc1)c1ccncc1] | (βR)-N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-L-phenylalaninamide | M + 1, +ESI = 645.1 |
| | | (βS)-N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-D-phenylalaninamide | |
| 70 | 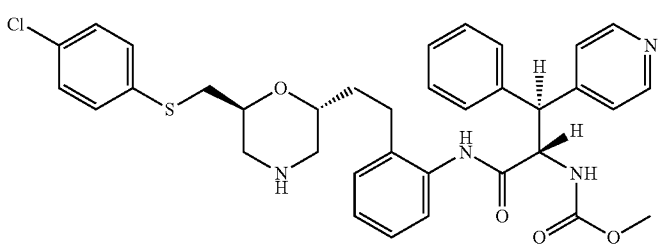 [SMILES: COC(=O)N[C@H](C(=O)Nc1ccccc1CC[C@@H]1CNC[C@@H](CSc2ccc(Cl)cc2)O1)[C@@H](c1ccccc1)c1ccncc1] | (βR)-N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-D-phenylalaninamide | M + 1, +ESI = 645.1 |
| | | (βS)-N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-L-phenylalaninamide | |

EXAMPLES 71 to 77

The following examples (71 to 77) were synthesized from (2S,6S)-4-benzyl-6-({[tert-butyl(dimethyl)silyl]oxy}methyl)morpholine-2-carbaldehyde according to the procedures described in steps 7 to 13 in Example 7 and by using the appropriate wittig reagent and the appropriate phenol or thiophenol.

| Ex. | Structure | IUPAC name | LCMS data |
|---|---|---|---|
| 71 | 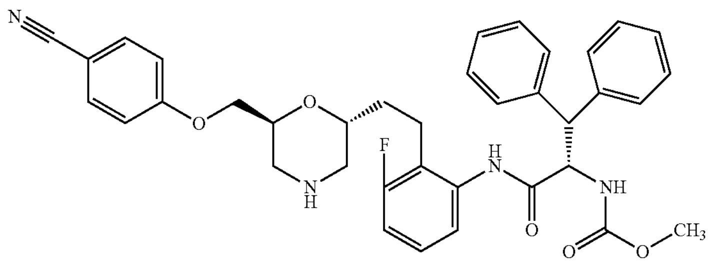 [SMILES: COC(=O)N[C@H](C(=O)Nc1cccc(F)c1CC[C@@H]1CNC[C@@H](COc2ccc(C#N)cc2)O1)C(c1ccccc1)c1ccccc1] | N-[2-(2-{(2R,6S)-6-[(4-cyanophenoxy)methyl]morpholin-2-yl}ethyl)-3-fluorophenyl]-Nα-(methoxycarbonyl)-β-phenyl-L-phenylalaninamide | M + 1, +ESI = 637 |
| 72 | 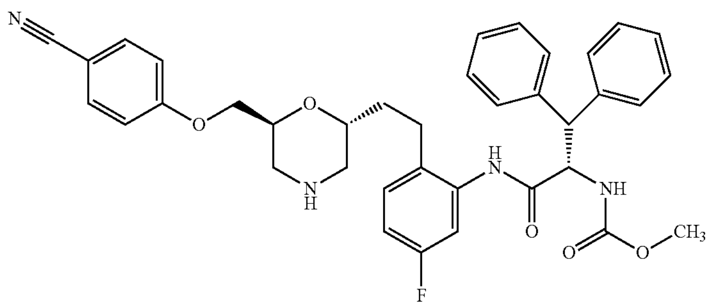 [SMILES: COC(=O)N[C@H](C(=O)Nc1cc(F)ccc1CC[C@@H]1CNC[C@@H](COc2ccc(C#N)cc2)O1)C(c1ccccc1)c1ccccc1] | N-[2-(2-{(2R,6S)-6-[(4-cyanophenoxy)methyl]morpholin-2-yl}ethyl)-5-fluorophenyl]-Nα-(methoxycarbonyl)-β-phenyl-L-phenylalaninamide | M + 1, +ESI = 637 |
| 73 | 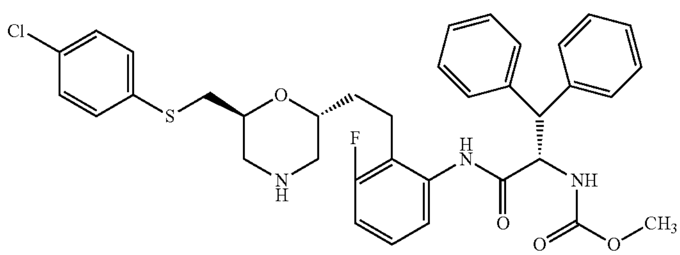 [SMILES: COC(=O)N[C@H](C(=O)Nc1cccc(F)c1CC[C@@H]1CNC[C@@H](CSc2ccc(Cl)cc2)O1)C(c1ccccc1)c1ccccc1] | N-(2-{2-[(2R,6S)-6-{[(4-chlorophenyl)sulfanyl]methyl}morpholin-2-yl]ethyl}-3-fluorophenyl)-Nα-(methoxycarbonyl)-β-phenyl-L-phenylalaninamide | M + 1, +ESI = 662 |
| 74 | 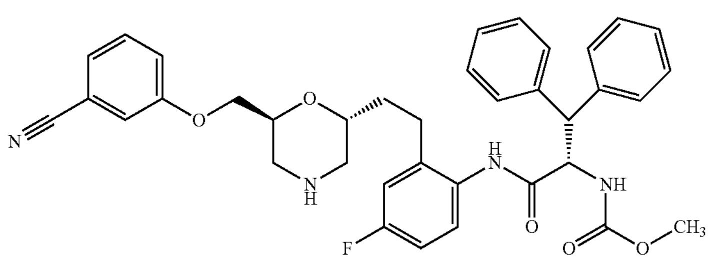 [SMILES: COC(=O)N[C@H](C(=O)Nc1ccc(F)cc1CC[C@@H]1CNC[C@@H](COc2cccc(C#N)c2)O1)C(c1ccccc1)c1ccccc1] | N-[2-(2-{(2R,6S)-6-[(3-cyanophenoxy)methyl]morpholin-2-yl}ethyl)-4-fluorophenyl]-Nα-(methoxycarbonyl)-β-phenyl-L-phenylalaninamide | M + 1, +ESI = 637.3 |
| 75 | 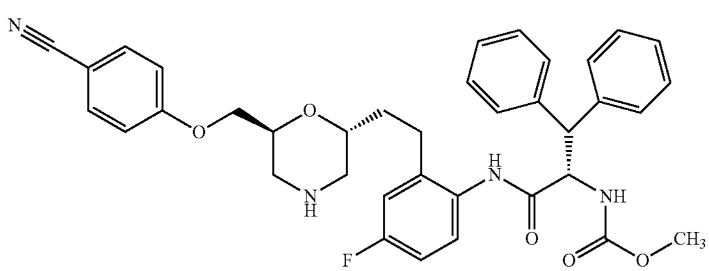 [SMILES: COC(=O)N[C@H](C(=O)Nc1ccc(F)cc1CC[C@@H]1CNC[C@@H](COc2ccc(C#N)cc2)O1)C(c1ccccc1)c1ccccc1] | N-[2-(2-{(2R,6S)-6-[(4-cyanophenoxy)methyl]morpholin-2-yl}ethyl)-4-fluorophenyl]-Nα-(methoxycarbonyl)-β-phenyl-L-phenylalaninamide | M + 1, +ESI = 637.3 |

| Ex. | Structure | IUPAC name | LCMS data |
|---|---|---|---|
| 76 | 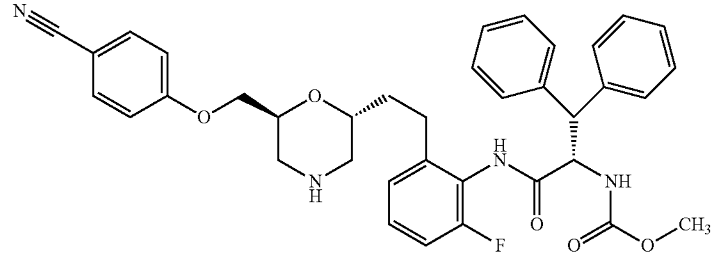 [SMILES: COC(=O)N[C@H](C(=O)Nc1c(F)cccc1CC[C@@H]1CNC[C@@H](COc2ccc(C#N)cc2)O1)C(c1ccccc1)c1ccccc1] | N-[2-(2-{(2R,6S)-6-[(4-cyanophenoxy)methyl]morpholin-2-yl}ethyl)-6-fluorophenyl]-Nα-(methoxycarbonyl)-β-phenyl-L-phenylalaninamide | M + 1, +ESI = 637.3 |
| 77 | 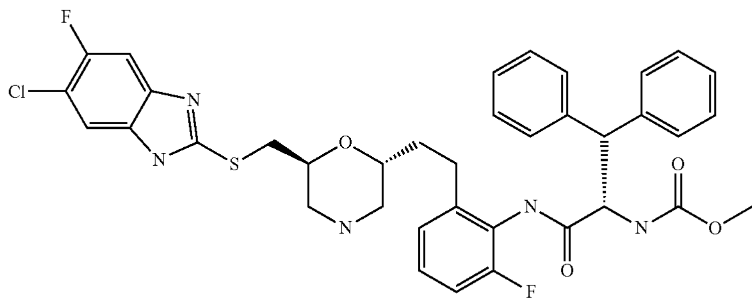 [SMILES: COC(=O)N[C@H](C(=O)Nc1c(F)cccc1CC[C@@H]1CNC[C@@H](CSc2nc3cc(F)c(Cl)cc3[nH]2)O1)C(c1ccccc1)c1ccccc1] | N-(2-{2-[(2R,6S)-6-{[(6-chloro-5-fluoro-1H-benzimidazol-2-yl)sulfanyl]methyl}morpholin-2-yl]ethyl}-6-fluorophenyl)-Nα-(methoxycarbonyl)-β-phenyl-L-phenylalaninamide | M + 1, +ESI = 720.1 |

EXAMPLE 78

Preparation of Compound 78 (N-[2-(2-{(2R,6S)-6-[(4-cyanophenoxy)methyl]morpholin-2-yl}ethyl)-5-fluoropyridin-3-yl]-Nα-(methoxycarbonyl)-β-phenyl-L-phenylalaninamide)

C-78

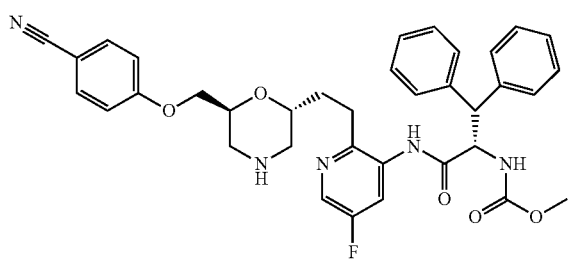

Step 1-Synthesis of Intermediate Compound Int-78a ((2S,6R)-4-benzyl-2-({[tert-butyl(dimethyl)silyl]oxy}methyl)-6-ethynylmorpholine)

To a stirred solution of dimethyl (1-diazo-2-oxopropyl)phosphonate (2.1 eq) in THF (0.1 M) at −78° C. was added 4N sodium methoxide in MeOH (2.3 eq) over 10 minutes. The reaction mixture was stirred at −78° C. for 15 minutes. A solution of (2S,6S)-4-benzyl-6-({[tert-butyl(dimethyl)silyl]oxy}methyl)morpholine-2-carbaldehyde (1 eq) in THF (0.3M) was slowly added over 20 minutes. The reaction mixture was stirred at −78° C. for 1.5 hours and then allowed to stand at room temperature overnight prior to be concentrated under reduced pressure. The residue was diluted with aqueous sodium hydrogen carbonate and EtOAc and the aqueous layer was extracted EtOAc. The combined organic layers were washed with brine, dried with MgSO₄ and concentrated under vacuum. The crude product was purified by automated SiO₂ flash chromatography system using solvent gradient of 0% to 40% EtOAc/Hex to afford the desired compound (Int-78a).

Step 2-Synthesis of Intermediate Compound Int-78b (2-{[(2R,6S)-4-benzyl-6-({[tert-butyl(dimethyl)silyl]oxy}methyl)morpholin-2-yl]ethynyl}-5-fluoropyridin-3-amine)

A solution of intermediate compound Int-78a (1 eq) and 5-fluoro-2-iodopyridin-3-amine (1.4 eq) in acetonitrile (0.1M) and triethylamine (25 eq) was flushed with nitrogen for 10 minutes. Then bis(triphenylphosphine)palladium(ii) chloride (0.1 eq) and copper(i) iodide (1.2 eq) were added and the mixture was flushed again with nitrogen for 10 minutes. The reaction mixture was stirred at 60° C. for 2 hours in the dark. It was concentrated to dryness and the residue was purified by automated SiO₂ flash chromatography system using solvent gradient of 0% to 50% EtOAc/Hex to afford the compound Int-78b.

Step 3-Synthesis of Compound 78 (N-[2-(2-{(2R,6S)-6-[(4-cyanophenoxy)methyl]morpholin-2-yl}ethyl)-5-fluoropyridin-3-yl]-Nα-(methoxycarbonyl)-β-phenyl-L-phenylalaninamide)

Compound 78 was prepared from intermediate compound Int-78b according to the same procedure described in Steps 8 to 13 from Example 7 and by using the appropriate reagents.

M+1 (+ESI)=638.3.

The following compounds (79 to 85) were synthesized from (2S,6R)-4-benzyl-2-({[tert-butyl(dimethyl)silyl]oxy}methyl)-6-ethynylmorpholine (Int-78a) according to the procedures described in steps 1 to 3 from Example 78 and by using the appropriate reagents.

| Ex. | Structure | IUPAC name | LCMS data |
|---|---|---|---|
| 79 | 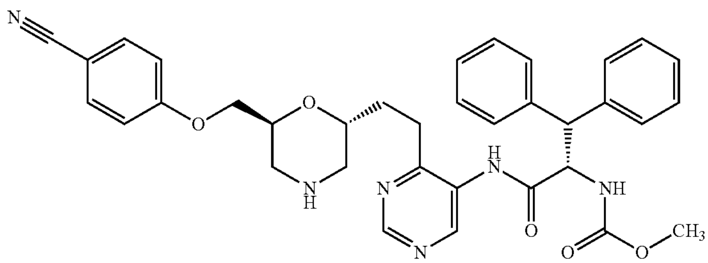 [SMILES: COC(=O)N[C@H](C(=O)Nc1cncnc1CC[C@@H]1CNC[C@@H](COc2ccc(C#N)cc2)O1)C(c1ccccc1)c1ccccc1] | N-[4-(2-{(2R,6S)-6-[(4-cyanophenoxy)methyl]morpholin-2-yl}ethyl)pyrimidin-5-yl]-Nα-(methoxycarbonyl)-β-phenyl-L-phenylalaninamide | M + 1, +ESI = 621 |
| 80 | 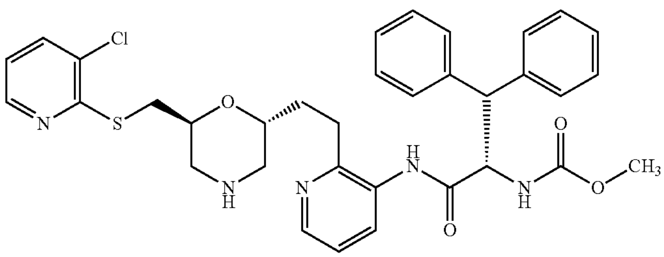 [SMILES: COC(=O)N[C@H](C(=O)Nc1cccnc1CC[C@@H]1CNC[C@@H](CSc2ncccc2Cl)O1)C(c1ccccc1)c1ccccc1] | N-(2-{2-[(2R,6S)-6-{[(3-chloropyridin-2-yl)sulfanyl]methyl}morpholin-2-yl]ethyl}pyridin-3-yl)-Nα-(methoxycarbonyl)-β-phenyl-L-phenylalaninamide | M + 1, +ESI = 646.2 |
| 81 | 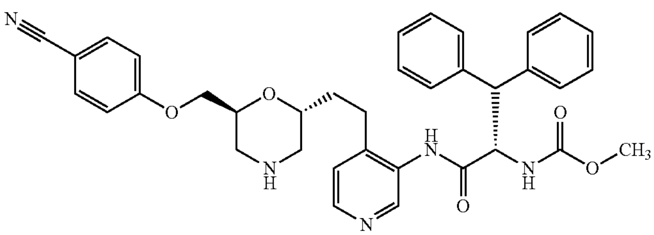 [SMILES: COC(=O)N[C@H](C(=O)Nc1cnccc1CC[C@@H]1CNC[C@@H](COc2ccc(C#N)cc2)O1)C(c1ccccc1)c1ccccc1] | N-[4-(2-{(2R,6S)-6-[(4-cyanophenoxy)methyl]morpholin-2-yl}ethyl)pyridin-3-yl]-Nα-(methoxycarbonyl)-β-phenyl-L-phenylalaninamide | M + 1, +ESI = 620.2 |
| 82 | 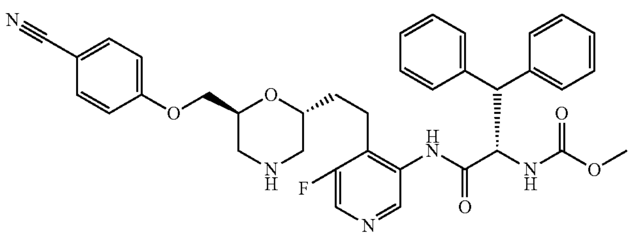 [SMILES: COC(=O)N[C@H](C(=O)Nc1cncc(F)c1CC[C@@H]1CNC[C@@H](COc2ccc(C#N)cc2)O1)C(c1ccccc1)c1ccccc1] | Methyl[(1S)-2-{[4-(2-{(2R,6S)-6-[(4-cyanophenoxy)methyl]morpholin-2-yl}ethyl)-5-fluoropyridin-3-yl]amino}-1-(diphenylmethyl)-2-oxoethyl]carbamate | M + 1, +ESI = 638.25 |
| 83 | 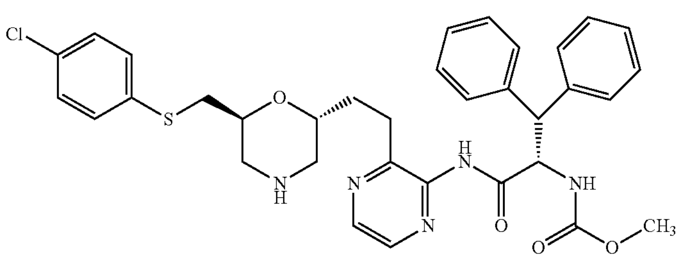 [SMILES: COC(=O)N[C@H](C(=O)Nc1nccnc1CC[C@@H]1CNC[C@@H](CSc2ccc(Cl)cc2)O1)C(c1ccccc1)c1ccccc1] | methyl N-[(1S)-1-benzhydryl-2-[[3-[2-[(2R,6S)-6-[(4-chlorophenyl)sulfanylmethyl]morpholin-2-yl]ethyl]pyrazin-2-yl]amino]-2-oxo-ethyl]carbamate | M + 1, +ESI = 646.2 |
| 84 | 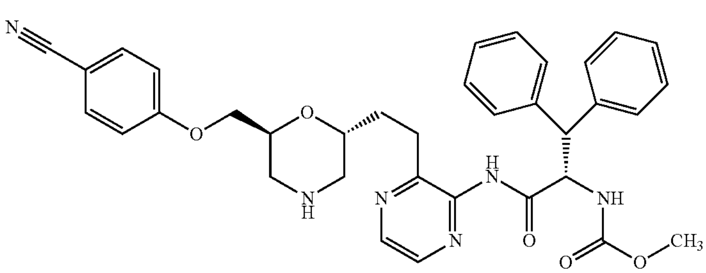 [SMILES: COC(=O)N[C@H](C(=O)Nc1nccnc1CC[C@@H]1CNC[C@@H](COc2ccc(C#N)cc2)O1)C(c1ccccc1)c1ccccc1] | methyl N-[(1S)-1-benzhydryl-2-[[3-[2-[(2R,6S)-6-[(4-cyanophenoxy)methyl]morpholin-2-yl]ethyl]pyrazin-2-yl]amino]-2-oxo-ethyl]carbamate | M + 1, +ESI = 621.3 |

| Ex. | Structure | IUPAC name | LCMS data |
|---|---|---|---|
| 85 | 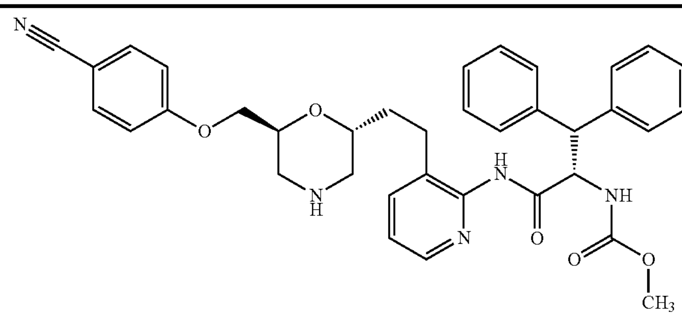 | N-[3-(2-{(2R,6S)-6-[(4-cyanophenoxy)methyl]morpholin-2-yl}ethyl)pyridin-2-yl]-Nα-(methoxycarbonyl)-β-phenyl-L-phenylalaninamide | M + 1, +ESI = 620.2 |

EXAMPLE 86

Preparation of Compound 86 (N-[4-(2-{(2R,6S)-6-[(4-cyanophenoxy)methyl]morpholin-2-yl}ethyl)-2-oxo-1,2-dihydropyridin-3-yl]-Nα-(methoxycarbonyl)-β-phenyl-L-phenylalaninamide)

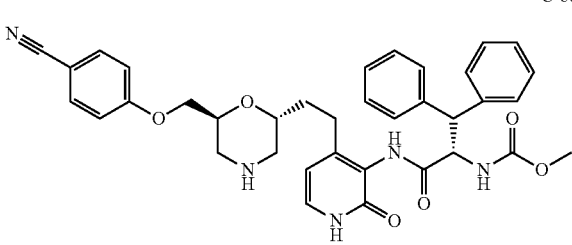

C-86

Step 1-Synthesis of Intermediate Compound Int-86a (4-{[(2R,6S)-4-benzyl-6-({[tert-butyl(dimethyl)silyl]oxy}methyl)morpholin-2-yl]ethynyl}-2-methoxypyridin-3-amine)

To a degassed solution of intermediate compound Int-78a (1 eq) in tetrahydrofuran (0.3M) was added 4-iodo-2-methoxypyridin-3-amine (1.1 eq.), piperidine (3.0 eq.), Pd(Ph₃P)₄ (0.08 eq.) and copper(I) iodide (0.13 eq.). The flask was purged from air and stirred at 60° C. for 3 hours. The reaction was quenched with water and the aqueous phase extracted with dichloromethane. The combined organic layers were co-evaporated with toluene and the residue was purified by automated SiO₂ flash chromatography system using solvent gradient of 0% to 50% EtOAc/Hex to afford the compound Int-86a.

Step 2-Synthesis of Intermediate Compound Int-86b (4-{2-[(2R,6S)-6-({[tert-butyl(dimethyl)silyl]oxy}methyl)morpholin-2-yl]ethyl}-2-methoxypyridin-3-amine)

To a solution of intermediate compound Int-86a (1 eq) in MeOH (0.27M) purged from air was added 10% Pd/C (0.4 eq.) and acetic acid (1.0 eq.). The reaction mixture was stirred at room temperature under 1 atm of hydrogen overnight, filtered on celite and the filtrate washed with MeOH. The evaporation residue was used as such for next step.

Step 3-Synthesis of Intermediate Compound Int-86c (tert-butyl (2S,6R)-2-[(4-cyanophenoxy)methyl]-6-[2-(2-methoxy-3-{[N-(methoxycarbonyl)-β-phenyl-L-phenylalanyl]amino}pyridin-4-yl)ethyl]morpholine-4-carboxylate)

Intermediate compound Int-86c was prepared from intermediate compound Int-86b by following procedures from steps 9 to 12 described in Example 7.

Step 4-Synthesis of Compound 86 (N-[4-(2-{(2R,6S)-6-[(4-cyanophenoxy)methyl]morpholin-2-yl}ethyl)-2-oxo-1,2-dihydropyridin-3-yl]-Nα-(methoxycarbonyl)-β-phenyl-L-phenylalaninamide)

To a solution of sodium iodide (7 eq.) in acetonitrile (0.03M) was added TMS-Cl (7 eq.). The reaction mixture was stirred for 15 minutes and then intermediate compound Int-86c (1 eq.) was added as a solution in acetonitrile (0.03M). The mixture was stirred at 60° C. for 60 minutes and then concentrated to dryness. The residue was purified by automated SiO₂ flash chromatography system using solvent gradient of 0% to 10% MeOH/CH₂Cl₂ containing 1% of NEt₃ to afford the desired compound.
M+1, +ESI=636.3.

EXAMPLE 87

Preparation of Compound 87 (N-(4-{2-[(2R,6S)-6-{[(4-chlorophenyl)sulfanyl]methyl}morpholin-2-yl]ethyl}-2-oxo-1,2-dihydropyridin-3-yl)-Nα-(methoxycarbonyl)-β-phenyl-L-phenylalaninamide)

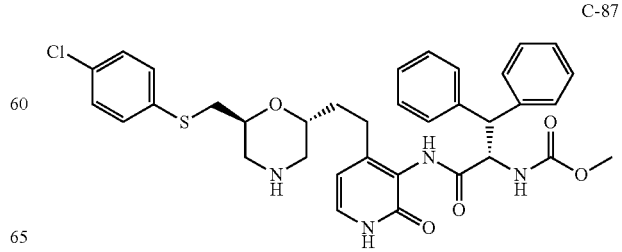

C-87

Step 1-Synthesis of Compound 87 (N-(4-{2-[(2R, 6S)-6-{[(4-chlorophenyl)sulfanyl]methyl}morpholin-2-yl]ethyl}-2-oxo-1,2-dihydropyridin-3-yl)-Nα-(methoxycarbonyl)-β-phenyl-L-phenylalaninamide)

Compound 87 was prepared from 4-{2-[(2R,6S)-6-({[tert-butyl(dimethyl)silyl]oxy}methyl)morpholin-2-yl]ethyl}-2-methoxypyridin-3-amine by following procedures from steps 2 to 4 described in Example 86. M+1, +ESI=661.2

EXAMPLE 88

Preparation of Compound 88 (N-(4-{2-[(2R,6S)-6-{[(4-chlorophenyl)sulfanyl]methyl}morpholin-2-yl]ethyl}-2-oxo-1,2-dihydropyridin-3-yl)-β-phenyl-L-phenylalaninamide)

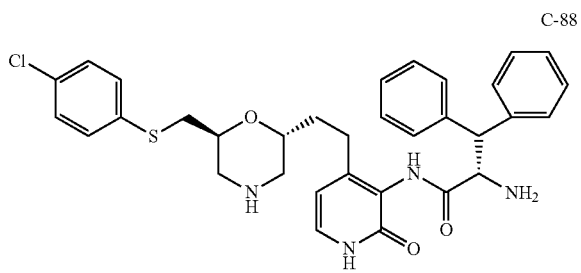 [SMILES: N[C@H](C(=O)Nc1c(CC[C@@H]2CNC[C@@H](CSc3ccc(Cl)cc3)O2)cc[nH]c1=O)C(c1ccccc1)c1ccccc1]

C-88

Step 1-Synthesis of Compound 88 (N-(4-{2-[(2R, 6S)-6-{[(4-chlorophenyl)sulfanyl]methyl}morpholin-2-yl]ethyl}-2-oxo-1,2-dihydropyridin-3-yl)-β-phenyl-L-phenylalaninamide)

To a solution of sodium iodide (7 eq.) acetonitrile (0.03M) was added TMS-Cl (7 eq.). The solution was stirred at room temperature for 15 minutes and then a solution of tert-butyl (2S,6R)-2-{[(4-chlorophenyl)sulfanyl]methyl}-6-[2-(2-methoxy-3-{[N-(methoxycarbonyl)-β-phenyl-L-phenylalanyl]amino}pyridin-4-yl)ethyl]morpholine-4-carboxylate in acetonitrile (0.03M) was added and the solution was stirred at 100° C. overnight. An additional 7 equivalent of premix TMSCl and NaI in acetonitrile was added to the reaction mixture and the mixture was heated in microwave for 10 minutes at 100° C. The reaction mixture was then concentrated and the residue was purified by automated C18 flash chromatography system using solvent gradient of 5% to 95% MeOH+0.1% TFA/water to afford compound 88.

M+1, +ESI=603.1.

EXAMPLE 89

Preparation of Compound 89 (N-(4-{2-[(2R,6S)-6-{[(4-chlorophenyl)sulfanyl]methyl}morpholin-2-yl]ethyl}-2-oxo-1,2-dihydropyridin-3-yl)-β-phenyl-Nα-(2,2,2-trifluoroethyl)-L-phenylalaninamide)

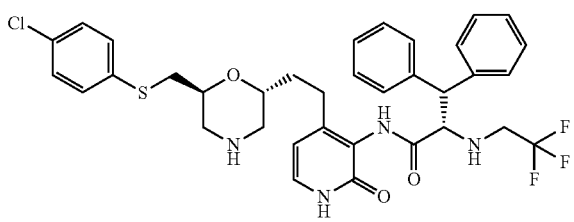

C-89

Step 1-Synthesis of Intermediate Compound Int-89a (methyl β-phenyl-N-(2,2,2-trifluoroethyl)-L-phenylalaninate)

To a solution of methyl β-phenyl-L-phenylalaninate (1 eq.) in toluene (0.5M) was added trifluoroacetadehyde ethyl hemiacetal (6.0 eq.). The solution was stirred at room temperature and T3P™ solution in ethyl acetate (6.6 eq,) was added. The solution was stirred at 60° C. for four hours and then cooled to 0° C. Sodium borohydride (20 eq.) was added and the suspension was warmed to room temperature. Methanol was then added slowly to quench the excess NaBH$_4$. Water was then added and the aqueous phase was extracted with EtOAc three times. The combined organic layers were then washed with water and brine and dried over Na$_2$SO$_4$ and concentrated. The evaporation residue was purified by automated SiO$_2$ flash chromatography system using solvent gradient of 0% to 20% EtOAc/Hex to afford the compound Int-89a.

Step 2-Synthesis of Intermediate Compound Int-89a (β-phenyl-N-(2,2,2-trifluoroethyl)-L-phenylalanine)

To a solution of methyl β-phenyl-N-(2,2,2-trifluoroethyl)-L-phenylalaninate (1 eq.) in THF (0.1 M) was added 1N aqueous NaOH (3 eq.). Methanol was then added dropwise until the reaction was homogenous. Once the reaction was judged completed by tlc, saturated aqueous ammonium chloride was added and the aqueous layer was extracted with ethyl acetate three times. The combined organic layers were then washed with water, dried over MgSO$_4$ filtered and concentrated to afford the desired product which was used as such for next step.

Step 3-Synthesis of Compound 89 (N-(4-{2-[(2R, 6S)-6-{[(4-chlorophenyl)sulfanyl]methyl}morpholin-2-yl]ethyl}-2-oxo-1,2-dihydropyridin-3-yl)-β-phenyl-Nα-(2,2,2-trifluoroethyl)-L-phenylalaninamide)

Compound 89 was prepared from 4-{2-[(2R,6S)-6-({[tert-butyl(dimethyl)silyl]oxy}methyl)morpholin-2-yl]ethyl}-2-methoxypyridin-3-amine and intermediate compound Int-89a by following procedures from steps 2 to 4 described in Example 86 and using the appropriate reagents. M+1, +ESI=685.2.

EXAMPLE 90

Preparation of Compound 90 (N-[6-(2-{(2R,6S)-6-[(4-cyanophenoxy)methyl]morpholin-2-yl}ethyl)-2-oxopyridin-1 (2H)-yl]-Nα-(methoxycarbonyl)-β-phenyl-L-phenylalaninamide)

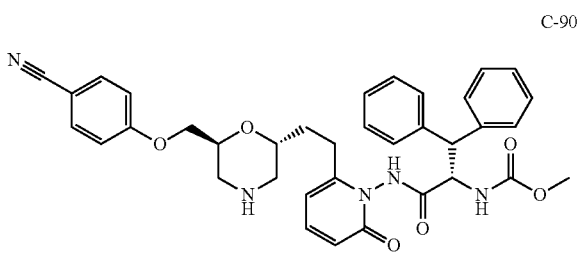 [SMILES: COC(=O)N[C@H](C(=O)Nn1c(CC[C@@H]2CNC[C@@H](COc3ccc(C#N)cc3)O2)cccc1=O)C(c1ccccc1)c1ccccc1]

C-90

Step 1-Synthesis of Intermediate Compound Int-90a ((2R,6S)-4-benzyl-2-{[6-(benzyloxy)pyridin-2-yl]ethynyl}-6-({[tert-butyl(dimethyl)silyl]oxy}methyl)morpholine)

To a degassed solution of intermediate compound Int-78a (1 eq.) in tetrahydrofuran (0.24M) was added 2-(benzyloxy)-6-bromopyridine (1.1 eq.), piperidine (3 eq.), Pd(Ph₃P)₄ (0.13 eq.) and copper(I) iodide (0.08 eq.). The flask was purged from air and stirred at 50° C. overnight. The reaction was concentrated under reduced pressure and coevaporated twice with toluene. The mixture was pumped overnight and the residue was purified by automated SiO₂ flash chromatography system using solvent gradient of 0% to 10% EtOAc/Hex to afford the desired compound.

Step 2-Synthesis of Intermediate Compound Int-90b (6-{2-[(2R,6S)-6-({[tert-butyl(dimethyl)silyl]oxy}methyl)morpholin-2-yl]ethyl}pyridin-2(1H)-one)

To a solution of intermediate compound Int-90a (1 eq.) in trifluoroethanol (0.2M) was bubbled nitrogen for 5 minutes. Palladium hydroxide on carbon 20% (0.3 eq.) was added and the reaction put under hydrogen atmosphere (1 atm). The reaction mixture was stirred for 4 hours, filtered on celite, concentrated and used as such for next step.

Step 3—Synthesis of Intermediate Compound Int-90c (tert-butyl (2S,6R)-2-({[tert-butyl(dimethyl)silyl]oxy}methyl)-6-[2-(6-oxo-1,6-dihydropyridin-2-yl)ethyl]morpholine-4-carboxylate)

To a solution of intermediate compound Int-90b (1 eq.) in tetrahydrofuran (0.2M) and water (0.2M) was added was added sodium bicarbonate (3 eq.) followed by BOC₂O (1.05 eq.). The mixture was stirred overnight and upon completion the mixture was diluted with ethyl acetate and the aqueous phase was further extracted with EtOAc. The combined organic phases were washed with water and brine and dried over MgSO₄. The residue was purified by automated SiO₂ flash chromatography system using solvent gradient of 30% to 100% EtOAc/Hex to afford the desired compound.

Step 4-Synthesis of Intermediate Compound Int-90d (tert-butyl (2R,6S)-2-[2-(1-amino-6-oxo-1,6-dihydropyridin-2-yl)ethyl]-6-({[tert-butyl(dimethyl)silyl]oxy}methyl)morpholine-4-carboxylate)

To a solution of intermediate compound Int-90c (1 eq.) in DMF (0.1M) was added cesium carbonate (4 eq.). The solution was stirred for 2 minutes and diphenyl phosphoryl-O-hydroxylamine (2 eq.) was added. The suspension was stirred for 30 minutes and filtered. The filtrate was diluted with water and was extracted with ethyl acetate. The combined organic layers were dried over MgSO₄, filtered and concentrated. The residue was purified by automated SiO₂ flash chromatography system using solvent gradient of 50% to 100% EtOAc/Hex to afford the desired compound (Int-90d).

Step 5-Synthesis of Intermediate Compound Int-90e (tert-butyl (2S,6R)-2-({[tert-butyl(dimethyl)silyl]oxy}methyl)-6-[2-(1-{[N-(methoxycarbonyl)-β-phenyl-L-phenylalanyl]amino}-6-oxo-1,6-dihydropyridin-2-yl)ethyl]morpholine-4-carboxylate)

To a solution of N-(methoxycarbonyl)-β-phenyl-L-phenylalanine (5 eq.) in DCM (0.5M) was added oxalyl chloride (8 eq.) and DMF (0.6 eq.) at room temperature. The reaction was stirred 20 minutes and then evaporated to dryness and dried on high vac. In a separated flask, to a solution of intermediate compound Int-90d (1 eq.) in THF (0.5M) was added 60% sodium hydride in oil (1.1 eq.). The mixture was stirred at 0° C. for 20 minutes and then removed from cooling bath. The sodium salt was then added dropwise to a −78° C. THF (0.1M) solution of the previously prepared acyl chloride. The reaction was then stirred at −78° C. for 1 hour. The reaction mixture was then diluted with saturated aqueous NH₄Cl and the aqueous layer was extracted with ethyl acetate. The combined organic layers were washed with brine, dried over MgSO₄, filtered and concentrated. The residue was purified by automated SiO₂ flash chromatography system using solvent gradient of 30% to 100% EtOAc/Hex to afford the compound Int-90e.

Step 6-Synthesis of Compound 90 (N-[6-(2-{(2R,6S)-6-[(4-cyanophenoxy)methyl]morpholin-2-yl}ethyl)-2-oxopyridin-1 (2H)-yl]-Nα-(methoxycarbonyl)-β-phenyl-L-phenylalaninamide)

Compound 90 was prepared from intermediate compound Int-90e by following procedures from steps 11 to 13 described in Example 7 and using the appropriate reagents.
M+1, +ESI=636.2.

EXAMPLE 91

4-fluoro-β-(4-fluorophenyl)-N-(3-fluoro-2-{2-[(2R,6S)-6-{[(5-pyridin-4-yl-1,3,4-oxadiazol-2-yl)sulfanyl]methyl}morpholin-2-yl]ethyl}phenyl)-L-phenylalaninamide

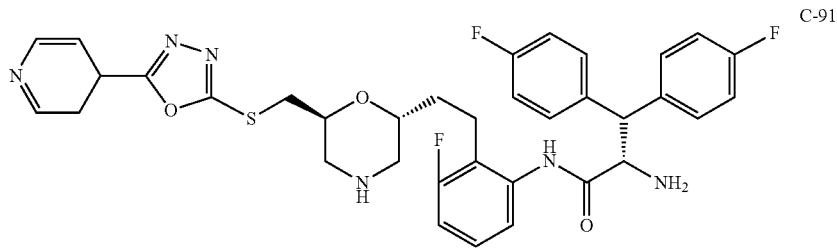 [SMILES: N[C@H](C(=O)Nc1cccc(F)c1CC[C@@H]1CNC[C@@H](CSc2nnc(C3C=CN=CC3)o2)O1)C(c1ccc(F)cc1)c1ccc(F)cc1]

Step 1-Synthesis of Intermediate Compound Int-91a ((2R,6S)-tert-butyl 2-(2-((S)-2-((tert-butoxycarbonyl)amino)-3,3-bis(4-fluorophenyl)propanamido)-6-fluorophenethyl)-6-(hydroxymethyl)morpholine-4-carboxylate)

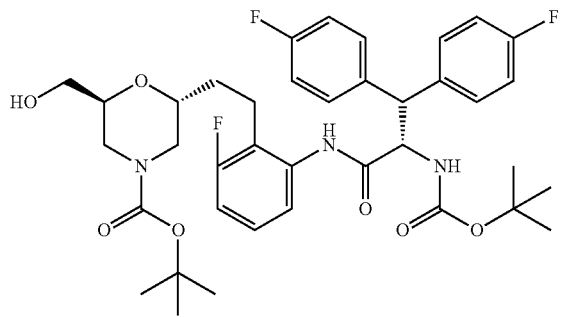 [SMILES: CC(C)(C)OC(=O)N[C@H](C(=O)Nc1cccc(F)c1CC[C@@H]1CN(C(=O)OC(C)(C)C)C[C@@H](CO)O1)C(c1ccc(F)cc1)c1ccc(F)cc1]

The title compound was prepared from (2R,6S)-tert-butyl 2-(2-((S)-2-((tert-butoxycarbonyl)amino)-3,3-bis(4-fluorophenyl)propanamido)-6-fluorophenethyl)-6-(((tert-butyldimethylsilyl)oxy)methyl)morpholine-4-carboxylate by following the procedure from step 11 described in Example 7.

Step 2-Synthesis of Intermediate Compound Int-91b ((2R,6S)-tert-butyl 2-(2-((S)-2-((tert-butoxycarbonyl)amino)-3,3-bis(4-fluorophenyl)propanamido)-6-fluorophenethyl)-6-(((5-(pyridin-4-yl)-1,3,4-oxadiazol-2-yl)thio)methyl)morpholine-4-carboxylate)

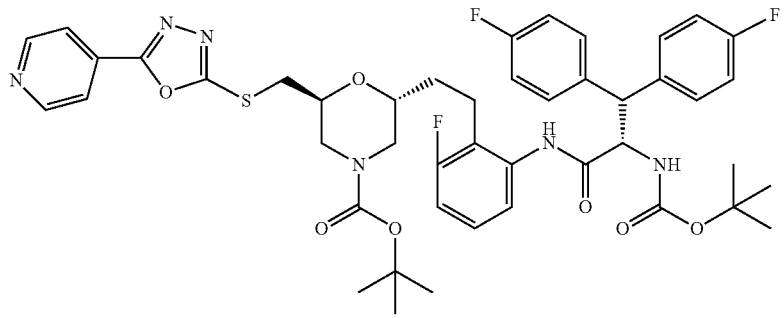 [SMILES: CC(C)(C)OC(=O)N[C@H](C(=O)Nc1cccc(F)c1CC[C@@H]1CN(C(=O)OC(C)(C)C)C[C@@H](CSc2nnc(-c3ccncc3)o2)O1)C(c1ccc(F)cc1)c1ccc(F)cc1]

To a solution of Int-91a (39.6 mg, 0.055 mmol) in toluene (555 μl) was added 5-(4-pyridinyl)-1,3,4-oxadiazole-2(3H)-thione (14.9 mg, 0.083 mmol) and cyanomethylenetributylphosphorane (26.8 mg, 0.111 mmol). The mixture was warmed to 80° C. After 20 hours, the reaction was concentrated and purified by automated silica gel column chromatography eluting with 0 to 20% EtOAc/hexanes on a 12 g Redisep Rf column to afford the product (Int-91b) as a tan foam. LRMS (ESI) m/z 875.3 [(M+H)+; calcd for $C_{45}H_{49}F_3N_6O_7S$: 875.0].

Step 3-Synthesis of Compound 91 (4-fluoro-β-(4-fluorophenyl)-N-(3-fluoro-2-{2-[(2R,6S)-6-{[(5-pyridin-4-yl-1,3,4-oxadiazol-2-yl)sulfanyl]methyl}morpholin-2-yl]ethyl}phenyl)-L-phenylalaninamide)

The title compound was prepared from Int-91b by following the procedure from step 6 described in Example 99. (ES+) m/z (M+H)⁺=675.1. ¹H NMR (400 MHz, DMSO) δ 10.45 (s, 1H), 9.51 (bs, 1H), 9.28 (bs, 1H), 8.80 (d, J=5.7 Hz, 2H), 8.56 (bs, 3H), 7.91 (d, J=6.0 Hz, 2H), 7.58-7.63 (m, 3H), 7.25 (t, J=8.7 Hz, 2H), 7.13 (t, J=8.7 Hz, 3H), 6.87 (t, J=8.1 Hz, 2H), 5.56 (m, 1H), 4.42 (d, J=11.4 Hz, 1H), 4.32 (m, 1H), 4.11 (m, 1H), 3.75 (d, J=7.0 Hz, 2H), 3.31 (m, 2H), 3.17 (m, 1H), 3.01 (m, 1H), 2.55 (m, 1H), 2.21 (m, 1H), 1.99 (m, 2H).

EXAMPLE 92

Methyl [(1S,2S)-2-(3,5-difluorophenyl)-1-[(3-fluoro-2-{2-[(2R)-8-oxo-1-oxa-4-azaspiro[5.5]undec-2-yl]ethyl}phenyl)carbamoyl]-2-(4-fluorophenyl)ethyl]carbamate

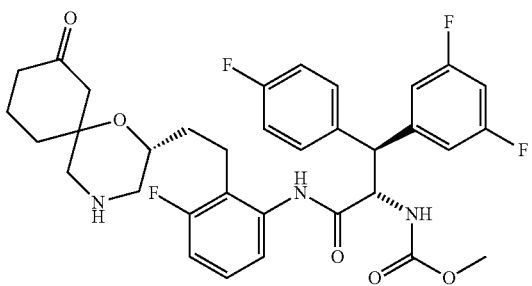 [SMILES: COC(=O)N[C@H](C(=O)Nc1cccc(F)c1CC[C@@H]1CNCC2(CCCC(=O)C2)O1)[C@@H](c1ccc(F)cc1)c1cc(F)cc(F)c1]

Step 1-Synthesis of 1,6,9-trioxadispiro[2.1.4.3]dodecane

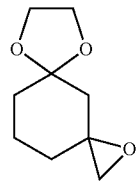

To a stirred solution of NaH (60% in mineral oil, 1.62 g, 39.8 mmol) in DMF (50.0 mL) at 0° C., was added Me₃S⁺I⁻ (7.71 g, 37.3 mmol) in one portion and stirred for 45 minutes. A solution of 1,4-dioxaspiro[4.5]decan-7-one (3.99 g, 25.5 mmol) in DMF (15.0 mL) was added slowly at 0° C. The reaction mixture was warmed to room temperature and stirred for 22 hours. The reaction was quenched with water (50.0 mL), saturated solution of NaHCO₃ (200 mL) and extracted with EtOAc (400 mL). The organic layer was washed with brine (400 mL), dried (Na₂SO₄), filtered and concentrated under reduced pressure to provide the product (2.87 g, crude) as yellow oil. MS: m/z=171 (M+H⁺).

Step 2-Synthesis of 7-(S)-((Benzylamino)methyl)-1,4-dioxaspiro[4.5]decan-7-ol

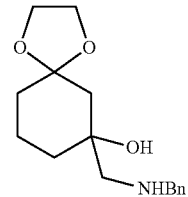

To a stirred solution of 1,6,9-trioxadispiro[2.1.4.3]dodecane (2.87 g, 16.9 mmol) in EtOH (50.0 mL) was added benzylamine (2.00 mL, 18.3 mmol) and heated to reflux for 13 hours. The reaction mixture was warmed to room temperature and stirred for 22 hours. The reaction mixture was concentrated under reduced pressure and the residue was purified by 40 g SiO₂ column using a gradient elution of 0-10% MeOH in dichloromethane. Fractions containing product were combined and the solvents were removed in vacuo to provide the product (3.45 g, 70%) as yellow oil. MS: m/z=278 (M+H⁺).

Step 3-Synthesis of (S)-1,4,8-Trioxa-9-(hydroxymethyl)-11-benzyl-11-azadispiro[4.1.5.3]pentadecane

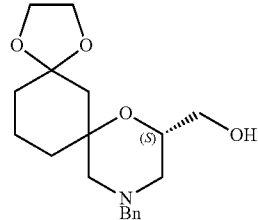

To a solution of 7-(S)-((benzylamino)methyl)-1,4-dioxaspiro[4.5]decan-7-ol (0.92 g, 3.33 mmol) in MeOH/H₂O (17.0 mL/8.00 mL) was added (R)-2-(chloromethyl)oxirane (0.63 mL, 5.77 mmol) at room temperature and stirred for 30 hours. To the reaction mixture was added KOH (0.618 g, 11.0 mmol) in one portion and stirred for additional 40 hours at room temperature. The reaction mixture was concentrated under reduced pressure and the residue was diluted with EtOAc (150 mL). The organic layer was washed with saturated solution of NaHCO₃ (20.0 mL), brine (50.0 mL), dried (Na₂SO₄), filtered and concentrated under reduced pressure. The residue and was purified by 12 g SiO₂ column using a gradient elution of 10-50% EtOAc in hexanes. Fractions containing product were combined and the solvents were removed in vacuo to provide the product (0.839 g, 70%) as yellow syrup. MS: m/z=334 (M+H⁺).

Step 4-Synthesis of (S)-1,4,8-Trioxa-11-benzyl-11-azadispiro[4.1.5.3]pentadecane-9-carbaldehyde

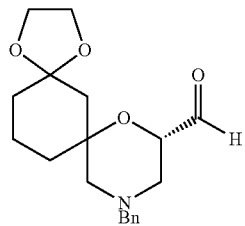 [SMILES: O=C[C@@H]1CN(Cc2ccccc2)CC2(CCCC3(C2)OCCO3)O1]

To a solution of (S)-1,4,8-trioxa-9-(hydroxymethyl)-11-benzyl-11-azadispiro[4.1.5.3]pentadecane (0.86 g, 2.65 mmol) and pyridine (1.95 mL, 24.11 mmol) in CH$_2$Cl$_2$ (10.0 mL) was added Dess-Martin periodinane (4.22 g, 9.80 mmol) at 0° C. and the reaction mixture was stirred for at room temperature for 8 hours. The reaction mixture was quenched with saturated solution of NaHCO$_3$ (50.0 mL), saturated Na$_2$S$_2$O$_3$ solution (80.0 mL) and extracted with EtOAc (250 mL). The organic layer was washed with brine (300 mL), dried (Na$_2$SO$_4$), filtered and concentrated under reduced pressure to provide the product (0.79 g, crude) as yellow syrup. MS: m/z=332 (M+H$^+$). The crude product was directly used in the next step without purification.

Step 5-Synthesis of 1,4,8-Trioxa-9-(R)-(2-fluoro-6-nitrostyryl)-11-benzyl-11-azadispiro[4.1.5.3]pentadecane

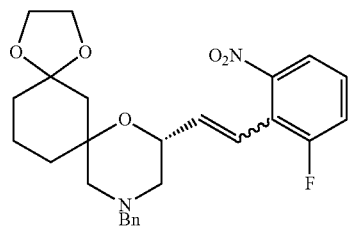 [SMILES: O=[N+]([O-])c1cccc(F)c1C=C[C@@H]1CN(Cc2ccccc2)CC2(CCCC3(C2)OCCO3)O1]

To a suspension of (2-fluoro-6-nitrobenzyl)triphenylphosphoranyl bromide (3.00 g, 6.05 mmol) in THF (10.0 mL) at 0° C. was added KO$^t$Bu (1M in THF, 5.40 mL, 5.40 mmol) slowly and stirred at room temperature for 2 hours. A solution of (S)-1,4,8-trioxa-11-benzyl-11-azadispiro[4.1.5.3]pentadecane-9-carbaldehyde (0.91 g, 2.73 mmol) in THF (12.0 mL) was added to the above reaction mixture at 0° C. and stirred at room temperature for 36 hours. The solids precipitated in the reaction were filtered using a celite pad and washed with a mixture of THF/CH$_2$Cl$_2$ (60 mL/40 mL). The filtrate was concentrated under reduced pressure and the residue was purified by 40 g SiO$_2$ column using a gradient elution of 0-30% EtOAc in hexanes. Fractions containing product were combined and the solvents were removed in vacuo to provide the product (0.89 g, 69%) as yellow syrup. MS: m/z=469 (M+H$^+$).

Step 6-Synthesis of tert-Butyl 1,4,8-trioxa-9-(R)-(2-fluoro-6-aminophenethyl)-11-azadispiro[4.1.5.3]pentadecane-11-carboxylate

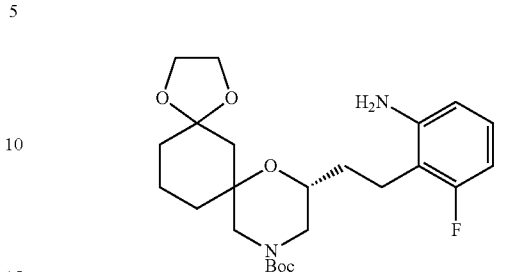

A solution of 1,4,8-trioxa-9-(R)-(2-fluoro-6-nitrostyryl)-11-benzyl-11-azadispiro[4.1.5.3]pentadecane (0.82 g, 1.75 mmol) and (Boc)$_2$O (0.56 mL, 2.44 mmol) in EtOAc (30.0 mL) was de-gassed with N$_2$ (g) for 10 minutes. To the solution, 10% palladium on carbon (82.0 mg) was added and the reaction mixture was hydrogenated at 1 atm pressure at room temperature for 24 hours. The reaction mixture was diluted with EtOAc (30.0 mL) and filtered through a pad of celite and the pad was washed with EtOAc (100 mL). The filtrate was concentrated under reduced pressure and the residue was purified by 12 g SiO$_2$ column using a gradient elution of 20-50% EtOAc in hexanes. Fractions containing the product were combined and the solvents were removed in vacuo to provide the product (0.27 g, 35%) as yellow syrup. MS: m/z=451 (M+H$^+$).

Step 7-Synthesis of tert-Butyl 9(R)-(2-((2S,3S)-3-(3,5-difluorophenyl)-3-(4-fluorophenyl)-2-azidopropanamido)-6-fluorophenethyl)-1,4,8-trioxa-11-azadispiro[4.1.5.3]pentadecane-11-carboxylate

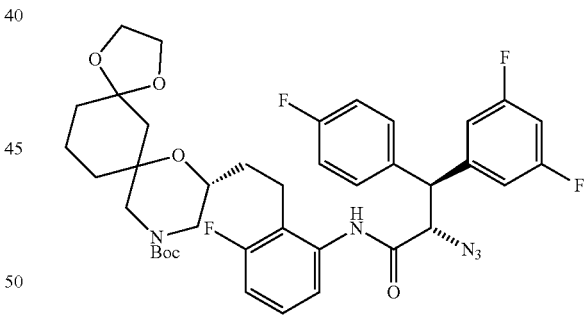

To a stirred solution of tert-butyl 1,4,8-trioxa-9-(R)-(2-fluoro-6-aminophenethyl)-11-azadispiro[4.1.5.3]pentadecane-11-carboxylate (0.27 g, 0.61 mmol) and (2S,3S)-2-azido-3-(3,5-difluorophenyl)-3-(4-fluorophenyl)propanoic acid (0.26 g, 0.83 mmol) in pyridine (6.00 mL) at −20° C. was added POCl$_3$ (0.08 mL, 0.91 mmol) slowly and the reaction mixture was allowed to reach 0° C. and stirred for 4 hours. The reaction was quenched with a saturated solution of KH$_2$PO$_4$ (2 mL) and extracted with EtOAc (100 mL). The organic layer was washed with brine (80.0 mL), dried (Na$_2$SO$_4$), filtered and concentrated under reduced pressure. The residue was purified by 12 g SiO$_2$ column using a gradient elution of 0-30% EtOAc in hexanes. Fractions containing product were combined and the solvents were removed in vacuo to provide the product (0.31 g, 69%) as a pale yellow solid. MS: m/z=776 (M+Na+).

Step 8-Synthesis of tert-Butyl 9(R)-(2-((2S,3S)-3-(3,5-difluorophenyl)-3-(4-fluorophenyl)-2-(amino) propanamido)-6-fluorophenethyl)-1,4,8-trioxa-11-azadispiro[4.1.5.3]pentadecane-11-carboxylate

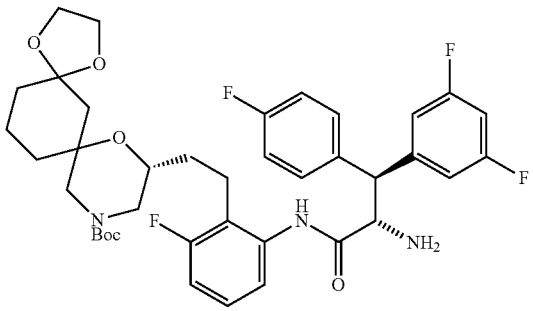 [SMILES: CC(C)(C)OC(=O)N1C[C@@H](CCc2c(F)cccc2NC(=O)[C@@H](N)[C@@H](c2ccc(F)cc2)c2cc(F)cc(F)c2)OC2(CCCC3(C2)OCCO3)C1]

To a stirred solution of tert-butyl 9(R)-(2-((2S,3S)-3-(3,5-difluorophenyl)-3-(4-fluorophenyl)-2-azidopropanamido)-6-fluorophenethyl)-1,4,8-trioxa-11-azadispiro [4.1.5.3]pentadecane-11-carboxylate (0.31 g, 0.42 mmol) in a mixture of EtOAc (4.00 mL), water (3.00 mL) was added trimethyl phosphine (1M solution in THF, 2.15 mL, 2.15 mmol) and the reaction mixture was stirred at room temperature for 10 hours. The reaction mixture was diluted with water (5.00 mL) and EtOAc (40.0 mL) and the layers were separated. The organic layer was washed with brine (30.0 mL), dried (Na2SO4), filtered and concentrated under reduced pressure. The residue was purified by 4 g SiO2 column using a gradient elution of 0-40% EtOAc in hexanes. Fractions containing product were combined and the solvents were removed in vacuo to provide the product (0.28 g, 90%) as a light yellow solid. MS: m/z=728 (M+H+).

Step 9-Synthesis of tert-Butyl 9(R)-(2-((2S,3S)-3-(3,5-difluorophenyl)-3-(4-fluorophenyl)-2-((methoxycarbonyl)amino)propanamido)-6-fluorophenethyl)-1,4,8-trioxa-11-azadispiro[4.1.5.3] pentadecane-11-carboxylate

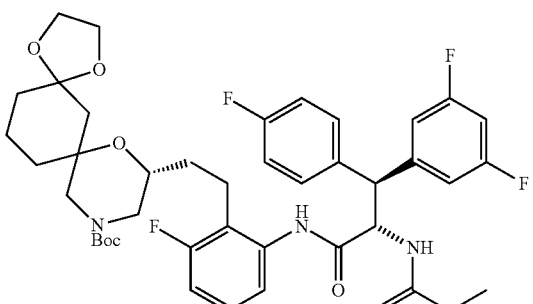

To a stirred solution of tert-butyl 9(R)-(2-((2S,3S)-3-(3,5-difluorophenyl)-3-(4-fluorophenyl)-2-(amino)propanamido)-6-fluorophenethyl)-1,4,8-trioxa-11-azadispiro [4.1.5.3]pentadecane-11-carboxylate (0.14 g, 0.19 mmol) in dichloromethane (5.00 mL) was added diisopropylethylamine (0.08 mL, 0.48 mmol), methylchloroformate (0.02 mL, 0.26 mmol) at 0° C. and stirred for 3 hours. Water (5.00 mL) was added and extracted with dichloromethane (2×20.0 mL). The combined organic extracts were washed with brine (10.0 mL), dried (Na2SO4), filtered and concentrated under reduced pressure. The residue was purified by 4 g SiO2 column using a gradient elution of 0-50% EtOAc in hexanes. Fractions containing product were combined and the solvents were removed in vacuo to provide the product (0.15 g, 98%) as an off-white solid. MS: m/z=808 (M+Na+).

Step 10-Synthesis of Compound 92 (Methyl ((1S, 2S)-1-(3,5-difluorophenyl)-3-((3-fluoro-2-(2-((2R)-8-oxo-1-oxa-4-azaspiro[5.5]undecan-2-yl)ethyl)phenyl)amino)-1-(4-fluorophenyl)-3-oxopropan-2-yl) carbamate)

To a stirred solution of tert-butyl 9(R)-(2-((2S,3S)-3-(3,5-difluorophenyl)-3-(4-fluorophenyl)-2-((methoxycarbonyl)amino)propanamido)-6-fluorophenethyl)-1,4,8-trioxa-11-azadispiro[4.1.5.3]pentadecane-11-carboxylate (0.15 g, 0.19 mmol) in dichloromethane (7.00 mL), was added trifluoroacetic acid (0.32 mL) and stirred at room temperature for 8 hours. The reaction mixture was concentrated under reduced pressure and azeotroped with dichloromethane (2×5.00 mL). The residue was purified by prep HPLC (Phenomenex Luna C18(2) column, over 4 injections) using a gradient elution of 0-90% acetonitrile (with 0.05% TFA) in water (with 0.05% TFA). Fractions containing product were combined and the solvents were removed in vacuo to provide the product (Compound 92, 0.07 g, 50%) as an amorphous white solid. MS: m/z=642 (M+H+).

Intermediate A For Examples 93-95

(R, E)-tert-butyl 4-benzyl-2-(2-fluoro-6-nitrostyryl)-1-oxa-4,9-diazaspiro[5.5]undecane-9-carboxylate

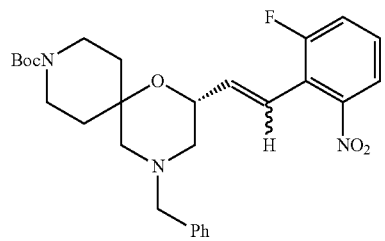 [SMILES: CC(C)(C)OC(=O)N1CCC2(CC1)CN(Cc1ccccc1)C[C@@H](C=Cc1c(F)cccc1[N+](=O)[O-])O2]

Step 1: tert-Butyl 1-oxa-6-azaspiro[2.5]octane-6-carboxylate

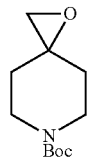

To a solution of NaH (1.68 g, 42.0 mmol) in dry DMF (70 mL) at 0° C., (CH3)3SI (8.56 g, 42.0 mmol) was added and allowed to stirred at room temperature for 30 minutes. tert-Butyl 4-oxopiperidine-1-carboxylate (7.00 g, 35.0 mmol) was added at 0° C. and the reaction mixture was stirred at room temperature for 16 hours. The reaction mixture was quenched with water (50.0 mL) and extracted with EtOAc (2×100 mL). The combined organic extracts were dried (Na₂SO₄), filtered and concentrated under reduced pressure to give the product (7.40 g, 98%) as colorless oil. MS: m/z=214 (M+H⁺).

Step 2: tert-Butyl 4-((benzylamino)methyl)-4-hydroxypiperidine-1-carboxylate

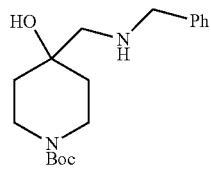 [SMILES: CC(C)(C)OC(=O)N1CCC(O)(CNCc2ccccc2)CC1]

To a solution of tert-butyl 1-oxa-6-azaspiro[2.5]octane-6-carboxylate (7.40 g, 34.7 mmol) in EtOH (70.0 mL) at room temperature was added benzyl amine (4.20 mL, 38.0 mmol) in portion-wise over a period of 10 minutes and the reaction mixture was heated at 85° C. for 16 hours. The reaction mixture was concentrated under reduced pressure. The residue was purified by 120 g SiO₂ column using a gradient elution of 0-50% EtOAc in hexanes. Fractions containing the product were combined and concentrated under reduced pressure to provide the product (9.20 g, 83%) as colorless oil. MS: m/z=321 (M+H⁺).

Step 3: (S)-tert-Butyl 4-benzyl-2-(hydroxymethyl)-1-oxa-4,9-diazaspiro[5.5]undecane-9-carboxylate

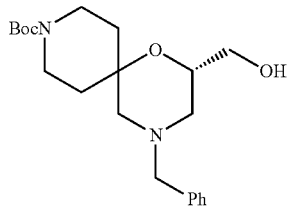

To a solution of tert-butyl 4-((benzylamino)methyl)-4-hydroxypiperidine-1-carboxylate (9.28 g, 29.0 mmol) in MeOH: H₂O (90.0 mL: 40.0 mL) was added (R)-2-(chloromethyl)oxirane (2.40 mL, 30.0 mmol) and the reaction mixture was stirred at room temperature for 16 hours. Potassium hydroxide (4.80 g, 87.0 mmol) was added and the reaction mixture was stirred at room temperature for additional 6 hours. The reaction mixture was concentrated under reduced pressure and diluted with EtOAc (200 mL), washed with saturated solution of NaHCO₃ (100 mL), water (100 mL) and concentrated under reduced pressure. The residue was purified by 120 g SiO₂ column using a gradient elution of 0-30% EtOAc in hexanes. Fractions containing the product were combined and concentrated under reduced pressure to provide the product (6.50 g, 60%) as colorless oil. MS: m/z=377 (M+H⁺).

Step 4: (S)-tert-Butyl 4-benzyl-2-formyl-1-oxa-4,9-diazaspiro[5.5]undecane-9-carboxylate

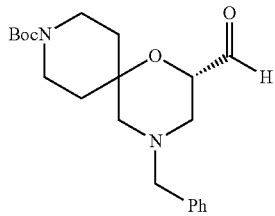

To a solution of oxalyl chloride (0.50 mL, 5.58 mmol) in dichloromethane (10.0 mL) at −78° C., was added DMSO (0.80 mL, 11.1 mmol) and stirred for 15 mins. A solution of (S)-tert-butyl 4-benzyl-2-(hydroxymethyl)-1-oxa-4,9-diazaspiro[5.5]undecane-9-carboxylate (1.05 g, 2.79 mmol) in dichloromethane (10.0 mL) was added followed by triethyl amine (1.90 mL, 13.9 mmoL), and the reaction mixture was stirred at 0° C. for 1 hour. The reaction mixture was diluted with dichloromethane (200 mL), washed with saturated solution of NaHCO₃ (100 mL), water (100 mL), dried (Na₂SO₄), filtered and concentrated under reduced pressure. The residue was purified by 24 g SiO₂ column using a gradient elution of 0-20% EtOAc in hexanes. Fractions containing the product were combined and concentrated under reduced pressure to provide the product (1.00 g, 98%) as colorless oil. MS: m/z=375 (M+H⁺).

Step 5: (R, E)-tert-Butyl 4-benzyl-2-(2-fluoro-6-nitrostyryl)-1-oxa-4,9-diazaspiro[5.5]undecane-9-carboxylate

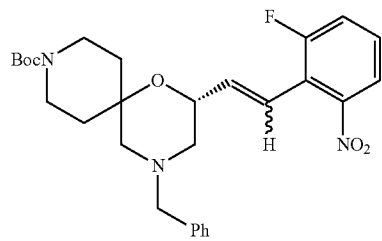 [SMILES: CC(C)(C)OC(=O)N1CCC2(CC1)CN(Cc1ccccc1)C[C@@H](C=Cc1c(F)cccc1[N+](=O)[O-])O2]

To a solution of (2-fluoro-6-nitrobenzyl)triphenylphosphonium bromide (3.50 g, 7.00 mmol) in a mixture of 1,2-dimetoxyethane/acetonitrile (30.0 mL: 10.0 mL) was added 18-crown-6 (0.18 g, 0.69 mmol) followed by potassium carbonate (1.90 g, 13.8 mmol) and stirred at room temperature for 30 minutes. A solution of (S)-tert-butyl 4-benzyl-2-formyl-1-oxa-4,9-diazaspiro[5.5]undecane-9-carboxylate (2.60 g, 6.90 mmol) in DME (5.00 mL) was added slowly and the reaction mixture was stirred at room temperature for 16 hours. The reaction mixture was filtered through a pad of celite and washed with EtOAc (100 mL). The filtrate was concentrated under reduced pressure. The residue was purified by 12 g SiO₂ column using a gradient elution of 10-20% EtOAc in hexanes. Fractions containing the compound were combined and concentrated under reduced pressure to provide the product (2.80 g, 80%) as a racemic mixture. The product was used directly in the next step without purification. MS: m/z=512 (M+H⁺).

EXAMPLE 93

(βS)-4-chloro-β-(3,5-difluorophenyl)-N-(3-fluoro-2-{2-[(2R)-9-(methylsulfonyl)-1-oxa-4,9-diazaspiro[5.5]undec-2-yl]ethyl}phenyl)-L-phenylalaninamide

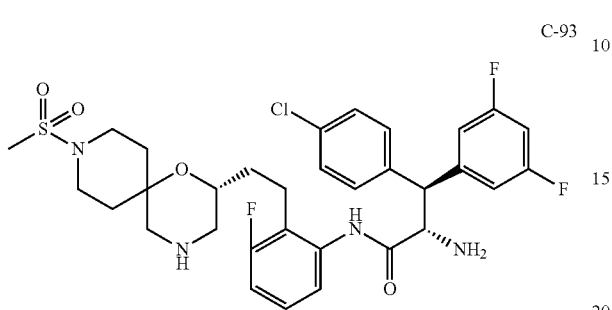

C-93

Step 1: (R, E)-4-Benzyl-2-(2-fluoro-6-nitrostyryl)-9-(methylsulfonyl)-1-oxa-4,9-diazaspiro[5.5]undecane

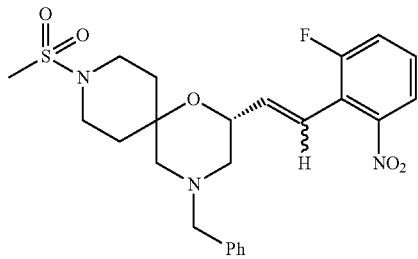 [SMILES: CS(=O)(=O)N1CCC2(CC1)CN(Cc1ccccc1)C[C@@H](C=Cc1c(F)cccc1[N+](=O)[O-])O2]

To a stirred solution of (R, E)-tert-butyl 4-benzyl-2-(2-fluoro-6-nitrostyryl)-1-oxa-4,9-diazaspiro[5.5]undecane-9-carboxylate (0.50 g, 0.97 mmol) in dichloromethane (10.0 mL) at room temperature, was added trifluoroacetic acid (1.00 mL, 13.0 mmol) and stirred for 30 minutes at room temperature and the reaction mixture was concentrated under reduced pressure.

The residue was dissolved in dichloromethane (10.0 mL) at 0° C. and di-isopropylamine (0.90 mL, 4.80 mmol) followed by methanesulfonyl chloride (0.10 mL, 1.10 mmol) was added and stirred at 0° C. for 1 hour. The reaction mixture was quenched with saturated solution of NaHCO₃ (20.0 mL) and extracted with dichloromethane (2×50.0 mL). The combined organic extracts were washed with brine (20.0 mL), dried (Na₂SO₄) and concentrated under reduced pressure. The residue was purified by 24 g SiO₂ column using a gradient elution of 0-20% EtOAc in hexanes. Fractions containing product were combined and the solvents were removed in vacuum to provide the product (0.40 g, 83%) as a colorless semi-solid. MS: m/z=490 (M+H⁺).

Step 2: (R)-tert-Butyl 2-(2-amino-6-fluorophenethyl)-9-(methylsulfonyl)-1-oxa-4,9-diazaspiro[5.5]undecane-4-carboxylate

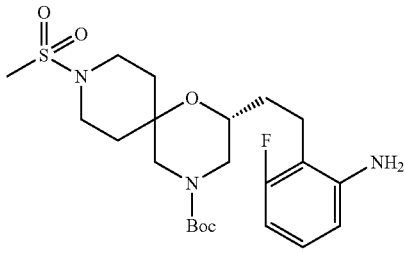 [SMILES: CC(C)(C)OC(=O)N1C[C@@H](CCc2c(N)cccc2F)OC2(CCN(S(C)(=O)=O)CC2)C1]

A solution of (R, E)-4-Benzyl-2-(2-fluoro-6-nitrostyryl)-9-(methylsulfonyl)-1-oxa-4,9-diazaspiro[5.5]undecane (0.40 g, 0.81 mmol) and (Boc)₂O (0.20 mL, 0.89 mmol) in EtOAc (10.0 mL) was de-gassed with N₂ (g) for 10 minutes, and palladium hydroxide on carbon (0.10 g) was added and the reaction mixture was hydrogenated at 1 atm pressure at room temperature for 24 hours. The reaction mixture was diluted with EtOAc (10.0 mL) and filtered through a pad of celite and the pad was washed with EtOAc (50.0 mL). The filtrate was concentrated under reduced pressure and the residue was purified by 12 g SiO₂ column using a gradient elution of 20-50% EtOAc in hexanes. Fractions containing the product were combined and concentrated under reduced pressure to provide the product (0.25 g, 65%) as white solid. MS: m/z=472 (M+H⁺).

Step 3: (R)-tert-Butyl 2-(2-((2S,3S)-2-azido-3-(4-chlorophenyl)-3-(3,5-difluorophenyl)propanamido)-6-fluorophenethyl)-9-(methylsulfonyl)-1-oxa-4,9-diazaspiro[5.5]undecane-4-carboxylate

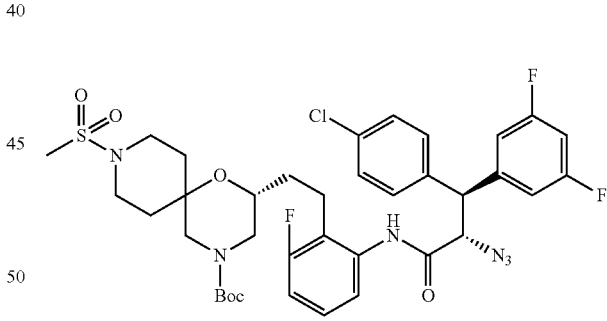

To a stirred solution of (R)-tert-butyl 2-(2-amino-6-fluorophenethyl)-9-(methylsulfonyl)-1-oxa-4,9-diazaspiro[5.5]undecane-4-carboxylate (0.25 g, 0.53 mmol) and (2S,3S)-2-azido-3-(4-chlorophenyl)-3-(3,5-difluorophenyl)propanoic acid (0.19 mg, 0.58 mmol) in pyridine (5.00 mL) at −20° C. was added POCl₃ (0.06 mL, 0.63 mmol) and the reaction solution was allowed to reach 0° C. over a period of 2 hours. The reaction mixture was quenched with saturated solution of KH₂PO₄ (1.00 mL), extracted with EtOAc (3×20.0 mL) and the combined organic extracts were washed with brine (20.0 mL), dried (Na₂SO₄), filtered and concentrated under reduced pressure. The residue was purified by 12 g SiO₂ column using a gradient elution of 0-100% EtOAc in hexanes. Fractions containing product were com- Step 4: (R)-tert-Butyl 2-(2-((2S,3S)-2-amino-3-(4-chlorophenyl)-3-(3,5-difluorophenyl)propanamido)-6-fluorophenethyl)-9-(methylsulfonyl)-1-oxa-4,9-diazaspiro[5.5]undecane-4-carboxylate

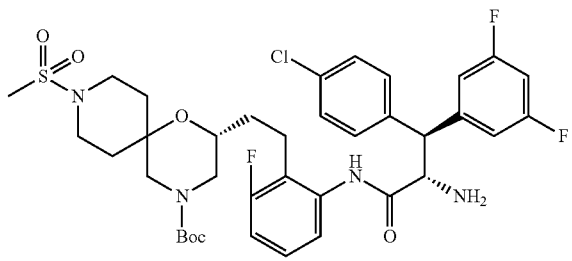 [SMILES: CC(C)(C)OC(=O)N1C[C@@H](CCc2c(F)cccc2NC(=O)[C@@H](N)[C@@H](c2ccc(Cl)cc2)c2cc(F)cc(F)c2)OC2(CCN(S(C)(=O)=O)CC2)C1]

To a stirred solution of (R)-tert-butyl 2-(2-((2S,3S)-2-azido-3-(4-chlorophenyl)-3-(3,5-difluorophenyl)propanamido)-6-fluorophenethyl)-9-(methylsulfonyl)-1-oxa-4,9-diazaspiro[5.5]undecane-4-carboxylate (0.30 g, 0.25 mmol) in a mixture of EtOAc (5.00 mL), water (1.00 mL) was added trimethylphosphine (2.50 mL, 1M solution in THF, 2.50 mmol) and stirred at room temperature for 16 hours. Water (20.0 mL) was added and extracted with EtOAc (2×50.0 mL). The organic layer was washed with brine (20.0 mL), dried (Na$_2$SO$_4$), filtered and concentrated under reduced pressure. The crude product (0.30 g) used directly in the next step without purification. MS: m/z 766 (M+H$^+$).

Step 5: (2S,3S)-2-Amino-3-(4-chlorophenyl)-3-(3,5-difluorophenyl)-N-(3-fluoro-2-(2-((R)-9-(methylsulfonyl)-1-oxa-4,9-diazaspiro[5.5]undecan-2-yl)ethyl)phenyl)propanamide To a stirred solution of (R)-tert-butyl 2-(2-((2S,3S)-2-amino-3-(4-chlorophenyl)-3-(3,5-difluorophenyl)propanamido)-6-fluorophenethyl)-9-(methylsulfonyl)-1-oxa-4,9-diazaspiro[5.5]undecane-4-carboxylate (0.10 g, 0.76 mmol) in dichloromethane (3.00 mL), added trifluoroacetic acid (0.50 mL) and stirred at room temperature for 2 hours. The reaction mixture was concentrated to dryness under reduced pressure and azeotroped with dichloromethane (5.00 mL). The residue was purified by 30 g C18 column using a gradient elution of 0-100% acetonitrile in water. Fractions containing product were combined and the solvents were removed in vacuum to provide the product (0.64 g, 65%) as an amorphous white solid. MS: m/z 665 (M+H$^+$).

EXAMPLE 94 methyl {(1S,2S)-2-(4-chlorophenyl)-2-(3,5-difluorophenyl)-1-[(3-fluoro-2-{2-[(2R)-9-(methylsulfonyl)-1-oxa-4,9-diazaspiro[5.5]undec-2-yl]ethyl}phenyl)carbamoyl]ethyl}carbamate

C-94

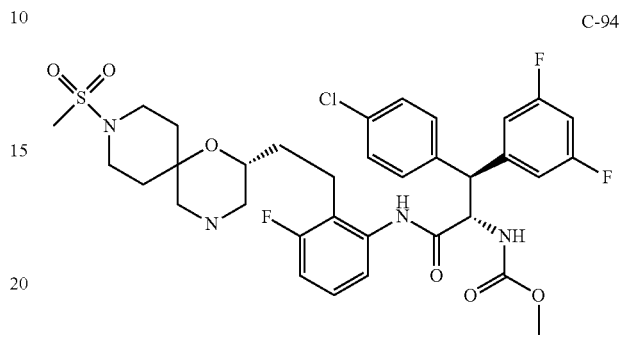

Step 1: (R)-tert-Butyl 2-(2-((2S,3S)-3-(4-chlorophenyl)-3-(3,5-difluorophenyl)-2-((methoxycarbonyl)amino)propanamido)-6-fluorophenethyl)-9-(methylsulfonyl)-1-oxa-4,9-diazaspiro[5.5]undecane-4-carboxylate

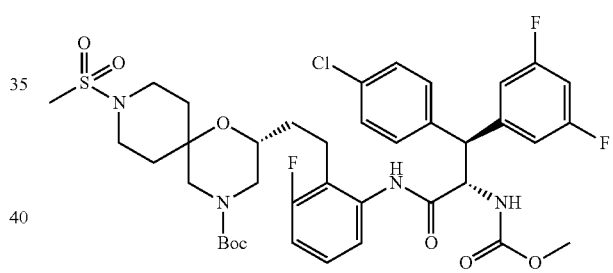

To a stirred solution of (R)-tert-butyl 2-(2-((2S,3S)-2-amino-3-(4-chlorophenyl)-3-(3,5-difluorophenyl)propanamido)-6-fluorophenethyl)-9-(methylsulfonyl)-1-oxa-4,9-diazaspiro[5.5]undecane-4-carboxylate (0.20 g, 0.16 mmol) in dichloromethane (3.00 mL) was added diisopropylethylamine (0.10 mL, 0.52 mmol), methylchloroformate (0.24 mL, 0.31 mmol) at 0° C. and stirred for 15 min. Water (5.00 mL) was added and extracted with dichloromethane (2×20.0 mL). The organic layer was washed with brine (10.0 mL), dried (Na$_2$SO$_4$), filtered and concentrated under reduced pressure. The residue was purified by 12 g SiO$_2$ column using a gradient elution of 0-100% EtOAc in hexanes. Fractions containing product were combined and the solvents were removed in vacuum to provide the product (0.20 g, 81%) as an off-white solid. MS: m/z 823 (M+H$^+$).

Step 2: Methyl ((1S,2S)-1-(4-chlorophenyl)-1-(3,5-difluorophenyl)-3-((3-fluoro-2-(2-((R)-9-(methylsulfonyl)-1-oxa-4,9-diazaspiro[5.5]undecan-2-yl)ethyl)phenyl)amino)-3-oxopropan-2-yl)carbamate To a stirred solution of (R)-tert-butyl 2-(2-((2S,3S)-3-(4-chlorophenyl)-3-(3,5-difluorophenyl)-2-((methoxycarbonyl)amino)propanamido)-6-fluorophenethyl)-9-(methylsulfonyl)-1-oxa-4,9-diazaspiro[5.5]undecane-4-carboxylate (0.20 g, 0.24 mmol) in dichloromethane (2.00 mL), added trifluoroacetic acid (1.00 mL) and stirred at room temperature for 2 hours. The reaction mixture was concentrated under reduced pressure and azeotroped with dichloromethane (5.00 mL). The residue was purified by 30 g C18 column using a gradient elution of 0-100% acetonitrile in water. Fractions containing product were combined and the solvents were removed in vacuum to provide the product (0.10 g, 55%) as an amorphous white solid. MS: m/z 723 (M+H$^+$).

EXAMPLE 95

(2S,3S)—N-(2-(2-((R)-9-Acetyl-1-oxa-4,9-diazaspiro[5.5]undecan-2-yl)ethyl)-3-fluorophenyl)-2-amino-3-(4-chlorophenyl)-3-(3,5-difluorophenyl)propanamide

C-95

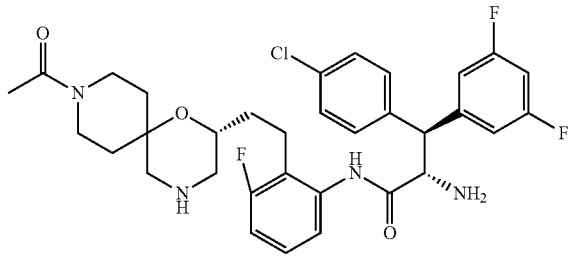

Step 1: (R, E)-1-(4-Benzyl-2-(2-fluoro-6-nitrostyryl)-1-oxa-4,9-diazaspiro[5.5]undecan-9-yl)ethanone

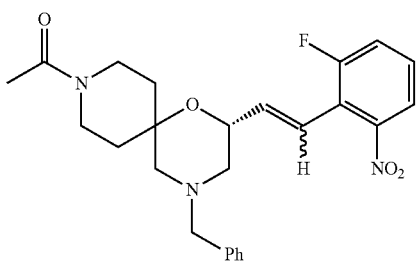 [SMILES: CC(=O)N1CCC2(CC1)CN(Cc1ccccc1)C[C@@H](C=Cc1c(F)cccc1[N+](=O)[O-])O2]

To a stirred solution of (R, E)-tert-butyl 4-benzyl-2-(2-fluoro-6-nitrostyryl)-1-oxa-4,9-diazaspiro[5.5]undecane-9-carboxylate (1.30 g, 2.50 mmol) in dichlorormethane (10.0 mL) was added trifluoroacetic acid (1.00 mL, 13.0 mmol) and stirred at room temperature for 30 minutes and concentrated under reduced pressure. The residue was dissolved in dichloromethane (10.0 mL) and cooled to 0° C., Triethyl amine (1.00 mL, 7.50 mmol) and acetyl chloride (0.20 mL, 3.00 mmol) were added and stirred at 0° C. for 1 hour. The reaction mixture was quenched with saturated solution of NaHCO$_3$ (20.0 mL) and extracted with dichlormethane (2×50.0 mL). The combined organic extracts were washed with brine (20.0 mL), dried (Na$_2$SO$_4$), filtered and concentrated under reduced pressure. The residue was purified by 24 g SiO$_2$ column using a gradient elution of 0-20% EtOAc in hexanes. Fractions containing product were combined and the solvents were removed in vacuum to provide the product (800 mg, 69%) as a colorless semi-solid. MS: m/z=454 (M+H$^+$).

Step 2: (R)-tert-Butyl 9-acetyl-2-(2-amino-6-fluorophenethyl)-1-oxa-4,9-diazaspiro[5.5]undecane-4-carboxylate

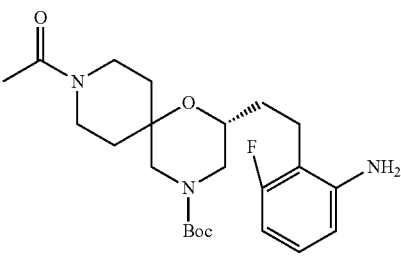 [SMILES: CC(=O)N1CCC2(CC1)CN(C(=O)OC(C)(C)C)C[C@@H](CCc1c(N)cccc1F)O2]

A solution of (R, E)-1-(4-benzyl-2-(2-fluoro-6-nitrostyryl)-1-oxa-4,9-diazaspiro[5.5]undecan-9-yl)ethanone (0.80 g, 1.70 mmol) and (Boc)$_2$O (0.42 g, 1.90 mmol) in EtOAc (10.0 mL) was de-gassed with N$_2$ (g) for 10 minutes. Palladium hydroxide on carbon (0.20 g) was added and the reaction mixture was hydrogenated at 1 atm pressure at room temperature for 24 hours. The reaction mixture was diluted with EtOAc and filtered through a pad of celite and washed with EtOAc (100 mL) and the filtrate was concentrated under reduced pressure. The residue was purified by 12 g SiO$_2$ column using a gradient elution of 20-50% EtOAc in hexanes. Fractions containing the product were combined and concentrated under reduced pressure to provide the product (0.29 g, 40%) as white solid. MS: m/z=436 (M+H$^+$).

Step 3: (R)-tert-Butyl 9-acetyl-2-(2-((2S,3S)-2-azido-3-(4-chlorophenyl)-3-(3,5-difluorophenyl)propanamido)-6-fluorophenethyl)-1-oxa-4,9-diazaspiro[5.5]undecane-4-carboxylate

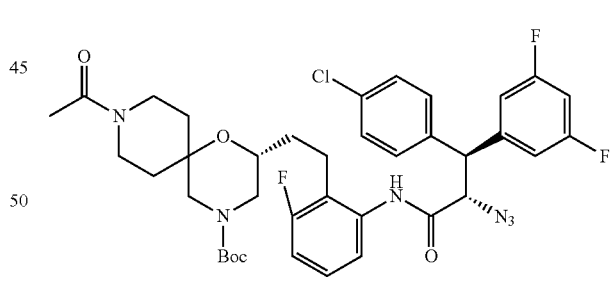

To a stirred solution of (R)-tert-butyl 9-acetyl-2-(2-amino-6-fluorophenethyl)-1-oxa-4,9-diazaspiro[5.5]undecane-4-carboxylate (0.29 g, 0.66 mmol) and (2S,3S)-2-azido-3-(4-chlorophenyl)-3-(3,5-difluorophenyl)propanoic acid (0.22 g, 0.66 mmol) in pyridine (5 mL) at −20° C. was added POCl$_3$ (0.12 mL, 0.79 mmol) dropwise and the reaction solution was allowed to reach 0° C. over a period of 2 hours. The reaction mixture was quenched with saturated solution of KH$_2$PO$_4$ (1.00 mL), extracted with EtOAc (3×20.0 mL) and the combined organic extracts were washed with brine (20.0 mL), dried (Na$_2$SO$_4$), filtered and concentrated under reduced pressure. The residue was purified by 12 g SiO$_2$ column using a gradient elution of 0-100%

EtOAc in hexanes. Fractions containing the product were combined and concentrated under reduced pressure to provide the product (0.35 g, 70%) as a white semi-solid. MS: m/z=755 (M+H⁺).

Step 4: (R)-tert-Butyl 9-acetyl-2-(2-((2S,3S)-2-amino-3-(4-chlorophenyl)-3-(3,5-difluorophenyl)propanamido)-6-fluorophenethyl)-1-oxa-4,9-diazaspiro[5.5]undecane-4-carboxylate

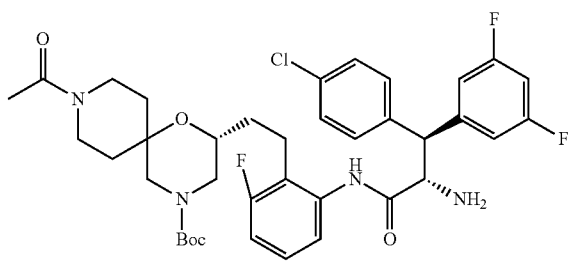 [SMILES: CC(=O)N1CCC2(CC1)CN(C(=O)OC(C)(C)C)C[C@@H](CCc1c(F)cccc1NC(=O)[C@@H](N)[C@@H](c1ccc(Cl)cc1)c1cc(F)cc(F)c1)O2]

To a stirred solution of (R)-tert-butyl 9-acetyl-2-(2-((2S,3S)-2-azido-3-(4-chlorophenyl)-3-(3,5-difluorophenyl)propanamido)-6-fluorophenethyl)-1-oxa-4,9-diazaspiro[5.5]undecane-4-carboxylate (0.35 g, 0.46 mmol) in a mixture of EtOAc (5.00 mL), water (1.00 mL), was added trimethylphosphine (4.60 mL, 1M solution in THF, 4.60 mmol) and stirred at room temperature for 16 hours. Water (20.0 mL) was added and extracted with EtOAc (2×50.0 mL). The organic layer was washed with brine (20.0 mL), dried (Na₂SO₄), filtered and concentrated under reduced pressure. The crude product (0.36 g) was used directly in the next step without any purification. MS: m/z 729 (M+H⁺).

Step 5: (2S,3S)—N-(2-(2-((R)-9-Acetyl-1-oxa-4,9-diazaspiro[5.5]undecan-2-yl)ethyl)-3-fluorophenyl)-2-amino-3-(4-chlorophenyl)-3-(3,5-difluorophenyl)propanamide To a stirred solution of (R)-tert-butyl 9-acetyl-2-(2-((2S,3S)-2-amino-3-(4-chlorophenyl)-3-(3,5-difluorophenyl)propanamido)-6-fluorophenethyl)-1-oxa-4,9-diazaspiro[5.5]undecane-4-carboxylate (0.11 g, 0.15 mmol) in dichloromethane (3.00 mL), added trifluoroacetic acid (0.50 mL) and stirred at room temperature for 2 hours. The reaction mixture was concentrated to dryness under reduced pressure and azeotroped with dichloromethane (5.00 mL). The residue was purified by 30 g C18 column using a gradient elution of 0-100% acetonitrile in water. Fractions containing product were combined and concentrated under reduced pressure to provide the product (0.07 g, 70%) as an amorphous white solid. MS: m/z 629 (M+H⁺).

Intermediate B for Examples 96-98

(R)-tert-Butyl 2-ethynyl-1,9-dioxa-4-azaspiro[5.5]undecane-4-carboxylate

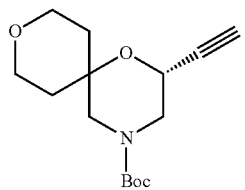 [SMILES: C#C[C@@H]1CN(C(=O)OC(C)(C)C)CC2(CCOCC2)O1]

Step 1:
4-Hydroxytetrahydro-2H-pyran-4-carbonitrile

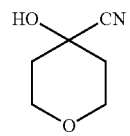

To a solution of dihydro-2H-pyran-4(3H)-one (20.0 g, 199 mmol) in toluene (200 mL) under N₂ atmosphere, was added zinc iodide (0.64 g, 1.99 mmol) and stirred at room temperature for 15 minutes. The reaction mixture was cooled to 0° C. and TMSCN (19.8 g, 199 mmol) was added dropwise over a period of 30 minutes. The cooling bath was removed and the reaction mixture was stirred at room temperature for 16 hours. The reaction mixture was concentrated to half the volume and cooled to 0° C. A solution of aqueous 2 N HCl (300 mL) was added slowly and stirred at room temperature for additional 1 hour. The reaction mixture was diluted with EtOAc (500 mL), and the organic layer was separated. The organic layer was washed with H₂O (3×50 mL), brine (50 mL), dried (Na₂SO₄), filtered and concentrated under reduced pressure to afford crude product (25.0 g, 98%) as a pale brown liquid. MS: m/z=128 (M+H⁺). The crude product was directly used in the next step without purification.

Step 2: 4-(Aminomethyl)tetrahydro-2H-pyran-4-ol hydrochloride

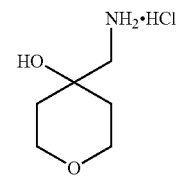

To a 2 L 3-neck RBF equipped with over head stirrer, thermocouple, dropping funnel and nitrogen inlet, charged LiAlH₄ (18.7 g, 492 mmol) and cooled to 0° C., was added anhydrous THF. To this reaction mixture was added a solution of 4-hydroxytetrahydro-2H-pyran-4-carbonitrile (25.0 g, 196 mmol) in anhydrous THF (250 mL) slowly over a period of 1 hour. After complete addition, the reaction mixture was warmed up to room temperature; and the dropping funnel was replaced with reflux condenser and heated to reflux at 70° C. for 4 hours. The reaction mixture was cooled to room temperature and cooled further to −10° C. using dry-ice acetone bath and quenched with 2N NaOH solution (150 mL) until white precipitation occurred. The reaction mixture was warmed up to room temperature, diluted with ethyl acetate (500 mL) and stirred for 10 minutes. The precipitated while solid was filtered through celite pad and the pad was washed with EtOAc (300 mL). The filtrate was evaporated under reduced pressure to provide a gummy liquid, which was dissolved in MTBE (100 mL) and cooled to 0° C. To the reaction mixture was added HCl (4 N in dioxane, 100 mL) dropwise and stirred at 0° C. for 30 minutes and at room temperature for an additional 30 minutes. The precipitated solid was collected by filtration under vacuum, with a constant flow of N₂ gas, to provide the product (21.0 g, 64%) as an off white solid; MS: m/z=132 (M+H⁺).

Step 3: 4-((Benzylamino)methyl)tetrahydro-2H-pyran-4-ol

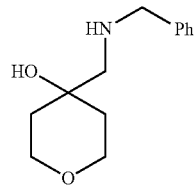 [SMILES: OC1(CNCc2ccccc2)CCOCC1]

To an ice cooled solution of 4-(aminomethyl)tetrahydro-2H-pyran-4-ol hydrochloride (16.0 g, 95.5 mmol) in CH₂Cl₂ (200 mL), Et₃N (9.66 g, 95.5 mmol) was added and stirred for 30 minutes. The reaction mixture was concentrated under reduced pressure and the solid residue was dissolved in anhydrous MeOH (150 mL). Benzaldehyde (10.1 g, 105 mmol) was added in one portion and stirred at room temperature for 2 hours. To this reaction mixture NaCNBH₃ (17.9 g, 286 mmol) was added portion wise and stirred at room temperature for 16 hours. The reaction mixture was concentrated under reduced pressure, dissolved the suspension in water (100 mL) and extracted EtOAc (3×200 mL). The combined organic extracts were washed with water (2×100 mL), brine (100 mL), dried (Na₂SO₄), filtered and concentrated under reduced pressure. The residue was purified by 120 g SiO₂ column using a gradient elution of 0-80% EtOAc in hexanes. Fractions containing the product were combined and concentrated under vacuo to provide the product (14.7 g, 73%) as colorless foam. MS: m/z=222 (M+H⁺).

Step 4: (S)-(4-Benzyl-1,9-dioxa-4-azaspiro[5.5]undecan-2-yl)methanol

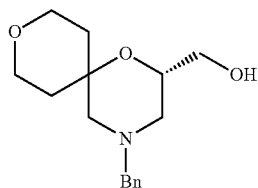 [SMILES: OC[C@@H]1CN(Cc2ccccc2)CC2(CCOCC2)O1]

To a solution of 4-((benzylamino)methyl)tetrahydro-2H-pyran-4-ol (14.7 g, 66.5 mmol) in a mixture of iso-proponol:H₂O (147 mL, 1:1) was added (R)-2-(chloromethyl)oxirane (6.15 g, 66.5 mmol) and stirred at room temperature for 48 hours. To this reaction mixture solid KOH (11.2 g, 199 mmol) was added in three portions and stirred at room temperature for 3 hours. The reaction mixture was concentrated under reduced pressure and the residue was dissolved in EtOAc (500 mL). The EtOAc layer was washed with H₂O (2×100 mL), brine (100 mL), dried (Na₂SO₄), filtered and concentrated under reduced pressure. The residue was purified by 120 g SiO₂ column using a gradient elution of 0-60% EtOAc in hexanes. Fractions containing the product were combined and concentrated under vacuo to provide the product (14.8 g, 81%) as colorless liquid.

Step 5: (S)-tert-Butyl 2-(hydroxymethyl)-1,9-dioxa-4-azaspiro[5.5]undecane-4-carboxylate

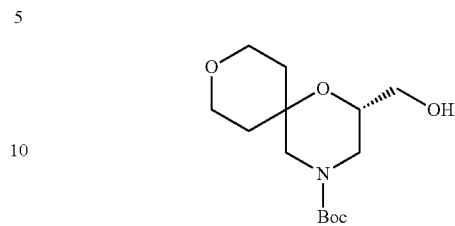

A solution of (S)-(4-benzyl-1,9-dioxa-4-azaspiro[5.5]undecan-2-yl)methanol (14.8 g, 53.2 mmol) and Boc₂O (14.0 g, 63.8 mmol) in methanol (150 mL) was de-gassed with N₂ for 10 minutes. To this reaction mixture 10% Pd/C (6.00 g, 40% wt/wt) was added portion wise and hydrogenated at 45 psi for 18 hours. The reaction mixture was filtered through celite pad and the pad was washed with methanol (200 mL). The filtrate was concentrated under reduced pressure and the residue was purified by 120 g SiO₂ column using a gradient elution of 0-70% EtOAc in hexanes. Fractions containing the product were combined and concentrated under vacuo to provide the product (13.4 g, 87%) as colorless foam. MS: m/z=278 (M+H⁺).

Step 6: (S)-tert-Butyl 2-formyl-1,9-dioxa-4-azaspiro[5.5]undecane-4-carboxylate

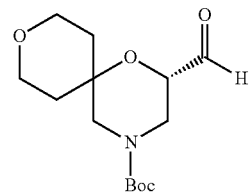 [SMILES: CC(C)(C)OC(=O)N1C[C@@H](C=O)OC2(CCOCC2)C1]

A 500 mL 3-neck RBF equipped with thermocouple, dropping funnel and nitrogen inlet, was charged with CH₂Cl₂ (100 mL). The reaction mixture was cooled to −74° C. and oxalyl chloride (11.8 g, 93.0 mmol) was added, followed by a solution of DMSO (14.5 g, 186.1 mmol) in CH₂Cl₂ (50.0 mL). The reaction mixture was stirred at −74° C. for another 30 minutes and a solution of (S)-tert-butyl 2-(hydroxymethyl)-1,9-dioxa-4-azaspiro[5.5]undecane-4-carboxylate (13.4 g, 46.5 mmol) in CH₂Cl₂ (50.0 mL) was added in a dropwise manner. The reaction mixture was stirred at −74° C. for additional 1 hour and quenched with a solution of Et₃N (28.3 g, 279 mmol) in CH₂Cl₂ (50.0 mL) and stirred at −74° C. for 30 minutes and allowed to reach room temperature gradually. The reaction mixture was poured into ice cold H₂O (200 mL) and the organic layer was separated. The aqueous layer was extracted with CH₂Cl₂ (2×200 mL). The combined organic extracts were dried (Na₂SO₄), filtered and evaporated under reduced pressure to provide the product (15.1 g, crude). The crude product was directly used in the next step without further purification. MS: m/z=276 (M+H⁺).

Step 7: (R)-tert-Butyl 2-ethynyl-1,9-dioxa-4-azaspiro[5.5]undecane-4-carboxylate

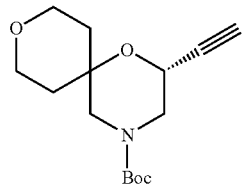 [SMILES: C#C[C@@H]1CN(C(=O)OC(C)(C)C)CC2(CCOCC2)O1]

To a solution of (S)-tert-butyl 2-formyl-1,9-dioxa-4-azaspiro[5.5]undecane-4-carboxylate (4.20 g, 14.7 mmol) in anhydrous MeOH (63.0 mL), $K_2CO_3$ (6.1 g, 44.20 mmol) was added under nitrogen atmosphere and stirred at room temperature for 10 minutes. The reaction mixture was cooled to +5° C. and Bestmann-Ohira reagent (4.24 g, 22.10 mmol) was added. The reaction mixture was allowed to gradually reach to room temperature and stirred for 16 hours. The reaction mixture was quenched with $H_2O$ (50.0 mL) and concentrated the solvents under reduced pressure. The aqueous layer was diluted further with $H_2O$ (100 mL) and extracted with EtOAc (3×150 mL). The combined organic extracts were washed with brine (100 mL), dried ($NaSO_4$), filtered and concentrated under reduced pressure. The residue was purified by 40 g $SiO_2$ column using a gradient elution of 0-20% EtOAc in hexanes. Fractions containing the product were combined and concentrated under vacuo to provide the product (1.80 g, 44%) as pale brown foam. MS: m/z=282 (M+H$^+$).

EXAMPLE 96

(βS)-4-chloro-β-(3,5-difluorophenyl)-N-(2-{2-[(2R)-1,9-dioxa-4-azaspiro[5.5]undec-2-yl]ethyl}-3-fluorophenyl)-L-phenylalaninamide

C-96

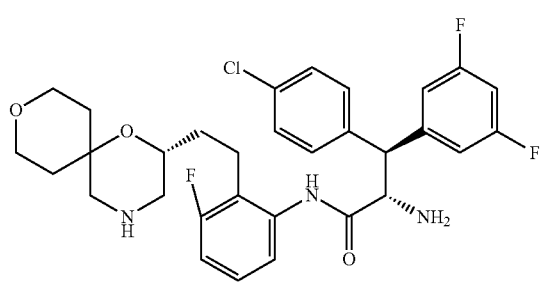

Step 1: (R)-tert-Butyl 2-((2-amino-6-fluorophenyl)ethynyl)-1,9-dioxa-4-azaspiro[5.5]undecane-4-carboxylate

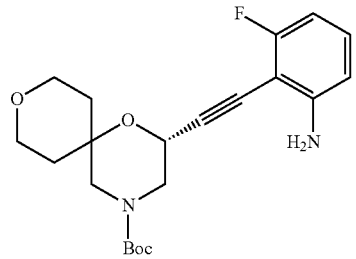 [SMILES: CC(C)(C)OC(=O)N1C[C@@H](C#Cc2c(N)cccc2F)OC2(CCOCC2)C1]

To a solution of (R)-tert-butyl 2-ethynyl-1,9-dioxa-4-azaspiro[5.5]undecane-4-carboxylate (3.00 g, 10.7 mmol) in anhydrous $CH_3CN$ (36.0 mL) in a sealed tube was added 3-fluoro-2-iodoaniline (3.0 g, 12.811 mmol). The reaction mixture was degassed with Ar(g) for 15 minutes and added bis(triphenylphosphine)palladium(II) dichloride (0.52 g, 0.74 mmol) and CuI (0.20 g, 1.06 mmol). The reaction mixture was degassed for an additional 5 min and $Et_3N$ (3.24 g, 32.1 mmol) was added and the mixture was heated to 80° C. for 2 hours. The reaction mixture was cooled to room temperature and concentrated the solvents under reduced pressure. The residue was purified by 40 g $SiO_2$ column using a gradient elution of 0-40% EtOAc in hexanes. Fractions containing the product were combined and concentrated under vacuo to provide the product (2.60 g, 62%); MS: m/z=391 (M+H$^+$).

Step 2: (R)-tert-Butyl 2-(2-amino-6-fluorophenethyl)-1,9-dioxa-4-azaspiro[5.5]undecane-4-carboxylate

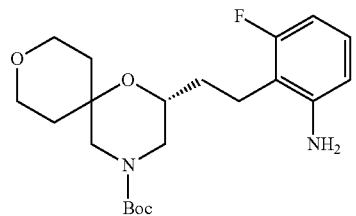 [SMILES: CC(C)(C)OC(=O)N1C[C@@H](CCc2c(N)cccc2F)OC2(CCOCC2)C1]

A solution of (R)-tert-butyl 2-((2-amino-6-fluorophenyl)ethynyl)-1,9-dioxa-4-azaspiro[5.5]undecane-4-carboxylate (0.48 g, 1.20 mmol) in methanol (10.0 mL) was degassed with $N_2$ for 15 min. To this reaction mixture 10% Pd/C (0.48 g, 30% wt/wt) was added portion wise and hydrogenated at 40 psi for 8 hours. The reaction mixture was filtered through celite pad and washed the pad with methanol (100 mL). The filtrate was concentrated under reduced pressure and the residue was purified by 12 g $SiO_2$ column using a gradient elution of 0-50% EtOAc in hexanes. Fractions containing the product were combined and concentrated under vacuo to provide the product (0.42 g, 87%) as off-white foam. MS: m/z=395 (M+H$^+$).

Step 3: (R)-tert-Butyl 2-(2-((2S,3S)-2-azido-3-(4-chlorophenyl)-3-(3,5-difluorophenyl)propanamido)-6-fluorophenethyl)-1,9-dioxa-4-azaspiro[5.5]undecane-4-carboxylate

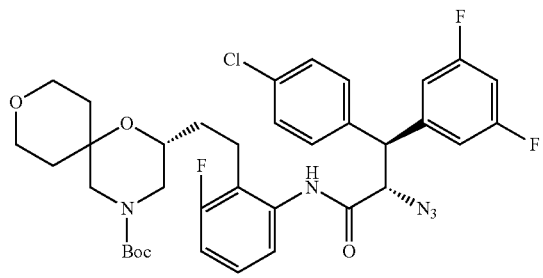 [SMILES: CC(C)(C)OC(=O)N1C[C@@H](CCc2c(F)cccc2NC(=O)[C@@H](N=[N+]=[N-])[C@@H](c2ccc(Cl)cc2)c2cc(F)cc(F)c2)OC2(CCOCC2)C1]

To a solution of (R)-tert-butyl 2-(2-amino-6-fluorophenethyl)-1,9-dioxa-4-azaspiro[5.5]undecane-4-carboxylate (0.25 g, 0.634 mmol) and (2S,3S)-2-azido-3-(4-chlorophenyl)-3-(3,5-difluorophenyl)propanoic acid (0.25 g, 0.761 mmol) in anhydrous pyridine (5.00 mL) at −20° C. was added POCl₃ (0.15 g, 0.95 mmol) dropwise over a period of 10 minutes. The reaction mixture was gradually allowed to reach room temperature and stirred for and stirred for 1 hour. The reaction mixture was quenched with a saturated solution of NaHCO₃ and diluted with EtOAc (100 mL). The organic layer was separated, washed with H₂O (2×25.0 mL), brine (25.0 mL), dried (Na₂SO₄), filtered and concentrated under reduced pressure. The residue was purified by 12 g SiO₂ column using a gradient elution of 0-40% EtOAc in hexanes. Fractions containing the product were combined and concentrated under vacuo to provide the product (0.40 g, 88%) as brown foam. MS: m/z=715 (M+H⁺).

Step 4: (R)-tert-Butyl 2-(2-((2S,3S)-2-amino-3-(4-chlorophenyl)-3-(3,5-difluorophenyl)propanamido)-6-fluorophenethyl)-1,9-dioxa-4-azaspiro[5.5]undecane-4-carboxylate

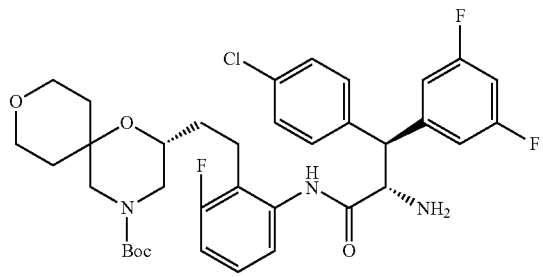 [SMILES: CC(C)(C)OC(=O)N1C[C@@H](CCc2c(F)cccc2NC(=O)[C@@H](N)[C@@H](c2ccc(Cl)cc2)c2cc(F)cc(F)c2)OC2(CCOCC2)C1]

To a solution of (R)-tert-butyl 2-(2-((2S,3S)-2-azido-3-(4-chlorophenyl)-3-(3,5-difluorophenyl)propanamido)-6-fluorophenethyl)-1,9-dioxa-4-azaspiro[5.5]undecane-4-carboxylate (0.40 g, 0.56 mmol) in EtOAc: H₂O (4.00 mL, 1:1) at room temperature, trimethyl phosphine (0.21 g, 2.80 mmol) was added in one portion and stirred at room temperature for 16 hours. The reaction mixture was diluted with EtOAc (100 mL), washed with H₂O (2×25.0 mL), brine (25.0 mL), dried (Na₂SO₄), filtered and concentrated under reduced pressure. The residue was purified by 12 g SiO₂ column using a gradient elution of 0-50% EtOAc in hexanes. Fractions containing the product were combined and concentrated under vacuo to provide the product (380 mg, 98%) as colorless foam. MS: m/z=689 (M+H⁺).

Step 5: (βS)-4-chloro-β-(3,5-difluorophenyl)-N-(2-{2-[(2R)-1,9-dioxa-4-azaspiro[5.5]undec-2-yl]ethyl}-3-fluorophenyl)-L-phenylalaninamide To a stirred solution of (R)-tert-butyl 2-(2-((2S,3S)-2-amino-3-(4-chlorophenyl)-3-(3,5-difluorophenyl)propanamido)-6-fluorophenethyl)-1,9-dioxa-4-azaspiro[5.5]undecane-4-carboxylate (0.15 g, 0.22 mmol) in dichloromethane (3.00 mL), added trifluoroacetic acid (0.12 g, 1.09 mmol) and stirred at room temperature for 16 hours. The reaction mixture was concentrated to dryness under reduced pressure and azeotroped with dichloromethane (5.00 mL). The residue was purified by 30 g C18 column using a gradient elution of 0-100% acetonitrile in water. Fractions containing product were combined and concentrated under redcuced pressure to provide the product (0.12 g, 94%) as an amorphous white solid. MS: m/z 589 (M+H⁺).

EXAMPLE 97 methyl {(1S,2S)-2-(4-chlorophenyl)-2-(3,5-difluorophenyl)-1-[(2-{2-[(2R)-1,9-dioxa-4-azaspiro[5.5]undec-2-yl]ethyl}-3-fluorophenyl)carbamoyl]ethyl}carbamate

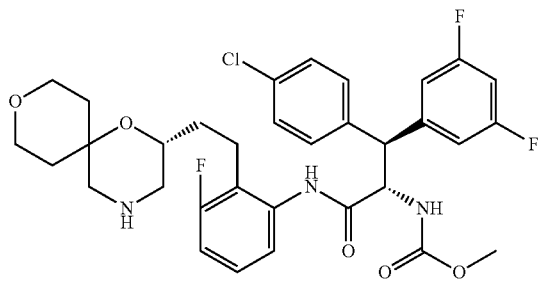

C-97

Step 1: (R)-tert-Butyl 2-(2-((2S,3S)-3-(4-chlorophenyl)-3-(3,5-difluorophenyl)-2-((methoxycarbonyl)amino)propanamido)-6-fluorophenethyl)-1,9-dioxa-4-azaspiro[5.5]undecane-4-carboxylate

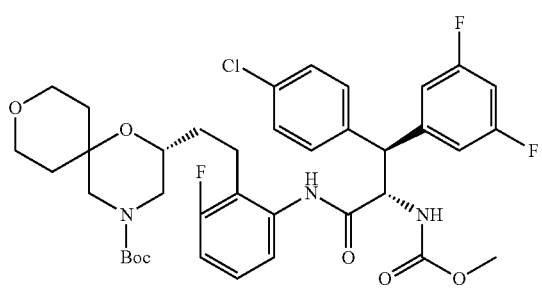 [SMILES: COC(=O)N[C@H](C(=O)Nc1cccc(F)c1CC[C@@H]1CN(C(=O)OC(C)(C)C)CC2(CCOCC2)O1)[C@@H](c1ccc(Cl)cc1)c1cc(F)cc(F)c1]

To a stirred solution of (R)-tert-butyl 2-(2-((2S,3S)-2-amino-3-(4-chlorophenyl)-3-(3,5-difluorophenyl)propanamido)-6-fluorophenethyl)-1,9-dioxa-4-azaspiro[5.5]undecane-4-carboxylate (0.23 g, 0.334 mmol) in dichloromethane (4.60 mL) was added triethylamine (87 mg, 0.68 mmol), methylchloroformate (35 mg, 0.37 mmol) at 0° C. and stirred for 2 hours. Water (5.00 mL) was added and extracted with dichloromethane (2×20.0 mL). The organic layer was washed with brine (10.0 mL), dried (Na₂SO₄), filtered and concentrated under reduced pressure. The residue was purified by 12 g SiO₂ column using a gradient elution of 0-100% EtOAc in hexanes. Fractions containing product were combined and the solvents were removed in vacuum to provide the product (0.18 g, 72%) as an off-white solid. MS: m/z 747 (M+H⁺).

Step 2: methyl {(1S,2S)-2-(4-chlorophenyl)-2-(3,5-difluorophenyl)-1-[(2-{2-[(2R)-1,9-dioxa-4-azaspiro [5.5]undec-2-yl]ethyl}-3-fluorophenyl)carbamoyl] ethyl}carbamate To a stirred solution of of (R)-tert-butyl 2-(2-((2S,3S)-3-(4-chlorophenyl)-3-(3,5-difluorophenyl)-2-((methoxycarbonyl)amino)propanamido)-6-fluorophenethyl)-1,9-dioxa-4-azaspiro[5.5]undecane-4-carboxylate (0.18 g, 0.24 mmol) in dichloromethane (5.00 mL), added trifluoroacetic acid (1.00 mL) and stirred at room temperature for 16 hours. The reaction mixture was concentrated under reduced pressure and azeotroped with dichloromethane (5.00 mL). The residue was purified by 30 g C18 column using a gradient elution of 0-100% acetonitrile in water. Fractions containing product were combined and the solvents were removed in vacuum to provide the product (45 mg, 29%) as an amorphous white solid. MS: m/z 647 (M+H⁺).

EXAMPLE 98 methyl {(1S,2S)-2-(4-chlorophenyl)-2-(3,5-difluorophenyl)-1-[(4-{2-[(2R)-1,9-dioxa-4-azaspiro[5.5] undec-2-yl]ethyl}-5-fluoropyridin-3-yl)carbamoyl] ethyl}carbamate

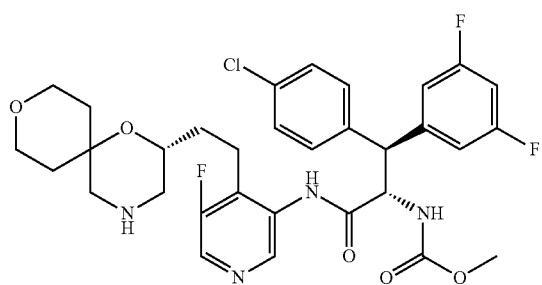

C-98

Step 1. (R)-tert-Butyl 2-((3-amino-5-fluoropyridin-4-yl)ethynyl)-1,9-dioxa-4-azaspiro[5.5]undecane-4-carboxylate

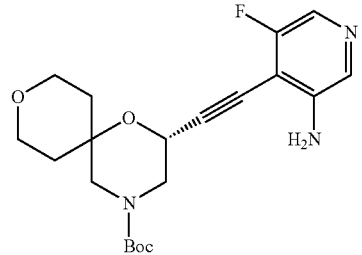 [SMILES: CC(C)(C)OC(=O)N1C[C@@H](C#Cc2c(N)cncc2F)OC2(CCOCC2)C1]

To a solution of (R)-tert-butyl 2-ethynyl-1,9-dioxa-4-azaspiro[5.5]undecane-4-carboxylate (0.75 g, 2.70 mmol) in anhydrous CH₃CN (14.0 mL) in a sealed tube was added 5-fluoro-4-iodopyridin-3-amine (0.75 g, 3.20 mmol). The reaction mixture was degassed with Ar(g) for 15 minutes and added bis(triphenylphosphine)palladium(II) dichloride (0.13 g, 0.07 mmol) and CuI (0.05 g, 0.26 mmol). The reaction mixture was degassed for an additional 5 minutes and Et₃N (1.35 g, 13.3 mmol) was added and the mixture was heated to 80° C. for 2 hours. The reaction mixture was cooled to room temperature and concentrated the solvents under reduced pressure. The residue was purified by 40 g SiO₂ column using a gradient elution of 0-60% EtOAc in hexanes. Fractions containing the product were combined and concentrated under vacuo to provide the product (0.90 g, 86%); MS: m/z=392 (M+H⁺).

Step 2: (R)-tert-Butyl 2-(2-(3-amino-5-fluoropyridin-4-yl)ethyl)-1,9-dioxa-4-azaspiro[5.5]undecane-4-carboxylate

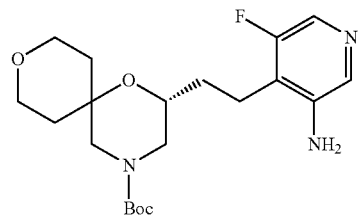 [SMILES: CC(C)(C)OC(=O)N1C[C@@H](CCc2c(N)cncc2F)OC2(CCOCC2)C1]

A solution of (R)-tert-butyl 2-((3-amino-5-fluoropyridin-4-yl)ethynyl)-1,9-dioxa-4-azaspiro[5.5]undecane-4-carboxylate (900 mg, 2.301 mmol) in methanol (20.0 mL) was degassed with N₂ for 15 minutes. To this reaction mixture 10% Pd/C (0.24 g, 30% wt/wt) was added portion wise and hydrogenated at 40 psi for 8 hours. The reaction mixture was filtered through celite pad and washed the pad with methanol (100 mL). The filtrate was concentrated under reduced pressure and the residue was purified by 12 g SiO₂ column using a gradient elution of 0-50% EtOAc in hexanes. Fractions containing the product were combined and concentrated under vacuo to provide the product (0.78 g, 86%) as off-white foam. MS: m/z=396 (M+H⁺).

Step 3: (R)-tert-Butyl 2-(2-(3-((2S,3S)-2-azido-3-(4-chlorophenyl)-3-(3,5-difluorophenyl)propanamido)-5-fluoropyridin-4-yl)ethyl)-1,9-dioxa-4-azaspiro[5.5]undecane-4-carboxylate

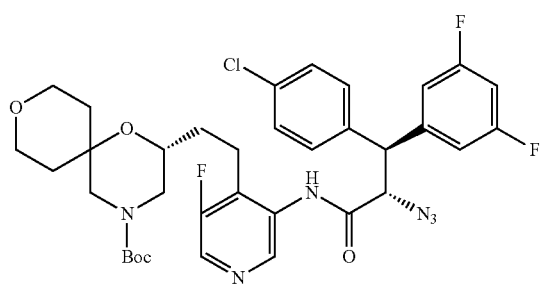 [SMILES: CC(C)(C)OC(=O)N1C[C@@H](CCc2c(F)cncc2NC(=O)[C@@H](N=[N+]=[N-])[C@@H](c2ccc(Cl)cc2)c2cc(F)cc(F)c2)OC2(CCOCC2)C1]

To a solution of (R)-tert-butyl 2-(2-(3-amino-5-fluoropyridin-4-yl)ethyl)-1,9-dioxa-4-azaspiro[5.5]undecane-4-carboxylate (0.32 g, 0.81 mmol) and (2S,3S)-2-azido-3-(4-chlorophenyl)-3-(3,5-difluorophenyl)propanoic acid (0.33 g, 0.97 mmol) in anhydrous pyridine (6.50 mL) at −20° C. was added $POCl_3$ (0.19 g, 1.22 mmol) dropwise over a period of 10 minutes. The reaction mixture was gradually allowed to reach room temperature and stirred for and stirred for 1 hour. The reaction mixture was quenched with a saturated solution of $NaHCO_3$ and diluted with EtOAc (100 mL). The organic layer was separated, washed with $H_2O$ (2×25.0 mL), brine (25.0 mL), dried ($Na_2SO_4$), filtered and concentrated under reduced pressure. The residue was purified by 12 g $SiO_2$ column using a gradient elution of 0-40% EtOAc in hexanes. Fractions containing the product were combined and concentrated under vacuo to provide the product (0.36 g, 62%) as brown foam. MS: m/z=716 (M+H$^+$).

Step 4: (R)-tert-Butyl 2-(2-(3-((2S,3S)-2-amino-3-(4-chlorophenyl)-3-(3,5-difluorophenyl)propanamido)-5-fluoropyridin-4-yl)ethyl)-1,9-dioxa-4-azaspiro[5.5]undecane-4-carboxylate

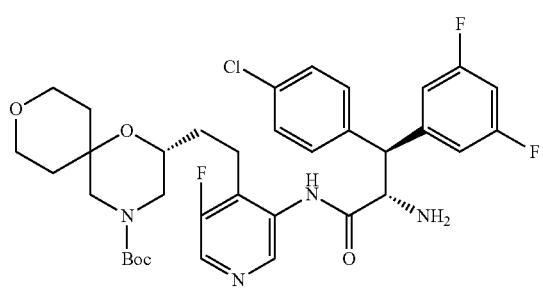 [SMILES: CC(C)(C)OC(=O)N1C[C@@H](CCc2c(F)cncc2NC(=O)[C@@H](N)[C@@H](c2ccc(Cl)cc2)c2cc(F)cc(F)c2)OC2(CCOCC2)C1]

To a solution of (R)-tert-butyl 2-(2-(3-((2S,3S)-2-azido-3-(4-chlorophenyl)-3-(3,5-difluorophenyl)propanamido)-5-fluoropyridin-4-yl)ethyl)-1,9-dioxa-4-azaspiro[5.5]undecane-4-carboxylate (0.36 g, 0.50 mmol) in EtOAc: $H_2O$ (4.00 mL, 1:1) at room temperature, trimethyl phosphine (0.11 g, 1.51 mmol) was added in one portion and stirred at room temperature for 16 hours. The reaction mixture was diluted with EtOAc (50.0 mL), washed with $H_2O$ (2×25.0 mL), brine (25.0 mL), dried ($Na_2SO_4$), filtered and concentrated under reduced pressure. The residue was purified by 12 g $SiO_2$ column using a gradient elution of 0-50% EtOAc in hexanes. Fractions containing the product were combined and concentrated under vacuo to provide the product (0.34 g, >99%) as colorless foam. MS: m/z=690 (M+H$^+$).

Step 5: (R)-tert-Butyl 2-(2-(3-((2S,3S)-3-(4-chlorophenyl)-3-(3,5-difluorophenyl)-2-((methoxycarbonyl)amino)propanamido)-5-fluoropyridin-4-yl)ethyl)-1,9-dioxa-4-azaspiro[5.5]undecane-4-carboxylate

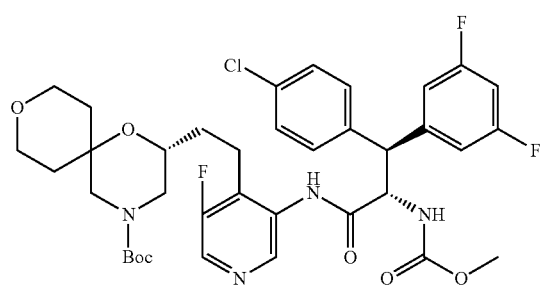

To a stirred solution of (R)-tert-butyl 2-(2-(3-((2S,3S)-2-amino-3-(4-chlorophenyl)-3-(3,5-difluorophenyl)propanamido)-5-fluoropyridin-4-yl)ethyl)-1,9-dioxa-4-azaspiro[5.5]undecane-4-carboxylate (0.19 g, 0.28 mmol) in dichloromethane (3.80 mL) was added triethylamine (74 mg, 0.57 mmol), methylchloroformate (30 mg, 0.31 mmol) at 0° C. and stirred for 2 hours. Water (5.00 mL) was added and extracted with dichloromethane (2×20.0 mL). The organic layer was washed with brine (10.0 mL), dried ($Na_2SO_4$), filtered and concentrated under reduced pressure. The residue was purified by 12 g $SiO_2$ column using a gradient elution of 0-100% EtOAc in hexanes. Fractions containing product were combined and the solvents were removed in vacuum to provide the product (0.11 g, 52%) as colourless foam. MS: m/z 748 (M+H$^+$).

Step 6: methyl {(1S,2S)-2-(4-chlorophenyl)-2-(3,5-difluorophenyl)-1-[(4-{2-[(2R)-1,9-dioxa-4-azaspiro[5.5]undec-2-yl]ethyl}-5-fluoropyridin-3-yl)carbamoyl]ethyl}carbamate To a stirred solution of of (R)-tert-butyl 2-(2-((2S,3S)-3-(4-chlorophenyl)-3-(3,5-difluorophenyl)-2-((methoxycarbonyl)amino)propanamido)-6-fluorophenethyl)-1,9-dioxa-4-azaspiro[5.5]undecane-4-carboxylate (0.11 g, 0.15 mmol) in dichloromethane (5.00 mL), added trifluoroacetic acid (1.00 mL) and stirred at room temperature for 16 hours. The reaction mixture was concentrated under reduced pressure and azeotroped with dichloromethane (5.00 mL). The residue was purified by 30 g C18 column using a gradient elution of 0-100% acetonitrile in water. Fractions containing product were combined and the solvents were removed in vacuum to provide the product (90 mg, 80%) as an amorphous white solid. MS: m/z 648 (M+H$^+$).

EXAMPLE 99

4-fluoro-β-(4-fluorophenyl)-N-(3-fluoro-2-{2-[(2R,6S)-6-({[(2,2,2-trifluoroethyl)carbamoyl]oxy}methyl)morpholin-2-yl]ethyl}phenyl)-L-phenylalaninamide

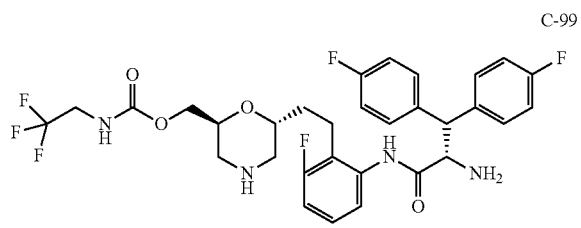 [SMILES: N[C@H](C(=O)Nc1cccc(F)c1CC[C@@H]1CNC[C@@H](COC(=O)NCC(F)(F)F)O1)C(c1ccc(F)cc1)c1ccc(F)cc1]

C-99

Step 1: (2S,6R)-4-benzyl-2-(((tert-butyldimethylsilyl)oxy)methyl)-6-((E)-2-fluoro-6-nitrostyryl)morpholine

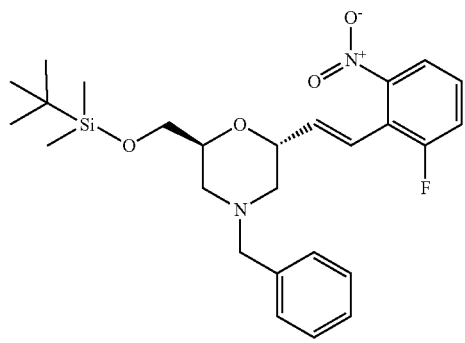 [SMILES: CC(C)(C)[Si](C)(C)OC[C@@H]1CN(Cc2ccccc2)C[C@@H](/C=C/c2c(F)cccc2[N+](=O)[O-])O1]

The title compound was prepared from (2S,6S)-4-benzyl-6-({[tert-butyl(dimethyl)silyl]oxy}methyl)morpholine-2-carbaldehyde using the appropriate (2-fluoro-6-nitrobenzyl)triphenylphosphonium bromide and by following the procedure from step 7 described in Example 7.

Step 2: (2R,6S)-tert-butyl 2-(2-amino-6-fluorophenethyl)-6-(((tert-butyldimethylsilyl)oxy)methyl)morpholine-4-carboxylate

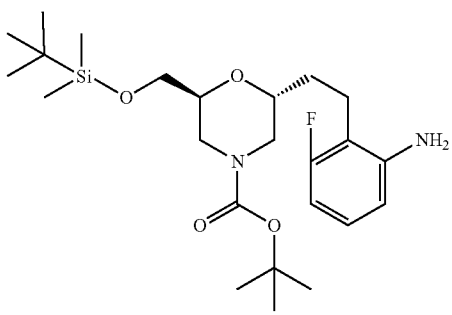 [SMILES: CC(C)(C)OC(=O)N1C[C@@H](CCc2c(N)cccc2F)O[C@H](CO[Si](C)(C)C(C)(C)C)C1]

The title compound was prepared from (2S,6R)-4-benzyl-2-(((tert-butyldimethylsilyl)oxy)methyl)-6-((E)-2-fluoro-6-nitrostyryl)morpholine by following procedures from steps 8 to 9 described in Example 7.

Step 3: (2R,6S)-tert-butyl 2-(2-((S)-2-((tert-butoxycarbonyl)amino)-3,3-bis(4-fluorophenyl)propanamido)-6-fluorophenethyl)-6-(((tert-butyldimethylsilyl)oxy)methyl)morpholine-4-carboxylate

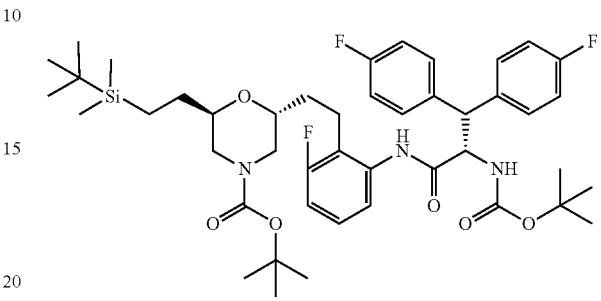

The title compound was prepared from (2R,6S)-tert-butyl 2-(2-amino-6-fluorophenethyl)-6-(((tert-butyldimethylsilyl)oxy)methyl)morpholine-4-carboxylate using the appropriate (S)-2-((tert-butoxycarbonyl)amino)-3,3-bis(4-fluorophenyl)propanoic acid and by following the procedure from step 10 described in Example 7.

Step 4: (2R,6S)-tert-butyl 2-(2-((S)-2-((tert-butoxycarbonyl)amino)-3,3-bis(4-fluorophenyl)propanamido)-6-fluorophenethyl)-6-(hydroxymethyl)morpholine-4-carboxylate

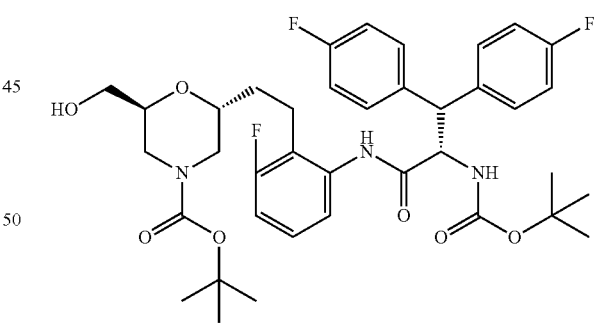

The title compound was prepared from (2R,6S)-tert-butyl 2-(2-((S)-2-((tert-butoxycarbonyl)amino)-3,3-bis(4-fluorophenyl)propanamido)-6-fluorophenethyl)-6-(((tert-butyldimethylsilyl)oxy)methyl)morpholine-4-carboxylate by following the procedure from step 11 described in Example 7.

Step 5: (2R,6S)-tert-butyl 2-(2-((S)-2-((tert-butoxycarbonyl)amino)-3,3-bis(4-fluorophenyl)propanamido)-6-fluorophenethyl)-6-((((2,2,2-trifluoroethyl)carbamoyl)oxy)methyl)morpholine-4-carboxylate

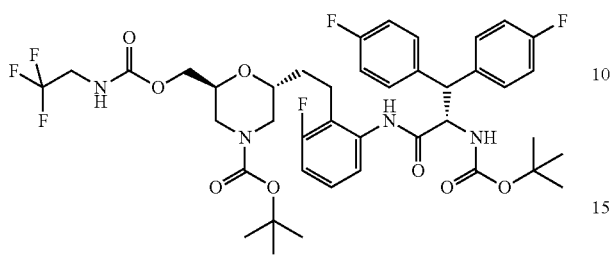

To a solution of (2R,6S)-tert-butyl 2-(2-((S)-2-((tert-butoxycarbonyl)amino)-3,3-bis(4-fluorophenyl)propanamido)-6-fluorophenethyl)-6-(hydroxymethyl)morpholine-4-carboxylate (40.4 mg, 0.057 mmol) in pyridine (566 μl) was added CDI (27.5 mg, 0.170 mmol). The mixture was warmed to 65° C. After 17 hours, to the resulting solution was added 2,2,2-trifluoroethylamine (140 mg, 1.415 mmol), which was heated at 65° C. After 23 hours, reaction was concentrated and purified by automated silica gel column chromatography eluting with 0 to 20% EtOAc/hexanes on a 12 g Redisep Rf column to afford the product as a white foam. LRMS (ESI) m/z 839.4 [(M+H)$^+$; calcd for $C_{41}H_{48}F_6N_4O_8$: 838.8].

Step 6: 4-fluoro-β-(4-fluorophenyl)-N-(3-fluoro-2-{2-[(2R,6S)-6-({[(2,2,2-trifluoroethyl)carbamoyl]oxy}methyl)morpholin-2-yl]ethyl}phenyl)-L-phenylalaninamide In an ice water bath, to a cooled solution of (2R,6S)-tert-butyl 2-(2-((S)-2-((tert-butoxycarbonyl)amino)-3,3-bis(4-fluorophenyl)propanamido)-6-fluorophenethyl)-6-((((2,2,2-trifluoroethyl)carbamoyl)oxy)methyl)morpholine-4-carboxylate (50 mg, 0.060 mmol) in EtOAc (0.6 mL) was added a cold saturated solution of HCl in EtOAc (0.6 mL). The reaction was allowed to warm to ambient temperature overnight. After 16 hours, the reaction was concentrated to dryness to afford the desired product as a white solid that gave a proton NMR spectrum consistent with theory and a low resolution mass spectrum (ES+) m/z of 639.0 (M+H)$^+$. $^1$H NMR (400 MHz, DMSO) δ 10.43 (s, 1H), 9.33 (bs, 1H), 8.57 (bs, 2H), 8.08 (t, J=6.4 Hz, 1H), 7.61 (m, 4H), 7.26 (t, J=8.8 Hz, 2H), 7.15 (m, 3H), 6.98 (t, J=8.9 Hz, 1H), 6.83 (d, J=8.1 Hz, 2H), 5.59 (d, J=9.5 Hz, 1H), 4.42 (d, J=11.2 Hz, 1H), 4.29 (m, 1H), 4.00-4.14 (m, 3H), 3.75-3.89 (m, 4H), 3.20 (m, 2H), 3.00 (m, 2H), 2.24 (m, 1H), 1.91 (m, 1H), 1.79 (m, 1H).

EXAMPLE 100 methyl {(1S)-1-[bis(4-fluorophenyl)methyl]-2-[(5-fluoro-4-{2-[(7R)-6-oxa-9-azaspiro[4.5]dec-7-yl]ethyl}pyridin-3-yl)amino]-2-oxoethyl}carbamate

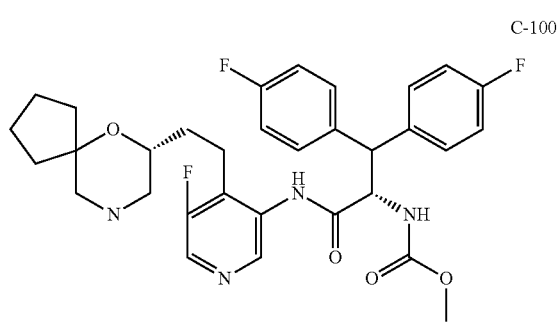 [SMILES: COC(=O)N[C@H](C(=O)Nc1cncc(F)c1CC[C@@H]1CNCC2(CCCC2)O1)C(c1ccc(F)cc1)c1ccc(F)cc1]

Step 1: 1-(Aminomethyl)cyclopentanol hydrochloride

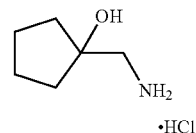

To an ice cooled mixture of cyclopentanone (5.50 g, 65.0 mmol) and ZnBr$_2$ (0.20 g, 8.00 mmol) was added TMSCN (10.0 mL, 73.4 mmol) and stirred at room temperature for 12 hours. The resulting cyanohydrin solution was added dropwise to a suspension of LiAlH$_4$ (8.34 g, 219 mmol) in THF (30.0 mL) at 0° C. and mixture was refluxed for 1 hour. The reaction mixture was cooled to room temperature, water (10.0 mL), 4 M aqueous NaOH solution (10.0 mL) followed by water (10.0 mL) was added slowly to the reaction mixture with vigorous stirring. The resultant precipitate was filtered through a pad of celite, the organic phase separated and dried over KOH. The solution was decanted, dried (Na$_2$SO$_4$), filtered and concentrated. The residue was dissolved in MTBE (100 mL), 4N HCl in dioxane (10.0 mL) was added and mixture was stirred at room temperature for 30 minutes. The resulting precipitate was collected by filtering through sintered funnel to provide product (6.68 g, 68%) as a white solid.

Step 2: 1-((Benzylamino)methyl)cyclopentanol

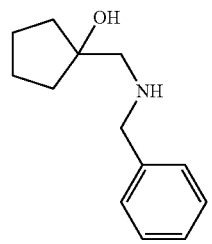 [SMILES: OC1(CNCc2ccccc2)CCCC1]

To a solution of 1-(aminomethyl)cyclopentanol hydrochloride (5.48 g, 36.1 mmol) in methanol (50.0 mL) was added Et₃N (5.00 mL) and the mixture was stirred for 20 minutes at room temperature followed by the addition of benzaldehyde (3.85 mL, 37.9 mmol). The mixture was stirred at room temperature for 20 minutes. NaCNBH₃ (5.40 g, 72.3 mmol) was added and mixture was stirred at room temperature for 16 hours. The solvent was removed under reduced pressure, quenched with saturated aqueous K₂CO₃ solution (25.0 mL) and stirred for 20 minutes. The resulting reaction mixture was diluted with EtOAc (150 mL), organic layers separated and aqueous layer extracted with EtOAc (2×150 mL). The combined organic layers was washed with brine (50.0 mL), dried (Na₂SO₄), concentrated under reduced pressure and purified by 80 g SiO₂ column using a gradient elution of 0-70% EtOAc in hexanes. Fractions containing product were combined and the solvents were removed in vacuo to provide the product (2.90 g, 39%) as a colourless oil MS, m/z=206 (M+H⁺).

Step 3: ((9-Benzyl-6-oxa-9-azaspiro[4.5]decan-7-yl)methanol

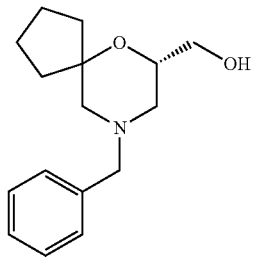 [SMILES: OC[C@@H]1CN(Cc2ccccc2)CC2(CCCC2)O1]

To a solution of 1-((benzylamino)methyl)cyclopentanol (3.80 g, 18.5 mmol) in MeOH (25.0 mL) was added (R)-2-(chloromethyl)oxirane (1.80 mL, 22.3 mmol) and reaction mixture was stirred at room temperature for 16 hours. Potassium hydroxide (3.12 g, 55.6 mmol) was added to the reaction mixture and allowed to stir at room temperature for 4 hours. The reaction mixture was evaporated to dryness, diluted with dichloromethane (200 mL) and water (50.0 mL). The organic layer was separated, washed with water (2×50.0 mL), brine (20.0 mL), dried (Na₂SO₄), filtered and concentrated under reduced pressure. The residue was purified by 80 g SiO₂ column using a gradient elution of 0-70% EtOAc in hexanes. Fractions containing product were combined and the solvents were removed in vacuo to provide the product (3.20 g, 67%) as colourless oil. MS: m/z=262 (M+H⁺).

Step 4: (S)-9-Benzyl-6-oxa-9-azaspiro[4.5]decane-7-carbaldehyde

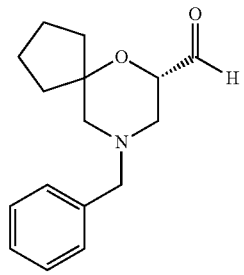 [SMILES: O=C[C@@H]1CN(Cc2ccccc2)CC2(CCCC2)O1]

To a solution of (9-benzyl-6-oxa-9-azaspiro[4.5]decan-7-yl)methanol (0.52 g, 1.97 mmol) in CH₂Cl₂ (15.0 mL) was added Dess-Martin periodinane (1.00 g, 2.37 mmol) and mixture was stirred at room temperature for 2 hours. The reaction mixture was diluted with CH₂Cl₂ (15.0 mL), quenched with saturated aqueous Na₂S₂O₃ solution (3.00 mL) and saturated aqueous NaHCO₃ (5.00 mL). The organic layer was separated, washed with brine (20.0 mL), dried (Na₂SO₄), filtered and concentrated under reduced pressure to provide the product (0.50 g, quantitative) as light yellow oil. MS: APCI, m/z=260 (M+H⁺).

Step 5: (S)-9-Benzyl-7-ethynyl-6-oxa-9-azaspiro[4.5]decane

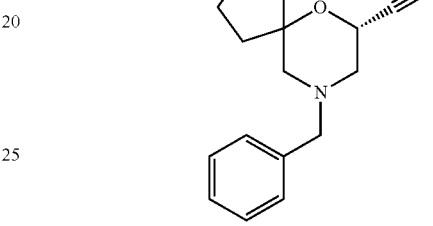

To a solution of (S)-9-benzyl-6-oxa-9-azaspiro[4.5]decane-7-carbaldehyde (0.51 g, 1.96 mmol) in MeOH (5.00 mL) was added dimethyl (1-diazo-2-oxopropyl)phosphonate (0.56 g, 2.94 mmol) and K₂CO₃ (0.54 g, 3.91 mmol). The reaction mixture was stirred at room temperature for 16 hours. The solvent was removed under reduced pressure and the residue was purified by 24 g SiO₂ column using a gradient elution of 0-40% EtOAc in hexanes. Fractions containing product were combined and the solvents were removed in vacuo to provide the product (0.13 g, 26%) as colourless oil. MS: m/z=256 (M+H⁺).

Step 6: tert-Butyl ((S)-1-((4-(((R)-9-benzyl-6-oxa-9-azaspiro[4.5]decan-7-yl)ethynyl)-5-fluoropyridin-3-yl)amino)-1-oxo-3,3-diphenylpropan-2-yl)carbamate

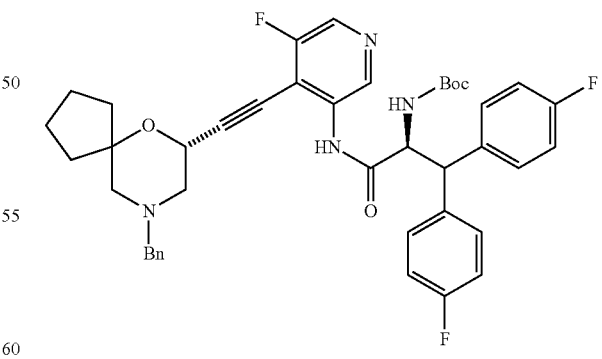

To a solution of 9-benzyl-7-ethynyl-6-oxa-9-azaspiro[4.5]decane (0.13 g, 0.50 mmol), (S)-tert-butyl (1-((5-fluoro-4-iodopyridin-3-yl)amino)-1-oxo-3,3-diphenylpropan-2-yl)carbamate (0.28 g, 0.50 mmol) and Et₃N (0.21 mL, 1.53 mmol) in degassed THF (10.0 mL) was added CuI (1.90 mg, 0.010 mmol) and PdCl₂(PPh₃)₂ (3.61 mg, 0.005 mmol).

The reaction mixture was stirred at 40° C. for 16 hours. The solvent was removed under reduced pressure and the residue was purified by 24 g SiO₂ column using a gradient elution of 0-50% EtOAc in hexanes. Fractions containing product were combined and the solvents were removed in vacuo to provide the product (0.11 g, 31%) as off-white solid. MS: m/z=725 (M+H⁺).

Step 7: 2-Amino-N-(4-(((R)-9-benzyl-6-oxa-9-azaspiro[4.5]decan-7-yl)ethynyl)-5-fluoropyridin-3-yl)-3,3-bis(4-fluorophenyl)propanamide

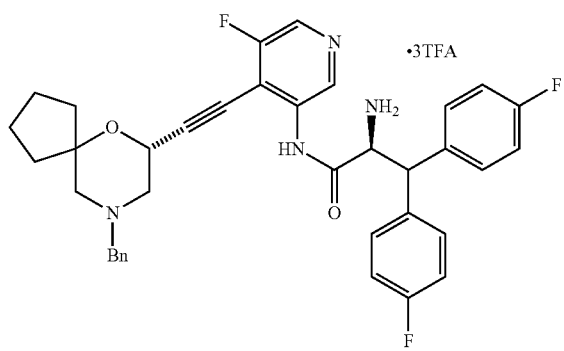 [SMILES: N[C@H](C(=O)Nc1cncc(F)c1C#C[C@@H]1CN(Cc2ccccc2)CC2(CCCC2)O1)C(c1ccc(F)cc1)c1ccc(F)cc1]

To a solution of tert-Butyl ((S)-1-((4-(((R)-9-benzyl-6-oxa-9-azaspiro[4.5]decan-7-yl)ethynyl)-5-fluoropyridin-3-yl)amino)-1-oxo-3,3-diphenylpropan-2-yl)carbamate (80.0 mg, 0.110 mmol) in CH₂Cl₂ (2.00 mL) was added TFA (0.08 mL, 1.10 mmol) and water (0.01 mL). The reaction mixture was stirred at room temperature for 24 hours. The solvent was removed under reduced pressure to provide product (106 mg, 100%) as an off-white solid. MS: m/z=625 (M+H)⁺

Step 8: Methyl (1-((4-(((R)-9-benzyl-6-oxa-9-azaspiro[4.5]decan-7-yl)ethynyl)-5-fluoropyridin-3-yl)amino)-3,3-bis(4-fluorophenyl)-1-oxopropan-2-yl)carbamate

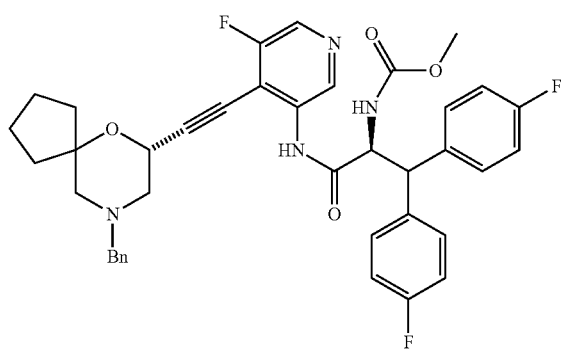 [SMILES: COC(=O)N[C@H](C(=O)Nc1cncc(F)c1C#C[C@@H]1CN(Cc2ccccc2)CC2(CCCC2)O1)C(c1ccc(F)cc1)c1ccc(F)cc1]

To a solution 2-amino-N-(4-(((R)-9-benzyl-6-oxa-9-azaspiro[4.5]decan-7-yl)ethynyl)-5-fluoropyridin-3-yl)-3,3-bis(4-fluorophenyl)propanamide (69.0 mg, 0.11 mmol) in CH₂Cl₂ (2.00 mL) at room temperature was added Hunig's base (0.07 mL, 0.44 mmol) and methylchloroformate (0.01 mL, 0.13 mmol). The reaction mixture was stirred at room temperature for 12 h. The solvent was removed under reduced pressure and residue was purified by 24 g C18 column using a gradient elution of 10-60% acetonitrile in water. Fractions containing product were combined and the solvents were removed in vacuo and lyophilized to provide the product (43 mg, 56%) as an off-white solid. MS: m/z=683 (M+H)⁺

Step 9: methyl {(1S)-1-[bis(4-fluorophenyl)methyl]-2-[(5-fluoro-4-{2-[(7R)-6-oxa-9-azaspiro[4.5]dec-7-yl]ethyl}pyridin-3-yl)amino]-2-oxoethyl}carbamate To a solution of methyl (1-((4-(((R)-9-benzyl-6-oxa-9-azaspiro[4.5]decan-7-yl)ethynyl)-5-fluoropyridin-3-yl)amino)-3,3-bis(4-fluorophenyl)-1-oxopropan-2-yl)carbamate (43.0 mg, 0.06 mmol) in MeOH (2.00 mL) was added Pd(OH)₂ on carbon (10%, 43.0 mg). The reaction mixture was stirred at room temperature for 24 hours. The solvent was removed under reduced pressure and residue was purified by 15 g C18 column using a gradient elution of 10-60% acetonitrile in water. Fractions containing product were combined and the solvents were removed in vacuo and lyophilized to provide the product (13.4 mg, 36%) as an off-white solid. MS: m/z=597 (M+H)⁺

EXAMPLE 101

N-(4-{2-[(2R)-1,9-dioxa-4-azaspiro[5.5]undec-2-yl]ethyl}-5-fluoropyridin-3-yl)-4-fluoro-β-(4-fluorophenyl)-L-phenylalaninamide

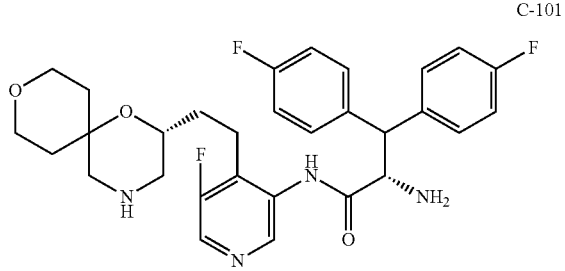 [SMILES: N[C@H](C(=O)Nc1cncc(F)c1CC[C@@H]1CNCC2(CCOCC2)O1)C(c1ccc(F)cc1)c1ccc(F)cc1]

C-101

Step 1: (S)-tert-Butyl (1-((5-fluoro-4-iodopyridin-3-yl)amino)-3,3-bis(4-fluorophenyl)-1-oxopropan-2-yl)carbamate

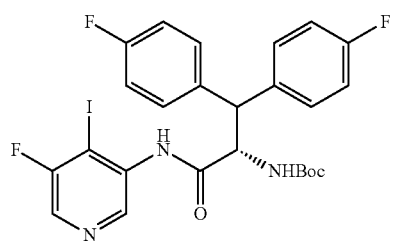 [SMILES: CC(C)(C)OC(=O)N[C@H](C(=O)Nc1cncc(F)c1I)C(c1ccc(F)cc1)c1ccc(F)cc1]

To a solution of 5-fluoro-4-iodopyridin-3-amine (1.00 g, 4.27 mmol) and 2-((tert-butoxycarbonyl)amino)-3,3-bis(4-fluorophenyl)propanoic acid (1.70 g, 4.49 mmol) in pyridine (15.0 mL) at −20° C. was added POCl₃ (0.72 g, 4.70 mmol) dropwise over a period of 10 minutes. The reaction mixture was gradually allowed to reach room temperature and stirred for 1 hour. The reaction mixture was quenched with a saturated solution of NaHCO₃ and diluted with EtOAc (100 mL). The organic layer was separated, washed with H₂O (2×25.0 mL), brine (25.0 mL), dried (Na₂SO₄), filtered and concentrated under reduced pressure. The residue was purified by 40 g SiO₂ column using a gradient elution of 0-45% EtOAc in hexanes. Fractions containing the product were combined and concentrated under vacuo to provide the product (0.68 g, 26%) as off-white solid MS: m/z=598 (M+H⁺).

Step 2: tert-Butyl (1-((4-(((R)-4-benzyl-1,9-dioxa-4-azaspiro[5.5]undecan-2-yl)ethynyl)-5-fluoropyridin-3-yl)amino)-3,3-bis(4-fluorophenyl)-1-oxopropan-2-yl)carbamate

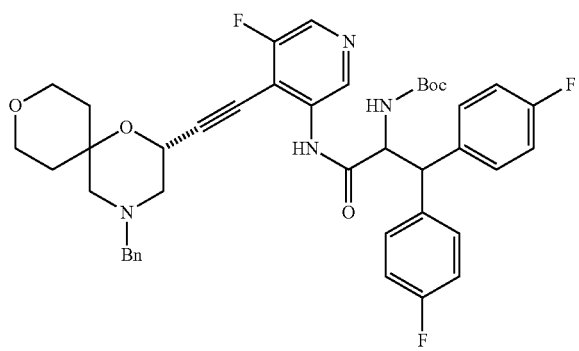 [SMILES: CC(C)(C)OC(=O)NC(C(=O)Nc1cncc(F)c1C#C[C@@H]1CN(Cc2ccccc2)CC2(CCOCC2)O1)C(c1ccc(F)cc1)c1ccc(F)cc1]

To a solution of (S)-tert-butyl (1-((5-fluoro-4-iodopyridin-3-yl)amino)-3,3-bis(4-fluorophenyl)-1-oxopropan-2-yl)carbamate (0.42 g, 0.71 mmol) in anhydrous CH₃CN (3.50 mL) in a sealed tube was added (R)-4-benzyl-2-ethynyl-1,9-dioxa-4-azaspiro[5.5]undecane (0.16 g, 0.59 mmol). The reaction mixture was degassed with Ar(g) for 15 minutes and added bis(triphenylphosphine)palladium(II) dichloride (29 mg, 0.04 mmol) and CuI (12 mg, 0.06 mmol). The reaction mixture was degassed for an additional 5 minutes and Et₃N (0.30 mg, 2.95 mmol) was added and the mixture was heated to 80° C. for 2 hours. The reaction mixture was cooled to room temperature and concentrated the solvents under reduced pressure. The residue was purified by 12 g SiO₂ column using a gradient elution of 0-55% EtOAc in hexanes. Fractions containing the product were combined and concentrated under vacuo to provide the product (0.15 g, 35%); MS: m/z=741 (M+H⁺).

Step 3: tert-Butyl ((S)-1-((4-(2-((R)-1,9-dioxa-4-azaspiro[5.5]undecan-2-yl)ethyl)-5-fluoropyridin-3-yl)amino)-3,3-bis(4-fluorophenyl)-1-oxopropan-2-yl)carbamate

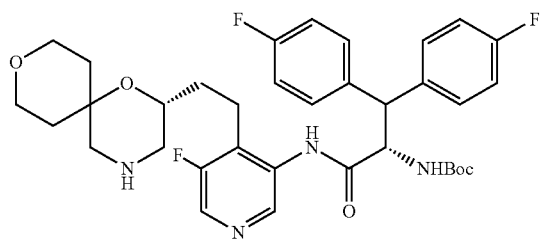 [SMILES: CC(C)(C)OC(=O)N[C@H](C(=O)Nc1cncc(F)c1CC[C@@H]1CNCC2(CCOCC2)O1)C(c1ccc(F)cc1)c1ccc(F)cc1]

A solution of tert-butyl (1-((4-(((R)-4-benzyl-1,9-dioxa-4-azaspiro[5.5]undecan-2-yl)ethynyl)-5-fluoropyridin-3-yl)amino)-3,3-bis(4-fluorophenyl)-1-oxopropan-2-yl)carbamate (0.07 g, 0.09 mmol) in methanol (2.00 mL) was degassed with N₂ for 10 minutes. To this reaction mixture 10% Pd/C (13 mg, 20% wt/wt) was added in one portion and hydrogenated at 1 atmosphere pressure at room temperature for 16 hour. The reaction mixture was filtered through celite pad and washed the pad with methanol (25 mL). The filtrate was concentrated under reduced pressure and the residue was purified by 4 g SiO₂ column using a gradient elution of 0-50% EtOAc in hexanes. Fractions containing the product were combined and concentrated under vacuo to provide the product (0.04 g, 65%) as off-white foam. MS: m/z=655 (M+H⁺).

Step 4: N-(4-{2-[(2R)-1,9-dioxa-4-azaspiro[5.5]undec-2-yl]ethyl}-5-fluoropyridin-3-yl)-4-fluoro-β-(4-fluorophenyl)-L-phenylalaninamide To a stirred solution of tert-butyl ((S)-1-((4-(2-((R)-1,9-dioxa-4-azaspiro[5.5]undecan-2-yl)ethyl)-5-fluoropyridin-3-yl)amino)-3,3-bis(4-fluorophenyl)-1-oxopropan-2-yl)carbamate (0.04 g, 0.05 mmol) in dichloromethane (2.00 mL), added trifluoroacetic acid (0.50 mL) and stirred at room temperature for 16 hours. The reaction mixture was concentrated under reduced pressure and azeotroped with dichloromethane (5.00 mL). The residue was purified by 30 g C18 column using a gradient elution of 0-100% acetonitrile in water. Fractions containing product were combined and the solvents were removed in vacuum to provide the product (0.01 g, 30%) as white solid. MS: m/z=555 (M+H⁺).

EXAMPLE 102

N-(4-{2-[(2R,6S)-6-{[(3-cyanophenyl)sulfanyl]methyl}morpholin-2-yl]ethyl}-5-fluoropyridin-3-yl)-4-fluoro-β-(4-fluorophenyl)-L-phenylalaninamide

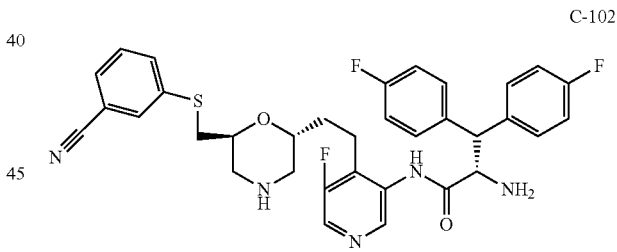

C-102

Step 1: (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(hydroxymethyl)morpholine-4-carboxylate

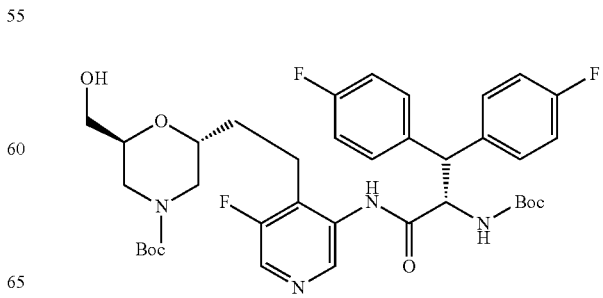

To a solution of (2R,6S)-tert-butyl 2-(2-(3-((S)-2-((tert-butoxycarbonyl)amino)-3,3-bis-4-fluorophenyl-propanamido)-5-fluoropyridin-4-yl)ethyl)-6-tert-butyldimethylsilyloxymethyl-morpholine-4-carboxylate (400 mg, 0.48 mmol) (prepared using a procedure similar to Example 99, step 4) in THF (4.8 mL) at room temperature was added TBAF (0.72 mL, 0.72 mmol, 1.0 M in THF). The mixture was stirred at room temperature for 3 hours. The resulting solution was quenched with brine and extracted with dichloromethane. The combined extracts were dried (Na$_2$SO$_4$), filtered and concentrated. Purification by isco silica gel chromatography (0-50% ethyl acetate/hexanes) on a 24 g RediSep Rf silica gel column afforded (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(hydroxymethyl)morpholine-4-carboxylate as an oil. LRMS (ESI) m/z 715.5 [(M+H$^+$) calcd for C$_{37}$H$_{46}$N$_4$O$_7$F$_3$: 715.3.

Step 2: (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(3-cyanophenylthio-methyl)morpholine-4-carboxylate

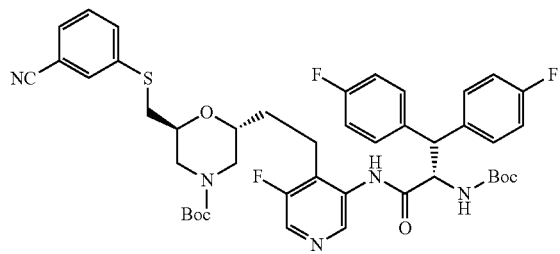 [SMILES: CC(C)(C)OC(=O)N[C@H](C(=O)Nc1cncc(F)c1CC[C@@H]1CN(C(=O)OC(C)(C)C)C[C@@H](CSc2cccc(C#N)c2)O1)C(c1ccc(F)cc1)c1ccc(F)cc1]

To a solution of (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(hydroxymethyl)morpholine-4-carboxylate (42 mg, 0.059 mmol) in Toluene (0.6 mL) at room temperature was added 3-mercaptobenzonitrile (12 mg, 0.088 mmol) and cyanomethylenetributylphosphorane (31 µL, 0.12 mmol). The mixture was heated to 80° C. for 2 hours. The resulting solution was concentrated and purified by isco silica gel chromatography (0-20% ethyl acetate/hexanes) on a 12 g RediSep Rf silica gel column to afford (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(3-cyanophenylthio-methyl)morpholine-4-carboxylate as a gummy solid. LRMS (ESI) m/z 832.7 [(M+H$^+$) calcd for C$_{44}$H$_{49}$N$_5$O$_6$SF$_3$: 832.4.

Step 3: N-(4-{2-[(2R,6S)-6-{[(3-cyanophenyl)sulfanyl]methyl}morpholin-2-yl]ethyl}-5-fluoropyridin-3-yl)-4-fluoro-β-(4-fluorophenyl)-L-phenylalaninamide A solution of (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(3-cyanophenylthio-methyl)morpholine-4-carboxylate (43 mg, 0.052 mmol) in ethyl acetate (1.0 mL) at 0° C. was bubbled with a stream of HCl (gas) for 5 minutes. The mixture was warmed to room temperature over 15 minutes and concentrated to afford (S)-2-amino-N-(4-(2-((2R,6S)-6-(((3-cyanophenyl)thio)methyl)morpholin-2-yl)ethyl)-5-fluoropyridin-3-yl)-3,3-bis-4-fluorophenylpropanamide as the bis HCl salt. LRMS (ESI) m/z 632.5 [(M+H$^+$) calcd for C$_{34}$H$_{33}$F$_3$N$_5$O$_2$S: 632.3. $^1$H NMR (500 MHz, d6-DMSO) δ 1.85 (m, 2 H), 2.35 (m, 1 H), 2.59 (m, 1 H) 3.03 (m, 2 H), 3.24 (m, 2 H), 3.41 (dd, J=5.6, 13.9 Hz, 1 H), 3.48 (dd, J=8.0, 13.9 Hz, 1 H), 4.08 (m, 1 H), 4.43 (d, J=11.2 Hz, 1 H), 5.64 (m, 1 H), 7.13 (t, J=8.6 Hz, 2 H), 7.25 (t, J=8.6 Hz, 2 H), 7.51 (t, J=7.9 Hz, 1 H), 7.59-7.69 (m, 6 H), 7.83 (s, 1 H), 8.00 (s, 1 H), 8.29 (s, 1 H), 8.67 (m, 2 H), 9.32 (s, 1 H), 9.62 (s, 1 H), 10.94 (s, 1 H).

The following compounds were prepared from (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(hydroxymethyl)morpholine-4-carboxylate by following the procedures detailed in Example 102, Steps 2-3.

| Example IUPAC Name | Structure | LCMS Data |
|---|---|---|
| Example 103<br>(S)-2-amino-N-(5-fluoro-4-(2-((2R,6S)-6-(((5-(pyridin-4-yl)-1,3,4-oxadiazol-2-yl)thio)methyl)morpholin-2-yl)ethyl)pyridin-3-yl)-3,3-bis(4-fluorophenyl)propanamide | | M + 1,<br>+ESI = 676.5 |

| Example IUPAC Name | Structure | LCMS Data |
|---|---|---|
| Example 104 (S)-2-amino-N-(4-(2-((2R,6S)-6-(((4-chlorophenyl)thio)methyl)morpholin-2-yl)ethyl)-5-fluoropyridin-3-yl)-3,3-bis(4-fluorophenyl)propanamide | 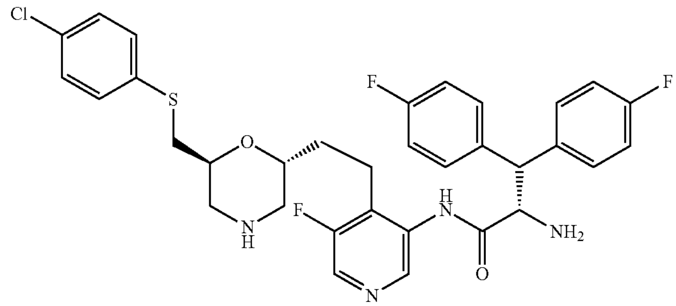 [SMILES: N[C@H](C(=O)Nc1cncc(F)c1CC[C@@H]1CNC[C@@H](CSc2ccc(Cl)cc2)O1)C(c1ccc(F)cc1)c1ccc(F)cc1] | M + 1, +ESI = 641.4 |

EXAMPLE 105

{(2S,6R)-6-[2-(3-fluoro-5-{[4-fluoro-β-(4-fluorophenyl)-L-phenylalanyl]amino}pyridin-4-yl)ethyl]morpholin-2-yl}methyl morpholine-4-carboxylate

C-105

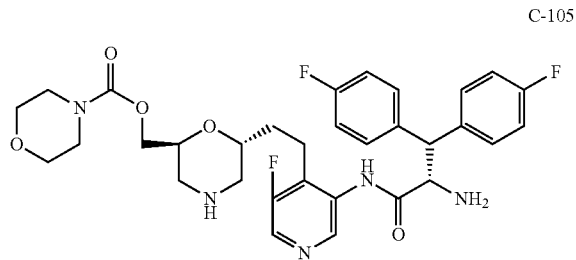 [SMILES: N[C@H](C(=O)Nc1cncc(F)c1CC[C@@H]1CNC[C@@H](COC(=O)N2CCOCC2)O1)C(c1ccc(F)cc1)c1ccc(F)cc1]

Step 1: (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(((morpholine-4-carbonyl)oxy)methyl)morpholine-4-carboxylate

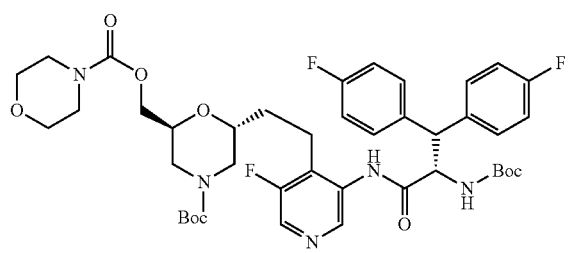 [SMILES: CC(C)(C)OC(=O)N[C@H](C(=O)Nc1cncc(F)c1CC[C@@H]1CN(C(=O)OC(C)(C)C)C[C@@H](COC(=O)N2CCOCC2)O1)C(c1ccc(F)cc1)c1ccc(F)cc1]

To a solution of (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(hydroxymethyl)morpholine-4-carboxylate (Example 102, step 1) (39 mg, 0.055 mmol) in pyridine (0.5 mL) at room temperature was added 1,1'-carbonyldiimidazole (18 mg, 0.11 mmol). The mixture was warmed to 65° C. for 2 hours. The resulting solution was cooled to room temperature and morpholine (19 L, 0.22 mmol) was added. The solution was stirred at 65° C. for 12 hours. The solution was concentrated and purified by isco silica gel chromatography (0-5% MeOH/DCM) on a 12 g RediSep Rf silica gel column to afford (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(((morpholine-4-carbonyl)oxy)methyl)morpholine-4-carboxylate as a white solid. LRMS (ESI) m/z 828.3 [(M+H$^+$) calcd for $C_{42}H_{53}F_3N_5O_9$: 828.5.

Step 2: {(2S,6R)-6-[2-(3-fluoro-5-{[4-fluoro-β-(4-fluorophenyl)-L-phenylalanyl]amino}pyridin-4-yl)ethyl]morpholin-2-yl}methyl morpholine-4-carboxylate ((2S,6R)-6-(2-(3-((S)-2-amino-3,3-bis(4-fluorophenyl)propanamido)-5-fluoropyridin-4-yl)ethyl)morpholin-2-yl)methyl morpholine-4-carboxylate as the bis HCl salt was prepared from (2R,6S)-tert-butyl 2-(2-(3-((S)-2-((tert-butoxycarbonyl)amino)-3,3-bis(4-fluorophenyl)propanamido)-5-fluoropyridin-4-yl)ethyl)-6-(((morpholine-4-carbonyl)oxy)methyl)morpholine-4-carboxylate following the procedure detailed in Example 102, Step 3. LRMS (ESI) m/z 628.1 [(M+H$^+$) calcd for $C_{32}H_{37}F_3N_5O_5$: 628.4. $^1$H NMR (500 MHz, d6-DMSO) δ 1.90 (m, 2 H), 2.35 (m, 1 H), 2.55 (m, 1 H), 3.00 (m, 2 H), 3.19 (m, 2 H), 3.34 (m, 4 H), 3.45 (m, 4 H), 4.04-4.16 (m, 3 H), 4.24 (m, 1 H), 4.44 (d, J=11.1 Hz, 1 H), 5.69 (m, 1 H), 7.14 (t, J=8.6 Hz, 2 H), 7.25 (t, J=8.6 Hz, 2 H), 7.61-7.67 (m, 4 H), 7.83 (s, 1 H), 8.02 (s, 1 H), 8.33 (s, 1 H), 8.67 (m, 2 H), 9.35 (s, 1 H), 9.55 (s, 1 H), 10.98 (s, 1 H).

The following compound was prepared from (2R,6S)-tert-butyl 2-(2-(3-amino-5-fluoropyridin-4-yl)ethyl)-6-(((tert-butyldimethylsilyl)oxy)methyl)morpholine-4-carboxylate and (S)-3-(3,5-difluorophenyl)-3-(4-fluorophenyl)propanoic acid following the procedures detailed in Example 102, Step 1 and Example 105, Steps 1-2.

| Compound_ID | Structure | LCMS Data |
|---|---|---|
| Example 106<br>((2S,6R)-6-(2-(3-((S)-3-(3,5-difluorophenyl)-3-(4-fluorophenyl)propanamido)-5-fluoropyridin-4-yl)ethyl)morpholin-2-yl)methyl(2,2-trifluoroethyl)carbamate | | M + 1,<br>+ESI = 643.1 |
| Example 107<br>N-(3-{(6R)-6-[2-(4-chlorophenyl)ethyl]morpholin-2-yl}propyl)-Nα-(methoxycarbonyl)-β-phenyl-L-phenylalaninamide | | 564.3 |
| Example 108<br>N-(2-{2-[(2R,6S)-6-{[4-(1H-imidazol-1-yl)phenoxy]methyl}morpholin-2-yl]ethyl}phenyl)-Nα-(methoxycarbonyl)-β-phenyl-L-phenylalaninamide | | 660.3 |
| Example 109<br>N-(2-{2-[(2S,6S)-6-{[(4-chlorophenyl)sulfonyl]methyl}morpholin-2-yl]ethyl}phenyl)-Nα-(methoxycarbonyl)-β-phenyl-L-phenylalaninamide | | 676.2 |
| Example 110<br>Nα-(methoxycarbonyl)-β-phenyl-N-(2-{2-[(2R,6S)-6-{[2-(1H-pyrazol-3-yl)phenoxy]methyl}morpholin-2-yl]ethyl}phenyl)-L-phenylalaninamide | | 660.3 |

-continued

| Compound_ID | Structure | LCMS Data |
|---|---|---|
| Example 111<br>N-(2-{2-[(2R,6R)-6-ethynylmorpholin-2-yl]ethyl}phenyl)-Nα-(methoxycarbonyl)-β-phenyl-L-phenylalaninamide | | 512.3 |
| Example 112<br>N-(2-{2-[(2R,6S)-6-(5,6-dimethyl-1H-benzimidazol-2-yl)morpholin-2-yl]ethyl}phenyl)-Nα-(methoxycarbonyl)-β-phenyl-L-phenylalaninamide | | 632.3 |
| Example 113<br>N-[2-(2-{(2R,6S)-6-[(3-cyanophenoxy)methyl]morpholin-2-yl}ethyl)pyridin-3-yl]-Nα-(methoxycarbonyl)-β-phenyl-L-phenylalaninamide | | 620.3 |
| Example 114<br>N-[5-(2-{(2R,6S)-6-[(4-cyanophenoxy)methyl]morpholin-2-yl}ethyl)pyrimidin-4-yl]-Nα-(methoxycarbonyl)-β-phenyl-L-phenylalaninamide | | 621.3 |
| Example 115<br>Nα-(methoxycarbonyl)-N-(4-{2-[(2R,6S)-6-{[4-(methylsulfonyl)phenoxy]methyl}morpholin-2-yl]ethyl}-1H-pyrazol-3-yl)-β-phenyl-L-phenylalaninamide | | 662.3 |
| Example 116<br>N-[2-(2-{(2R,6R)-6-[2-(4-chlorophenyl)ethyl]morpholin-2-yl}ethyl)phenyl]-Nα-(methoxycarbonyl)-β-phenyl-L-phenylalaninamide | | 626.3 |

| Compound_ID | Structure | LCMS Data |
|---|---|---|
| Example 117<br>N-[2-({(2S,6S)-6-[(4-cyanophenoxy)methyl]morpholin-2-yl}methyl)phenyl]-Nα-(methoxycarbonyl)-β-phenyl-L-phenylalaninamide | | 605.3 |
| Example 118<br>N-(2-{2-[(2R,6S)-6-{[(4-chlorophenyl)sulfanyl]methyl}morpholin-2-yl]ethyl}phenyl)-Nα-(methoxycarbonyl)-β-pyridin-4-ylphenylalaninamide | | 645.2 |
| Example 119<br>N-(2-{2-[(2R,6S)-6-{[(4-chlorophenyl)sulfanyl]methyl}morpholin-2-yl]ethyl}phenyl)-Nα-(methoxycarbonyl)-β-pyridin-4-ylphenylalaninamide | | 645.2 |
| Example 120<br>4-fluoro-N-(5-fluoro-4-{2-[(2R,6S)-6-(hydroxymethyl)morpholin-2-yl]ethyl}pyridin-3-yl)-β-(4-fluorophenyl)-L-phenylalaninamide | | 515.2 |
| Example 121<br>N-(2-{2-[(2R,6S)-6-{[(4-chlorophenyl)sulfanyl]methyl}morpholin-2-yl]ethyl}-3-fluorophenyl)-4-fluoro-β-(4-fluorophenyl)-L-phenylalaninamide | | 640.2 |

-continued

| Compound_ID | Structure | LCMS Data |
|---|---|---|
| Example 122<br>N-(4-{2-[(2R,6S)-6-{[(4-chlorophenyl)sulfanyl]methyl}morpholin-2-yl]ethyl}-5-fluoropyridin-3-yl)-4-fluoro-β-(4-fluorophenyl)-D-phenylalaninamide | 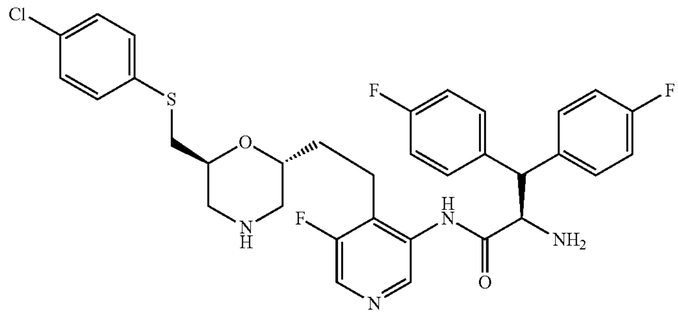 [SMILES: N[C@@H](C(=O)Nc1cncc(F)c1CC[C@@H]1CNC[C@@H](CSc2ccc(Cl)cc2)O1)C(c1ccc(F)cc1)c1ccc(F)cc1] | 641.2 |
| Example 123<br>4-fluoro-β-(4-fluorophenyl)-N-(5-fluoro-4-{2-[(2R,6S)-6-({[(2,2,2-trifluoroethyl)carbamoyl]oxy}methyl)morpholin-2-yl]ethyl}pyridin-3-yl)-L-phenylalaninamide | 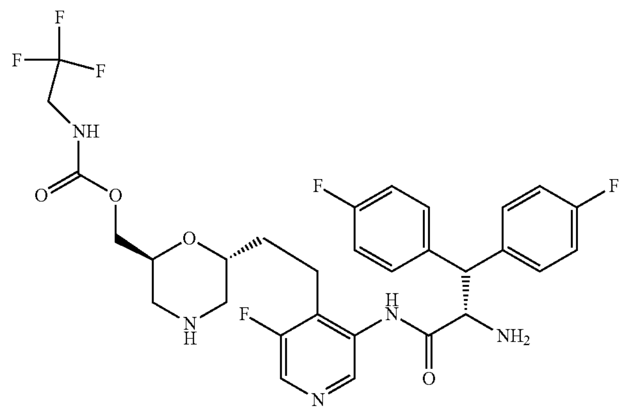 [SMILES: N[C@H](C(=O)Nc1cncc(F)c1CC[C@@H]1CNC[C@@H](COC(=O)NCC(F)(F)F)O1)C(c1ccc(F)cc1)c1ccc(F)cc1] | 640.2 |
| Example 124<br>N-[4-(2-{(2R,6S)-6-[(carbamoyloxy)methyl]morpholin-2-yl}ethyl)-5-fluoropyridin-3-yl]-4-fluoro-β-(4-fluorophenyl)-L-phenylalaninamide | 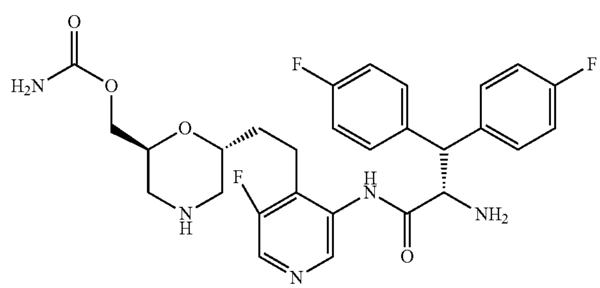 [SMILES: NC(=O)OC[C@@H]1CNC[C@@H](CCc2c(F)cncc2NC(=O)[C@@H](N)C(c2ccc(F)cc2)c2ccc(F)cc2)O1] | 558.2 |
| Example 125<br>4-fluoro-N-(5-fluoro-4-{2-[(2R,6S)-6-({[(4-fluorobenzyl)carbamoyl]oxy}methyl)morpholin-2-yl]ethyl}pyridin-3-yl)-β-(4-fluorophenyl)-L-phenylalaninamide | 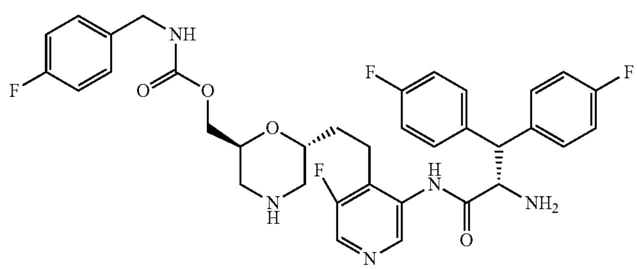 [SMILES: N[C@H](C(=O)Nc1cncc(F)c1CC[C@@H]1CNC[C@@H](COC(=O)NCc2ccc(F)cc2)O1)C(c1ccc(F)cc1)c1ccc(F)cc1] | 666.3 |
| Example 126<br>{(2S,6R)-6-[2-(2-{[(3S)-3-(3,5-difluorophenyl)-3-(4-fluorophenyl)propanoyl]amino}-6-fluorophenyl)ethyl]morpholin-2-yl}methyl (2,2,2-trifluoroethyl)carbamate | 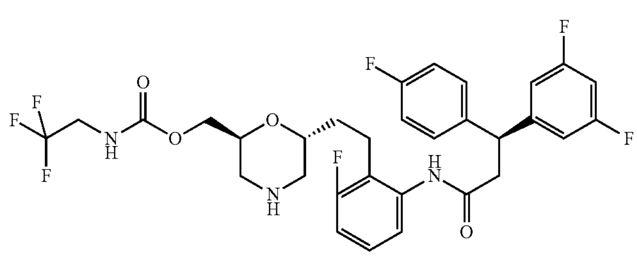 [SMILES: O=C(C[C@@H](c1ccc(F)cc1)c1cc(F)cc(F)c1)Nc1cccc(F)c1CC[C@@H]1CNC[C@@H](COC(=O)NCC(F)(F)F)O1] | 642.2 |

-continued

| Compound_ID | Structure | LCMS Data |
|---|---|---|
| Example 127<br>{(2S,6R)-6-[2-(2-{[3,3-bis(4-fluorophenyl)propanoyl]amino}-6-fluorophenyl)ethyl]morpholin-2-yl}methyl(2,2,2-trifluoroethyl)carbamate | 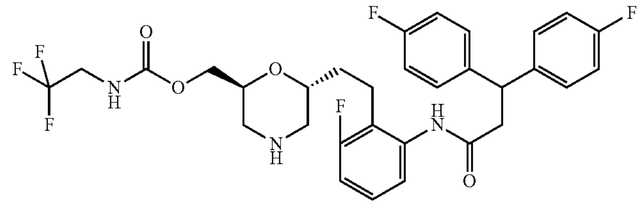 [SMILES: O=C(CC(c1ccc(F)cc1)c1ccc(F)cc1)Nc1cccc(F)c1CC[C@@H]1CNC[C@@H](COC(=O)NCC(F)(F)F)O1] | 624.2 |
| Example 128<br>{(2S,6R)-6-[2-(3-{[3,3-bis(4-fluorophenyl)propanoyl]amino}-5-fluoropyridin-4-yl)ethyl]morpholin-2-yl}methyl(2,2,2-trifluoroethyl)carbamate | 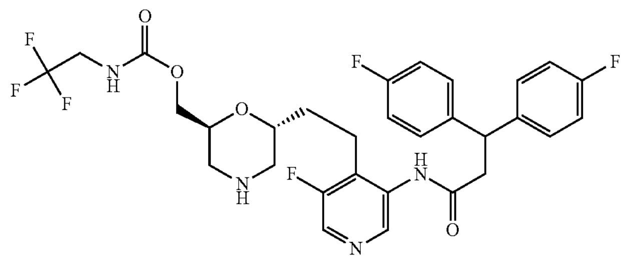 [SMILES: O=C(CC(c1ccc(F)cc1)c1ccc(F)cc1)Nc1cncc(F)c1CC[C@@H]1CNC[C@@H](COC(=O)NCC(F)(F)F)O1] | 625.2 |
| Example 129<br>[(2S,6R)-6-(2-{3-[(3,3-diphenylpropanoyl)amino]-5-fluoropyridin-4-yl}ethyl)morpholin-2-yl]methyl(2,2,2-trifluoroethyl)carbamate | 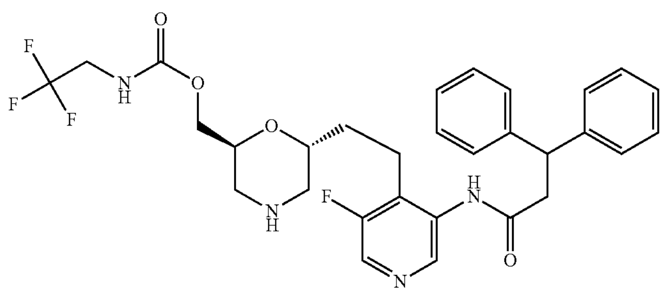 [SMILES: O=C(CC(c1ccccc1)c1ccccc1)Nc1cncc(F)c1CC[C@@H]1CNC[C@@H](COC(=O)NCC(F)(F)F)O1] | 589.2 |
| Example 130<br>4-fluoro-β-(4-fluorophenyl)-N-(5-fluoro-4-{2-[(2R,6S)-6-({[(2-phenylethyl)carbamoyl]oxy}methyl)morpholin-2-yl]ethyl}pyridin-3-yl)-L-phenylalaninamide | 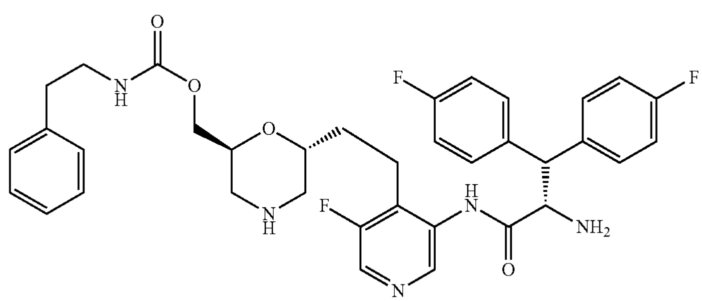 [SMILES: N[C@H](C(=O)Nc1cncc(F)c1CC[C@@H]1CNC[C@@H](COC(=O)NCCc2ccccc2)O1)C(c1ccc(F)cc1)c1ccc(F)cc1] | 662.3 |
| Example 131<br>N-(5-fluoro-4-{2-[(7R)-6-oxa-9-azaspiro[4.5]dec-7-yl]ethyl}pyridin-3-yl)-β-phenyl-L-phenylalaninamide | 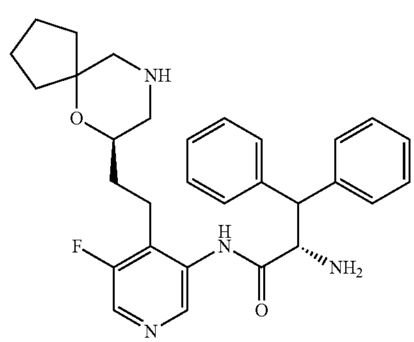 [SMILES: N[C@H](C(=O)Nc1cncc(F)c1CC[C@@H]1CNCC2(CCCC2)O1)C(c1ccccc1)c1ccccc1] | 503.3 |

-continued

| Compound_ID | Structure | LCMS Data |
|---|---|---|
| Example 132<br>4-fluoro-N-[5-fluoro-4-(2-{(2R,6S)-6-[(2-methylpropoxy)methyl]morpholin-2-yl}ethyl)pyridin-3-yl]-β-(4-fluorophenyl)-L-phenylalaninamide | | 571.3 |
| Example 133<br>N-(5-fluoro-4-{2-[(2R)-1-oxa-4-azaspiro[5.5]undec-2-yl]ethyl}pyridin-3-yl)-β-phenyl-L-phenylalaninamide | | 517.3 |
| Example 134<br>N-(4-{2-[(2R,6S)-6-({[(cyclohexylmethyl)carbamoyl]oxy}methyl)morpholin-2-yl]ethyl}-5-fluoropyridin-3-yl)-4-fluoro-β-(4-fluorophenyl)phenylalaninamide | | 654.3 |
| Example 135<br>N-(4-{2-[(2R,6S)-6-({[(2-chlorobenzyl)carbamoyl]oxy}methyl)morpholin-2-yl]ethyl}-5-fluoropyridin-3-yl)-4-fluoro-β-(4-fluorophenyl)phenylalaninamide | | 682.2 |

-continued

| Compound_ID | Structure | LCMS Data |
|---|---|---|
| Example 136<br>4-fluoro-N-(5-fluoro-4-{2-[(2R,6S)-6-({[(3-hydroxy-2,2-dimethylpropyl)carbamoyl]oxy}methyl)morpholin-2-yl]ethyl}pyridin-3-yl)-β-(4-fluorophenyl)phenylalaninamide | | 644.3 |
| Example 137<br>4-fluoro-N-(5-fluoro-4-{2-[(2R,6S)-6-({[(6-methylpyridin-3-yl)carbamoyl]oxy}methyl)morpholin-2-yl]ethyl}pyridin-3-yl)-β-(4-fluorophenyl)phenylalaninamide | | 649.3 |
| Example 138<br>4-fluoro-N-(5-fluoro-4-{2-[(2R,6S)-6-({[(3-fluoropropyl)carbamoyl]oxy}methyl)morpholin-2-yl]ethyl}pyridin-3-yl)-β-(4-fluorophenyl)phenylalaninamide | | 618.3 |
| Example 139<br>N-[4-(2-{(2R,6S)-6-[({[2-(3,5-dimethyl-1H-pyrazol-1-yl)ethyl]carbamoyl}oxy)methyl]morpholin-2-yl}ethyl)-5-fluoropyridin-3-yl]-4-fluoro-β-(4-fluorophenyl)phenylalaninamide | | 680.3 |

| Compound_ID | Structure | LCMS Data |
|---|---|---|
| 4-fluoro-N-[5-fluoro-4-(2-{(2R,6S)-6-[({[(2-methyltetrahydrofuran-2-yl)methyl]carbamoyl}oxy)methyl]morpholin-2-yl}ethyl)pyridin-3-yl]-β-(4-fluorophenyl)phenylalaninamide | 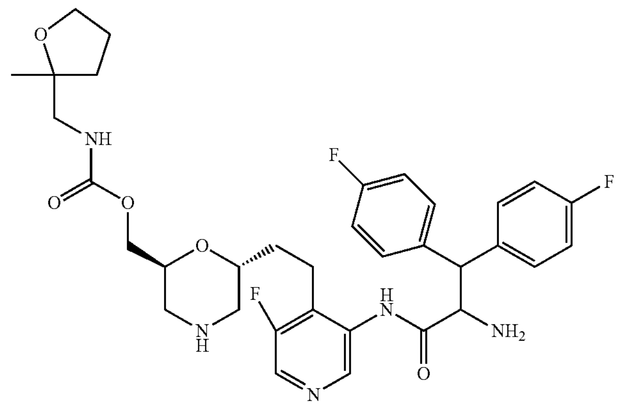 [SMILES: CC1(CNC(=O)OC[C@@H]2CNC[C@@H](CCc3c(F)cncc3NC(=O)C(N)C(c3ccc(F)cc3)c3ccc(F)cc3)O2)CCCO1] | 656.3 |
| Example 141<br>4-fluoro-N-[5-fluoro-4-(2-{(2R,6S)-6-[({[(4-methylmorpholin-2-yl)methyl]carbamoyl}oxy)methyl]morpholin-2-yl}ethyl)pyridin-3-yl]-β-(4-fluorophenyl)phenylalaninamide | 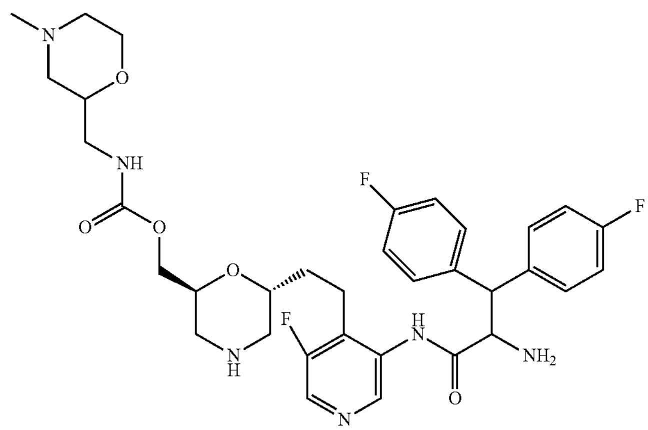 [SMILES: CN1CCOC(CNC(=O)OC[C@@H]2CNC[C@@H](CCc3c(F)cncc3NC(=O)C(N)C(c3ccc(F)cc3)c3ccc(F)cc3)O2)C1] | 671.3 |
| Example 142<br>4-fluoro-β-(4-fluorophenyl)-N-(5-fluoro-4-{2-[(2R,6S)-6-({[(tetrahydrofuran-3-ylmethyl)carbamoyl]oxy}methyl)morpholin-2-yl]ethyl}pyridin-3-yl)phenylalaninamide | 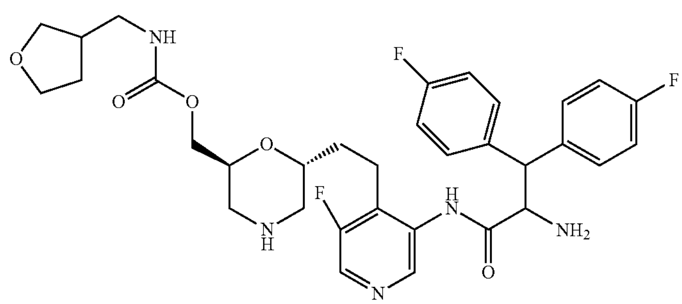 [SMILES: NC(C(=O)Nc1cncc(F)c1CC[C@@H]1CNC[C@@H](COC(=O)NCC2CCOC2)O1)C(c1ccc(F)cc1)c1ccc(F)cc1] | 642.3 |
| Example 143<br>N-(4-{2-[(2R,6R)-6-{[(2-chlorobenzyl)amino]methyl}morpholin-2-yl]ethyl}-5-fluoropyridin-3-yl)-4-fluoro-β-(4-fluorophenyl)phenylalaninamide | 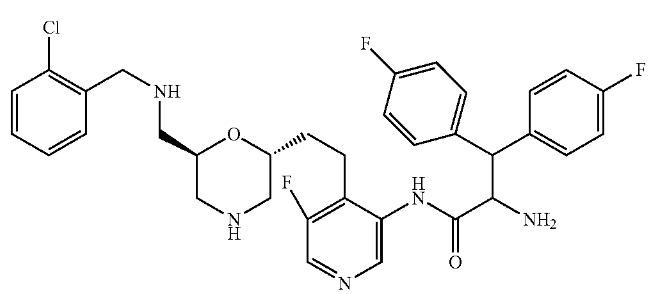 [SMILES: NC(C(=O)Nc1cncc(F)c1CC[C@@H]1CNC[C@@H](CNCc2ccccc2Cl)O1)C(c1ccc(F)cc1)c1ccc(F)cc1] | 638.3 |

-continued

| Compound_ID | Structure | LCMS Data |
|---|---|---|
| Example 144<br>N-(5-fluoro-4-{2-[(7R)-6-oxa-9-azaspiro[4.5]dec-7-yl]ethyl}pyridin-3-yl)-3,3-bis(4-fluorophenyl)propanamide | 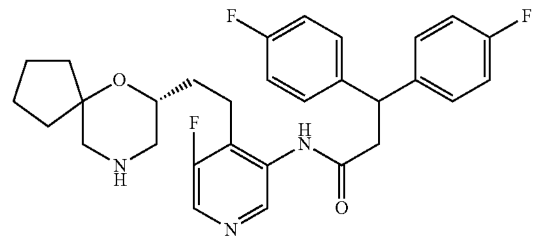 [SMILES: O=C(CC(c1ccc(F)cc1)c1ccc(F)cc1)Nc1cncc(F)c1CC[C@@H]1CNCC2(CCCC2)O1] | 524.3 |
| Example 145<br>(βS)-3,5-difluoro-β-(4-fluorophenyl)-N-(3-fluoro-2-{2-[(2R,6S)-6-({[(2,2,2-trifluoroethyl)carbamoyl]oxy}methyl)morpholin-2-yl]ethyl}phenyl)-L-phenylalaninamide | 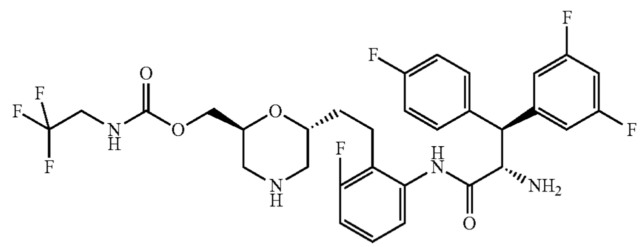 [SMILES: N[C@H](C(=O)Nc1cccc(F)c1CC[C@@H]1CNC[C@@H](COC(=O)NCC(F)(F)F)O1)[C@@H](c1ccc(F)cc1)c1cc(F)cc(F)c1] | 657.2 |
| Example 146<br>4-fluoro-N-(5-fluoro-4-{2-[(2R,6R)-6-{[(3-fluoropropyl)amino]methyl}morpholin-2-yl]ethyl}pyridin-3-yl)-β-(4-fluorophenyl)-L-phenylalaninamide | 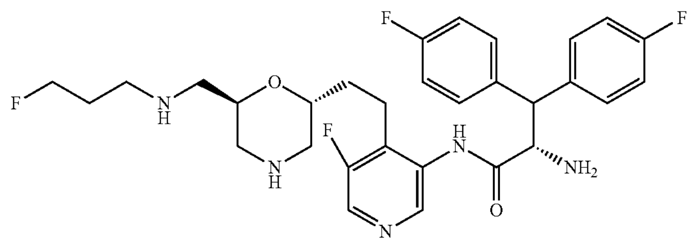 [SMILES: N[C@H](C(=O)Nc1cncc(F)c1CC[C@@H]1CNC[C@@H](CNCCCF)O1)C(c1ccc(F)cc1)c1ccc(F)cc1] | 574.3 |
| Example 147<br>N-(4-{2-[(2R,6R)-6-({[2-(3,5-dimethyl-1H-pyrazol-1-yl)ethyl]amino}methyl)morpholin-2-yl]ethyl}-5-fluoropyridin-3-yl)-4-fluoro-β-(4-fluorophenyl)-L-phenylalaninamide | 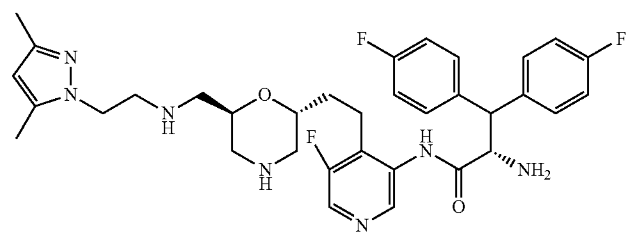 [SMILES: Cc1cc(C)n(CCNC[C@@H]2CNC[C@@H](CCc3c(F)cncc3NC(=O)[C@@H](N)C(c3ccc(F)cc3)c3ccc(F)cc3)O2)n1] | 636.3 |
| Example 148<br>N-(4-{2-[(2R,6S)-6-{[(1,4-dioxan-2-ylmethyl)(methyl)amino]methyl}morpholin-2-yl]ethyl}-5-fluoropyridin-3-yl)-4-fluoro-β-(4-fluorophenyl)-L-phenylalaninamide | 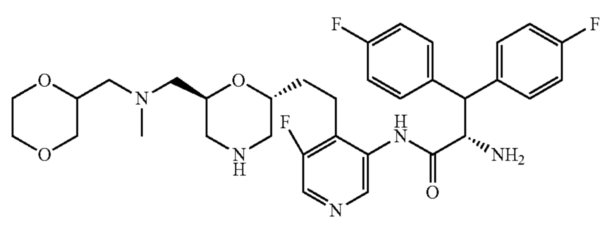 [SMILES: CN(CC1COCCO1)C[C@@H]1CNC[C@@H](CCc2c(F)cncc2NC(=O)[C@@H](N)C(c2ccc(F)cc2)c2ccc(F)cc2)O1] | 628.3 |
| Example 149<br>(βS)-3-fluoro-N-(3-fluoro-2-{2-[(7R)-6-oxa-9-azaspiro[4.5]dec-7-yl]ethyl}phenyl)-β-(4-fluorophenyl)-L-phenylalaninamide | 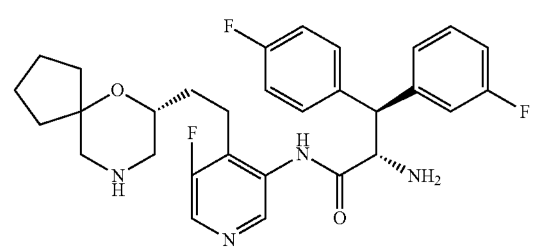 [SMILES: N[C@H](C(=O)Nc1cncc(F)c1CC[C@@H]1CNCC2(CCCC2)O1)[C@@H](c1ccc(F)cc1)c1cccc(F)c1] | 538.3 |

| Compound_ID | Structure | LCMS Data |
|---|---|---|
| Example 150<br>4-fluoro-N-(5-fluoro-4-{2-[(7R)-6-oxa-9-azaspiro[4.5]dec-7-yl]ethyl}pyridin-3-yl)-β-(4-fluorophenyl)-L-phenylalaninamide | | 539.3 |
| Example 151<br>methyl{(1S)-2-[(2-{2-[(2R)-9-acetyl-1-oxa-4,9-diazaspiro[5.5]undec-2-yl]ethyl}-3-fluorophenyl)amino]-1-[(S)-(4-chlorophenyl)(3,5-difluorophenyl)methyl]-2-oxoethyl}carbamate | | 687.3 |
| Example 152<br>(βS)-N-(4-{2-[(2R)-9-acetyl-1-oxa-4,9-diazaspiro[5.5]undec-2-yl]ethyl}-5-fluoropyridin-3-yl)-4-chloro-β-(3,5-difluorophenyl)-L-phenylalaninamide | | 630.2 |
| Example 153<br>methyl{(1S)-2-[(4-{2-[(2R)-9-acetyl-1-oxa-4,9-diazaspiro[5.5]undec-2-yl]ethyl}-5-fluoropyridin-3-yl)amino]-1-[(S)-(4-chlorophenyl)(3,5-difluorophenyl)methyl]-2-oxoethyl}carbamate | | 688.3 |
| Example 154<br>(βS)-β-(4-chlorophenyl)-N-(5-fluoro-4-{2-[(2R)-9-(methylsulfonyl)-1-oxa-4,9-diazaspiro[5.5]undec-2-yl]ethyl}pyridin-3-yl)-3-(trifluoromethoxy)-L-phenylalaninamide | | 714.2 |

-continued

| Compound_ID | Structure | LCMS Data |
|---|---|---|
| Example 155<br>(βS)-4-chloro-β-(3,5-difluorophenyl)-N-(4-{2-[(2R)-1,9-dioxa-4-azaspiro[5.5]undec-2-yl]ethyl}-5-fluoropyridin-3-yl)-L-phenylalaninamide | | 589.2 |
| Example 156<br>(βS)-4-chloro-N-(4-{2-[(2R)-1,9-dioxa-4-azaspiro[5.5]undec-2-yl]ethyl}-5-fluoropyridin-3-yl)-β-[3-(trifluoromethoxy)phenyl]-L-phenylalaninamide | | 637.2 |
| Example 157<br>methyl{(1S,2S)-2-(4-chlorophenyl)-1-[(4-{2-[(2R)-1,9-dioxa-4-azaspiro[5.5]undec-2-yl]ethyl}-5-fluoropyridin-3-yl)carbamoyl]-2-[3-(trifluoromethoxy)phenyl]ethyl}carbamate | | 695.2 |
| Example 158<br>(βR)-4-chloro-N-(4-{2-[(2R)-1,9-dioxa-4-azaspiro[5.5]undec-2-yl]ethyl}-5-fluoropyridin-3-yl)-β-(tetrahydro-2H-pyran-4-yl)-L-phenylalaninamide | | 561.3 |
| Example 159<br>(βR)-4-chloro-N-(2-{2-[(2R)-1,9-dioxa-4-azaspiro[5.5]undec-2-yl]ethyl}-3-fluorophenyl)-β-(tetrahydro-2H-pyran-4-yl)-L-phenylalaninamide | | 560.3 |

| Compound_ID | Structure | LCMS Data |
|---|---|---|
| Example 160<br>methyl[(1S,2R)-2-(4-chlorophenyl)-1-[(4-{2-[(2R)-1,9-dioxa-4-azaspiro[5.5]undec-2-yl]ethyl}-5-fluoropyridin-3-yl)carbamoyl]-2-(tetrahydro-2H-pyran-4-yl)ethyl]carbamate | | 619.3 |
| Example 161<br>methyl[(1S,2R)-2-(4-chlorophenyl)-1-[(2-{2-[(2R)-1,9-dioxa-4-azaspiro[5.5]undec-2-yl]ethyl}-3-fluorophenyl)carbamoyl]-2-(tetrahydro-2H-pyran-4-yl)ethyl]carbamate | | 618.3 |
| Example 162<br>(βS)-4-chloro-β-(3,5-difluorophenyl)-N-(2-{2-[(7R)-2,6-dioxa-9-azaspiro[4.5]dec-7-yl]ethyl}-3-fluorophenyl)-L-phenylalaninamide | | 574.2 |
| Example 163<br>methyl{(1S,2S)-2-(4-chlorophenyl)-2-(3,5-difluorophenyl)-1-[(2-{2-[(7R)-2,6-dioxa-9-azaspiro[4.5]dec-7-yl]ethyl}-3-fluorophenyl)carbamoyl]ethyl}carbamate | | 632.2 |

EXAMPLE 164

Assay for Inhibition of Microbial Expressed HIV Protease ("Pepcleav")

Studies of the inhibition of the wildtype HIV-1 protease (which was expressed in *Escherichia coli*) were carried out with a peptide substrate [Val-Ser-Gln-Asn-(βnaphtyl)Ala-Pro-Ile-Val (SEQ ID NO 1)]. The inhibitor was first preincubated with the HIV-1 protease (wild type) enzyme in assay buffer (50 mM sodium acetate, pH 5.5, 100 mM NaCl, and 0.1% BSA) for 30 minutes at room temperature. Substrate was added to 400 micromolar in a total volume of 20 microliters containing 20 picomolar HIV-1 protease (final) and the reaction is incubated for 1 hour at 30° C. The reaction was quenched with the addition of formic acid and indinavir to 0.012% and 150 nM final concentrations, respectively. Product formation was determined after separation of product and substrate on a Zorbax Eclipse XDB-C18 column connected to an API 4000 mass spectrometer (Applied Biosystems) with multiple reaction monitoring (transitions were 644.5/428.9 and 615.4/422.2 (M1/M3) for product and indinavir respectively). The extent of inhibition of the reaction was determined from the peak area of the products. Analysis of the products, independently synthesized, provided quantitation standards and confirmation of the product composition. Representative compounds of the present invention exhibit inhibition of HIV-1 protease in this assay.

EXAMPLE 165

Antiviral Assays in Cell Culture ("Spread")

Acute Infection Assay ("Spread") data were generated using HIV-1 (H9IIIB strain) infection of MT-4 human T-lymphoid cells in 10% FBS, and according to the methods disclosed by J. P. Vacca et al, "L-735,524: An orally bioavailable human immunodeficiency virus type 1 protease inhibitor," *Proc. Natl. Acad. Sci. USA*, Vol. 91, pp. 4096-4100 (April 1994).

EXAMPLE 166

Viral Kinetics GFP Reporter (ViKinG) Assay

The ViKinG assay is an in vitro kinetic assay that employs the MT4-gag-GFP reporter cell line (Wang et al., "Assessment of the susceptibility of mutant HIV-1 to antiviral agents." *J Virological Methods* 165:230-37 (2010)) to quantify the number of new cells infected in each round of replication. The purpose of the ViKinG assay is to identify agents that inhibit HIV progression. Briefly, HIV infection results in tat transactivation of the stably expressed HIV LTR promoter to drive gagGFP expression. Thus, an increase in the number of GFP-MT4 cells results following HIV infection. Compounds dose dependently inhibit the number of GFP cells.

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended RPMI+ 10% or 50% normal human serum (NHS). Test compounds were serial-diluted in DMSO on an ECHO® liquid handling platform (Labcyte Corp., Sunnyvale, Calif.), along with a triple drug control (integrase, protease and NNRTI compounds). The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen® eX3 (TTP Labtech Ltd., Hertfordshire, United Kingdom). Viral reproductive ratio ($R_0$) was determined using the number of infected cells at 48 hours divided by the number of infected cells at 24 hours. Percent viral growth inhibition was calculated by $[1-(R-R_{tripledrug})/(RDMSO-R_{tripledrug})]*100$. Compound potency IP or IC50 was determined by a 4-parameter dose response curve analysis.

Representative compounds of the present invention exhibit inhibition of HIV replication in this assay. For example, as shown by their ViKinG values (nm) in Data Table 1 below, compounds set forth in the foregoing Examples were tested in this assay and found to exhibit inhibition of HIV-1 replication to varying degrees.

Data Table 1 provides data from the Pepcleave, Spread, and Viking assays for each of the example compounds. Each column of data in the table reflects the mean of at least two independent experiments.

DATA TABLE 1

| Example | Pepcleav (nM) | Spread 50% NHS (nM) | Viking 50% NHS (nM) |
|---|---|---|---|
| 1 | 450 | | |
| 2 | 300 | | |
| 3 | 420 | | |
| 4 | 62 | | |
| 5 | 58 | | |
| 6 | 1.9 | | |
| 7 | 2.0 | | |
| 8 | 2.1 | | |
| 9 | 18 | | |
| 10 | 120 | | |
| 11 | 6.6 | | |
| 12 | 24 | | |
| 13 | 21 | | |
| 14 | 32 | | |
| 15 | 12 | | |
| 16 | 19 | | |
| 17 | 21 | | |
| 18 | 1.9 | | |
| 19 | 8.7 | | |
| 20 | 2.9 | | |
| 21 | 0.86 | | |
| 22 | 1.1 | | |
| 23 | 0.8 | | |
| 24 | 2.1 | | |
| 25 | 1.5 | | |
| 26 | 1.3 | | |
| 27 | 0.53 | | |
| 28 | 18 | | |
| 29 | 17 | | |
| 30 | 130 | | |
| 31 | 36 | | |
| 32 | 8.0 | | |
| 33 | 0.67 | | |
| 34 | 0.42 | | |
| 35 | 2.1 | | |
| 36 | 0.93 | | |
| 37 | 21 | | |
| 38 | 240 | | |
| 39 | 100 | | |
| 40 | 68 | | |
| 41 | 26 | | |
| 42 | 0.94 | | |
| 43 | 4.7 | | |
| 44 | 14 | | |
| 45 | 11 | | |
| 46 | 23 | | |
| 47 | 12 | | |
| 48 | 5.5 | | |
| 49 | 14 | | |
| 50 | 130 | | |
| 51 | 14 | | |
| 52 | 4.0 | | |
| 53 | 13 | | |
| 54 | 0.93 | | |
| 55 | 12 | | |
| 56 | 110 | | |
| 57 | 280 | | |
| 58 | 8.1 | | |
| 59 | 62 | | |
| 60 | 19 | | |
| 61 | 5.9 | | |
| 62 | 1.4 | | |
| 63 | 8.8 | | |
| 64 | 28 | | |
| 65 | 50 | | |
| 66 | 0.20 | | |
| 67 | 0.11 | | |
| 68 | 0.03 | | |
| 69 | 0.30 | | |
| 70 | 0.74 | | |
| 71 | 7.4 | | |
| 72 | 23 | | |
| 73 | 0.89 | | |
| 74 | 39 | | |
| 75 | 46 | | |
| 76 | 9.1 | | |
| 77 | 11 | | |
| 78 | 150 | | |
| 79 | 120 | | |
| 80 | 58 | | |
| 81 | 53 | | |
| 82 | 9.8 | | |
| 83 | 27 | | |
| 84 | 430 | | |

DATA TABLE 1-continued

| Example | Pepcleav (nM) | Spread 50% NHS (nM) | Viking 50% NHS (nM) |
|---|---|---|---|
| 85 | 88 | | |
| 86 | 4.1 | | |
| 87 | 0.05 | | |
| 88 | 0.04 | | |
| 89 | 12.3 | | |
| 90 | 53.29 | | |
| 91 | 0.25 | | 20 |
| 92 | | | 35 |
| 93 | 11 | | 46 |
| 94 | 11 | | 42 |
| 95 | | | 150 |
| 96 | | | 80 |
| 97 | | | 55 |
| 98 | 29 | | 88 |
| 99 | 15 | | 59 |
| 100 | | | 71 |
| 101 | | | 110 |
| 102 | 0.47 | | |
| 103 | 0.49 | | 37 |
| 104 | 0.28 | | |
| 105 | 29 | | |
| 106 | | 38 | |
| 107 | 1000 | | |
| 108 | 37 | | |
| 109 | 770 | | |
| 110 | 250 | | |
| 111 | 580 | | |
| 112 | 850 | | |
| 113 | 510 | | |
| 114 | 1000 | | |
| 115 | 370 | | |
| 116 | 4.5 | | |
| 117 | 180 | | |
| 118 | 0.47 | | |
| 119 | 43 | | |
| 120 | 380 | | |
| 121 | 5.2 | | |
| 122 | 9.0 | | |
| 123 | 16 | | |
| 124 | 120 | | |
| 125 | 15 | | |
| 126 | | 1000 | |
| 127 | | 3400 | |
| 128 | | 350 | |
| 129 | | 210 | |
| 130 | 8.8 | 160 | |
| 131 | 300 | | |
| 132 | 430 | | |
| 133 | 290 | | |
| 134 | | 620 | |
| 135 | | 210 | |
| 136 | | 760 | |
| 137 | | 280 | |
| 138 | | 540 | |
| 139 | | 380 | |
| 140 | | 170 | |
| 141 | | 2200 | |
| 142 | | 240 | |
| 143 | | 730 | |
| 144 | | 740 | |
| 145 | | 140 | |
| 146 | | 2200 | |
| 147 | | 1900 | |
| 148 | | 460 | |
| 149 | | 1300 | |
| 150 | | | 270 |
| 151 | | | 170 |
| 152 | | | 320 |
| 153 | | | 310 |
| 154 | | | 300 |
| 155 | | | 140 |
| 156 | | | 480 |
| 157 | | | 210 |
| 158 | | | 390 |
| 159 | | | 490 |
| 160 | | | 350 |
| 161 | | | 130 |
| 162 | | | 180 |
| 163 | | | 150 |

---

What is claimed is:

1. A compound of Formula I:

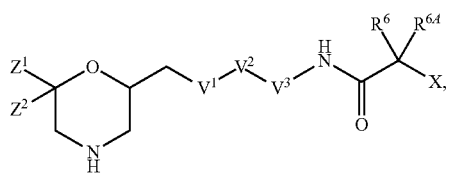
(I)

or a pharmaceutically acceptable salt thereof, wherein:

$V^1$ is a bond, $CH_2$, or O;

$V^2$ is $CH_2$;

$V^3$ is $CH_2$; or alternatively, $V^2$ and $V^3$ may come together to form (i) a phenyl group, which is optionally substituted with up to 4 occurrences of $X^D$, or (ii) HetA, wherein $V^2$ is C or CH and $V^3$ is C, CH, or N;

X is H or $NR^1R^2$;

each occurrence of $X^D$ is independently selected from halo, hydroxy, =O, $C_1$-$C_4$ alkyl, $C_1$-$C_4$ alkoxy, —S(O)$_k$ $C_1$-$C_4$ alkyl, CF3, CN, $C_0$-$C_4$ alkyl-phenyl;

each k is independently 0, 1 or 2;

$Z^1$ is selected from the group consisting of:

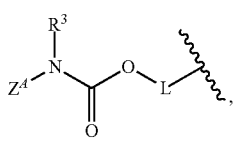
(1)

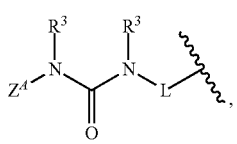
(2)

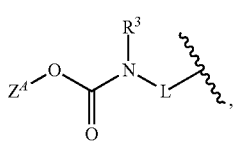
(3)

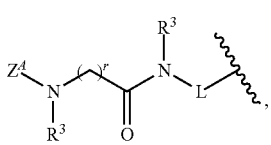
(4)

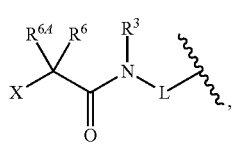
(5)

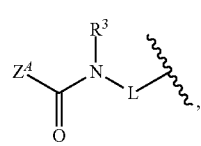
(6)

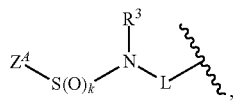
(7)

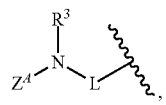
(8)

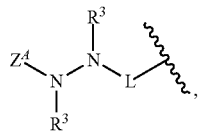
(9)

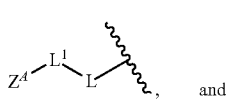
and
(10)

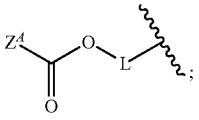
;
(11)

L is a linker selected from
(a) a bond,
(b) —$C_1$-$C_3$ alkylene-,
(c) —$C_2$-$C_4$ alkenylene-,
(d) —$CH_2$—$CF_2$—
(e) —C(O)—,
(f) —CH2—C(O)—,
(g) —CH2—CH2—C(O)—, and
(h)

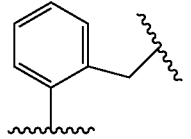 or 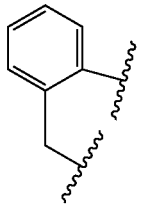 ;

$L^1$ is selected from the group consisting of: S, S(O), $S(O)_2$, O, $C_1$-$C_3$ alkylene, and a bond; each r is independently 1, 2, 3 or 4;

$Z^A$ is selected from the group consisting of:
(a) hydrogen,
(b) $C_1$-$C_{10}$ alkyl,
(c) $C_2$-$C_{10}$ alkenyl,
(d) $C_2$-$C_{10}$ alkynyl,
(e) $C_3$-$C_7$ cycloalkyl,
(f) AryA,
(g) HetB, and
(h) HetC, wherein said $C_1$-$C_{10}$ alkyl, $C_2$-$C_{10}$ alkenyl, $C_2$-$C_{10}$ alkynyl, and $C_3$-$C_7$ cycloalkyl, are optionally substituted with 1 to 6 substituents independently selected from the group consisting of: fluoro, hydroxyl, carbomoyl, $C_3$-$C_6$ cycloalkyl, C(O)O—$C_1$-$C_6$ alkyl, C(O)OH, C(O)—$C_1$-$C_6$ alkyl, N(H)—$C_1$-$C_6$ alkyl, N(—$C_1$-$C_6$ alkyl)$_2$, AryA, HetB and HetC;

each $R^3$ is independently H or $C_1$-$C_6$ alkyl;

$Z^2$ is H; or alternatively $Z^1$ and $Z^2$, together with the carbon atom to which they are attached may form a spirocyclic 3- to 6-membered monocyclic heterocycloalkyl group, a spirocyclic 5- or 6-membered monocyclic heterocycloalkenyl group, or a spirocyclic 3- to 6-membered cycloalkyl group; wherein said 3- to 6-membered monocyclic heterocycloalkyl group, said 5- or 6-membered monocyclic heterocycloalkenyl group, or said 3- to 6-membered cycloalkyl group may be optionally substituted with $X^A$ from one up to the maximum number of substitutable positions as allowed by valence;

$R^6$ is selected from

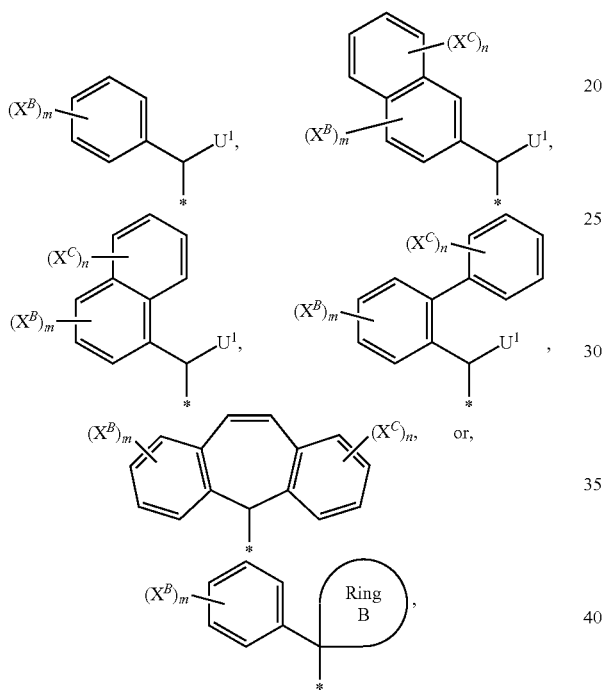

wherein the asterisk (*) denotes the point of attachment to the rest of the compound and U1 is selected from (1) H, (2) $C_1$-$C_{10}$ alkyl, wherein said $C_1$-$C_{10}$ alkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (3) $C_3$-$C_7$ cycloalkyl, wherein said $C_3$-$C_7$ cycloalkyl is optionally substituted with 1 to 4 substituents independently selected from halo, $C_1$-$C_4$ alkyl, $C_1$-$C_4$ haloalkyl, hydroxy and $C_1$-$C_4$ alkoxy, (4) AryA, (5) HetB, (6) HetC, (7) $C_1$-$C_{10}$ alkyl substituted with AryA, (8) $C_1$-$C_{10}$ alkyl substituted with HetB, and (9) $C_1$-$C_{10}$ alkyl substituted with HetC; and Ring B is selected from $C_3$-$C_7$ cycloalkyl, HetB, and HetC, wherein $C_3$-$C_7$ cycloalkyl is optionally substituted with 1 to 4 substituents independently selected from halo, OH, $C_1$-$C_4$ alkyl, $C_1$-$C_4$ fluorolkyl and $C_1$-$C_4$ alkoxy;

$R^{6A}$ is selected from H or $C_1$-$C_6$ alkyl;

alternatively, $R^6$ and $R^{6A}$ together with the carbon to which they are attached form a $C_3$-$C_6$ cycloalkyl, which is optionally substituted with phenyl, wherein the phenyl is optionally substituted with from 1 to 3 $X^E$;

each occurrence of $X^A$, $X^B$, $X^C$, $X^E$, $Y^B$ and $Y^C$ are independently selected from the group consisting of:
(1) $C_1$-$C_6$ alkyl,
(2) $C_3$-$C_6$ cycloalkyl,
(3) $C_1$-$C_6$ haloalkyl,
(4) OH,
(5) O—$C_1$-$C_6$ alkyl,
(6) O—$C_1$-$C_6$ haloalkyl,
(7) O—$C_3$-$C_6$ cycloalkyl,
(8) SH,
(9) S—$C_1$-$C_6$ alkyl,
(10) S—$C_1$-$C_6$ haloalkyl,
(11) S—$C_3$-$C_6$ cycloalkyl,
(12) halo,
(13) CN,
(14) $NO_2$,
(15) $NH_2$,
(16) N(H)—$C_1$-$C_6$ alkyl,
(17) N(—$C_1$-$C_6$ alkyl)2,
(18) N(H)C(O)—$C_1$-$C_6$ alkyl,
(19) N(H)CH(O),
(20) CH(O),
(21) C(O)—$C_1$-$C_6$ alkyl,
(22) C(O)OH,
(23) C(O)O—$C_1$-$C_6$ alkyl,
(24) C(O)$NH_2$,
(25) C(O)N(H)—$C_1$-$C_6$ alkyl,
(26) C(O)N(—$C_1$-$C_6$ alkyl)$_2$,
(27) C(O)N(H)C(O)—$C_1$-$C_6$ alkyl,
(28) C(O)N(H)CH(O)
(29) $SO_2$H,
(30) $SO_2$— $C_1$-$C_6$ alkyl;
(31) phenyl, benzyl or phenoxy, each optionally substituted with 1 to 5 substituents independently selected from halo and $C_1$-$C_6$ alkyl,
(32) HetD, —O-HetD or —$CH_2$—HetD,
(33) trimethylsilyl,
(34) $C_2$-$C_6$ alkenyl, and
(35) $SO_2$—$NH_2$ wherein $C_1$-$C_6$ alkyl in each instance of (1), (3) (5), (6), (9), (10), (16), (17), (18), (21), (23), (25), (26), (27), (30), and (31) and $C_2$-$C_6$ alkenyl of (34) above is optionally substituted with 1 to 6 substituents independently selected from the group consisting of:
(a) $C_1$-$C_6$ haloalkyl,
(b) OH
(c) O—$C_1$-$C_6$ alkyl,
(d) O—$C_1$-$C_6$ haloalkyl,
(e) O—$C_3$-$C_6$ cycloalkyl,
(f) SH,
(g) S—$C_1$-$C_6$ alkyl,
(h) halo,
(i) CN,
(j) $NO_2$,
(k) $NH_2$,
(l) N(H)—C1-6 alkyl,
(m) N(—$C_1$-$C_6$ alkyl)$_2$,
(n) C(O)—$C_1$-$C_6$ alkyl,
(o) C(O)OH,
(p) C(O)O—$C_1$-$C_6$ alkyl, and
(q) $SO_2$— $C_1$-$C_6$ alkyl;

m is an integer equal to 0, 1, 2, or 3;
n is an integer equal to 0, 1, 2, or 3;
$R^1$ is H, $C_1$-$C_6$ alkyl, $C_3$-$C_6$ cycloalkyl, $C_1$-$C_6$ alkyl substituted with $C_3$-$C_6$ cycloalkyl, C(O)—$R^7$ or $SO_2$—$R^7$;
$R^2$ is H, $C_1$-$C_6$ alkyl, $C_1$-$C_6$ haloalkyl and $C_3$-$C_6$ cycloalkyl;

$R^7$ is:
(1) $C_1$-$C_6$ alkyl,
(2) $C_3$-$C_6$ cycloalkyl,
(3) $C_1$-$C_6$ alkyl substituted with $C_3$-$C_6$ cycloalkyl,
(4) O—$C_1$-$C_6$ alkyl,
(5) O—$C_1$-$C_6$ alkyl substituted with O—$C_1$-$C_6$ alkyl,
(6) O—$C_1$-$C_6$ fluoroalkyl,
(7) C(O)O—$C_1$-$C_6$ alkyl,
(8) $C_1$-$C_6$ alkyl substituted with C(O)O—$C_1$-$C_6$ alkyl,
(9) $C_1$-$C_6$ alkyl substituted with C(O)OH,
(10) $C_1$-$C_6$ alkyl substituted with C(O)—$C_1$-$C_6$ alkyl,
(11) N(H)—$C_1$-$C_6$ alkyl,
(12) N(—$C_1$-$C_6$ alkyl)$_2$,
(13) $C_1$-$C_6$ alkyl substituted with $NH_2$, N(H)—$C_1$-$C_6$ alkyl, or N(—$C_1$-$C_6$ alkyl)$_2$,
(14) AryA,
(15) $C_1$-$C_6$ alkyl substituted with AryA,
(16) O—$C_1$-$C_6$ alkyl substituted with AryA,
(17) HetB,
(18) $C_1$-$C_6$ alkyl substituted with HetB,
(19) O—$C_1$-$C_6$ alkyl substituted with HetB,
(20) HetC,
(21) O-HetC, or
(22) O—$C_1$-$C_6$ alkyl substituted with HetC;

each AryA is an aryl which is independently phenyl or naphthyl, wherein the phenyl or naphthyl is optionally substituted with $Y^B$ from one up to the maximum number of substitutable positions as allowed by valence;

each HetA is an independently a 5- or 6-membered monocyclic heteroaryl containing from 1 to 4 N, wherein the moncyclic ring is optionally substituted with up to 3 occurrences of $X^D$;

each HetB is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with $Y^C$ from one up to the maximum number of substitutable positions as allowed by valence; and each HetC is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with one or more substituents, up to the maximum number allowed by valance, each of which is independently halo, CN, $C_1$-$C_6$ alkyl, OH, oxo, O—$C_1$-$C_6$ alkyl, $C_1$-$C_6$ haloalkyl, O—$C_1$-$C_6$ haloalkyl, C(O)$NH_2$, C(O)N(H)—$C_1$-$C_6$ alkyl, C(O)N(—$C_1$-$C_6$ alkyl)$_2$, C(O)H, C(O)—$C_1$-$C_6$ alkyl, $CO_2$H, $CO_2$—$C_1$-$C_6$ alkyl, $SO_2$H, or $SO_2$—$C_1$-$C_6$ alkyl; and each HetD is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with 1 to 5 substituents independently selected from halo and $C_1$-$C_6$ alkyl.

2. The compound according to claim 1, or a pharmaceutically acceptable salt thereof, wherein R6 is:

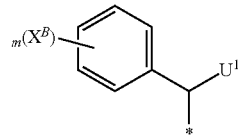

wherein U1 is selected from HetB or HetC, and R6A is H.

3. The compound according to claim 1, or a pharmaceutically acceptable salt thereof, wherein $R^6$ is:

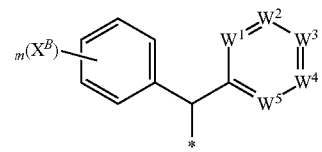

$W^1$ to $W^5$ are independently $CR^5$ or N, with the proviso that no more than four of $W^1$ to $W^5$ are N,
each $R^5$ is independently $X^C$ or H;
and $R^{6A}$ is H.

4. The compound according to claim 1, or a pharmaceutically acceptable salt thereof, having the formula

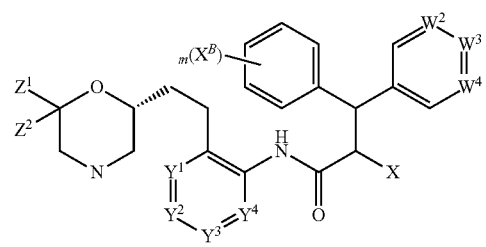

(Ia)

or

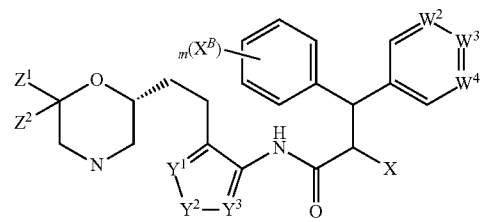

(Ib)

or a pharmaceutically acceptable salt thereof, wherein
$Y^1$, $Y^2$, $Y^3$, and $Y^4$ are independently $C(R^4)$ or N;
$W^2$, $W^3$, and $W^4$ are independently $CR^5$ or N;
each $R^5$ is independently $X^C$ or H; and
each occurrence of $R^4$ is independently selected from H, halo, hydroxy, =O, $C_1$-$C_4$ alkyl, $C_1$-$C_4$ alkoxy, $C_1$-$C_4$ alkyl-S(O)k-, CF3, CN, and benzyl.

5. The compound according to claim 4, or a pharmaceutically acceptable salt thereof, wherein:
each $R^4$ is independently H or fluoro,
each $X^B$ is independently selected from F, Cl, Br, —OCH$_3$, —CF$_3$, and —OCF$_3$,
each $R^5$ is independently selected from H, F, Cl, Br, —OCH$_3$, —CF$_3$, and —OCF$_3$, and
m is 0, 1 or 2.

6. The compound according to claim 3, or a pharmaceutically acceptable salt thereof, wherein each $X^B$ is independently F or Cl, and each $R^5$ is independently H, F, or Cl, provided that one $X^B$ group is present at the 4-position.

7. The compound according to claim 4, or a pharmaceutically acceptable salt thereof, wherein at least one of $Y^1$, $Y^2$, $Y^3$, and $Y^4$ is CF.

8. The compound according to claim 1, or a pharmaceutically acceptable salt thereof, wherein X is selected from: H, —$NH_2$, N(H)—$CH_2$—$CF_3$, and —N(H)—C(O)—$OC_1$-$C_6$ alkyl, and N(H)—C(O)—$OC_1$-$C_6$ fluoroalkyl.

9. The compound according to claim 1, or a pharmaceutically acceptable salt thereof, wherein $Z^1$ and $Z^2$, together with the carbon atom to which they are attached, form a spirocyclic 5- or 6-membered monocyclic heterocycloalkyl group, or a spirocyclic 5- or 6-membered cycloalkyl group; wherein said 5- or 6-membered monocyclic heterocycloalkyl group, or said 5- or 6-membered cycloalkyl group may be optionally substituted with one or two $X^A$, wherein each occurrence of $X^A$ is independently C(O)—$C_1$-$C_6$ alkyl, $SO_2$—$C_1$-$C_6$ alkyl, $C_1$-$C_6$ alkyl, and halo.

10. The compound according to claim 1, or a pharmaceutically acceptable salt thereof, wherein $Z^1$ is

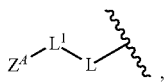

L is $C_1$-$C_3$ alkylene, $CH_2CF_2$, or a bond, and $Z^2$ is H.

11. The compound according to claim 1, or a pharmaceutically acceptable salt thereof, wherein $Z^2$ is H, and $Z^1$ is selected from the group consisting of:

(1)
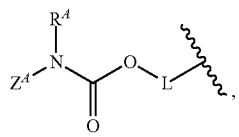

(2)
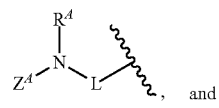
, and (3)
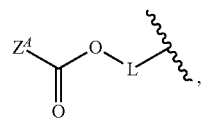
,

L is a linker selected from
(a) a bond,
(b) —CH2-,
(c) —$CH_2$—$CF_2$—, and
(d) —$CH_2CH_2$—.

12. The compound according to claim 1, or a pharmaceutically acceptable salt thereof, wherein $Z^A$ is:
(1) AryA optionally substituted with one or two substituents, independently selected from: (a) $C_1$-$C_6$ alkyl, (b) $C_1$-$C_6$ haloalkyl, (c) halo, (d) CN, (e) $NO_2$, (f) $NH_2$, (g) $SO_2$—$C_1$-$C_6$ alkyl, (h) $SO_2$—$NH_2$, (i) phenyl, benzyl or phenoxy, each optionally substituted with 1 or 2 substituents selected from halo and $C_1$-$C_6$ alkyl, and (j) HetD, —O-HetD or —$CH_2$-HetD;
(2) HetB, optionally substituted with one or two substituents, independently selected from: halo, $C_1$-$C_6$ alkyl, HetB, $C_1$-$C_6$ alkyl substituted with HetB, and phenyl; and (3) HetC, optionally substituted with one or two substituents, independently selected from: halo or $C_1$-$C_6$ alkyl.

13. A compound selected from the group consisting of:
N-(2-{2-[(2R,5R,6S)-6-{[(4-chlorophenyl)sulfanyl]methyl}-5-methylmorpholin-2-yl]ethyl}phenyl)-Nα-(methoxycarbonyl)-β-phenyl-L-phenylalaninamide;

methyl N-[(1S)-1-benzhydryl-2-[3-[(6S)-6-[(4-chlorophenyl)sulfanylmethyl]morpholin-2-yl]propylamino]-2-oxo-ethyl]carbamate;

methyl N-[(1S)-1-benzhydryl-2-[3-[(6S)-6-[(4-chloro-2-methyl-phenyl)sulfanylmethyl]morpholin-2-yl]propylamino]-2-oxo-ethyl]carbamate;

methyl N-[(1S)-1-benzhydryl-2-[[2-[2-[(6S)-6-(2-naphthylsulfonylmethyl)morpholin-2-yl]ethyl]phenyl]amino]-2-oxo-ethyl]carbamate;

methyl N-[(1S)-1-benzhydryl-2-[[2-[2-[(6S)-6-[(4-chlorophenoxy)methyl]morpholin-2-yl]ethyl]phenyl]amino]-2-oxo-ethyl]carbamate;

methyl N-[(1S)-1-benzhydryl-2-[[2-[2-[(6S)-6-[(4-chlorophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-chlorophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-bromophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-bromophenoxy)methyl]morpholin-2-yl]ethyl]phenyl]amino]-2-oxo-ethyl]carbamate;

methyl N-[(1S)-1-benzhydryl-2-[[2-[2-[(2R,6S)-6-[(4-bromo-2-nitro-phenoxy)methyl]morpholin-2-yl]ethyl]phenyl]amino]-2-oxo-ethyl]carbamate;

methyl N-[(1S)-1-benzhydryl-2-oxo-2-[[2-[2-[(2R,6S)-6-[(4-phenylphenoxy)methyl]morpholin-2-yl]ethyl]phenyl]amino]ethyl]carbamate;

methyl N-[(1S)-1-benzhydryl-2-[[2-[2-[(2R,6S)-6-[(4-benzylphenoxy)methyl]morpholin-2-yl]ethyl]phenyl]amino]-2-oxo-ethyl]carbamate;

methyl N-[(1S)-1-[[2-[2-[(2R,6S)-6-[(2-amino-4-bromophenoxy)methyl]morpholin-2-yl]ethyl]phenyl]carbamoyl]-2,2-diphenyl-ethyl]carbamate;

methyl N-[(1S)-1-benzhydryl-2-[[2-[2-[(2R,6S)-6-[(4-imidazol-1-ylphenoxy)methyl]morpholin-2-yl]ethyl]phenyl]amino]-2-oxo-ethyl]carbamate;

methyl N-[(1S)-1-benzhydryl-2-oxo-2-[[2-[2-[(2R,6S)-6-[[4-(1,2,4-triazol-1-yl)phenoxy]methyl]morpholin-2-yl]ethyl]phenyl]amino]ethyl]carbamate;

methyl N-[(1S)-1-benzhydryl-2-[[2-[2-[(2R,6S)-6-[(4-methylsulfonylphenoxy)methyl]morpholin-2-yl]ethyl]phenyl]amino]-2-oxo-ethyl]carbamate;

methyl N-[(1S)-1-benzhydryl-2-[[2-[2-[(2R,6S)-6-[(4-cyanophenoxy)methyl]morpholin-2-yl]ethyl]phenyl]amino]-2-oxo-ethyl]carbamate;

methyl N-[(1S)-1-benzhydryl-2-[[2-[2-[(2R,6S)-6-[(3-chlorophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(3,4-dichlorophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(3-bromophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-methylsulfonylphenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-cyanophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(3-methylsulfonylphenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(3-cyanophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(2,4-dichlorophenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-chloro-2-methyl-phenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-bromo-2-fluoro-phenyl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[(2-methyl-4-methylsulfonyl-phenoxy)methyl]morpholin-2-yl]ethyl]phenyl]amino]-2-oxo-ethyl]carbamate;

methyl N-[(1S)-1-benzhydryl-2-[[2-[2-[(2R,6S)-6-[(4-cyano-2-methyl-phenoxy)methyl]morpholin-2-yl]ethyl]phenyl]amino]-2-oxo-ethyl]carbamate;

methyl N-[(1S)-1-benzhydryl-2-[[2-[2-[(2R,6S)-6-(1H-indol-4-yloxymethyl)morpholin-2-yl]ethyl]phenyl]amino]-2-oxo-ethyl]carbamate;

methyl N-[(1S)-1-benzhydryl-2-[[2-[2-[(2R,6S)-6-(indan-4-yloxymethyl)morpholin-2-yl]ethyl]phenyl]amino]-2-oxo-ethyl]carbamate;

methyl N-[(1S)-1-benzhydryl-2-[[2-[2-[(2R,6S)-6-[[5-[(2-methylthiazol-4-yl)methyl]-1,3,4-oxadiazol-2-yl]sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[[5-[(5-methylpyrazol-1-yl)methyl]-1,3,4-oxadiazol-2-yl]sulfanylmethyl]morpholin-2-yl]ethyl]phenyl]amino]-2-oxo-ethyl]carbamate;

methyl N-[(1S)-1-benzhydryl-2-oxo-2-[[2-[2-[(2R,6S)-6-[[5-(4-pyridyl)-1,3,4-oxadiazol-2-yl]sulfanylmethyl]morpholin-2-yl]ethyl]phenyl]amino]ethyl]carbamate;

methyl N-[(1S)-1-benzhydryl-2-oxo-2-[[2-[2-[(2R,6S)-6-(1H-pyrazolo[3,4-d]pyrimidin-4-ylsulfanylmethyl)morpholin-2-yl]ethyl]phenyl]amino]ethyl]carbamate;

methyl N-[(1S)-1-benzhydryl-2-[[2-[2-[(2R,6S)-6-[(1-methylpyrazolo[3,4-d]pyrimidin-4-yl)sulfanylmethyl]morpholin-2-yl]ethyl]phenyl]amino]-2-oxo-ethyl]carbamate;

methyl N-[(1S)-1-benzhydryl-2-[[2-[2-[(2R,6S)-6-[[5-[(2-methylthiazol-4-yl)methyl]-1,3,4-oxadiazol-2-yl]oxymethyl]morpholin-2-yl]ethyl]phenyl]amino]-2-oxo-ethyl]carbamate;

N-[2-(2-{(2R,6S)-6-[(1H-indol-7-yloxy)methyl]morpholin-2-yl}ethyl)phenyl]-Nα-(methoxycarbonyl)-b-phenyl-L-phenylalaninamide;

N-[2-(2-{(2R,6S)-6-[(1H-indol-6-yloxy)methyl]morpholin-2-yl)}ethyl)phenyl]-Nα-(methoxycarbonyl)-b-phenyl-L-phenylalaninamide;

N-[2-(2-{(2R,6S)-6-[(1H-benzotriazol-7-yloxy)methyl]morpholin-2-yl}ethyl)phenyl]-Nα-(methoxycarbonyl)-b-phenyl-L-phenylalaninamide;

N-[2-(2-{(2R,6S)-6-[(1H-indazol-7-yloxy)methyl]morpholin-2-yl}ethyl)phenyl]-Nα-(methoxycarbonyl)-b-phenyl-L-phenylalaninamide;

methyl [(2S)-1-oxo-3,3-diphenyl-1-{[2-(2-{(2R,6S)-6-[(quinolin-5-ylsulfanyl)methyl]morpholin-2-yl}ethyl)phenyl]amino}propan-2-yl]carbamate;

N-α-(methoxycarbonyl)-β-phenyl-N-(2-{2-[(2R,6S)-6-{[4-(1H-pyrazol-1-yl)phenoxy]methyl}morpholin-2-yl]ethyl}phenyl)-L-phenylalaninamide;

N-α-(methoxycarbonyl)-β-phenyl-N-(2-{2-[(2R,6S)-6-{[4-(trifluoromethyl)phenoxy]methyl}morpholin-2-yl]ethyl}phenyl)-L-phenylalaninamide;

N-[2-(2-{(2R,6S)-6-[(1H-indazol-6-yloxy)methyl]morpholin-2-yl}ethyl)phenyl]-Nα-(methoxycarbonyl)-β-phenyl-L-phenylalaninamide;

N-[2-(2-{(2R,6S)-6-[(4-fluorophenoxy)methyl]morpholin-2-yl}ethyl)phenyl]-Nα-(methoxycarbonyl)-β-phenyl-L-phenylalaninamide;

N-[2-(2-{(2R,6S)-6-[(3-fluorophenoxy)methyl]morpholin-2-yl}ethyl)phenyl]-Nα-(methoxycarbonyl)-β-phenyl-L-phenylalaninamide;

N-[2-(2-{(2R,6S)-6-[(1,3-benzothiazol-6-yloxy)methyl]morpholin-2-yl}ethyl)phenyl]-Nα-(methoxycarbonyl)-β-phenyl-L-phenylalaninamide;

N-[2-(2-{(2R,6S)-6-[(2-fluorophenoxy)methyl]morpholin-2-yl}ethyl)phenyl]-Nα-(methoxycarbonyl)-β-phenyl-L-phenylalaninamide;

N-α-(methoxycarbonyl)-N-(2-{2-[(2R,6S)-6-{[(2-methylpyridin-3-yl)oxy]methyl}morpholin-2-yl]ethyl}phenyl)-β-phenyl-L-phenylalaninamide;

methyl [(2S)-1-oxo-3,3-diphenyl-1-{[2-(2-{(2R,6S)-6-[(quinolin-5-yloxy)methyl]morpholin-2-yl}ethyl)phenyl]amino}propan-2-yl]carbamate;

N-α-(methoxycarbonyl)-β-phenyl-N-(2-{2-[(2R,6S)-6-{[4-(pyridin-4-yl)phenoxy]methyl}morpholin-2-yl]ethyl}phenyl)-L-phenylalaninamide;

methyl [(2S)-1-oxo-3,3-diphenyl-1-{[2-(2-{(2R,6S)-6-[(1,2,3,4-tetrahydroquinolin-7-yloxy)methyl]morpholin-2-yl}ethyl)phenyl]amino}propan-2-yl]carbamate;

N-(2-{2-[(2R,6S)-6-{[(3-chloropyridin-2-yl)sulfanyl]methyl}morpholin-2-yl]ethyl}phenyl)-Nα-(methoxycarbonyl)-β-phenyl-L-phenylalaninamide;

N-α-(methoxycarbonyl)-β-phenyl-N-[2-(2-{(2R,6S)-6-[(4-sulfamoylphenoxy)methyl]morpholin-2-yl}ethyl)phenyl]-L-phenylalaninamide;

methyl N-[(1S)-1-benzhydryl-2-[[2-[2-[(2R,6S)-6-[(4-chlorophenyl)sulfonylmethyl]morpholin-2-yl]ethyl]phenyl]amino]-2-oxo-ethyl]carbamate;

methyl N-[(1S)-1-benzhydryl-2-[[2-[2-[(2R,6S)-6-[(4-chlorophenyl)sulfinylmethyl]morpholin-2-yl]ethyl]phenyl]amino]-2-oxo-ethyl]carbamate;

methyl N-[(1S)-1-benzhydryl-2-[[2-[[(2S,6S)-6-[(4-chlorophenyl)sulfanylmethyl]morpholin-2-yl]methoxy]phenyl]amino]-2-oxo-ethyl]carbamate;

methyl N-[(1S)-1-benzhydryl-2-[[2-[2-[(2R,6S)-6-[(4-chlorophenyl)methoxymethyl]morpholin-2-yl]ethyl]phenyl]amino]-2-oxo-ethyl]carbamate;

N-[2-(2-{(2R,6R)-6-[(E)-2-(4-chlorophenyl)ethenyl]morpholin-2-yl}ethyl)phenyl]-Nα-(methoxycarbonyl)-β-phenyl-L-phenylalaninamide;

N-α-(methoxycarbonyl)-N-(2-{2-[(2R,6R)-6-{(E)-2-[4-(methylsulfonyl)phenyl]ethenyl}morpholin-2-yl]ethyl}phenyl)-β-phenyl-L-phenylalaninamide;

N-[2-(2-{(2R,6R)-6-[2-(4-chlorophenyl)ethyl]morpholin-2-yl}ethyl)phenyl]-Nα-(methoxycarbonyl)-β-phenyl-L-phenylalaninamide;

N-[2-(2-{(2R,6R)-6-[2-(4-cyanophenyl)ethyl]morpholin-2-yl)}ethyl)phenyl]-N-α-(methoxycarbonyl)-β-phenyl-L-phenylalaninamide;

N-[2-(2-{(2R,6R)-6-[2-(4-cyanophenoxy)ethyl]morpholin-2-yl}ethyl)phenyl]-Nα-(methoxycarbonyl)-β-phenyl-L-phenylalaninamide;

N-[2-(2-{(2R,6S)-6-[2-(4-bromophenyl)-1,1-difluoroethyl]morpholin-2-yl}ethyl)phenyl]-Nα-(methoxycarbonyl)-β-phenyl-L-phenylalaninamide;

(βS)—N-(2-{2-[(2R,6S)-6-{[(4-chlorophenyl)sulfanyl]methyl}morpholin-2-yl]ethyl}phenyl)-Nα-(methoxycarbonyl)-β-pyridin-3-yl-L-phenylalaninamide;

(βS)—N-(2-{2-[(2R,6S)-6-{[(4-chlorophenyl)sulfanyl]methyl}morpholin-2-yl]ethyl}phenyl)-Nα-(methoxycarbonyl)-β-1H-pyrrolo[2,3-b]pyridin-3-yl-L-phenylalaninamide;

methyl [(2S,3S)-1-[(2-{2-[(2R,6S)-6-{[(4-chlorophenyl)sulfanyl]methyl}morpholin-2-yl]ethyl}phenyl)amino]-1-oxo-3-phenyl-3-(quinolin-4-yl)propan-2-yl]carbamate;

(βR)—N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-L-phenylalaninamide;

(βS)—N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-D-phenylalaninamide;

(βR)—N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-D-phenylalaninamide;

(βS)—N-(2-{2-[(2R,6S)-6-{[(4-chlorophenyl)sulfanyl]methyl}morpholin-2-yl]ethyl}phenyl)-Nα-(methoxycarbonyl)-β-pyridin-4-yl-L-phenylalaninamide;

N-[2-(2-{(2R,6 S)-6-[(4-cyanophenoxy)methyl]morpholin-2-yl}ethyl)-3-fluorophenyl]-Nα-(methoxycarbonyl)-β-phenyl-L-phenylalaninamide;

N-[2-(2-{(2R,6S)-6-[(4-cyanophenoxy)methyl]morpholin-2-yl}ethyl)-5-fluorophenyl]-Nα-(methoxycarbonyl)-β-phenyl-L-phenylalaninamide;

N-(2-{2-[(2R,6S)-6-{[(4-chlorophenyl)sulfanyl]methyl}morpholin-2-yl]ethyl}-3-fluorophenyl)-Nα-(methoxycarbonyl)-β-phenyl-L-phenylalaninamide;

N-[2-(2-{(2R,6S)-6-[(3-cyanophenoxy)methyl]morpholin-2-yl}ethyl)-4-fluorophenyl]-Nα-(methoxycarbonyl)-β-phenyl-L-phenylalaninamide;

N-[2-(2-{(2R,6S)-6-[(4-cyanophenoxy)methyl]morpholin-2-yl}ethyl)-4-fluorophenyl]-Nα-(methoxycarbonyl)-β-phenyl-L-phenylalaninamide;

N-[2-(2-{(2R,6S)-6-[(4-cyanophenoxy)methyl]morpholin-2-yl}ethyl)-6-fluorophenyl]-Nα-(methoxycarbonyl)-β-phenyl-L-phenylalaninamide;

N-(2-{2-[(2R,6S)-6-{[(6-chloro-5-fluoro-1H-benzimidazol-2-yl)sulfanyl]methyl}morpholin-2-yl]ethyl}-6-fluorophenyl)-Nα-(methoxycarbonyl)-β-phenyl-L-phenylalaninamide;

N-[2-(2-{(2R,6S)-6-[(4-cyanophenoxy)methyl]morpholin-2-yl}ethyl)-5-fluoropyridin-3-yl]-Nα-(methoxycarbonyl)-β-phenyl-L-phenylalaninamide;

N-[4-(2-{(2R,6S)-6-[(4-cyanophenoxy)methyl]morpholin-2-yl}ethyl)pyrimidin-5-yl]-Nα-(methoxycarbonyl)-β-phenyl-L-phenylalaninamide;

N-(2-{2-[(2R,6S)-6-{[(3-chloropyridin-2-yl)sulfanyl]methyl}morpholin-2-yl]ethyl}pyridin-3-yl)-Nα-(methoxycarbonyl)-β-phenyl-L-phenylalaninamide;

N-[4-(2-{(2R,6S)-6-[(4-cyanophenoxy)methyl]morpholin-2-yl}ethyl)pyridin-3-yl]-Nα-(methoxycarbonyl)-β-phenyl-L-phenylalaninamide;

Methyl [(1S)-2-{[4-(2-{(2R,6S)-6-[(4-cyanophenoxy)methyl]morpholin-2-yl}ethyl)-5-fluoropyridin-3-yl]amino}-1-(diphenylmethyl)-2-oxoethyl]carbamate;

methyl N-[(1S)-1-benzhydryl-2-[[3-[2-[(2R,6S)-6-[(4-chlorophenyl)sulfanylmethyl]morpholin-2-yl]ethyl]pyrazin-2-yl]amino]-2-oxo-ethyl]carbamate;

methyl N-[(1S)-1-benzhydryl-2-[[3-[2-[(2R,6S)-6-[(4-cyanophenoxy)methyl]morpholin-2-yl]ethyl]pyrazin-2-yl]amino]-2-oxo-ethyl]carbamate;

N-[3-(2-{(2R,6S)-6-[(4-cyanophenoxy)methyl]morpholin-2-yl}ethyl)pyridin-2-yl]-Nα-(methoxycarbonyl)-β-phenyl-L-phenylalaninamide;

N-[4-(2-{(2R,6S)-6-[(4-cyanophenoxy)methyl]morpholin-2-yl}ethyl)-2-oxo-1,2-dihydropyridin-3-yl]-Nα-(methoxycarbonyl)-β-phenyl-L-phenylalaninamide;

N-(4-{2-[(2R,6S)-6-{[(4-chlorophenyl)sulfanyl]methyl}morpholin-2-yl]ethyl}-2-oxo-1,2-dihydropyridin-3-yl)-Nα-(methoxycarbonyl)-β-phenyl-L-phenylalaninamide;

N-(4-{2-[(2R,6S)-6-{[(4-chlorophenyl)sulfanyl]methyl}morpholin-2-yl]ethyl}-2-oxo-1,2-dihydropyridin-3-yl)-β-phenyl-L-phenylalaninamide;

N-(4-{2-[(2R,6S)-6-{[(4-chlorophenyl)sulfanyl]methyl}morpholin-2-yl]ethyl}-2-oxo-1,2-dihydropyridin-3-yl)-β-phenyl-Nα-(2,2,2-trifluoroethyl)-L-phenylalaninamide;

N-[6-(2-{(2R,6S)-6-[(4-cyanophenoxy)methyl]morpholin-2-yl}ethyl)-2-oxopyridin-1(2H)-yl]-Nα-(methoxycarbonyl)-β-phenyl-L-phenylalaninamide;

4-fluoro-β-(4-fluorophenyl)-N-(3-fluoro-2-{2-[(2R,6S)-6-{[(5-pyridin-4-yl-1,3,4-oxadiazol-2-yl)sulfanyl]methyl}morpholin-2-yl]ethyl}phenyl)-L-phenylalaninamide;

Methyl [(1S,2S)-2-(3,5-difluorophenyl)-1-[(3-fluoro-2-{2-[(2R)-8-oxo-1-oxa-4-azaspiro[5.5]undec-2-yl]ethyl}phenyl)carbamoyl]-2-(4-fluorophenyl)ethyl]carbamate;

(βS)-4-chloro-β-(3,5-difluorophenyl)-N-(3-fluoro-2-{2-[(2R)-9-(methylsulfonyl)-1-oxa-4,9-diazaspiro[5.5]undec-2-yl]ethyl}phenyl)-L-phenylalaninamide;

methyl {(1S,2S)-2-(4-chlorophenyl)-2-(3,5-difluorophenyl)-1-[(3-fluoro-2-{2-[(2R)-9-(methylsulfonyl)-1-oxa-4,9-diazaspiro[5.5]undec-2-yl]ethyl}phenyl)carbamoyl]ethyl}carbamate;

(2S,3S)—N-(2-(2-((R)-9-Acetyl-1-oxa-4,9-diazaspiro[5.5]undecan-2-yl)ethyl)-3-fluorophenyl)-2-amino-3-(4-chlorophenyl)-3-(3,5-difluorophenyl)propanamide;

(βS)-4-chloro-β-(3,5-difluorophenyl)-N-(2-{2-[(2R)-1,9-dioxa-4-azaspiro[5.5]undec-2-yl]ethyl}-3-fluorophenyl)-L-phenylalaninamide;

methyl {(1S,2S)-2-(4-chlorophenyl)-2-(3,5-difluorophenyl)-1-[(2-{2-[(2R)-1,9-dioxa-4-azaspiro[5.5]undec-2-yl]ethyl}-3-fluorophenyl)carbamoyl]ethyl}carbamate;

methyl {(1S,2S)-2-(4-chlorophenyl)-2-(3,5-difluorophenyl)-1-[(4-{2-[(2R)-1,9-dioxa-4-azaspiro[5.5]undec-2-yl]ethyl}-5-fluoropyridin-3-yl)carbamoyl]ethyl}carbamate;

4-fluoro-β-(4-fluorophenyl)-N-(3-fluoro-2-{2-[(2R,6S)-6-({[(2,2,2-trifluoroethyl)carbamoyl]oxy}methyl)morpholin-2-yl]ethyl}phenyl)-L-phenylalaninamide;

methyl {(1S)-1-[bis(4-fluorophenyl)methyl]-2-[(5-fluoro-4-{2-[(7R)-6-oxa-9-azaspiro[4.5]dec-7-yl]ethyl}pyridin-3-yl)amino]-2-oxoethyl}carbamate;

N-(4-{2-[(2R)-1,9-dioxa-4-azaspiro[5.5]undec-2-yl]ethyl}-5-fluoropyridin-3-yl)-4-fluoro-β-(4-fluorophenyl)-L-phenylalaninamide;

N-(4-{2-[(2R,6S)-6-{[(3-cyanophenyl)sulfanyl]methyl}morpholin-2-yl]ethyl}-5-fluoropyridin-3-yl)-4-fluoro-β-(4-fluorophenyl)-L-phenylalaninamide;

(S)-2-amino-N-(5-fluoro-4-(2-((2R,6S)-6-(((5-(pyridin-4-yl)-1,3,4-oxadiazol-2-yl)thio)methyl)morpholin-2-yl)ethyl)pyridin-3-yl)-3,3-bis(4-fluorophenyl)propanamide;

(S)-2-amino-N-(4-(2-((2R,6S)-6-(((4-chlorophenyl)thio)methyl)morpholin-2-yl)ethyl)-5-fluoropyridin-3-yl)-3,3-bis(4-fluorophenyl)propanamide;

{(2S,6R)-6-[2-(3-fluoro-5-{[4-fluoro-β-(4-fluorophenyl)-L-phenylalanyl]amino}pyridin-4-yl)ethyl]morpholin-2-yl}methyl morpholine-4-carboxylate;

((2S,6R)-6-(2-(3-((S)-3-(3,5-difluorophenyl)-3-(4-fluorophenyl)propanamido)-5-fluoropyridin-4-yl)ethyl)morpholin-2-yl)methyl (2,2,2-trifluoroethyl)carbamate;

N-(3-{(6R)-6-[2-(4-chlorophenyl)ethyl]morpholin-2-yl}propyl)-Nα-(methoxycarbonyl)-β-phenyl-L-phenylalaninamide;

N-(2-{2-[(2R,6S)-6-{[4-(1H-imidazol-1-yl)phenoxy]methyl}morpholin-2-yl]ethyl}phenyl)-Nα-(methoxycarbonyl)-β-phenyl-L-phenylalaninamide;

N-(2-{2-[(2S,6S)-6-{[(4-chlorophenyl)sulfonyl]methyl}morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,6S)-6-{[2-(1H-pyrazol-3-yl)phenoxy]methyl}morpholin-2-yl]ethyl}phenyl)-L-phenylalaninamide;

N-(2-{2-[(2R,6R)-6-ethynylmorpholin-2-yl]ethyl}phenyl)-Nα-(methoxycarbonyl)-β-phenyl-L-phenylalaninamide;

N-(2-{2-[(2R,6S)-6-(5,6-dimethyl-1H-benzimidazol-2-yl)morpholin-2-yl]ethyl}phenyl)-Nα-(methoxycarbonyl)-β-phenyl-L-phenylalaninamide;

N-[2-(2-{(2R,6S)-6-[(3-cyanophenoxy)methyl]morpholin-2-yl}ethyl)pyridin-3-yl]-Nα-(methoxycarbonyl)-β-phenyl-L-phenylalaninamide;

N-[5-(2-{(2R,6S)-6-[(4-cyanophenoxy)methyl]morpholin-2-yl}ethyl)pyrimidin-4-yl]-Nα-(methoxycarbonyl)-β-phenyl-L-phenylalaninamide;

Nα-(methoxycarbonyl)-N-(4-{2-[(2R,6S)-6-{[4-(methylsulfonyl)phenoxy]methyl}morpholin-2-yl]ethyl}-1H-pyrazol-3-yl)-β-phenyl-L-phenylalaninamide;

N-[2-(2-{(2R,6R)-6-[2-(4-chlorophenyl)ethyl]morpholin-2-yl}ethyl)phenyl]-Nα-(methoxycarbonyl)-β-phenyl-L-phenylalaninamide;

N-[2-({(2S,6S)-6-[(4-cyanophenoxy)methyl]morpholin-2-yl}methyl)phenyl]-Nα-(methoxycarbonyl)-β-phenyl-L-phenylalaninamide;

N-(2-{2-[(2R,6S)-6-{[(4-chlorophenyl)sulfanyl]methyl}morpholin-2-yl]ethyl}phenyl)-Nα-(methoxycarbonyl)-β-pyridin-4-ylphenylalaninamide;

N-(2-{2-[(2R,6S)-6-{[(4-chlorophenyl)sulfanyl]methyl}morpholin-2-yl]ethyl}phenyl)-Nα-(methoxycarbonyl)-β-pyridin-4-ylphenylalaninamide;

4-fluoro-N-(5-fluoro-4-{2-[(2R,6S)-6-(hydroxymethyl)morpholin-2-yl]ethyl}pyridin-3-yl)-β-(4-fluorophenyl)-L-phenylalaninamide;

N-(2-{2-[(2R,6S)-6-{[(4-chlorophenyl)sulfanyl]methyl}morpholin-2-yl]ethyl}-3-fluorophenyl)-4-fluoro-β-(4-fluorophenyl)-L-phenylalaninamide;

N-(4-{2-[(2R,6S)-6-{[(4-chlorophenyl)sulfanyl]methyl}morpholin-2-yl]ethyl}-5-fluoropyridin-3-yl)-4-fluoro-β-(4-fluorophenyl)-D-phenylalaninamide;

4-fluoro-β-(4-fluorophenyl)-N-(5-fluoro-4-{2-[(2R,6S)-6-({[(2,2,2-trifluoroethyl)carbamoyl]oxy}methyl)morpholin-2-yl]ethyl}pyridin-3-yl)-L-phenylalaninamide;

N-[4-(2-{(2R,6S)-6-[(carbamoyloxy)methyl]morpholin-2-yl}ethyl)-5-fluoropyridin-3-yl]-4-fluoro-β-(4-fluorophenyl)-L-phenylalaninamide;

4-fluoro-N-(5-fluoro-4-{2-[(2R,6S)-6-({[(4-fluorobenzyl)carbamoyl]oxy}methyl)morpholin-2-yl]ethyl}pyridin-3-yl)-β-(4-fluorophenyl)-L-phenylalaninamide;

{(2S,6R)-6-[2-(2-{[(3S)-3-(3,5-difluorophenyl)-3-(4-fluorophenyl)propanoyl]amino}-6-fluorophenyl)ethyl]morpholin-2-yl}methyl (2,2,2-trifluoroethyl)carbamate;

{(2S,6R)-6-[2-(2-{[3,3-bis(4-fluorophenyl)propanoyl]amino}-6-fluorophenyl)ethyl]morpholin-2-yl}methyl (2,2,2-trifluoroethyl)carbamate;

{(2S,6R)-6-[2-(3-{[3,3-bis(4-fluorophenyl)propanoyl]amino}-5-fluoropyridin-4-yl)ethyl]morpholin-2-yl}methyl (2,2,2-trifluoroethyl)carbamate;

[(2S,6R)-6-(2-{3-[(3,3-diphenylpropanoyl)amino]-5-fluoropyridin-4-yl}ethyl)morpholin-2-yl]methyl (2,2,2-trifluoroethyl)carbamate;

4-fluoro-β-(4-fluorophenyl)-N-(5-fluoro-4-{2-[(2R,6S)-6-({[(2-phenylethyl)carbamoyl]oxy}methyl)morpholin-2-yl]ethyl}pyridin-3-yl)-L-phenylalaninamide;

N-(5-fluoro-4-{2-[(7R)-6-oxa-9-azaspiro[4.5]dec-7-yl]ethyl}pyridin-3-yl)-β-phenyl-L-phenylalaninamide;

4-fluoro-N-[5-fluoro-4-(2-{(2R,6S)-6-[(2-methylpropoxy)methyl]morpholin-2-yl}ethyl)pyridin-3-yl]-β-(4-fluorophenyl)-L-phenylalaninamide;

N-(5-fluoro-4-{2-[(2R)-1-oxa-4-azaspiro[5.5]undec-2-yl]ethyl}pyridin-3-yl)-β-phenyl-L-phenylalaninamide;

N-(4-{2-[(2R,6S)-6-({[(cyclohexylmethyl)carbamoyl]oxy}methyl)morpholin-2-yl]ethyl}-5-fluoropyridin-3-yl)-4-fluoro-β-(4-fluorophenyl)phenylalaninamide;

N-(4-{2-[(2R,6S)-6-({[(2-chlorobenzyl)carbamoyl]oxy}methyl)morpholin-2-yl]ethyl}-5-fluoropyridin-3-yl)-4-fluoro-β-(4-fluorophenyl)phenylalaninamide;

4-fluoro-N-(5-fluoro-4-{2-[(2R,6S)-6-({[(3-hydroxy-2,2-dimethylpropyl)carbamoyl]oxy}methyl)morpholin-2-yl]ethyl}pyridin-3-yl)-β-(4-fluorophenyl)phenylalaninamide;

4-fluoro-N-(5-fluoro-4-{2-[(2R,6S)-6-({[(6-methylpyridin-3-yl)carbamoyl]oxy}methyl)morpholin-2-yl]ethyl}pyridin-3-yl)-β-(4-fluorophenyl)phenylalaninamide;

4-fluoro-N-(5-fluoro-4-{2-[(2R,6S)-6-({[(3-fluoropropyl)carbamoyl]oxy}methyl)morpholin-2-yl]ethyl}pyridin-3-yl)-β-(4-fluorophenyl)phenylalaninamide;

N-[4-(2-{(2R,6S)-6-[({[2-(3,5-dimethyl-1H-pyrazol-1-yl)ethyl]carbamoyl}oxy)methyl]morpholin-2-yl}ethyl)-5-fluoropyridin-3-yl]-4-fluoro-β-(4-fluorophenyl)phenylalaninamide;

4-fluoro-N-[5-fluoro-4-(2-{(2R,6S)-6-[({[(2-methyltetrahydrofuran-2-yl)methyl]carbamoyl}oxy)methyl]morpholin-2-yl}ethyl)pyridin-3-yl]-β-(4-fluorophenyl)phenylalaninamide;

4-fluoro-N-[5-fluoro-4-(2-{(2R,6S)-6-[({[(4-methylmorpholin-2-yl)methyl]carbamoyl}oxy)methyl]morpholin-2-yl}ethyl)pyridin-3-yl]-β-(4-fluorophenyl)phenylalaninamide;

4-fluoro-β-(4-fluorophenyl)-N-(5-fluoro-4-{2-[(2R,6S)-6-({[(tetrahydrofuran-3-ylmethyl)carbamoyl]oxy}methyl)morpholin-2-yl]ethyl}pyridin-3-yl)phenylalaninamide;

N-(4-{2-[(2R,6R)-6-{[(2-chlorobenzyl)amino]methyl}morpholin-2-yl]ethyl}-5-fluoropyridin-3-yl)-4-fluoro-β-(4-fluorophenyl)phenylalaninamide;

N-(5-fluoro-4-{2-[(7R)-6-oxa-9-azaspiro[4.5]dec-7-yl]ethyl}pyridin-3-yl)-3,3-bis(4-fluorophenyl)propanamide;

(βS)-3,5-difluoro-β-(4-fluorophenyl)-N-(3-fluoro-2-{2-[(2R,6S)-6-({[(2,2,2-trifluoroethyl)carbamoyl]oxy}methyl)morpholin-2-yl]ethyl}phenyl)-L-phenylalaninamide;

4-fluoro-N-(5-fluoro-4-{2-[(2R,6R)-6-{[(3-fluoropropyl)amino]methyl}morpholin-2-yl]ethyl}pyridin-3-yl)-β-(4-fluorophenyl)-L-phenylalaninamide;

N-(4-{2-[(2R,6R)-6-({[2-(3,5-dimethyl-1H-pyrazol-1-yl)ethyl]amino}methyl)morpholin-2-yl]ethyl}-5-fluoropyridin-3-yl)-4-fluoro-β-(4-fluorophenyl)-L-phenylalaninamide;

N-(4-{2-[(2R,6S)-6-{[(1,4-dioxan-2-ylmethyl)(methyl)amino]methyl}morpholin-2-yl]ethyl}-5-fluoropyridin-3-yl)-4-fluoro-β-(4-fluorophenyl)-L-phenylalaninamide;

(βS)-3-fluoro-N-(3-fluoro-2-{2-[(7R)-6-oxa-9-azaspiro[4.5]dec-7-yl]ethyl}phenyl)-β-(4-fluorophenyl)-L-phenylalaninamide;

4-fluoro-N-(5-fluoro-4-{2-[(7R)-6-oxa-9-azaspiro[4.5]dec-7-yl]ethyl}pyridin-3-yl)-β-(4-fluorophenyl)-L-phenylalaninamide;

methyl {(1S)-2-[(2-{2-[(2R)-9-acetyl-1-oxa-4,9-diazaspiro[5.5]undec-2-yl]ethyl}-3-fluorophenyl)amino]-1-[(S)-(4-chlorophenyl)(3,5-difluorophenyl)methyl]-2-oxoethyl)}carbamate;

(βS)—N-(4-{2-[(2R)-9-acetyl-1-oxa-4,9-diazaspiro[5.5]undec-2-yl]ethyl}-5-fluoropyridin-3-yl)-4-chloro-β-(3,5-difluorophenyl)-L-phenylalaninamide;

methyl {(1S)-2-[(4-{2-[(2R)-9-acetyl-1-oxa-4,9-diazaspiro[5.5]undec-2-yl]ethyl}-5-fluoropyridin-3-yl)amino]-1-[(S)-(4-chlorophenyl)(3,5-difluorophenyl)methyl]-2-oxoethyl}carbamate;

(βS)-β-(4-chlorophenyl)-N-(5-fluoro-4-{2-[(2R)-9-(methylsulfonyl)-1-oxa-4,9-diazaspiro[5.5]undec-2-yl]ethyl}pyridin-3-yl)-3-(trifluoromethoxy)-L-phenylalaninamide;

(βS)-4-chloro-β-(3,5-difluorophenyl)-N-(4-{2-[(2R)-1,9-dioxa-4-azaspiro[5.5]undec-2-yl]ethyl}-5-fluoropyridin-3-yl)-L-phenylalaninamide;

(βS)-4-chloro-N-(4-{2-[(2R)-1,9-dioxa-4-azaspiro[5.5]undec-2-yl]ethyl}-5-fluoropyridin-3-yl)-β-[3-(trifluoromethoxy)phenyl]-L-phenylalaninamide;

methyl {(1S,2S)-2-(4-chlorophenyl)-1-[(4-{2-[(2R)-1,9-dioxa-4-azaspiro[5.5]undec-2-yl]ethyl}-5-fluoropyridin-3-yl)carbamoyl]-2-[3-(trifluoromethoxy)phenyl]ethyl}) carbamate;

(βR)-4-chloro-N-(4-{2-[(2R)-1,9-dioxa-4-azaspiro[5.5]undec-2-yl]ethyl}-5-fluoropyridin-3-yl)-β-(tetrahydro-2H-pyran-4-yl)-L-phenylalaninamide;

(βR)-4-chloro-N-(2-{2-[(2R)-1,9-dioxa-4-azaspiro[5.5]undec-2-yl]ethyl}-3-fluorophenyl)-β-(tetrahydro-2H-pyran-4-yl)-L-phenylalaninamide;

methyl [(1S,2R)-2-(4-chlorophenyl)-1-[(4-{2-[(2R)-1,9-dioxa-4-azaspiro[5.5]undec-2-yl]ethyl}-5-fluoropyridin-3-yl)carbamoyl]-2-(tetrahydro-2H-pyran-4-yl)ethyl]carbamate;

methyl [(1S,2R)-2-(4-chlorophenyl)-1-[(2-{2-[(2R)-1,9-dioxa-4-azaspiro[5.5]undec-2-yl]ethyl}-3-fluorophenyl)carbamoyl]-2-(tetrahydro-2H-pyran-4-yl)ethyl]carbamate;

(βS)-4-chloro-β-(3,5-difluorophenyl)-N-(2-{2-[(7R)-2,6-dioxa-9-azaspiro[4.5]dec-7-yl]ethyl}-3-fluorophenyl)-L-phenylalaninamide;

methyl {(1S,2S)-2-(4-chlorophenyl)-2-(3,5-difluorophenyl)-1-[(2-{2-[(7R)-2,6-dioxa-9-azaspiro[4.5]dec-7-yl]ethyl}-3-fluorophenyl)carbamoyl]ethyl}carbamate;

or a pharmaceutically acceptable salt thereof.

14. A pharmaceutical composition comprising an effective amount of a compound according to claim 1, or a pharmaceutically acceptable salt thereof, and a pharmaceutically acceptable carrier.

15. A method for the treatment of infection by HIV in a subject in need thereof, which comprises administering to the subject an effective amount of the compound according to claim 1 or a pharmaceutically acceptable salt thereof.

16. A pharmaceutical composition comprising an effective amount of a compound according to claim 1, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents.

17. The pharmaceutical composition of claim 16, wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: HIV-1 protease peptide substrate
<220> FEATURE:
<221> NAME/KEY: MISC_FEATURE
<222> LOCATION: (5)..(5)
<223> OTHER INFORMATION: Xaa is beta napthylalanine

<400> SEQUENCE: 1

Val Ser Gln Asn Xaa Pro Ile Val
1               5